US012043860B2

(12) United States Patent
Poulos et al.

(10) Patent No.: US 12,043,860 B2
(45) Date of Patent: Jul. 23, 2024

(54) ADVANCED PRODUCTION OF CANNABINOIDS IN YEAST

(71) Applicant: Lygos, Inc., Berkeley, CA (US)

(72) Inventors: Jason L. Poulos, Los Angeles, CA (US); Anthony N. Farina, Pasadena, CA (US)

(73) Assignee: Lygos, Inc., Berkeley, CA (US)

( * ) Notice: Subject to any disclaimer, the term of this patent is extended or adjusted under 35 U.S.C. 154(b) by 0 days.

(21) Appl. No.: 17/711,993

(22) Filed: Apr. 1, 2022

(65) Prior Publication Data

US 2022/0220515 A1 Jul. 14, 2022

Related U.S. Application Data

(63) Continuation of application No. 16/679,637, filed on Nov. 11, 2019, now Pat. No. 11,293,038, which is a continuation-in-part of application No. 16/539,436, filed on Aug. 13, 2019, now Pat. No. 10,954,534, which is a continuation-in-part of application No. 16/122,702, filed on Sep. 5, 2018, now Pat. No. 10,392,635, which is a continuation of application No. 15/815,651, filed on Nov. 16, 2017, now Pat. No.
(Continued)

(51) Int. Cl.

| | |
|---|---|
| ***C12P 7/42*** | (2006.01) |
| ***C12N 1/14*** | (2006.01) |
| ***C12N 1/20*** | (2006.01) |
| ***C12N 9/00*** | (2006.01) |
| ***C12N 9/10*** | (2006.01) |
| ***C12N 9/88*** | (2006.01) |
| ***C12N 15/00*** | (2006.01) |
| ***C12N 15/81*** | (2006.01) |

(52) U.S. Cl.
CPC .............. *C12P 7/42* (2013.01); *C12N 9/1029* (2013.01); *C12N 9/1085* (2013.01); *C12N 9/88* (2013.01); *C12N 9/93* (2013.01); *C12N 15/81* (2013.01); *C12Y 203/01206* (2015.07); *C12Y 205/01* (2013.01); *C12Y 504/99* (2013.01); *C12Y 602/01* (2013.01)

(58) Field of Classification Search
CPC ...... C12N 9/1085; C12N 9/88; C12N 9/1029; C12N 15/81
See application file for complete search history.

(56) References Cited

U.S. PATENT DOCUMENTS

| | | | |
|---|---|---|---|
| 6,630,507 | B1 | 10/2003 | Hampson et al. |
| 7,186,850 | B2 | 3/2007 | Silverberg |
| 8,673,368 | B2 | 3/2014 | Guy et al. |

(Continued)

FOREIGN PATENT DOCUMENTS

| | | |
|---|---|---|
| WO | WO2013006953 | 1/2013 |
| WO | WO2014134281 | 9/2014 |

OTHER PUBLICATIONS

Gagne, S.J. et al. Identification of olivetolic acid cyclase from Cannabis sativa reveals a unique catalytic route to plant polyketides. Proceedings of the National Academy of Sciences of the United States of America 109, 12811-12816 (2012).

(Continued)

*Primary Examiner* — Yong D Pak
(74) *Attorney, Agent, or Firm* — Carr & Ferrell LLP

(57) ABSTRACT

Exemplary embodiments provided herein include genetically engineering microorganisms, such as yeast or bacteria, to produce cannabinoids by inserting genes that produce the appropriate enzymes for the metabolic production of a desired compound.

3 Claims, 8 Drawing Sheets

Specification includes a Sequence Listing.

Related U.S. Application Data

10,093,949, which is a continuation of application No. 14/795,816, filed on Jul. 9, 2015, now Pat. No. 9,822,384.

(60) Provisional application No. 62/024,099, filed on Jul. 14, 2014.

(56) References Cited

U.S. PATENT DOCUMENTS

| | | | |
|---|---|---|---|
| 8,884,100 | B2 | 11/2014 | Page et al. |
| 9,611,460 | B2 | 4/2017 | Page et al. |
| 9,822,384 | B2 | 11/2017 | Poulos et al. |
| 10,093,949 | B2 | 10/2018 | Poulos et al. |
| 10,392,635 | B2 | 8/2019 | Poulos et al. |
| 10,954,534 | B2 | 3/2021 | Poulos et al. |
| 11,293,038 | B2 | 7/2022 | Poulos et al. |
| 2009/0226991 | A1 | 9/2009 | Feldman et al. |
| 2012/0144523 | A1 | 6/2012 | Page et al. |
| 2013/0067619 | A1 | 3/2013 | Page et al. |
| 2013/0210107 | A1 | 8/2013 | Akada et al. |
| 2014/0178954 | A1 | 6/2014 | Hitz et al. |
| 2016/0010126 | A1 | 1/2016 | Poulos et al. |
| 2018/0073043 | A1 | 3/2018 | Poulos et al. |
| 2018/0371507 | A1 | 12/2018 | Poulos et al. |
| 2020/0017889 | A1 | 1/2020 | Poulos et al. |
| 2020/0071732 | A1 | 3/2020 | Poulos et al. |

OTHER PUBLICATIONS

Stout, J.M., Boubakir, Z., Ambrose, S.J., Purves, R.W. & Page, J.E. The hexanoyl-CoA precursor for cannabinoid biosynthesis is formed by an acyl-activating enzyme in Cannabis sativa trichomes. The Plant Journal 71, 353-365 (2012).

Shoyama, Y. et al. Structure and function of 1-Tetrahydrocannabinolic Acid (THCA) synthase, the enzyme controlling the psychoactivity of cannabis sativa. J. Mol. Biol., 423 (1), 96-105 (2012).

ElSohly et al. Chemical constituents of marijuana: The complex mixture of natural cannabinoids. National Center for Natural Products Research, School of Pharmacy, The University of Mississippi, University, MS 38677. Life Sciences (78), 539-548 (2005).

Ignea et al. Engineering monoterpene production in yeast using a synthetic dominant negative geranyl diphosphate synthase. ACS Synth Biol, May 16, 2014. vol. 3, No. 5. pp. 298-306.

Fonseca et al. The yeast Kluyveromyces marxianus and its biotechnological potential. Appl Microbiol Biotechnol, Jun. 2008, vol. 79, No. 3, pp. 339-354.

"Recombinase expression vector pSH68, complete sequence", GenBank entry HQ401270.1, [retrieved on Nov. 18, 2015 from http://www.ncbi.nlm.nih.gov/nuccore/HW401270] Sep. 12, 2011 (Sep. 12, 2011), 3 pages.

Fischer, Marc et al., Metabolic Engineering of Monoterpene Synthesis in 2011, Biotechnology and Bioengineering, vol. 108, No. 8, Aug. 2011, 10 pages.

ADVANCED PRODUCTION OF CANNABINOIDS IN YEAST

CROSS-REFERENCE TO RELATED APPLICATIONS

This patent application is a continuation of U.S. Non-Provisional patent application Ser. No. 16/679,637, filed on Nov. 11, 2019, titled "Production of Cannabinoids in Yeast," now U.S. Pat. No. 11,293,038, which is a continuation-in-part of U.S. Non-Provisional patent application Ser. No. 16/539,436, filed Aug. 13, 2019, titled "Production of Cannabigerolic Acid in Yeast," now U.S. Pat. No. 10,954,534, issued on Mar. 23, 2021, which is a continuation-in-part of U.S. Non-Provisional patent application Ser. No. 16/122,702, filed Sep. 5, 2018, titled "Production of Tetrahydrocannabinolic Acid in Yeast," now U.S. Pat. No. 10,392,635, issued on Aug. 27, 2019, which is a continuation of U.S. Non-Provisional patent application Ser. No. 15/815,651, filed Nov. 16, 2017, titled "Production of Cannabidiolic Acid in Yeast," now U.S. Pat. No. 10,093,949, issued on Oct. 9, 2018, which is a continuation of U.S. Non-Provisional patent application Ser. No. 14/795,816, filed Jul. 9, 2015, titled "Production of Cannabinoids in Yeast," now U.S. Pat. No. 9,822,384, issued on Nov. 21, 2017, which in turn claims the benefit and priority of U.S. Provisional Patent Application Ser. No. 62/024,099, filed Jul. 14, 2014, titled "Terpenophenolic Production in Microorganisms." All of the aforementioned disclosures are hereby incorporated by reference herein in their entireties including all references and appendices cited therein.

REFERENCE TO SEQUENCE LISTINGS

The present application is filed with sequence listing(s) attached hereto and incorporated by reference, including Appendix 1A titled "Additional Examples," Appendix 1B titled "Sequence IDs," Appendix 1C titled "Additional Sequence IDs," and Appendix 1D titled "Sequence IDs."

The present application is filed with a ST.25 formatted sequence listing attached hereto and incorporated by reference comprising sequences 1 through 124.

FIELD OF THE INVENTION

This invention relates to molecular biology, and more specifically to the transformation of yeast cells and the production of cannabinoids.

SUMMARY OF THE INVENTION

Exemplary embodiments provided herein include genetically engineering microorganisms, such as yeast or bacteria, to produce cannabinoids by inserting genes that produce the appropriate enzymes for the metabolic production of a desired compound.

DETAILED DESCRIPTION OF EXEMPLARY EMBODIMENTS

Figure 1:
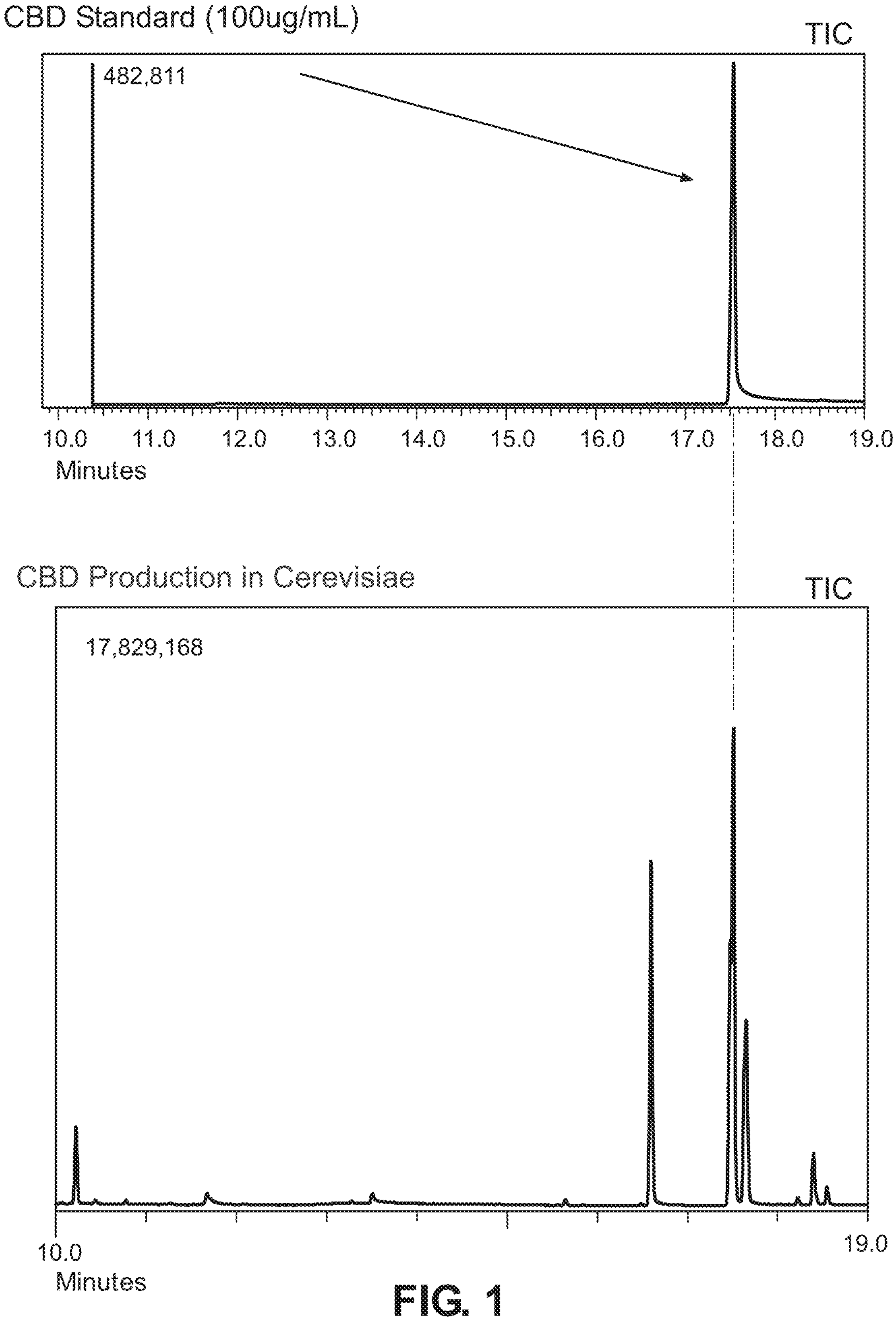
FIG. 1 shows exemplary experimental data achieved in connection with Example 1 of Appendix 1A titled "Additional Examples" for cannabidiol ("CBD")/cannabidiolic acid ("CBDA") production in *S. cerevisiae.*

The present application relates to the field of cannabinoid production in yeasts. Cannabinoids are a general class of chemicals that act on cannabinoid receptors and other target molecules to modulate a wide range of physiological behavior such as neurotransmitter release. Cannabinoids are produced naturally in humans (called endocannabinoids) and by several plant species (called phytocannabinoids) including *Cannabis sativa*. Cannabinoids have been shown to have several beneficial medical/therapeutic effects and therefore they are an active area of investigation by the pharmaceutical industry for use as pharmaceutical products for various diseases.

Currently the production of cannabinoids for pharmaceutical or other use is done by chemical synthesis or through the extraction of cannabinoids from plants that are producing these cannabinoids, for example *Cannabis sativa*. There are several drawbacks to the current methods of cannabinoid production. The chemical synthesis of various cannabinoids is a costly process when compared to the extraction of cannabinoids from naturally occurring plants. The chemical synthesis of cannabinoids also involves the use of chemicals that are not environmentally friendly, which can be considered as an additional cost to their production. Furthermore, the synthetic chemical production of various cannabinoids has been classified as less pharmacologically active as those extracted from plants such as *Cannabis sativa*. Although there are drawbacks to chemically synthesized cannabinoids, the benefit of this production method is that the end product is a highly pure single cannabinoid. This level of purity is preferred for pharmaceutical use. The level of purity required by the pharmaceutical industry is reflected by the fact that no plant extract based cannabinoid production has received FDA approval yet and only synthetic compounds have been approved.

In contrast to the synthetic chemical production of cannabinoids, the other method that is currently used to produce cannabinoids is production of cannabinoids in plants that naturally produce these chemicals; the most used plant for this is *Cannabis sativa*. In this method, the plant *Cannabis sativa* is cultivated and during the flowering cycle various cannabinoids are produced naturally by the plant. The plant can be harvested and the cannabinoids can be ingested for pharmaceutical purposes in various methods directly from the plant itself or the cannabinoids can be extracted from the plant. There are multiple methods to extract the cannabinoids from the plant *Cannabis sativa*. All of these methods typically involve placing the plant, *Cannabis sativa* that contains the cannabinoids, into a chemical solution that selectively solubilizes the cannabinoids into this solution. There are various chemical solutions used to do this such as hexane, cold water extraction methods, CO2 extraction methods, and others. This chemical solution, now containing all the different cannabinoids, can then be removed, leaving behind the excess plant material. The cannabinoid containing solution can then be further processed for use.

There are several drawbacks of the natural production and extraction of cannabinoids in plants such as *Cannabis sativa*. Since there are numerous cannabinoids produced by *Cannabis sativa* it is often difficult to reproduce identical cannabinoid profiles in plants using an extraction process. Furthermore, variations in plant growth will lead to different levels of cannabinoids in the plant itself making reproducible extraction difficult. Different cannabinoid profiles will have different pharmaceutical effects which are not desired for a pharmaceutical product. Furthermore, the extraction of cannabinoids from *Cannabis sativa* extracts produces a mixture of cannabinoids and not a highly pure single pharmaceutical compound. Since many cannabinoids are similar in structure it is difficult to purify these mixtures to a high level resulting in cannabinoid contamination of the end product.

Disclosed herein are strategies for creating cannabinoids in microorganisms such as yeast and methods to produce various cannabinoids in yeast from a simple sugar source. The general methods involve genetically engineering yeast to produce various cannabinoids, where the main carbon source available to the yeast is a sugar (glucose, galactose, fructose, sucrose, honey, molasses, raw sugar, etc.). Genetic engineering of the microorganism involves inserting various genes that produce the appropriate enzymes and/or altering the natural metabolic pathway in the microorganism to achieve the production of a desired compound. Through genetic engineering of microorganisms these metabolic pathways can be introduced into these microorganisms and the same metabolic products that are produced in the plant *Cannabis sativa* can be produced by the microorganisms. The benefit of this method is that once the microorganism is produced, the production of the cannabinoid is low cost and reliable, only a specific cannabinoid is produced or a subset is produced, depending on the organism. The purification of the cannabinoid is straight forward since there is only a single cannabinoid or a selected few cannabinoids present in the microorganism. The process is a sustainable process which is more environmentally friendly than synthetic production.

FIG. 1 shows exemplary experimental data achieved in connection with Example 1 of Appendix 1A titled "Additional Examples" for cannabidiol ("CBD")/cannabidiolic acid ("CBDA") production in *S. cerevisiae*.

FIG. 1 shows gas chromatography—mass spectrometry of cannabidiol (CBD) produced in *S. cerevisiae*. After processing the yeast cells, as described in Example 1 of Appendix 1A, the whole cell ethyl acetate extract is analyzed for the presences of CBD. The samples were prepared in a way similar to that shown in Appendix A1 except that no MSTFA derivatization was used in this sample (therefore CBDA turns into CBD upon heating), the oven protocol was also slightly different than that shown in Appendix 1A. Initially, a standard CBD solution is run (100 ug/mL; TOP). After running the standard the inventors determined the run time of 17.5 minutes. After running the standard the inventors repeated the GC-MS experiment with their whole cell extract (BOTTOM). At a run time of 17.5 minutes, the inventors saw the same peak as in the standard. Mass spectrometry analysis of the peaks showed identical mass for the two samples (standard and extract) indicating the presence of CBD in their whole cell extract.

Figure 2:
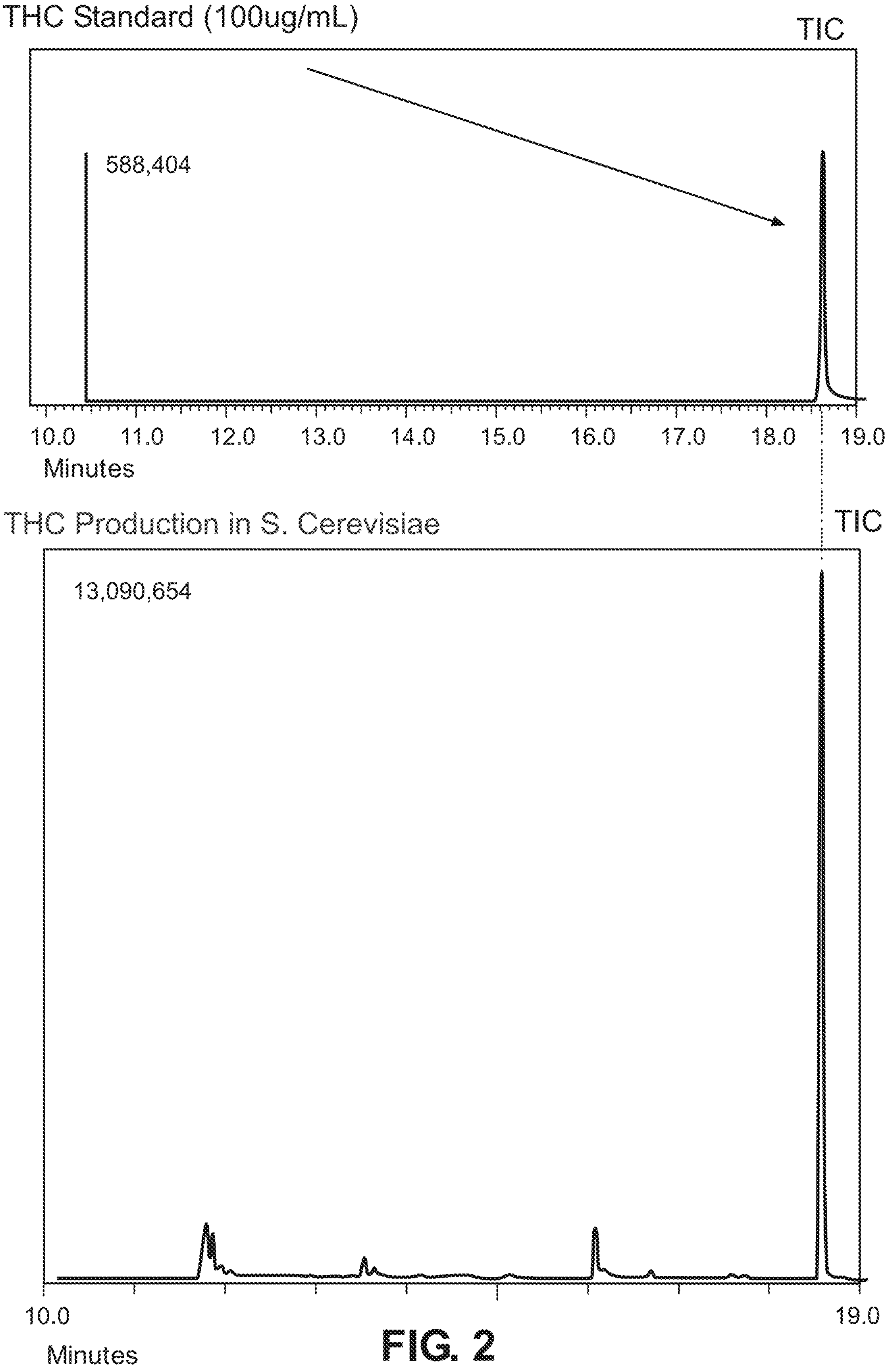
FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae.*

FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae.*

FIG. 2 shows gas chromatography—mass spectrometry of tetrahydrocannabinol (THC) produced in *S. cerevisiae*. After processing the yeast cells, as described in Example 2 of Appendix 1A, the whole cell ethyl acetate extract was analyzed for the presences of THC. The samples were prepared in a way similar to that shown in Appendix 1A except that no MSTFA derivatization was used in this sample (therefore THCA turns into THC upon heating), the oven protocol was also slightly different than that shown in Appendix 1A. Initially, a standard CBD solution was run (100 ug/mL; TOP). After running the standard the inventors determined the run time of 18.5 minutes. After running the standard the inventors repeated the GC-MS experiment with their whole cell extract (BOTTOM). At a run time of 18.5 minutes, the inventors saw the same peak as in the standard. Mass spectrometry analysis of the peaks showed identical mass for the two samples (standard and extract) indicating the presence of THC in their whole cell extract.

Figure 3:
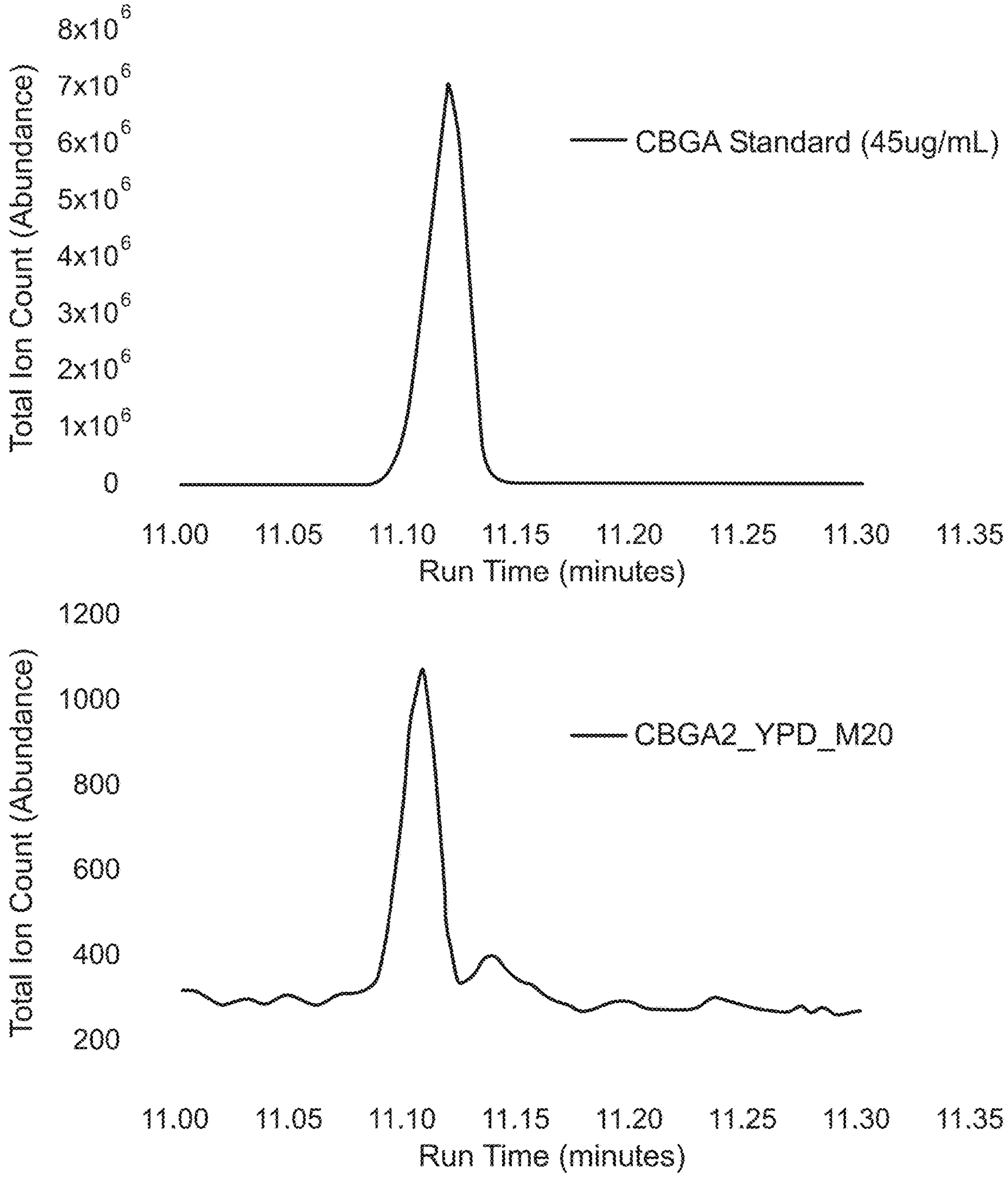
FIG. 3 shows exemplary experimental data achieved in connection with Example 3 of Appendix 1A titled "Additional Examples" for cannabigerol ("CBG")/cannabigerolic acid ("CBGA") production in *S. cerevisiae.*

FIG. 3 shows exemplary experimental data achieved in connection with Example 3 of Appendix 1A titled "Additional Examples" for cannabigerol ("CBG")/cannabigerolic acid ("CBGA") production in *S. cerevisiae.*

FIG. 3 shows gas chromatography—mass spectrometry of cannabigerolic acid (CBGA) produced in *S. cerevisiae*. After processing the yeast cells, as described in Example 3 of Appendix 1A, the whole cell ethyl acetate extract was analyzed for the presences of CBGA. The samples were prepared in a way as described in Appendix 1A, but the oven protocol was also slightly different than that shown in Appendix 1A. Initially, a standard CBGA solution was run (45 ug/mL; TOP). After running the standard, the inventors determined the run time of 11.1 minutes. After running the standard, the inventors repeated the GC-MS experiment with their whole cell extract (BOTTOM). At a run time of 11.1 minutes, the inventors saw the same peak as in the standard. Mass spectrometry analysis of the peaks showed identical mass for the two samples (standard and extract) indicating the presence of CBGA in their whole cell extract.

Figure 4:
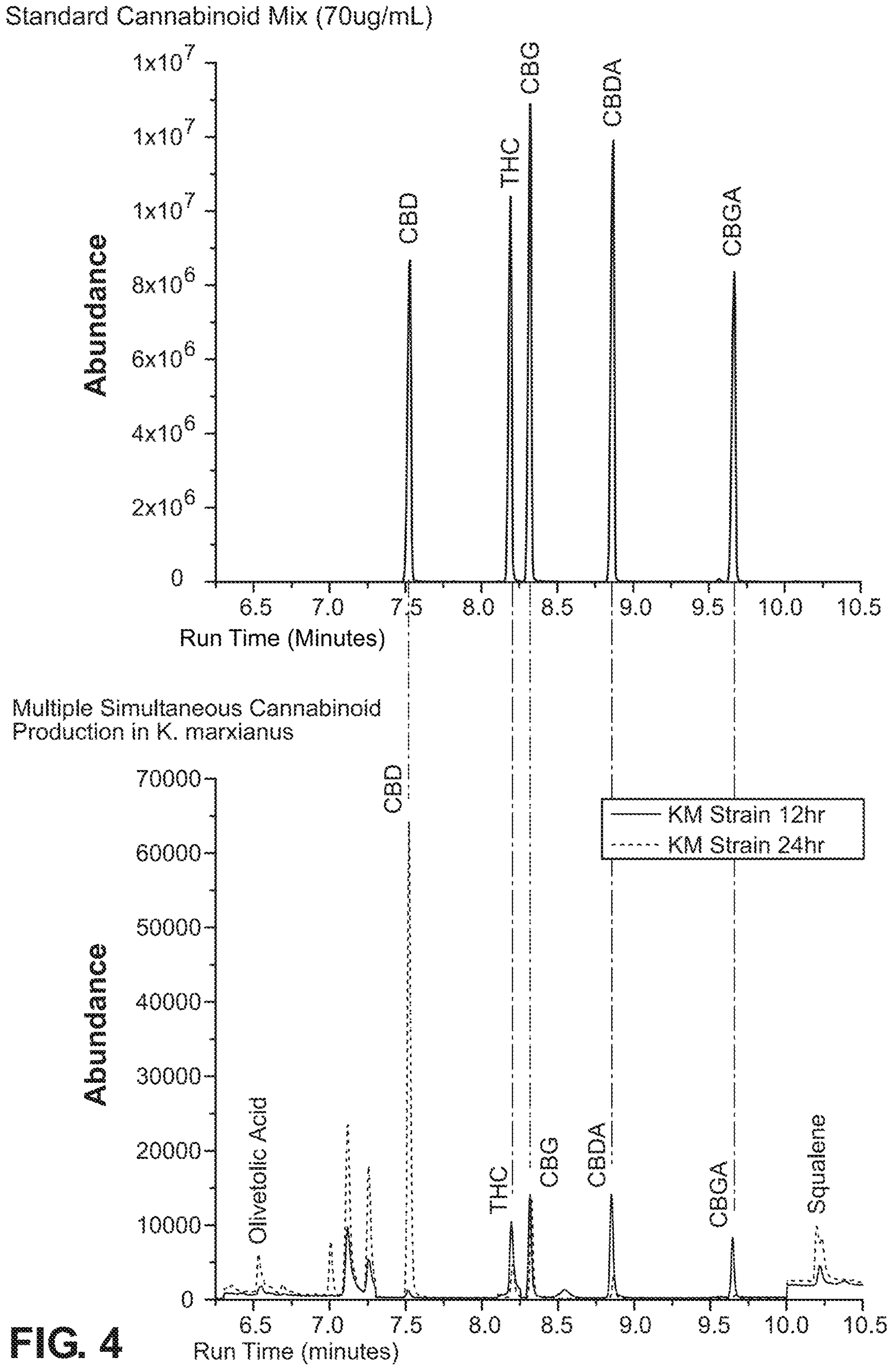
FIG. 4 shows exemplary experimental data achieved in connection with Example 4 of Appendix 1A titled "Additional Examples" for CBGA, CBDA, CBD, CBG and THC production in *K. marxianus.*

FIG. 4 shows exemplary experimental data achieved in connection with Example 4 of Appendix 1A titled "Additional Examples" for CBGA, CBDA, CBD, CBG and THC production in *K. marxianus.*

FIG. 4 shows gas chromatography—mass spectrometry of cannabinoid production (CBGA, CBDA, CBD, CBG, THC) produced in *K. marxianus*. After processing the yeast cells, as described in Example 4 of Appendix 1A, the whole cell ethyl acetate extract was analyzed for the presence of cannabinoids. The samples were prepared in a way as described in Appendix 1A, but the oven protocol was also slightly different than that shown in Appendix 1A. Initially, a standard solution containing CBD, CBG, THC, CBDA, and CBGA was run (70 ug/mL each; TOP). After running the standard, the inventors determined the run time for each compounds. After running the standard, the inventors repeated the GC-MS experiment with their whole cell extract (BOTTOM). At each run time the inventors saw the same peaks as in the standard. Mass spectrometry analysis of the peaks showed identical mass for the two samples (standard and extract) indicating the presence of cannabinoids in their whole cell extract.

Figure 5:
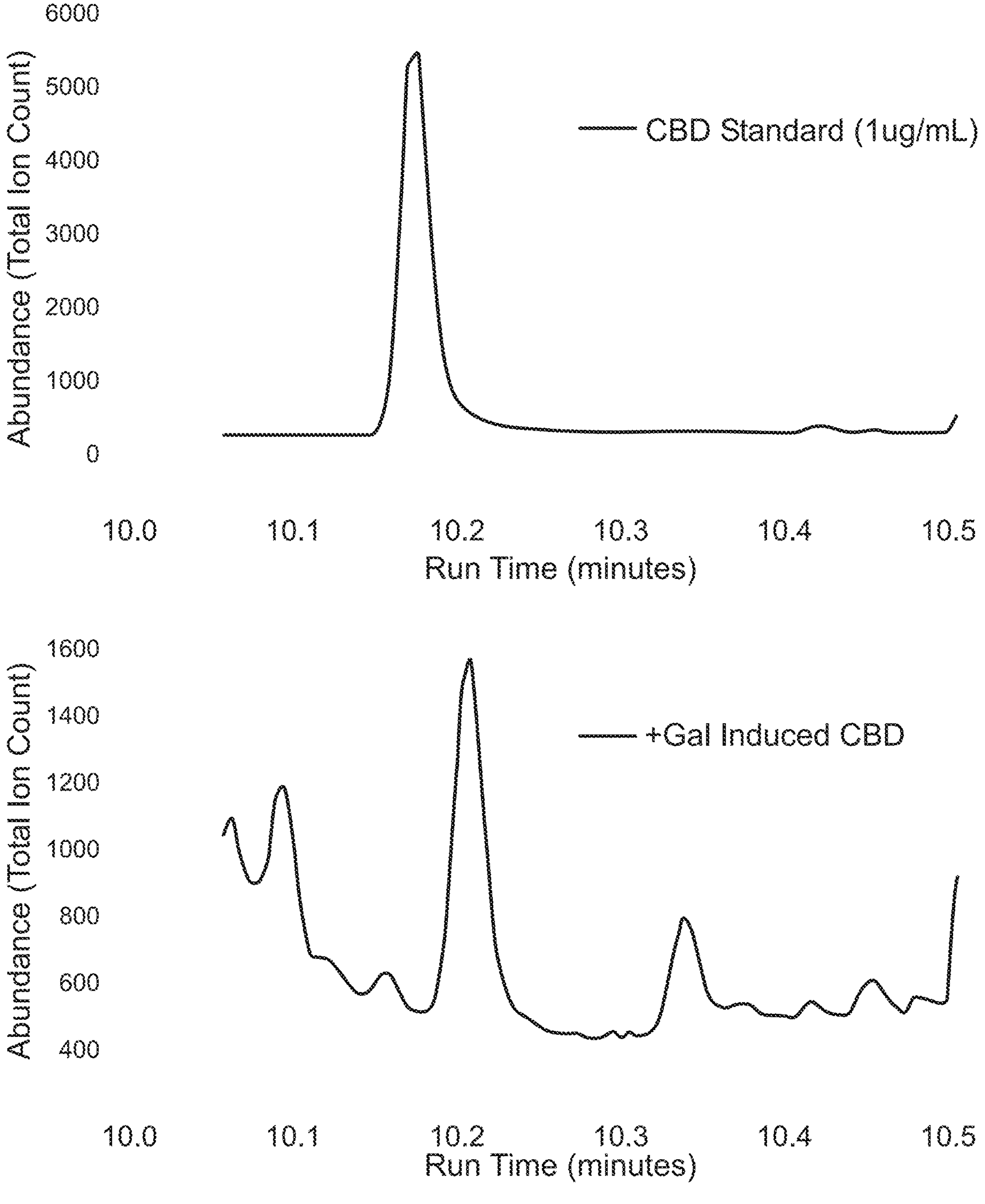
FIG. 5 show exemplary experimental data achieved in connection with Example 5 of Appendix 1A titled "Additional Examples" for galactose induced CBD production in *S. cerevisiae.*

FIG. 5 show exemplary experimental data achieved in connection with Example 5 of Appendix 1A titled "Additional Examples" for galactose induced CBD production in *S. cerevisiae.*

FIG. 5 shows gas chromatography—mass spectrometry of induced cannabidiol (CBD) production in *S. cerevisiae*. After processing yeast cells, as described in Example 5 of Appendix 1A, the whole cell ethyl acetate extract was analyzed for the presences of CBD. The samples were prepared in a way as described in Appendix 1A. Initially, a standard solution containing CBD was run (1 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Figure 6:
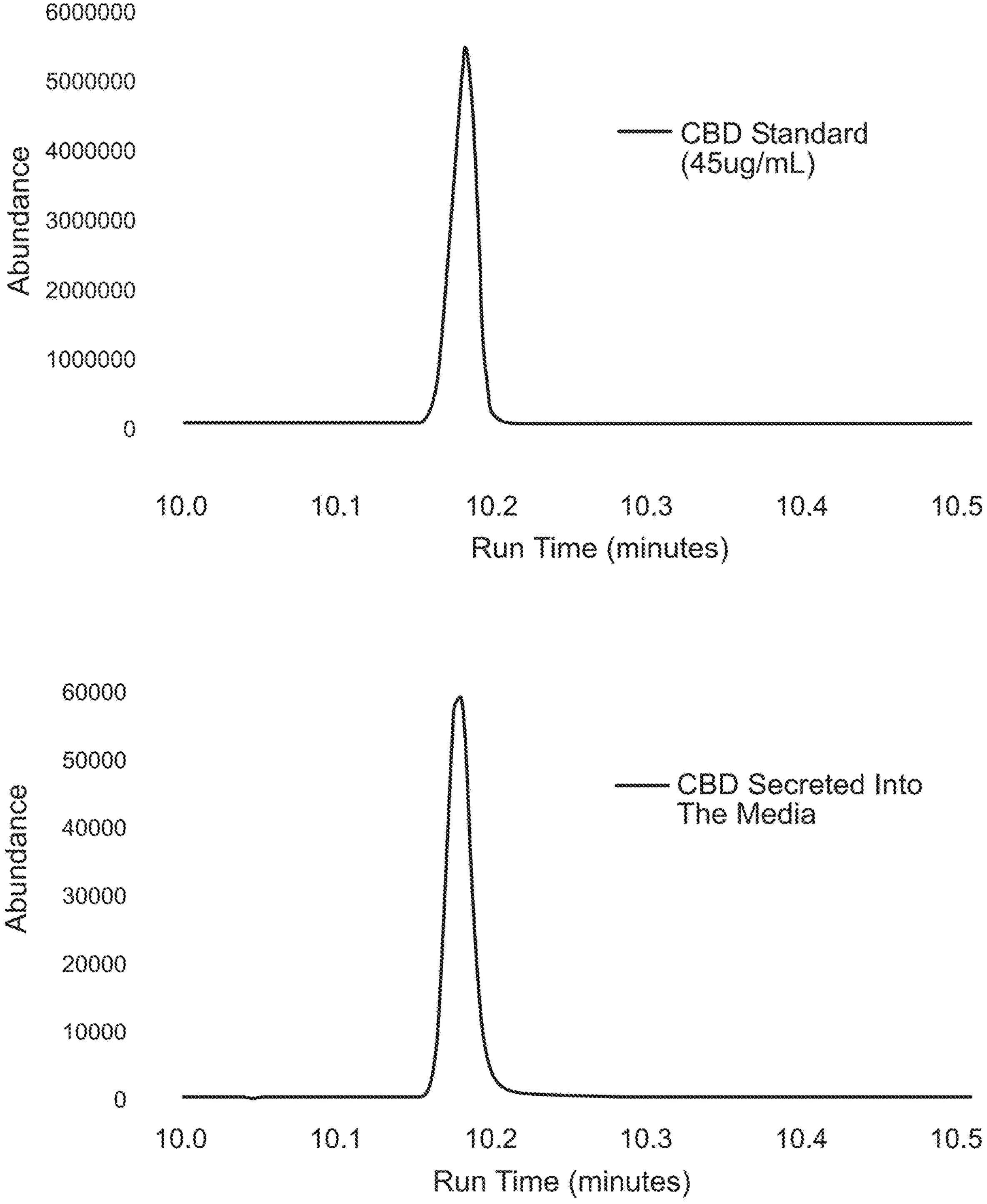
FIG. 6 shows exemplary experimental data achieved in connection with Example 6 of Appendix 1A titled "Additional Examples" for secretion of CBD into media by *S. cerevisiae.*

FIG. 6 shows exemplary experimental data achieved in connection with Example 6 of Appendix 1A titled "Additional Examples" for secretion of CBD into media by *S. cerevisiae.*

FIG. 6 shows gas chromatography—mass spectrometry of induced cannabidiol production (CBD) produced in *S. cerevisiae* and secreted into the media. After processing the growth media, as described in Example 6 of Appendix 1A, the media ethyl acetate extract was analyzed for the presence of CBD. The samples were prepared in a way as described in Appendix 1A. Initially, a standard solution containing CBD was run (45 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Biosynthetic Production of Cannabidiolic Acid (CBDA) in *S. cerevisiae.*

Through genetic engineering the inventors have reconstituted the cannabidiolic acid (CBDA) metabolic pathway found in *Cannabis sativa* into *S. cerevisiae* (a species of yeast).

Producing CBGA is an initial step in producing many cannabinoids from *Cannabis sativa* in *S. cerevisiae*. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Figure 7:
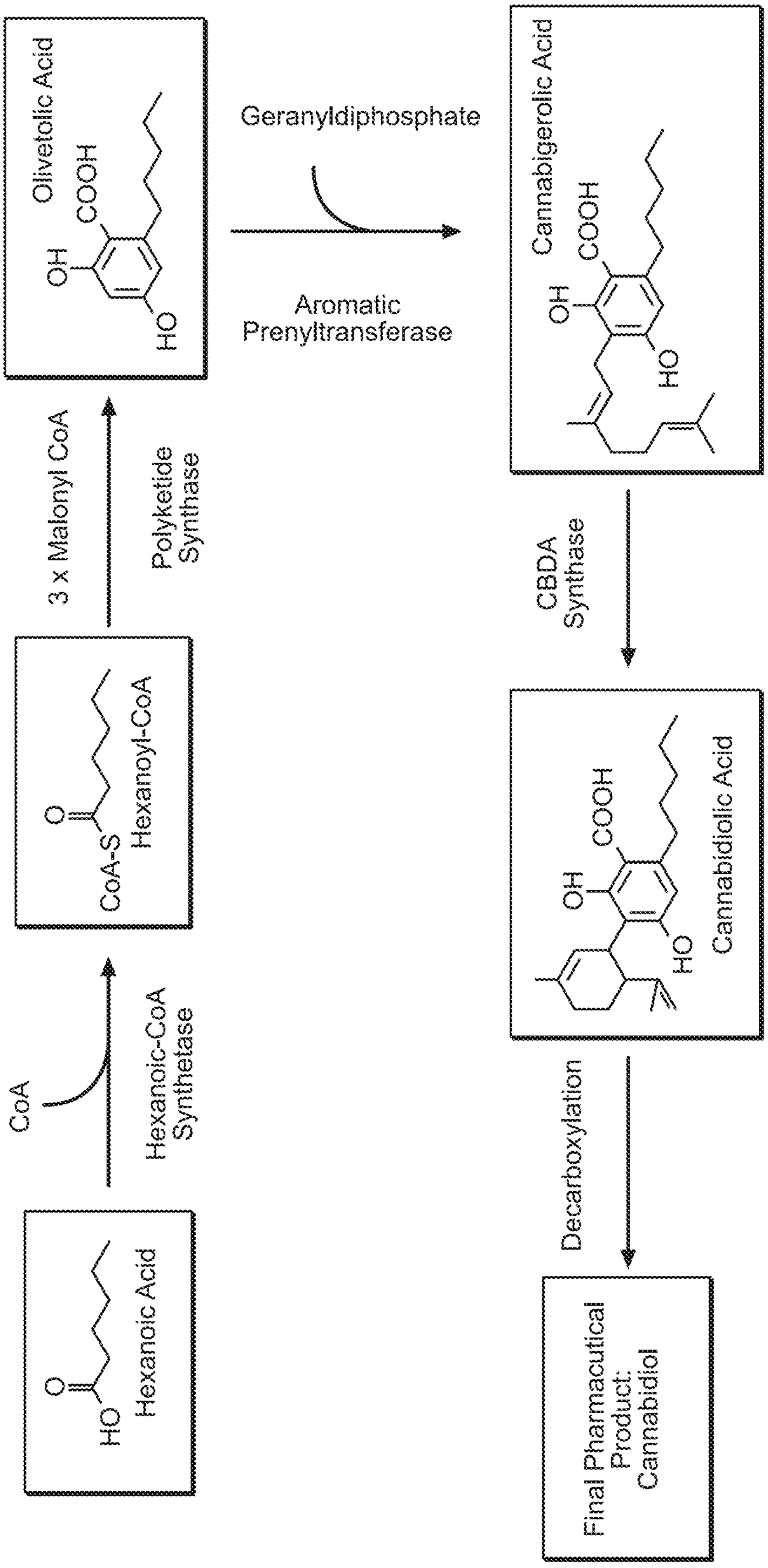
FIG. 7 shows an exemplary metabolic pathway for the production of cannabinoids by *Cannabis sativa.*

FIG. 7 shows an exemplary metabolic pathway for the production of cannabinoids by *Cannabis sativa.*

The biosynthetic route for the production of cannabidiolic acid in *Cannabis sativa* is shown in FIG. 7. The pathway begins with the conversion of Hexanoic acid (a simple fatty acid) to Hexanoyl-CoA by Hexanoyl-CoA Synthetase. Hexanoyl-CoA is converted to Oleviolic acid (OA), a polyketide, by a Polyketide synthase. OA is then prenylated with the monoterpene geranyl diphosphate to cannabigerolic acid by an Aromatic prenyltransferase. Finally, cannabidiolic acid (CBDA) is produced by cyclizing cannabigerolic acid via CBDA synthase (CBDAs). In summary, it takes four enzymatic steps to produce CBDA from Hexanoic acid. The inventors have engineered this metabolic pathway into *S. cerevisiae* (a species of yeast) for the production of CBDA.

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, through genetic engineering many of the required enzymes can be added and the production of GPP can be increased. In order to add the required enzymes for CBDA production in yeast the inventors created plasmids that contain the essential genes in the CBDA biosynthetic pathway. The inventors have transformed these genes into *S. cerevisiae.*

Synthesis of Fusion Genes Required for CBDA Production in *S. cerevisiae.*

The genome of *Cannabis sativa* has been investigated and the acyl-activating enzymes CsAAE1 was determined to convert hexanoic acid to hexanoyl-CoA (Step 1 in FIG. 7). The inventors have overexpressed CsAAE1 in yeast while simultaneously supplementing the growth media with Hexanoic acid. By supplementing the media with hexanoic acid, the inventors ensured that the yeast have the required starting materials for the production of hexanoyl-CoA. In addition to CsEE1, the *cannabis* plant has several other acyl-activating enzymes with sequences that are similar to CsEE1. These enzymes can also be used for the conversation of hexanoic acid to hexanoyl-CoA. These are listed in Appendix 1C.

The next enzymatic step that was engineered into the yeast strain was for the production of Olivetolic acid (OA) from hexanoyl-CoA. This step requires the substrates hexanoyl-CoA and 3 malonyl-CoA molecules, with the malonyl-CoA molecule produced by yeast naturally. Olivetolic acid production requires two enzymes for the condensation and subsequent cyclization of malonyl-CoA with hexanoyl-CoA. This process requires the tetraketide synthase, olivetolic synthase (OS), and the polyketide cyclase, olivetolic acid cyclase (OAC). In some embodiments, stoichiometric amounts of both of these enzymes are preferred; as it has been experimentally determined that OAC binds a chemical intermediate made by OS. In various embodiments, in order to ensure the proper amounts of OS and OAC the inventors have created a single gene that is a fusion of OS, a self cleaving T2A peptide, and the OAC gene (OS-T2A-OAC) and in certain cases an HA tag was inserted at the C-terminus of OAC to verify protein expression. This entire fusion protein was produced in yeast and the self cleaving peptide is spliced in vivo to produce OS and OAC. In addition to the tetraketide synthase, olivetolic synthase (OS), and the polyketide cyclase, olivetolic acid cyclase (OAC), the *cannabis* plant has several other enzymes with sequences that are similar to the tetraketide synthase, olivetolic synthase (OS), and the polyketide cyclase, olivetolic acid cyclase (OAC). These enzymes can also be used for the conversation of hexanoyl-CoA to olivetolic acid. These are listed in Appendix 1C.

The next enzymatic step requires the production of geranyl pyrophosphate (GPP). In yeast the prenyltransferace Erg20 condenses isopentenyl diphosphate (IPP) and dimethylallyl diphosphate (DMAP) to geranyl pyrophosphate (GPP) and feranyl pyrophosphate (FPP) naturally. While only these two products are produced in yeast, a greater quantity of FPP when compared to GPP is produced. More GPP is required for the production of CBDA. In order to increase the production of GPP compared to FPP the inventors inserted a mutant prenyltransferase, Erg20(K179E) in the yeast strain. This mutant has been shown to shift the ratio of GPP:FPP to 70:30. This Erg20(K179E) mutant was placed on a fusion gene with CsAAE1, the enzyme for hexanoyl-CoA, and a self-cleaving peptide, T2A (CsAAE1-T2A-Erg20(K179E). We also added a FLAG tag to the C-terminus of the Erg20p (K197E) enzyme (CsAAE1-T2A-Erg20(K179E)-FLAG) to verify expression of this fusion protein in yeast in certain yeast strains. After production in yeast the self-cleaving peptide was cut producing CsAAE1 and Erg20(K179E).

Once the inventors verified that they had enough GPP to prenylate Olivetolic acid to cannabigerolic acid the inventors inserted the aromatic prenyltransferase (CsPt1) gene into the yeast. In this final enzymatic step the inventors placed the cannabidiolic acid synthase (CBDAs) gene into yeast for the conversion of cannabigerolic acid to CBDA. Similar to the inventors' previous approach, they introduced a single gene containing CsPt1, a self-cleaving peptide T2A, CBDs, and in certain cases a MYC tag was inserted at the C-terminus of CBDs in order to verify production of each enzyme (CsPt1-T2A-CBDs-MYC). In addition to the aromatic prenyltransferase (CsPt1) the *cannabis* plant has several other enzymes with sequences that are similar to the aromatic prenyltransferase (CsPt1). These enzymes can also be used for the conversation of olivetolic acid to CBGA. These are listed in Appendix 1C.

Creation of a Stable Yeast Strain Producing the Metabolic Pathway for CBDA.

Three stable transformations of *S. cerevesaie* where created utilizing selection for leucine, uracil and tryptophan. The inventors first transformed an auxotrophic yeast strain (his3D1/leu2/trp1-289/ura3-52) with the CsAAE1-T2A-Erg20(K197E)-FLAG gene in an integrating vector; other sequences listed in Appendix 1C number 85-91 can replace CsAAE1. 5 μg of CsAAE1-T2A-Erg20(K197E)-FLAG in a vector containing a gene for tryptophan depletion resistance was linearized with the restriction enzyme EcoRV, transformed into chemically competent InVSc1, and grown on Yeast Nitrogen Base without amino acids and 0.5% ammonium sulfate (YNBA) agar plates supplemented with histidine, leucine, tryptophan, 1% glucose and 2% lactic acid are grown at 30° C. until colonies are formed. Any yeast colonies that did not incorporate the plasmid, that contains the CsAAE1-T2A-Erg20(K197E)-FLAG gene died since the starting yeast strain is a tryptophan auxotroph. All colonies, with successful plasmid incorporation, where picked and grown in YNBA supplemented with histidine, leucine and uracil, 1% glucose and 2% lactic acid. All colonies were screened for protein production by taking whole cell extracts of each induced clone and the total protein was subjected to SDS-PAGE followed by western blotting against the c-terminal tag of Erg20(K197E). Positive clones where stored at −80° C. in glycerol stocks. The highest expressing clone was taken for the second transformation and was designated as VscGPHA.

Using the VscGPHA strains the inventors added 5 μg of OS-T2A-OAC-HA in the a vector containing a gene for leucine depletion resistance; other sequences listed in Appendix 1C number 60-84 can replace OS and OAC. This plasmid was linearized with the restriction enzyme AseI and transformed into chemically competent VscGPHA and grown on YNBA agar plates supplemented with histidine and uracil, 1% glucose and 2% lactic acid and grown at 30° C. until colonies were formed. Any yeast colonies that did not incorporate the plasmid that contains the OS-T2A-OAC-HA gene died since the VscGPHA is a leucine auxotroph. All colonies, with successful plasmid incorporation, were picked and grown in YNBA supplemented with histidine, and leucine. All colonies were screened for protein production by taking whole cell extracts of each induced clone and subjected the total protein to SDS-PAGE followed by western blotting against the c-terminal HA tag of OAC. Positive clones were stored at −80° C. in glycerol stocks. The highest expressing clone was taken for the second stable transformation and was designated VscGPHOA.

The final stable transformation was done in a similar way as the previous transformation. The CsPT-T2A-CBDAs-MYC gene was placed in the vector containing a gene for uracil depletion resistance 5 μg of this plasmid was linearized with EcorV and transformed into chemically competent VscGPHOA; other sequences listed in Appendix 1C number 30-59 can replace CsPT. Transformed VscGPHOA was grown in YNBA supplemented with histidine, 1% glucose and 2% lactic acid. Any yeast colonies that did not incorporate the plasmid that contains the CsPT-T2A-CBDAs-MYC gene died since they lacked leucine. All colonies were picked and grown in YNBA supplemented with histidine, 1% glucose and 2% lactic acid. All colonies were screened for protein production by taking whole cell extracts of each induced clone and subjecting the total protein to SDS-PAGE followed by western blotting against the c-terminal Myc tag of CBDAs. Positive clones are stored at −80° C. in glycerol stocks. The highest expressing CBDAs was taken for the final strain and designated VscCBDA.

Production of CBDA in Yeast.

To initiate the reconstituted metabolic pathway of CBDA a colony of VscCBDA was freshly streaked on a plate of a frozen glycerol stock of VscCBDA. A small culture of VscCBDA was grown in YNBA supplemented with 0.05% histidine, 1% glucose, 2% lactic acid, and 0.03% hexanoic acid overnight at 30° C. The overnight culture was transferred to 1 L of YNBA supplemented with 0.05% histidine, 1% glucose, 2% lactic acid, and 0.03% hexanoic acid and was grown at 30° C. until mid-log phase. Cells were pelleted by centrifugation then washed with 200 ml of phosphate buffered saline (PBS) and repelleted. Pelleted cells were resuspended with 1 L of YNBA supplemented with 0.05% histidine, 2% galactose, and 0.03% hexanoic acid and grown at 30° C. overnight.

Overnight 1 L cultures were pelleted by centrifugation, resuspended, washed one time in PBS and pelleted. Cell pellets were resuspended in 40% (wt/vol) KOH and 50% (vol/vol) ethanol solution and boiled for 10 minutes. Metabolite extraction was done by extracting from the boiled extracts 3 times with hexane, then 3 times with ethyl acetate. The spent supernatant broth was extracted in a similar fashion as described above. Organic phases of extracts of each sample were pooled then dried by a rotary evaporator and stored for liquid chromatography mass spectrometry (LC-MS) and gas chromatography mass spectrometry (GC-MS) analysis to confirm and quantitate how much CBDA is produced from strain VscCBDA.

Biosynthetic Production of Cannabidiolic Acid (CBDA) in *K. marxianus.*

Through genetic engineering the inventors have reconstituted the cannabidiolic acid (CBDA) metabolic pathway found in *Cannabis sativa* into *K. marxianus* (a species of yeast). Producing CBGA is an initial step in producing many cannabinoids from *Cannabis sativa* in *K. marxianus*. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Synthesis of Fusion Genes Required for CBDA Production in *K. Marxianus.*

Figure 8:
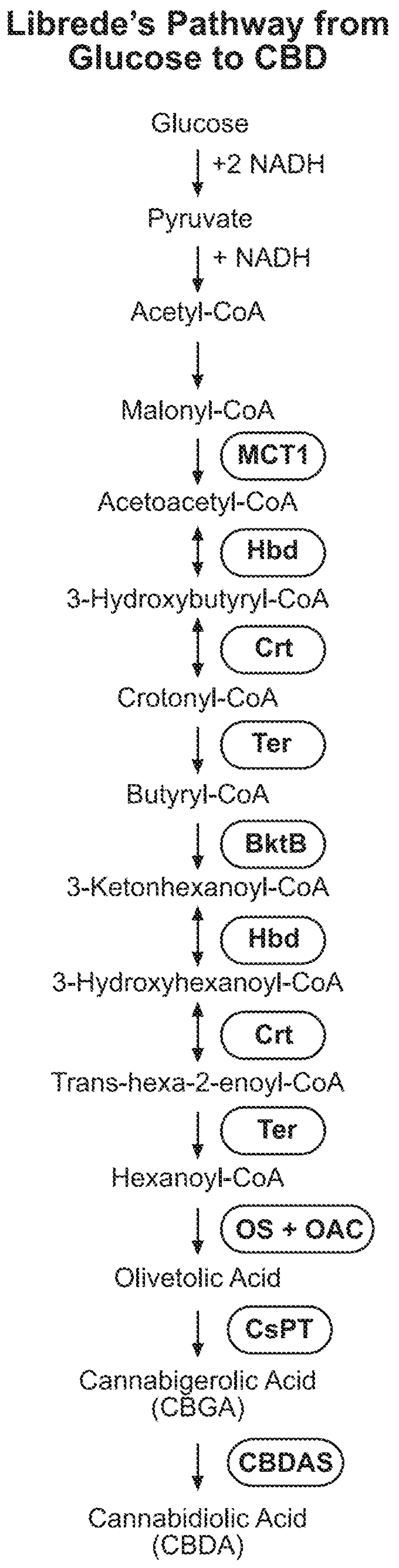
FIG. 8 shows an exemplary biosynthetic route for the production of CBDA from glucose.

FIG. 8 shows an exemplary biosynthetic route for the production of CBDA from glucose. The biosynthetic route for the production of cannabidiolic acid in *Cannabis sativa*, from glucose to CBDA is shown in FIG. 8. The pathway begins with the conversion of glucose to malonyl-CoA through a series of steps that are common to many strains of yeast. The conversion of malonyl-CoA to Acetoacetyl-CoA is conducted by the enzyme MCT1, an acyl-carrier-protein. Acetoacetyl-CoA is converted to 3-Hydroxybutyryl-CoA by the enzyme 3-hydroxybutyryl-CoA dehydrogenase (Hbd) from *Clostridium acetobutylicum*. Next, 3-Hydroxybutyryl-CoA is converted into Crotonyl-CoA by the enzyme crotonase (Crt) from *Clostridium acetobutylicum* and the conversion of Crotonyl-CoA to Butyryl-CoA is controlled by the enzyme trans-enoyl-CoA reducatase (Ter) from *Treponema denticola*. The Butyryl-CoA is converted to 3-Keton-hexanoyl-CoA by the enzyme β-ketothiolase (Bktb) from *Ralstonia Eutropha.* 3-Ketonhexanoyl-CoA is converted to 3-Hydroxyhexanoyl-CoA by the enzyme Hbd. Hydroxy-hexanoyl-CoA is converted to Trans-hexa-2-enoyl-CoA by the enzyme Crt. Trans-hexa-2-enoyl-CoA is converted to Hexanoyl-CoA by the enzyme Ter. Hexanoyl-CoA, with 3 malonyl-CoAs, is converted to Oleviolic acid (OA) by a Polyketide synthase and cyclase, OA and OAC respectively. OA is then prenylated with the monoterpene geranyl diphosphate to cannabigerolic acid by an Aromatic prenyltransferase, CsPT. Finally, cannabidiolic acid (CBDA) is produced by cyclizing cannabigerolic acid via CBDA synthase (CBDAS). We have engineered this metabolic pathway into *K. marxianus* (a species of yeast) for the production of CBDA (FIG. 8).

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, the inventors through genetic engineering created many of the required enzymes that can be added so the production of GPP was increased. In order to add the required enzymes for CBDA production in yeast the inventors created plasmids that contain the essential genes in the CBDA biosynthetic pathway. The inventors have transformed these genes into *K. marxianus.*

Creation of a Stable *K. marxianus* Strain Producing the Metabolic Pathways for Hexonyl-coA and CBDA.

Two stable transformations of *K. marxianus* were created utilizing selection for uracil and G418 (Genenticin). The inventors first transformed an auxotrophic *K. marxianus* strain (ATCC 17555 KM5) with 5 different genes needed to produce high levels of hexanoyl-CoA. After functional conformation of the genes required for hexanoyl-CoA the inventors did a second transformation with the genes responsible for CBDA production. The molecular biology methods required for biosynthetic production of CBDA in *K. marxianus* are outlined below.

Gene names Crt, Bktb, MCT1, TeR, Hbd, Erg20p(K179E) were codon optimized, synthesized and subclonned into puc57 and p426 ATCC with the restriction enzymes SpeI and SalI.

Genes Crt, Bktb, MCT1, TeR, Hbd, and Erg20p(K179E) were amplified via PCR using the primers GPD_F and URA_R and all 6 amplicons were electroporated into *K. marxianus* ATCC 17555 KM5 at a concentration of 200 nM and selected onto yeast nitrogen base (YNB) supplemented with amino acid dropout mix (DO supplement—Ura Clonetech 630416) 2% glucose, and 2% Agar plates.

Gene integration and functional gene expression of Crt, Bktb, MCT1, TeR, Hbd, and Erg20p(K179E) was validated by genomic PCR and RT-PCR methods respectively. The final strain produced containing the functional expression of Crt, Bktb, MCT1, TeR, Hbd, and Erg20p(K179E) was labeled kMarxHex1.

Gene names CBDAs, CsPt, OS, and OAC were codon optimized and synthesized by Genscript. The codon optimized gene sequences of CBDAs and CsPt were cloned in frame with a nucleotide sequence containing a self cleaving T2A peptide and designated as CstTCbds. The codon optimized gene sequences of OS and OAC were cloned in frame with a nucleotide sequence containing a self cleaving T2A peptide and designated as OSTOc. CsTCbds and OSTOc were cloned in frame with an *S. cerevisiae* internal ribosomal entry site (IRES), Ure2, into a galactose inducible vector and the final gene sequence pcen/arsGal-OSTOc-IRES-CsTCbds plasmid can be seen below. The plasmid pcen/arsGal-OSTOc-IRES-CstTCbds was used to synthesize a functional gene fragment that expresses the enzymes CBDAs, CsPt, OS, and OAC by using the primers GalIRES_F, GalIRES_R.

The Gibson Assembly method (from the following paragraph above: "Genes Crt, Bktb, MCT1, TeR, Hbd, and Erg20p(K179E) were amplified via PCR using the primers GPD_F and URA_R and all 6 amplicons were electroporated into *K. marxianus* ATCC 17555 KM5 at a concentration of 200 nM and selected onto yeast nitrogen base (YNB) supplemented with amino acid dropout mix (DO supplement-Ura Clonetech 630416) 2% glucose, and 2% Agar plates") was used to subclone the PCR fragment into the plasmid HO-polyKanMx4-HO (ATCC 87804) using the primers KmXIRES_F and KmXIRES_R to create the plasmid pHOOSCstKnMxHO.

The plasmid pHOOSCstKnMxHO was digested with NotI and transformed into kMarxHex1 using standard electroporation methods. The selection of stable integrants was done with yeast nitrogen base (YNB) supplemented with amino acid dropout mix (DO supplement—Ura Clonetech 630416) 2% glucose, 1 mg/ml G418 (Gibco) and 2% Agar plates.

Gene integration and functional gene expression of pHOOSCstKnMxHO validated by genomic PCR and RT-PCR methods respectively. The final strain produced containing the functional expression of Crt, Bktb, MCT1, TeR, Hbd, Erg20p(K179E) CBDAs, CsPt, OS, and OAC was labeled k.MarxCBDA.

Production of CBDA in *K. marxianus*.

To initiate the reconstituted metabolic pathway of CBDA, a colony from k.Marx CBDA was freshly streaked onto an agar plate from a frozen glycerol stock of k.Marx CBDA. A small culture of VscCBDA was grown in YNBA base (YNB) supplemented with amino acid dropout mix (DO supplement—Ura Clonetech 630416) 2% glucose, 1 mg/ml G418 (Gibco) and 2% Agar plates was grown overnight at 30° C. The overnight culture was transferred to 1 L of YNBA supplemented with base (YNB) supplemented with amino acid dropout mix (DO supplement—Ura Clonetech 630416) 2% glucose, and 1 mg/ml G418 (Gibco) and was grown at 30° C. until mid-log phase. Cells were pelleted by centrifugation then washed with 200 ml of phosphate buffered saline (PBS) and repelleted. Pelleted cells were resuspended with 1 L of YNBA supplemented with base (YNB) supplemented with amino acid dropout mix (DO supplement—Ura Clonetech 630416) 2% galactose, and 1 mg/ml G418 (Gibco) and grown at 30° C. overnight.

Processing CBDA for Analysis of Cannabinoid Production.

Overnight 1 L cultures were pelleted by centrifugation, resuspended, washed one time in PBS and pelleted. The process for extracting cannabinoids from the yeast generally follows the following basic steps:

1. Remove the yeast cells from the media by centrifugation or filtration.
2. Lysis the cells using either chemical or mechanical methods or a combination of methods. Mechanical methods can include a French Press or glass bead milling or other standard methods. Chemical methods can include enzymatic cell lysis, solvent cell lysis, or detergent based cell lysis.
3. Perform a liquid-liquid extraction of the cannabinoids form the cell lysate using the appropriate chemical solvent. An appropriate solvent is any solvent where the cannabinoids are highly soluble in this solvent and the solvent is not miscible in water. Examples of this are hexane, ethyl acetate, and cyclohexane. Preferred solvents can be straight or branched alkane chains (C5-C8) work well; mixtures of these solvents can also be use.

Protocol Used for Cannabinoid Extraction from Yeast Cell Lysate

1. After lysising the cells using any mechanical technique, add 1 mL of 4M KCl, pH2.0 to each 1 mL of cell lysate.
2. Add 1-2 mLs of ethyl acetate for each 1 mL of cell lysate.
3. Rigorously mix for 1 min.
4. Centrifuge the mixture for 5 min at 1000×g.
5. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for Cannabinoid Extraction from Growth Media (for Secreted Cannabinoid Samples)

1. Add 1 mL of ethyl acetate for every 1 mL of growth media.
2. Rigorously mix for 1 min.
3. Centrifuge the mixture for 5 min at 1000×g.
4. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for GC-MS Analysis of Cannabinoid Extracts for k.Marx CBDA

1. Remove solvent from samples under vacuum.
2. Re-suspend dry samples in either 100 uL of dry hexane or dry ethyl acetate
3. Add 20 uL of N-Methyl-N-(trimethylsilyl) trifluoroacetamide (MSTFA)
4. Briefly mix
5. Heat solution to 60° C. for 10-15 minutes
6. GC-MS Method a. Instrument Agilent 6890-5975 GC-MS (Model Number: Agilent 19091S-433)
b. Column HP-5MS 5% Phenyl Methyl Siloxane
c. OVEN:
   i. Initial temp: 100' C. (On) Maximum temp: 300' C.
   ii. Initial time: 3.00 min Equilibration time: 0.50 min
   iii. Ramps:

| # | Rate | Final temp | Final time |
|---|---|---|---|
| 1 | 30.00 | 280 | 1.00 |
| 2 | 70.00 | 300 | 5.00 |
| 3 | 0.0(Off) | | |

iv. Post temp: 0' C.
   v. Post time: 0.00 min
   vi. Run time: 15.29 min

What is claimed is:

1. A method for making Cannabigerovarinic Acid in yeast or fungi, the method comprising:

converting glucose to malonyl-CoA with a first nucleotide sequence comprising the nucleotide sequence of SEQ. ID. NO. 124 expressing Meningitis associated and temperature regulated Fimbria (MatB);

converting the malonyl-CoA to Acetoacetyl-CoA with a second nucleotide sequence comprising the nucleotide sequence of SEQ. ID. NO. 118 expressing Monocarboxylate Transporter 1 (MCT1);

converting the Acetoacetyl-CoA to 3-Hydroxybutyryl-CoA with a third nucleotide sequence comprising the nucleotide sequence of SEQ. ID. NO. 119 expressing 3-hydroxybutyryl-CoA dehydrogenase (Hbd);

converting the 3-Hydroxybutyryl-CoA to Crotonyl-CoA with a fourth nucleotide sequence comprising the nucleotide sequence of SEQ. ID. NO. 120 expressing crotonase (Crt);

converting the Crotonyl-CoA to Butyryl-CoA with a fifth nucleotide sequence comprising the nucleotide sequence of SEQ. ID. NO. 123 expressing trans-enoyl-CoA reducatase (Ter);

converting the Butyryl-CoA to divarinic acid with a sixth nucleotide sequence comprising the nucleotide sequence of SEQ. ID. NO. 60 expressing Polyketide synthase and with a seventh nucleotide sequence of SEQ. ID. NO. 92 or SEQ. ID. NO. 93 expressing olivetolic acid cyclase; and converting the divarinic acid to Cannabigerovarinic Acid with an eighth nucleotide sequence comprising the nucleotide sequence of SEQ. ID. NO. 30 expressing an Aromatic prenyltransferase, wherein the yeast or fungi is selected from the group consisting of *S. cerevisiae, K. marxianus, Y. lipolytica, Aspergillus oryzae, Aspergillus nidulans,* and *Komagataella pastoris.*

2. The method of claim 1, the method further comprising:

converting the Cannabigerovarinic Acid to Tetrahydrocannabivarinic acid with a ninth nucleotide sequence comprising the nucleotide sequence of SEQ. ID. NO. 29 expressing THCA synthase.

3. The method of claim 1, the method further comprising:

converting the Cannabigerovarinic Acid to Cannabidivarinic acid with a ninth nucleotide sequence comprising the nucleotide sequence of SEQ. ID. NO. 28 expressing CBDA synthase.

* * * * *

UNITED STATES PATENT AND TRADEMARK OFFICE

CERTIFICATE OF CORRECTION

PATENT NO. : 12,043,860 B2
APPLICATION NO. : 17/711993
DATED : July 23, 2024
INVENTOR(S) : Jason L. Poulos and Anthony N. Farina It is certified that error appears in the above-identified patent and that said Letters Patent is hereby corrected as shown below:

On the Title Page

Item (45) reading "(45) Date of Patent: Jul. 23, 2024"
Should read: "(45) Date of Patent: *Jul. 23, 2024"

The section reading "(*) Notice: Subject to any disclaimer, the term of this patent is extended by or adjusted under 35 U.S.C. 154(b) by 0 days."
Should be followed by: "This patent is subject to a terminal disclaimer."

In the Specification

In Column 1, Line 10:
The phrase: "now U.S. Pat. No. 11,293,038, which is a continuation-in-part..."
Should read: "now U.S. Pat. No. 11,293,038, issued on Apr. 5, 2022, which is a continuation-in-part..."

Signed and Sealed this
Eleventh Day of February, 2025

Coke Morgan Stewart
*Acting Director of the United States Patent and Trademark Office*

SEQUENCE LISTING

<160> NUMBER OF SEQ ID NOS: 124

<210> SEQ ID NO 1
<211> LENGTH: 7969
<212> TYPE: DNA
<213> ORGANISM: Artificial Sequence
<220> FEATURE:
<223> OTHER INFORMATION: Codon Optimized

<400> SEQUENCE: 1
tcgcgcgttt cggtgatgac ggtgaaaacc tctgacacat gcagctcccg gagacggtca 60
cagcttgtct gtaagcggat gccgggagca gacaagcccg tcagggcgcg tcagcgcgtg 120
ttggcgggtg tcggggctgg cttaactatg cggcatcaga gcagattgta ctgagagtgc 180

```
accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat attttttat gcctcggtaa tgattttcat    360

ttttttttt cccctagcgg atgactcttt ttttttctta gcgattggca ttatcacata    420

atgaattata cattatataa agtaatgtga tttcttcgaa gaatatacta aaaaatgagc    480

aggcaagata aacgaaggca aagatgacag agcagaaagc cctagtaaag cgtattacaa    540

atgaaaccaa gattcagatt gcgatctctt taaagggtgg tcccctagcg atagagcact    600

cgatcttccc agaaaaagag gcagaagcag tagcagaaca ggccacacaa tcgcaagtga    660

ttaacgtcca cacaggtata gggtttctgg accatatgat acatgctctg gccaagcatt    720

ccggctggtc gctaatcgtt gagtgcattg gtgacttaca catagacgac catcacacca    780

ctgaagactg cgggattgct ctcggtcaag cttttaaaga ggccctactg gcgcgtggag    840

taaaaaggtt tggatcagga tttgcgcctt tggatgaggc actttccaga gcggtggtag    900

atctttcgaa caggccgtac gcagttgtcg aacttggttt gcaaagggag aaagtaggag    960

atctctcttg cgagatgatc ccgcattttc ttgaaagctt tgcagaggct agcagaatta   1020

ccctccacgt tgattgtctg cgaggcaaga atgatcatca ccgtagtgag agtgcgttca   1080

aggctcttgc ggttgccata agagaagcca cctcgcccaa tggtaccaac gatgttccct   1140

ccaccaaagg tgttcttatg tagtgacacc gattatttaa agctgcagca tacgatatat   1200

atacatgtgt atatatgtat acctatgaat gtcagtaagt atgtatacga acagtatgat   1260

actgaagatg acaaggtaat gcatcattct atacgtgtca ttctgaacga ggcgcgcttt   1320

cctttttct ttttgctttt tctttttttt tctcttgaac tcgacggatc tatgcggtgt   1380

gaaataccgc acagatgcgt aaggagaaaa taccgcatca ggaaattgta aacgttaata   1440

ttttgttaaa attcgcgtta aatttttgtt aaatcagctc atttttaac caataggccg   1500

aaatcggcaa aatcccttat aaatcaaaag aatagaccga gatagggttg agtgttgttc   1560

cagtttggaa caagagtcca ctattaaaga acgtggactc caacgtcaaa gggcgaaaaa   1620

ccgtctatca gggcgatggc ccactacgtg aaccatcacc ctaatcaagt tttttggggt   1680

cgaggtgccg taaagcacta aatcggaacc ctaaagggag cccccgattt agagcttgac   1740

ggggaaagcc ggcgaacgtg gcgagaaagg aagggaagaa agcgaaagga gcgggcgcta   1800

gggcgctggc aagtgtagcg gtcacgctgc gcgtaaccac cacacccgcc gcgcttaatg   1860

cgccgctaca gggcgcgtcg cgccattcgc cattcaggct gcgcaactgt tgggaagggc   1920

gatcggtgcg ggcctcttcg ctattacgcc agctggcgaa agggggatgt gctgcaaggc   1980

gattaagttg ggtaacgcca gggttttccc agtcacgacg ttgtaaaacg acggccagtg   2040

agcgcgcgta atacgactca ctatagggcg aattgggtac cggccgcaaa ttaaagcctt   2100

cgagcgtccc aaaaccttct caagcaaggt tttcagtata atgttacatg cgtacacgcg   2160

tctgtacaga aaaaaaagaa aaatttgaaa tataaataac gttcttaata ctaacataac   2220

tataaaaaaa taaataggga cctagacttc aggttgtcta actccttcct tttcggttag   2280

agcggatgtg gggggagggc gtgaatgtaa gcgtgacata actaattaca tgactcgagg   2340

tcgactcatt cgaaatgact gaattgttgt ctcaaaactc ttctcatgat cttgtttgtt   2400

gcagttctag gtaaggatga caatgggaca actctagtaa ctttgaataa tgggttcaat   2460

ttcttttgca aacccaagtt aaaggataat ctcaattggt tcaaatcaat ggttgtgtcg   2520
```

-continued

```
tttgaatcct tcaatacgaa aaatatgacc aattgttctg gaccaccacc caaaggtgga   2580
acaccaatag cagtggtttc aaaaactctg tcatctactt cattacagac tctttcgatt   2640
tcgatagaac taattttgat accaccgatg ttcatagtgt catcggctct accgtgtgca   2700
tggtagtaac cgttagaggt caattcgaaa atgtcaccat gtcttctcaa tacttcacca   2760
ttcaaggttg gcataccctt gaaatagaca tcgtgatgat taccgtttaa caatgttttt   2820
gaggcaccaa acataacagg acctaatgcc aattcaccga tacctggctt atttttaggc   2880
attgggtaac cgttcttatc taatatgtac aaggtgcaac ccatacattg ggatgaaaaa   2940
gaacttaaag attgagcttg caaaaatgaa ccagcagaaa aagcaccacc gatttctgta   3000
ccaccacaca tttctataac tggcttgtag ttagctctac ccattaacca caaatattcg   3060
tctacattag aggcttcacc ggatgaagaa aagcatctta tggtggacca atcgtaacct   3120
gaaacacaat ttgtggattt ccatgatctt acaatagatg gtacgacacc caacattgtg   3180
acctttgcat cttgaacaaa tttagcgaaa ccagagacta aaggactacc gttgtacaag   3240
gcaatagatg caccatttaa caaactagca taaaccaacc aaggacccat catccaaccc   3300
aaattagttg gccatactat aacgtcacct tttctaatat ccaaatgaga ccaaccatca   3360
gcagcagcct tcaatggggt ggcttgtgtc caaggaattg cttttggttc acctgtagta   3420
ccactggaga ataagatgtt agtataagca tcaacaggtt gttctctggc agtaaactcg   3480
cagtttttaa actccttggc tctttctaaa aagtaatccc aagatatgtc accatctctc   3540
aattctgcac caatgttaga accactacaa gggataacta ttgccattgg ggatttagct   3600
tcaactactc ttgaatacaa tggtattctc tttttacctc tgatgatgtg atcttgtgtg   3660
aaaattgcct tagctttgga taatctcaat ctagttgaga tttcaggggc ggaaaatgaa   3720
tctgctatag agacaactac gtaaccagcc aatactatgg ccaaatatat aacaacagca   3780
tcaacatgca ttggcatatc gatggctatt gcacaacctt tttctaaacc catttcttcc   3840
aatgcataac caaccaacca aactctcttt ctcaattgat ctaatgtcaa cttattcaaa   3900
ggcaagtcat cgttaccctc gtctctccaa acgatcatag tatcgttcaa tttcttattg   3960
gagtttacgt tcaagcaatt tttagctgag ttcaagtaac caccaggtaa ccattcagaa   4020
ccacctgggt tgttgatgtc atctcttctc aagatacatt ctgggtcctt agagaaacta   4080
attttcattt catccatcaa tactgttctc caatagactt cagggtttct aacagaaaat   4140
tcttggaagt gagaaaaaga agaaattgga tctttgtact ttacacccaa aaattcttta   4200
cctctctttt ccaacaaagc acccaaatta gttgacttga ctttttcagg gtctggaatc   4260
caagcaggtg gggctggacc gaaatccttg tagcaaccat aaaacaacat ttggtgtaag   4320
gagaaaggca aatctggtga caagatatgg ttagcgatgt tgatccaagt ttgaggggtt   4380
gcagcaccat aattacaaac gatttctgcc aatctaccat gtaatgtttc tgctacttct   4440
gaggtgatac ccaatgcgat gaaatctgag gcaacgactg aatccaagga cttatagttt   4500
ttacccatac tagttctaga tccgtcgaaa ctaagttctt ggtgttttaa aactaaaaaa   4560
aagactaact ataaaagtag aatttaagaa gtttaagaaa tagatttaca gaattacaat   4620
caatacctac cgtctttata tacttattag tcaagtaggg gaataatttc agggaactgg   4680
tttaaacctt ttttttcagc tttttccaaa tcagagagag cagaaggtaa tagaaggtgt   4740
aagaaaatga gatagataca tgcgtgggtc aattgccttg tgtcatcatt tactccaggc   4800
aggttgcatc actccattga ggttgtgccc gttttttgcc tgtttgtgcc ctgttctctg   4860
tagttgcgct aagagaatgg acctatgaac tgatggttgg tgaagaaaac aatattttgg   4920
```

-continued tgctgggatt cttttttttt ctggatgcca gcttaaaaag cgggctccat tatatttagt 4980
ggatgccagg aataaacctg ttcacccaag caccatcagt gttatatatt ctgtgtaacc 5040
cgccccctat tttggcatgt acgggttaca gcagaattaa aaggctaatt ttttgactaa 5100
ataaagttag gaaaatcact actattaatt atttacgtat tctttgaaat ggcagtattg 5160
ataatgataa actcgagagc tccagctttt gttcccttta gtgagggtta attgcgcgct 5220
tggcgtaatc atggtcatag ctgtttcctg tgtgaaattg ttatccgctc acaattccac 5280
acaacatagg agccggaagc ataaagtgta aagcctgggg tgcctaatga gtgaggtaac 5340
tcacattaat tgcgttgcgc tcactgcccg ctttccagtc gggaaacctg tcgtgccagc 5400
tgcattaatg aatcggccaa cgcgcgggga gaggcggttt gcgtattggg cgctcttccg 5460
cttcctcgct cactgactcg ctgcgctcgg tcgttcggct gcggcgagcg gtatcagctc 5520
actcaaaggc ggtaatacgg ttatccacag aatcagggga taacgcagga aagaacatgt 5580
gagcaaaagg ccagcaaaag gccaggaacc gtaaaaaggc cgcgttgctg gcgtttttcc 5640
ataggctccg cccccctgac gagcatcaca aaaatcgacg ctcaagtcag aggtggcgaa 5700
acccgacagg actataaaga taccaggcgt ttccccctgg aagctccctc gtgcgctctc 5760
ctgttccgac cctgccgctt accggatacc tgtccgcctt tctcccttcg ggaagcgtgg 5820
cgctttctca tagctcacgc tgtaggtatc tcagttcggt gtaggtcgtt cgctccaagc 5880
tgggctgtgt gcacgaaccc cccgttcagc ccgaccgctg cgccttatcc ggtaactatc 5940
gtcttgagtc caacccggta agacacgact tatcgccact ggcagcagcc actggtaaca 6000
ggattagcag agcgaggtat gtaggcggtg ctacagagtt cttgaagtgg tggcctaact 6060
acggctacac tagaaggaca gtatttggta tctgcgctct gctgaagcca gttaccttcg 6120
gaaaaagagt tggtagctct tgatccggca aacaaaccac cgctggtagc ggtggttttt 6180
ttgtttgcaa gcagcagatt acgcgcagaa aaaaaggatc tcaagaagat cctttgatct 6240
tttctacggg gtctgacgct cagtggaacg aaaactcacg ttaagggatt ttggtcatga 6300
gattatcaaa aaggatcttc acctagatcc ttttaaatta aaaatgaagt tttaaatcaa 6360
tctaaagtat atatgagtaa acttggtctg acagttacca atgcttaatc agtgaggcac 6420
ctatctcagc gatctgtcta tttcgttcat ccatagttgc ctgactcccc gtcgtgtaga 6480
taactacgat acgggagggc ttaccatctg gccccagtgc tgcaatgata ccgcgagacc 6540
cacgctcacc ggctccagat ttatcagcaa taaaccagcc agccggaagg gccgagcgca 6600
gaagtggtcc tgcaacttta tccgcctcca tccagtctat taattgttgc cgggaagcta 6660
gagtaagtag ttcgccagtt aatagtttgc gcaacgttgt tgccattgct acaggcatcg 6720
tggtgtcacg ctcgtcgttt ggtatggctt cattcagctc cggttcccaa cgatcaaggc 6780
gagttacatg atcccccatg ttgtgcaaaa aagcggttag ctccttcggt cctccgatcg 6840
ttgtcagaag taagttggcc gcagtgttat cactcatggt tatggcagca ctgcataatt 6900
ctcttactgt catgccatcc gtaagatgct tttctgtgac tggtgagtac tcaaccaagt 6960
cattctgaga atagtgtatg cggcgaccga gttgctcttg cccggcgtca atacgggata 7020
ataccgcgcc acatagcaga actttaaaag tgctcatcat tggaaaacgt tcttcggggc 7080
gaaaactctc aaggatctta ccgctgttga gatccagttc gatgtaaccc actcgtgcac 7140
ccaactgatc ttcagcatct tttactttca ccagcgtttc tgggtgagca aaaacaggaa 7200
ggcaaaatgc cgcaaaaaag ggaataaggg cgacacggaa atgttgaata ctcatactct 7260
tcctttttca atattattga agcatttatc agggttattg tctcatgagc ggatacatat 7320
ttgaatgtat ttagaaaaat aaacaaatag gggttccgcg cacatttccc cgaaaagtgc 7380
cacctgggtc cttttcatca cgtgctataa aaataattat aatttaaatt ttttaatata 7440
aatatataaa ttaaaaatag aaagtaaaaa aagaaattaa agaaaaaata gtttttgttt 7500
tccgaagatg taaaagactc tagggggatc gccaacaaat actacctttt atcttgctct 7560
tcctgctctc aggtattaat gccgaattgt ttcatcttgt ctgtgtagaa gaccacacac 7620
gaaaatcctg tgattttaca ttttacttat cgttaatcga atgtatatct atttaatctg 7680
cttttcttgt ctaataaata tatatgtaaa gtacgctttt tgttgaaatt ttttaaacct 7740
ttgtttattt tttttcttc attccgtaac tcttctacct tctttattta ctttctaaaa 7800
tccaaataca aaacataaaa ataaataaac acagagtaaa ttcccaaatt attccatcat 7860
taaaagatac gaggcgcgtg taagttacag gcaagcgatc cgtcctaaga aaccattatt 7920
atcatgacat taacctataa aaataggcgt atcacgaggc cctttcgtc 7969

<210> SEQ ID NO 2
<211> LENGTH: 10004
<212> TYPE: DNA
<213> ORGANISM: Artificial Sequence
<220> FEATURE:
<223> OTHER INFORMATION: Codon Optimized

<400> SEQUENCE: 2
tcgcgcgttt cggtgatgac ggtgaaaacc tctgacacat gcagctcccg gagacggtca 60
cagcttgtct gtaagcggat gccgggagca gacaagcccg tcagggcgcg tcagcgcgtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctttca attcatcatt tttttttat tcttttttt gatttcggtt 360 tctttgaaat ttttttgatt cggtaatctc cgaacagaag gaagaacgaa ggaaggagca 420
cagacttaga ttggtatata tacgcatatg tagtgttgaa gaaacatgaa attgcccagt 480
attcttaacc caactgcaca gaacaaaaac ctgcaggaaa cgaagataaa tcatgtcgaa 540
agctacatat aaggaacgtg ctgctactca tcctagtcct gttgctgcca agctatttaa 600
tatcatgcac gaaaagcaaa caaacttgtg tgcttcattg gatgttcgta ccaccaagga 660
attactggag ttagttgaag cattaggtcc caaaatttgt ttactaaaaa cacatgtgga 720
tatcttgact gatttttcca tggagggcac agttaagccg ctaaaggcat tatccgccaa 780
gtacaatttt ttactcttcg aagacagaaa atttgctgac attggtaata cagtcaaatt 840
gcagtactct gcgggtgtat acagaatagc agaatgggca gacattacga atgcacacgg 900
tgtggtgggc ccaggtattg ttagcggttt gaagcaggcg gcagaagaag taacaaagga 960
acctagaggc cttttgatgt tagcagaatt gtcatgcaag ggctccctat ctactggaga 1020
atatactaag ggtactgttg acattgcgaa gagcgacaaa gattttgtta tcggctttat 1080
tgctcaaaga gacatgggtg gaagagatga aggttacgat tggttgatta tgacacccgg 1140
tgtgggttta gatgacaagg gagacgcatt gggtcaacag tatagaaccg tggatgatgt 1200
ggtctctaca ggatctgaca ttattattgt tggaagagga ctatttgcaa agggaaggga 1260
tgctaaggta gagggtgaac gttacagaaa agcaggctgg gaagcatatt tgagaagatg 1320
cggccagcaa aactaatgac accgattatt taaagctgca gcatacgata tatatacatg 1380

-continued tgtatatatg tatacctatg aatgtcagta agtatgtata cgaacagtat gatactgaag 1440
atgacaaggt aatgcatcat tctatacgtg tcattctgaa cgaggcgcgc tttccttttt 1500
tctttttgct ttttcttttt ttttctcttg aactcgacgg atctatgcgg tgtgaaatac 1560
cgcacagatg cgtaaggaga aaataccgca tcaggaaatt gtaaacgtta atattttgtt 1620
aaaattcgcg ttaaattttt gttaaatcag ctcatttttt aaccaatagg ccgaaatcgg 1680
caaaatccct tataaatcaa aagaatagac cgagataggg ttgagtgttg ttccagtttg 1740
gaacaagagt ccactattaa agaacgtgga ctccaacgtc aaagggcgaa aaaccgtcta 1800
tcagggcgat ggcccactac gtgaaccatc accctaatca agttttttgg ggtcgaggtg 1860
ccgtaaagca ctaaatcgga accctaaagg gagcccccga tttagagctt gacggggaaa 1920
gccggcgaac gtggcgagaa aggaagggaa gaaagcgaaa ggagcgggcg ctagggcgct 1980
ggcaagtgta gcggtcacgc tgcgcgtaac caccacaccc gccgcgctta atgcgccgct 2040
acagggcgcg tcgcgccatt cgccattcag gctgcgcaac tgttgggaag ggcgatcggt 2100
gcgggcctct tcgctattac gccagctggc gaaaggggga tgtgctgcaa ggcgattaag 2160
ttgggtaacg ccagggtttt cccagtcacg acgttgtaaa acgacggcca gtgagcgcgc 2220
gtaatacgac tcactatagg gcgaattggg taccggccgc aaattaaagc cttcgagcgt 2280
cccaaaacct tctcaagcaa ggttttcagt ataatgttac atgcgtacac gcgtctgtac 2340
agaaaaaaaa gaaaaatttg aaatataaat aacgttctta atactaacat aactataaaa 2400
aaataaatag ggacctagac ttcaggttgt ctaactcctt ccttttcggt tagagcggat 2460
gtgggggag ggcgtgaatg taagcgtgac ataactaatt acatgactcg aggtcgactt 2520
acttgtcatc gtcatctttg tagtcaatat cgtggtcttt atagtcaccg tcatgatcct 2580
tgtaatcctt tgatctcttg tagaccttat tcaagaaagc tgtcaaaacg tcggctttaa 2640
aacctcttga ttcatcaact tgactaatct ttgcctttaa gtctttagcg atggattctt 2700
cgtattcatg gtacaattgt tcaatcttca aatcattaaa aattttctta cactttgctt 2760
cagcaactga gtccttttta ccgtagtttt catccaaagt ctttctttgt tcggcagatg 2820
ctaattccaa agccttgtta ataacccaac tgcacttatt gtcttgaata tctgtaccga 2880
ttttacctat ttgttctgga gtaccgaaac agtctaagta gtcatcttgg atttggaagt 2940
attcacccaa aggtatcaaa acatctcttg cttgcttcaa gtctttttca tcagtaatac 3000
cagctacgta catagccaag gcgactggca aatagaagga gtaataagca gtttcaaagg 3060
tgacgatgaa tgaatgtttc ttcaaggaaa actttgacaa gtcaacttta tcttcaggtg 3120
cagttatcaa atccatcaat tgacccaatt ctgtttggaa agtaacttcg tggaataatt 3180
cggtaatatc gatgtagtac ttttcgtttc tgaaatgtga cttcaacaat ttatagatag 3240
cggcttccaa cataaaagca tcatttatgg ctatttcacc aacttctgga actttgtacc 3300
agcatggttg acctcttctt gttatagact tatccatcat gtcatcggca accaaaaagt 3360
atgcttgcaa caattcaata caccaaccca agatagcgac cttttcgtat tcttcttgac 3420
ctaattgttc aacggttttg ttagacaaga tagcataagt atcaactaca ctcaaacctc 3480
tattcaattt accacctgga gtattgtagt ttaaagagtg agcataccaa tcgcaggctt 3540
ctttaggcat accataagct aacaaactag cgttcaattc ttcaactaac tttgggaata 3600
cgttcaagaa tctttctctt cttatttcct tttctgaagc cataggacct ggatttctt 3660
caacgtcacc acatgttaac aaagaacctc taccttcttc gaaatgactg aattgttgtc 3720

-continued tcaaaactct tctcatgatc ttgtttgttg cagttctagg taaggatgac aatgggacaa 3780
ctctagtaac tttgaataat gggttcaatt tcttttgcaa acccaagtta aaggataatc 3840
tcaattggtt caaatcaatg gttgtgtcgt ttgaatcctt caatacgaaa aatatgacca 3900
attgttctgg accaccaccc aaaggtggaa caccaatagc agtggtttca aaaactctgt 3960
catctacttc attacagact ctttcgattt cgatagaact aattttgata ccaccgatgt 4020
tcatagtgtc atcggctcta ccgtgtgcat ggtagtaacc gttagaggtc aattcgaaaa 4080
tgtcaccatg tcttctcaat acttcaccat tcaaggttgg catacccttg aaatagacat 4140
cgtgatgatt accgtttaac aatgtttttg aggcaccaaa cataacagga cctaatgcca 4200
attcaccgat acctggctta tttttaggca ttgggtaacc gttcttatct aatatgtaca 4260
aggtgcaacc catacattgg gatgaaaaag aacttaaaga ttgagcttgc aaaaatgaac 4320
cagcagaaaa agcaccaccg atttctgtac caccacacat ttctataact ggcttgtagt 4380
tagctctacc cattaaccac aaatattcgt ctacattaga ggcttcaccg gatgaagaaa 4440
agcatcttat ggtggaccaa tcgtaacctg aaacacaatt tgtggatttc catgatctta 4500
caatagatgg tacgacaccc aacattgtga cctttgcatc ttgaacaaat ttagcgaaac 4560
cagagactaa aggactaccg ttgtacaagg caatagatgc accatttaac aaactagcat 4620
aaaccaacca aggacccatc atccaaccca aattagttgg ccatactata acgtcacctt 4680
ttctaatatc caaatgagac caaccatcag cagcagcctt caatggggtg gcttgtgtcc 4740
aaggaattgc ttttggttca cctgtagtac cactggagaa taagatgtta gtataagcat 4800
caacaggttg ttctctggca gtaaactcgc agtttttaaa ctccttggct ctttctaaaa 4860
agtaatccca agatatgtca ccatctctca attctgcacc aatgttagaa ccactacaag 4920
ggataactat tgccattggg gatttagctt caactactct tgaatacaat ggtattctct 4980
ttttacctct gatgatgtga tcttgtgtga aaattgcctt agctttggat aatctcaatc 5040
tagttgagat ttcaggggcg gaaaatgaat ctgctataga gacaactacg taaccagcca 5100
atactatggc caaatatata acaacagcat caacatgcat tggcatatcg atggctattg 5160
cacaaccttt ttctaaaccc atttcttcca atgcataacc aaccaaccaa actctctttc 5220
tcaattgatc taatgtcaac ttattcaaag gcaagtcatc gttaccctcg tctctccaaa 5280
cgatcatagt atcgttcaat ttcttattgg agtttacgtt caagcaattt ttagctgagt 5340
tcaagtaacc accaggtaac cattcagaac cacctgggtt gttgatgtca tctcttctca 5400
agatacattc tgggtcctta gagaaactaa ttttcatttc atccatcaat actgttctcc 5460
aatagacttc agggtttcta acagaaaatt cttggaagtg agaaaaagaa gaaattggat 5520
ctttgtactt tacacccaaa aattctttac ctctctttc caacaaagca cccaaattag 5580
ttgacttgac tttttcaggg tctggaatcc aagcaggtgg ggctggaccg aaatccttgt 5640
agcaaccata aaacaacatt tggtgtaagg agaaaggcaa atctggtgac aagatatggt 5700
tagcgatgtt gatccaagtt tgaggggttg cagcaccata attacaaacg atttctgcca 5760
atctaccatg taatgtttct gctacttctg aggtgatacc caatgcgatg aaatctgagg 5820
caacgactga atccaaggac ttatagtttt tacccatact agttctagat ccgtcgaaac 5880
taagttcttg gtgttttaaa actaaaaaaa agactaacta taaaagtaga atttaagaag 5940
tttaagaaat agatttacag aattacaatc aatacctacc gtctttatat acttattagt 6000
caagtagggg aataatttca gggaactggt ttaaaccttt tttttcagct ttttccaaat 6060
cagagagagc agaaggtaat agaaggtgta agaaaatgag atagatacat gcgtgggtca 6120

-continued attgccttgt gtcatcattt actccaggca ggttgcatca ctccattgag gttgtgcccg 6180
ttttttgcct gtttgtgccc tgttctctgt agttgcgcta agagaatgga cctatgaact 6240
gatggttggt gaagaaaaca atattttggt gctgggattc ttttttttttc tggatgccag 6300 cttaaaaagc gggctccatt atatttagtg gatgccagga ataaacctgt tcacccaagc 6360
accatcagtg ttatatattc tgtgtaaccc gccccctatt ttggcatgta cgggttacag 6420
cagaattaaa aggctaattt tttgactaaa taaagttagg aaaatcacta ctattaatta 6480
tttacgtatt ctttgaaatg gcagtattga taatgataaa ctcgagagct ccagcttttg 6540
ttcagttgat tgtatgcttg gtatagcttg aaatattgtg cagaaaaaga aacaaggaag 6600
aaagggaacg agaacaatga cgaggaaaca aaagattaat aattgcaggt ctatttatac 6660
ttgatagcaa gacagcaaac ttttttttat ttcaaattca agtaactgga aggaaggccg 6720
tataccgttg ctcattagag agtagtgtgc gtgaatgaag gaaggaaaaa gtttcgtgtg 6780
cttcgagata cccctcatca gctctggaac aacgacatct gttggtgctg tctttgtcgt 6840 taatttttttc ctttagtgtc ttccatcatt tttttgtcat tgcggatatg gtgagacaac 6900
aacgggggag agagaaaaga aaaaaaaaga aaagaagttg catgcgccta ttattacttc 6960
aatagatggc aaatggaaaa agggtagtga aacttcgata tgatgatggc tatcaagtct 7020
agggctacag tattagttcg ttatgtacca ccatcaatga ggcagtgtaa ttggtgtagt 7080
cttgtttagc ccattatgtc ttgtctggta tctgttctat tgtatatctc ccctccgcca 7140
cctacatgtt agggagacca acgaaggtat tataggaatc ccgatgtatg ggtttggttg 7200
ccagaaaaga ggaagtccat attgtacacc cggaaacaac aaaaggatgc gcgcttggcg 7260
taatcatggt catagctgtt tcctgtgtga aattgttatc cgctcacaat tccacacaac 7320
ataggagccg gaagcataaa gtgtaaagcc tggggtgcct aatgagtgag gtaactcaca 7380
ttaattgcgt tgcgctcact gcccgctttc cagtcgggaa acctgtcgtg ccagctgcat 7440
taatgaatcg gccaacgcgc ggggagaggc ggtttgcgta ttgggcgctc ttccgcttcc 7500
tcgctcactg actcgctgcg ctcggtcgtt cggctgcggc gagcggtatc agctcactca 7560
aaggcggtaa tacggttatc cacagaatca ggggataacg caggaaagaa catgtgagca 7620
aaaggccagc aaaaggccag gaaccgtaaa aaggccgcgt tgctggcgtt tttccatagg 7680
ctccgccccc ctgacgagca tcacaaaaat cgacgctcaa gtcagaggtg gcgaaacccg 7740
acaggactat aaagatacca ggcgtttccc cctggaagct ccctcgtgcg ctctcctgtt 7800
ccgaccctgc cgcttaccgg atacctgtcc gcctttctcc cttcgggaag cgtggcgctt 7860
tctcatagct cacgctgtag gtatctcagt tcggtgtagg tcgttcgctc caagctgggc 7920
tgtgtgcacg aaccccccgt tcagcccgac cgctgcgcct tatccggtaa ctatcgtctt 7980
gagtccaacc cggtaagaca cgacttatcg ccactggcag cagccactgg taacaggatt 8040
agcagagcga ggtatgtagg cggtgctaca gagttcttga agtggtggcc taactacggc 8100
tacactagaa ggacagtatt tggtatctgc gctctgctga agccagttac cttcggaaaa 8160
agagttggta gctcttgatc cggcaaacaa accaccgctg gtagcggtgg tttttttgtt 8220
tgcaagcagc agattacgcg cagaaaaaaa ggatctcaag aagatccttt gatcttttct 8280
acggggtctg acgctcagtg gaacgaaaac tcacgttaag ggattttggt catgagatta 8340
tcaaaaagga tcttcaccta gatcctttta aattaaaaat gaagttttaa atcaatctaa 8400
agtatatatg agtaaacttg gtctgacagt taccaatgct taatcagtga ggcacctatc 8460

-continued

```
tcagcgatct gtctatttcg ttcatccata gttgcctgac tccccgtcgt gtagataact   8520

acgatacggg agggcttacc atctggcccc agtgctgcaa tgataccgcg agacccacgc   8580

tcaccggctc cagatttatc agcaataaac cagccagccg gaagggccga gcgcagaagt   8640

ggtcctgcaa ctttatccgc ctccatccag tctattaatt gttgccggga agctagagta   8700

agtagttcgc cagttaatag tttgcgcaac gttgttgcca ttgctacagg catcgtggtg   8760

tcacgctcgt cgtttggtat ggcttcattc agctccggtt cccaacgatc aaggcgagtt   8820

acatgatccc ccatgttgtg caaaaaagcg gttagctcct tcggtcctcc gatcgttgtc   8880

agaagtaagt tggccgcagt gttatcactc atggttatgg cagcactgca taattctctt   8940

actgtcatgc catccgtaag atgcttttct gtgactggtg agtactcaac caagtcattc   9000

tgagaatagt gtatgcggcg accgagttgc tcttgcccgg cgtcaatacg ggataatacc   9060

gcgccacata gcagaacttt aaaagtgctc atcattggaa aacgttcttc ggggcgaaaa   9120

ctctcaagga tcttaccgct gttgagatcc agttcgatgt aacccactcg tgcacccaac   9180

tgatcttcag catcttttac tttcaccagc gtttctgggt gagcaaaaac aggaaggcaa   9240

aatgccgcaa aaaagggaat aagggcgaca cggaaatgtt gaatactcat actcttcctt   9300

tttcaatatt attgaagcat ttatcagggt tattgtctca tgagcggata catatttgaa   9360

tgtatttaga aaaataaaca aataggggtt ccgcgcacat ttccccgaaa agtgccacct   9420

gggtcctttt catcacgtgc tataaaaata attataattt aaatttttta atataaatat   9480

ataaattaaa aatagaaagt aaaaaaagaa attaaagaaa aaatagtttt tgttttccga   9540

agatgtaaaa gactctaggg ggatcgccaa caaatactac cttttatctt gctcttcctg   9600

ctctcaggta ttaatgccga attgtttcat cttgtctgtg tagaagacca cacacgaaaa   9660

tcctgtgatt ttacatttta cttatcgtta atcgaatgta tatctattta atctgctttt   9720

cttgtctaat aaatatatat gtaaagtacg ctttttgttg aaattttttta aacctttgtt   9780

tattttttttt tcttcattcc gtaactcttc taccttcttt atttactttc taaaatccaa   9840

atacaaaaca taaaaataaa taaacacaga gtaaattccc aaattattcc atcattaaaa   9900

gatacgaggc gcgtgtaagt tacaggcaag cgatccgtcc taagaaacca ttattatcat   9960

gacattaacc tataaaaata ggcgtatcac gaggcccttt cgtc                    10004
```

```
<210> SEQ ID NO 3
<211> LENGTH: 9508
<212> TYPE: DNA
<213> ORGANISM: Artificial Sequence
<220> FEATURE:
<223> OTHER INFORMATION: Codon Optimized

<400> SEQUENCE: 3

tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctaacg acattactat atatataata taggaagcat ttaatagaca    360

gcatcgtaat atatgtgtac tttgcagtta tgacgccaga tggcagtagt ggaagatatt    420

ctttattgaa aaatagcttg tcaccttacg tacaatcttg atccggagct tttctttttt    480

tgccgattaa gaattaattc ggtcgaaaaa agaaaaggag agggccaaga gggagggcat    540
```

-continued

```
tggtgactat tgagcacgtg agtatacgtg attaagcaca caaaggcagc ttggagtatg    600
tctgttatta atttcacagg tagttctggt ccattggtga aagtttgcgg cttgcagagc    660
acagaggccg cagaatgtgc tctagattcc gatgctgact tgctgggtat tatatgtgtg    720
cccaatagaa agagaacaat tgacccggtt attgcaagga aaatttcaag tcttgtaaaa    780
gcatataaaa atagttcagg cactccgaaa tacttggttg gcgtgtttcg taatcaacct    840
aaggaggatg ttttggctct ggtcaatgat tacggcattg atatcgtcca actgcatgga    900
gatgagtcgt ggcaagaata ccaagagttc ctcggtttgc cagttattaa aagactcgta    960
tttccaaaag actgcaacat actactcagt gcagcttcac agaaacctca ttcgtttatt   1020
cccttgtttg attcagaagc aggtgggaca ggtgaacttt tggattggaa ctcgatttct   1080
gactgggttg gaaggcaaga gagccccgaa agcttacatt ttatgttagc tggtggactg   1140
acgccagaaa atgttggtga tgcgcttaga ttaaatggcg ttattggtgt tgatgtaagc   1200
ggaggtgtgg agacaaatgg tgtaaaagac tctaacaaaa tagcaaattt cgtcaaaaat   1260
gctaagaaat agtgacaccg attatttaaa gctgcagcat acgatatata tacatgtgta   1320
tatatgtata cctatgaatg tcagtaagta tgtatacgaa cagtatgata ctgaagatga   1380
caaggtaatg catcattcta tacgtgtcat tctgaacgag gcgcgctttc cttttttctt   1440
tttgcttttt cttttttttt ctcttgaact cgacggatct atgcggtgtg aaataccgca   1500
cagatgcgta aggagaaaat accgcatcag gaaattgtaa acgttaatat tttgttaaaa   1560
ttcgcgttaa atttttgtta aatcagctca ttttttaacc aataggccga aatcggcaaa   1620
atcccttata aatcaaaaga atagaccgag atagggttga gtgttgttcc agtttggaac   1680
aagagtccac tattaaagaa cgtggactcc aacgtcaaag ggcgaaaaac cgtctatcag   1740
ggcgatggcc cactacgtga accatcaccc taatcaagtt ttttggggtc gaggtgccgt   1800
aaagcactaa atcggaaccc taaagggagc ccccgattta gagcttgacg gggaaagccg   1860
gcgaacgtgg cgagaaagga agggaagaaa gcgaaaggag cgggcgctag ggcgctggca   1920
agtgtagcgg tcacgctgcg cgtaaccacc acacccgccg cgcttaatgc gccgctacag   1980
ggcgcgtcgc gccattcgcc attcaggctg cgcaactgtt gggaagggcg atcggtgcgg   2040
gcctcttcgc tattacgcca gctggcgaaa gggggatgtg ctgcaaggcg attaagttgg   2100
gtaacgccag ggttttccca gtcacgacgt tgtaaaacga cggccagtga gcgcgcgtaa   2160
tacgactcac tatagggcga attgggtacc ggccgcaaat taaagccttc gagcgtccca   2220
aaaccttctc aagcaaggtt ttcagtataa tgttacatgc gtacacgcgt ctgtacagaa   2280
aaaaaagaaa aatttgaaat ataaataacg ttcttaatac taacataact ataaaaaaat   2340
aaatagggac ctagacttca ggttgtctaa ctccttcctt ttcggttaga gcggatgtgg   2400
ggggagggcg tgaatgtaag cgtgacataa ctaattacat gactcgaggt cgacttacaa   2460
atcttcttca cttattaatt tttgttcgtg gtggtgaggt ggcaaaggtg ggatggattg   2520
ttcgtttctg aaaaagttgt tagggtcggc tttagtcttt actttaacta atctgttgaa   2580
atttttacca aagtactttt caccccaaat tcttgcttgt gtatagttat ttggagattc   2640
agggttagtt ttacctaagt ccaaatctct gtagttcaaa tatgccaatc ttgggttttg   2700
actaacgtaa ggtgtagtga agttgtaaac ggatctgacc cagttgatat gcttttcgtt   2760
atcttcttgc ttttcccatg aggctgtgta ccataattca tacatgatac cagctctgtg   2820
aggaaatggt atggctgatt cagatatttc ttccataata ccaccgtatg gatacaaaac   2880
```

-continued

```
gtacatgccg acacctacat cttcttcgta caacttttcc aatatcttga ccattgcagt   2940
ttcagggatt ggtttcttaa cgtagtccaa tttaatagaa aaagcggtct tttaccagc    3000
ggatctatcc aacaagattt cctttttgaa gttagcggtg ttgaagttta caacacctga   3060
atagaagatg gttgtgtcta tccaagaaaa ttccttgcaa tctgtctttt taatacccaa   3120
ttctgggaat gacttattca tcaaatcaac caaagaatct acaccaccat ggaaaattga   3180
agaaaaataa ccgtgaacag tggtcttatt tttaccatgg ttatctgtaa tatttttagt   3240
gatgaaatgg gtcatcaaaa ccaagtcctt atcgtacttg taagcgatgt tttgccactt   3300
attaaacaac ttaaccaaac cgtggatttc catgttcttt ttgacagaga aaatagtact   3360
tttggaagga acagcgacta acttaatttt ccaagcggca atgataccga aattttcacc   3420
accaccacct cttatggccc aaaacaaatc ttcacccata gactttctgt ccaaaacttt   3480
accatctacg ttaaccaaat gggcgtctat aatattatct gcagctaaac cgtagtttct   3540
catcaatgca ccataaccac caccagaaaa gtgaccaccg acacctactg ttggacagta   3600
accaccaggg aaagaaaagt tttcattctt ttcgttgatc cagtagtaaa cttcacccaa   3660
ggtggcacct gcttctaccc atgctgtttg actgtgaacg tcgatcttta tggaatgcat   3720
atttctcaaa tcgactacaa cgaatggaac ttgtgagatg taagacatgc cttctgcatc   3780
atgaccacct gatctagttc tgatttgcaa acctactttc ttagagcaca atatagaagc   3840
ttgaatgtga ctaacattgg aaggtgtaac aatgactaaa ggttttggtg tagtgtcaga   3900
agtgaatctc aaattttgga tggtactgtt caaaacggac atgtacaatt gatcatgttg   3960
agtatatata aactttgggt tagcagggtt gtttgggatg tattcggaga aacacttcaa   4020
aaagttttct tgtggatttg cgatggagat ttggatgttg aaggacaaga agaagaagat   4080
tattttacag acgaaccaga aagagaatgc ggagcagttc ataggacctg gattttcttc   4140
aacgtcacca caggtcaaca aagaacctct accttcaata aaaacgtata ccaaatattc   4200
agcgtagtac aatttccaca taaactcgta gaatcttcta cctgcttcag ggtcataatt   4260
tgtcaaagcg aaatctctag tttgcaagat caaccagaaa gccaagatgg catgtgacaa   4320
caacataacg ttagaattaa aggcttgtgg ccaaatgata cctgccaaaa tggctgcgac   4380
gtaacttaac aaaacgatac cggagcagaa caaagtcaaa tttcttgaac cgtacttaga   4440
agccaaggta ctaataccga actttgtgtc accttcaacg tcagaggcat ccttgatcaa   4500
ggctaatgca gaacccatac ttttcatgaa tgccaacaaa aatgtgaatg aaggtctcaa   4560
ttcgaatggc aaacctaaag cagctcttga agcgtagtag aaggtgaagt ttgtgatgat   4620
atgagctaag aaattcaaca aaaaggcagt actagggttt tgtttccatc taaaaggtgg   4680
tacggaatag acaataccac cgaagatacc gaaacagtaa ccgaagatgt acaatggacc   4740
acccttcatt ttaattgtga tgatcaaacc gaacaaggct actatgatag acatgatcca   4800
tgcagtattg acggatattt cacctgaagc caaaggcaaa tctggtttgt taattctgtc   4860
gatgtgcaaa tcgtatattt gattaattgt agtggtgaat gaagcgatgc acaagatggc   4920
aactaaaaag aaaaatgcct tgaacatcaa ggaccatgaa attaagttag tgttatgcaa   4980
caattcttta ccgaataaac cgcatgcaca agaagtaaaa gcgattatgg tgtatggtct   5040
ttgcaacttc caacatgctt taccgaagtt caaaattttt gtggcaacag agtgattatc   5100
actttcaggt ggttcagttt gatttgtagt tgcagctctg atagagttct tagctataga   5160
caaactttcg gagcacttat tttgtaagtg gaaggacttg gttgaacaat gttttgatgg   5220
aaagttgttg taagagtact taataggtgt ctttggatgt ctgtaacaca acaatgatgt   5280
```

ttttggattg ttgttgtgag gattcaataa ggtatgatag ttagtttgga aggagaaagt 5340
acagacggat gataaaccca tactagttct agatccgtcg aaactaagtt cttggtgttt 5400
taaaactaaa aaaaagacta actataaaag tagaatttaa gaagtttaag aaatagattt 5460
acagaattac aatcaatacc taccgtcttt atatacttat tagtcaagta ggggaataat 5520
ttcagggaac tggtttaaac cttttttttc agctttttcc aaatcagaga gagcagaagg 5580
taatagaagg tgtaagaaaa tgagatagat acatgcgtgg gtcaattgcc ttgtgtcatc 5640
atttactcca ggcaggttgc atcactccat tgaggttgtg cccgtttttt gcctgtttgt 5700
gccctgttct ctgtagttgc gctaagagaa tggacctatg aactgatggt tggtgaagaa 5760
aacaatattt tggtgctggg attctttttt tttctggatg ccagcttaaa aagcgggctc 5820
cattatattt agtggatgcc aggaataaac ctgttcaccc aagcaccatc agtgttatat 5880
attctgtgta acccgccccc tattttggca tgtacgggtt acagcagaat taaaaggcta 5940
attttttgac taaataaagt taggaaaatc actactatta attatttacg tattctttga 6000
aatggcagta ttgataatga taaactcgag agctccagct tttgttcagt tgattgtatg 6060
cttggtatag cttgaaatat tgtgcagaaa aagaaacaag gaagaaaggg aacgagaaca 6120
atgacgagga aacaaaagat taataattgc aggtctattt atacttgata gcaagacagc 6180
aaactttttt ttatttcaaa ttcaagtaac tggaaggaag gccgtatacc gttgctcatt 6240
agagagtagt gtgcgtgaat gaaggaagga aaaagtttcg tgtgcttcga gatacccctc 6300
atcagctctg gaacaacgac atctgttggt gctgtctttg tcgttaattt tttcctttag 6360
tgtcttccat catttttttg tcattgcgga tatggtgaga caacaacggg ggagagagaa 6420
aagaaaaaaa aagaaaagaa gttgcatgcg cctattatta cttcaataga tggcaaatgg 6480
aaaaagggta gtgaaacttc gatatgatga tggctatcaa gtctagggct acagtattag 6540
ttcgttatgt accaccatca atgaggcagt gtaattggtg tagtcttgtt tagcccatta 6600
tgtcttgtct ggtatctgtt ctattgtata tctcccctcc gccacctaca tgttagggag 6660
accaacgaag gtattatagg aatcccgatg tatgggtttg gttgccagaa aagaggaagt 6720
ccatattgta cacccggaaa caacaaaagg atgcgcgctt ggcgtaatca tggtcatagc 6780
tgtttcctgt gtgaaattgt tatccgctca caattccaca caacatagga gccggaagca 6840
taaagtgtaa agcctggggt gcctaatgag tgaggtaact cacattaatt gcgttgcgct 6900
cactgcccgc tttccagtcg ggaaacctgt cgtgccagct gcattaatga atcggccaac 6960
gcgcggggag aggcggtttg cgtattgggc gctcttccgc ttcctcgctc actgactcgc 7020
tgcgctcggt cgttcggctg cggcgagcgg tatcagctca ctcaaaggcg gtaatacggt 7080
tatccacaga atcaggggat aacgcaggaa agaacatgtg agcaaaaggc cagcaaaagg 7140
ccaggaaccg taaaaaggcc gcgttgctgg cgtttttcca taggctccgc ccccctgacg 7200
agcatcacaa aaatcgacgc tcaagtcaga ggtggcgaaa cccgacagga ctataaagat 7260
accaggcgtt tccccctgga agctccctcg tgcgctctcc tgttccgacc ctgccgctta 7320
ccggatacct gtccgccttt ctcccttcgg gaagcgtggc gctttctcat agctcacgct 7380
gtaggtatct cagttcggtg taggtcgttc gctccaagct gggctgtgtg cacgaacccc 7440
ccgttcagcc cgaccgctgc gccttatccg gtaactatcg tcttgagtcc aacccggtaa 7500
gacacgactt atcgccactg gcagcagcca ctggtaacag gattagcaga gcgaggtatg 7560
taggcggtgc tacagagttc ttgaagtggt ggcctaacta cggctacact agaaggacag 7620

-continued tatttggtat ctgcgctctg ctgaagccag ttaccttcgg aaaaagagtt ggtagctctt 7680
gatccggcaa acaaaccacc gctggtagcg gtggtttttt tgtttgcaag cagcagatta 7740
cgcgcagaaa aaaggatct caagaagatc ctttgatctt ttctacgggg tctgacgctc 7800
agtggaacga aaactcacgt taagggattt tggtcatgag attatcaaaa aggatcttca 7860
cctagatcct tttaaattaa aaatgaagtt ttaaatcaat ctaaagtata tatgagtaaa 7920
cttggtctga cagttaccaa tgcttaatca gtgaggcacc tatctcagcg atctgtctat 7980
ttcgttcatc catagttgcc tgactccccg tcgtgtagat aactacgata cgggagggct 8040
taccatctgg ccccagtgct gcaatgatac cgcgagaccc acgctcaccg gctccagatt 8100
tatcagcaat aaaccagcca gccggaaggg ccgagcgcag aagtggtcct gcaactttat 8160
ccgcctccat ccagtctatt aattgttgcc gggaagctag agtaagtagt tcgccagtta 8220
atagtttgcg caacgttgtt gccattgcta caggcatcgt ggtgtcacgc tcgtcgtttg 8280
gtatggcttc attcagctcc ggttcccaac gatcaaggcg agttacatga tcccccatgt 8340
tgtgcaaaaa agcggttagc tccttcggtc ctccgatcgt tgtcagaagt aagttggccg 8400
cagtgttatc actcatggtt atggcagcac tgcataattc tcttactgtc atgccatccg 8460
taagatgctt ttctgtgact ggtgagtact caaccaagtc attctgagaa tagtgtatgc 8520
ggcgaccgag ttgctcttgc ccggcgtcaa tacgggataa taccgcgcca catagcagaa 8580
ctttaaaagt gctcatcatt ggaaaacgtt cttcggggcg aaaactctca aggatcttac 8640
cgctgttgag atccagttcg atgtaaccca ctcgtgcacc caactgatct tcagcatctt 8700
ttactttcac cagcgtttct gggtgagcaa aaacaggaag gcaaaatgcc gcaaaaaagg 8760
gaataagggc gacacggaaa tgttgaatac tcatactctt cctttttcaa tattattgaa 8820
gcatttatca gggttattgt ctcatgagcg gatacatatt tgaatgtatt tagaaaaata 8880
aacaaatagg ggttccgcgc acatttcccc gaaaagtgcc acctgggtcc ttttcatcac 8940
gtgctataaa aataattata atttaaattt tttaatataa atatataaat taaaaataga 9000
aagtaaaaaa agaaattaaa gaaaaaatag tttttgtttt ccgaagatgt aaaagactct 9060
agggggatcg ccaacaaata ctacctttta tcttgctctt cctgctctca ggtattaatg 9120
ccgaattgtt tcatcttgtc tgtgtagaag accacacacg aaaatcctgt gattttacat 9180
tttacttatc gttaatcgaa tgtatatcta tttaatctgc ttttcttgtc taataaatat 9240
atatgtaaag tacgcttttt gttgaaattt tttaaacctt tgtttatttt tttttcttca 9300
ttccgtaact cttctacctt ctttatttac tttctaaaat ccaaatacaa aacataaaaa 9360
taaataaaca cagagtaaat tcccaaatta ttccatcatt aaaagatacg aggcgcgtgt 9420
aagttacagg caagcgatcc gtcctaagaa accattatta tcatgacatt aacctataaa 9480
aataggcgta tcacgaggcc ctttcgtc 9508

<210> SEQ ID NO 4
<211> LENGTH: 9505
<212> TYPE: DNA
<213> ORGANISM: Artificial Sequence
<220> FEATURE:
<223> OTHER INFORMATION: Codon Optimized

<400> SEQUENCE: 4
tcgcgcgttt cggtgatgac ggtgaaaacc tctgacacat gcagctcccg gagacggtca 60
cagcttgtct gtaagcggat gccgggagca gacaagcccg tcagggcgcg tcagcgcgtg 120
ttggcgggtg tcggggctgg cttaactatg cggcatcaga gcagattgta ctgagagtgc 180

-continued

```
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctaacg acattactat atatataata taggaagcat ttaatagaca    360
gcatcgtaat atatgtgtac tttgcagtta tgacgccaga tggcagtagt ggaagatatt    420
ctttattgaa aaatagcttg tcaccttacg tacaatcttg atccggagct tttctttttt    480
tgccgattaa gaattaattc ggtcgaaaaa agaaaaggag agggccaaga gggagggcat    540
tggtgactat tgagcacgtg agtatacgtg attaagcaca caaaggcagc ttggagtatg    600
tctgttatta atttcacagg tagttctggt ccattggtga aagtttgcgg cttgcagagc    660
acagaggccg cagaatgtgc tctagattcc gatgctgact tgctgggtat tatatgtgtg    720
cccaatagaa agagaacaat tgacccggtt attgcaagga aaatttcaag tcttgtaaaa    780
gcatataaaa atagttcagg cactccgaaa tacttggttg gcgtgtttcg taatcaacct    840
aaggaggatg ttttggctct ggtcaatgat tacggcattg atatcgtcca actgcatgga    900
gatgagtcgt ggcaagaata ccaagagttc ctcggtttgc cagttattaa aagactcgta    960
tttccaaaag actgcaacat actactcagt gcagcttcac agaaacctca ttcgtttatt   1020
cccttgtttg attcagaagc aggtgggaca ggtgaacttt tggattggaa ctcgatttct   1080
gactgggttg gaaggcaaga gagccccgaa agcttacatt ttatgttagc tggtggactg   1140
acgccagaaa atgttggtga tgcgcttaga ttaaatggcg ttattggtgt tgatgtaagc   1200
ggaggtgtgg agacaaatgg tgtaaaagac tctaacaaaa tagcaaattt cgtcaaaaat   1260
gctaagaaat agtgacaccg attatttaaa gctgcagcat acgatatata tacatgtgta   1320
tatatgtata cctatgaatg tcagtaagta tgtatacgaa cagtatgata ctgaagatga   1380
caaggtaatg catcattcta tacgtgtcat tctgaacgag gcgcgctttc cttttttctt   1440
tttgcttttt cttttttttt ctcttgaact cgacggatct atgcggtgtg aaataccgca   1500
cagatgcgta aggagaaaat accgcatcag gaaattgtaa acgttaatat tttgttaaaa   1560
ttcgcgttaa atttttgtta aatcagctca ttttttaacc aataggccga aatcggcaaa   1620
atcccttata aatcaaaaga atagaccgag atagggttga gtgttgttcc agtttggaac   1680
aagagtccac tattaaagaa cgtggactcc aacgtcaaag ggcgaaaaac cgtctatcag   1740
ggcgatggcc cactacgtga accatcaccc taatcaagtt ttttggggtc gaggtgccgt   1800
aaagcactaa atcggaaccc taaagggagc ccccgattta gagcttgacg gggaaagccg   1860
gcgaacgtgg cgagaaagga agggaagaaa gcgaaaggag cgggcgctag ggcgctggca   1920
agtgtagcgg tcacgctgcg cgtaaccacc acacccgccg cgcttaatgc gccgctacag   1980
ggcgcgtcgc gccattcgcc attcaggctg cgcaactgtt gggaagggcg atcggtgcgg   2040
gcctcttcgc tattacgcca gctggcgaaa gggggatgtg ctgcaaggcg attaagttgg   2100
gtaacgccag ggttttccca gtcacgacgt tgtaaaacga cggccagtga gcgcgcgtaa   2160
tacgactcac tatagggcga attgggtacc ggccgcaaat taaagccttc gagcgtccca   2220
aaaccttctc aagcaaggtt ttcagtataa tgttacatgc gtacacgcgt ctgtacagaa   2280
aaaaaagaaa aatttgaaat ataaataacg ttcttaatac taacataact ataaaaaaat   2340
aaatagggac ctagacttca ggttgtctaa ctccttcctt ttcggttaga gcggatgtgg   2400
ggggagggcg tgaatgtaag cgtgacataa ctaattacat gactcgaggt cgacttacaa   2460
atcttcttca cttattaatt tttgttcgtg tctatgtcta ggtaaaggtg gaatggattg   2520
```

-continued ttcgtttcta aagaagttgt ttgggtcaac caatgtctta acctttacta atctatcgaa 2580
atttttaccg aagtattttt caccccaaat tctagcttgg gtatagttgt taggattctt 2640
tggatcgtta ataccgatgt ccaaatctct gtagttcaaa tatgccaatc tagggttttt 2700
agaaacgtat ggagtcatga agttatagat gtttctaatc cagtttaagt gcttttcgtt 2760
atcttcttgc ttttcccatg aacaaatgta ccacaattcg tataagatac cagctctatg 2820
aggaaatgga atggcagatt cactgatttc gtccattata ccaccgtatg gatacaaggc 2880
gtacatgcct gcaccaatat cttcttcgta caatttttct aagatttgga cgaaaactga 2940
ttcaggtatt ggctttttaa cgtagtctaa cttaatttta aaggcaccgt tttgacctgc 3000
ggatctatcc aataatattt ctttgttgaa gttgtctgta tcgtagttga caacacctga 3060
ataaaagatg atggtgtcga tccaagacaa ttgtctacaa tcagttttct taatacctaa 3120
ttctggaaaa gacttattca tcaagtctac taaggaatcg acaccaccca agaaaactga 3180
agaaaagtat gtgtggatag cagtcttatt tttaccttgg ttatcggtga tgtttcttgt 3240
gatgaaatga gtcatcaaca acaagtcctt atcgtacttg tatgcgatgt tttgccactt 3300
attgaccaat ttaactaatt catggatttc cattatcttt ttgactgaga acatagtaga 3360
ctttggtact gcgactaatc ttatcttcca agcaactatg ataccgaatg attctgcacc 3420
accacctctc aaagcccaaa ataagtcttc acccatagac tttctatcca aaactttacc 3480
gtgaacattt accaaatgag cgtcgattat gttatcagcg gccaaaccgt agtttctcat 3540
taaaggacca taaccaccac caccaaaatg accacctgcg caaactgttg gacagtaacc 3600
agcagccaat gataagtttt cattcttttc gttaacccag tagtatactt cacccaatgt 3660
tgcaccagct tcaacccaag cagtttgtga gtgtacgtct attttaattg atctcatgtt 3720
tctcaaatca acgataacga atggaacttg ggagatgtat gacatgcctt cactatcatg 3780
accaccggat ctagttctaa tttgcaaacc aacctttta gaacataaga tagtaccttg 3840
gatgtgagat acatgactag gggttacaat gaccaaaggt tttggagtgg tatcagaagt 3900
gaatctcaaa ttatggattg tactgttcaa gacggacatg tacaatgggt tgttttgagt 3960
gtaaaccaac ttcaaattgg tggcgttatt aggtatgtat tgtgagaagc acttcaaaaa 4020
gttttctctt gggtttgcga tacttgtttg gatgttaaag gaaaagaaaa agaagatgat 4080
cttgcatacg aaccaaaagg agaaagttga acatttcata ggacctggat tttcttcaac 4140
gtcaccacag gtcaacaaag aacctctacc ttcaataaaa acgtatacca aatattcagc 4200
gtagtacaat ttccacataa actcgtagaa tcttctacct gcttcagggt cataatttgt 4260
caaagcgaaa tctctagttt gcaagatcaa ccagaaagcc aagatggcat gtgacaacaa 4320
cataacgtta gaattaaagg cttgtggcca aatgatacct gccaaaatgg ctgcgacgta 4380
acttaacaaa acgataccgg agcagaacaa agtcaaattt cttgaaccgt acttagaagc 4440
caaggtacta ataccgaact ttgtgtcacc ttcaacgtca gaggcatcct tgatcaaggc 4500
taatgcagaa cccatacttt tcatgaatgc caacaaaaat gtgaatgaag gtctcaattc 4560
gaatggcaaa cctaaagcag ctcttgaagc gtagtagaag gtgaagtttg tgatgatatg 4620
agctaagaaa ttcaacaaaa aggcagtact agggttttgt ttccatctaa aaggtggtac 4680
ggaatagaca ataccaccga agataccgaa acagtaaccg aagatgtaca atggaccacc 4740
cttcatttta attgtgatga tcaaaccgaa caaggctact atgatagaca tgatccatgc 4800
agtattgacg gatatttcac ctgaagccaa aggcaaatct ggtttgttaa ttctgtcgat 4860
gtgcaaatcg tatatttgat taattgtagt ggtgaatgaa gcgatgcaca agatggcaac 4920

-continued taaaaagaaa aatgccttga acatcaagga ccatgaaatt aagttagtgt tatgcaacaa 4980
ttctttaccg aataaaccgc atgcacaaga agtaaaagcg attatggtgt atggtctttg 5040
caacttccaa catgctttac cgaagttcaa aatttttgtg gcaacagagt gattatcact 5100
ttcaggtggt tcagtttgat ttgtagttgc agctctgata gagttcttag ctatagacaa 5160
actttcggag cacttatttt gtaagtggaa ggacttggtt gaacaatgtt ttgatggaaa 5220
gttgttgtaa gagtacttaa taggtgtctt tggatgtctg taacacaaca atgatgtttt 5280
tggattgttg ttgtgaggat tcaataaggt atgatagtta gtttggaagg agaaagtaca 5340
gacggatgat aaacccatac tagttctaga tccgtcgaaa ctaagttctt ggtgttttaa 5400
aactaaaaaa aagactaact ataaaagtag aatttaagaa gtttaagaaa tagatttaca 5460
gaattacaat caatacctac cgtctttata tacttattag tcaagtaggg gaataatttc 5520
agggaactgg tttaaacctt ttttttcagc tttttccaaa tcagagagag cagaaggtaa 5580
tagaaggtgt aagaaaatga gatagataca tgcgtgggtc aattgccttg tgtcatcatt 5640
tactccaggc aggttgcatc actccattga ggttgtgccc gtttttttgcc tgtttgtgcc 5700
ctgttctctg tagttgcgct aagagaatgg acctatgaac tgatggttgg tgaagaaaac 5760
aatattttgg tgctgggatt cttttttttt ctggatgcca gcttaaaaag cgggctccat 5820
tatatttagt ggatgccagg aataaacctg ttcacccaag caccatcagt gttatatatt 5880
ctgtgtaacc cgccccctat tttggcatgt acgggttaca gcagaattaa aaggctaatt 5940
ttttgactaa ataaagttag gaaaatcact actattaatt atttacgtat tctttgaaat 6000
ggcagtattg ataatgataa actcgagagc tccagctttt gttcagttga ttgtatgctt 6060
ggtatagctt gaaatattgt gcagaaaaag aaacaaggaa gaaagggaac gagaacaatg 6120
acgaggaaac aaaagattaa taattgcagg tctatttata cttgatagca agacagcaaa 6180
cttttttttta tttcaaattc aagtaactgg aaggaaggcc gtataccgtt gctcattaga 6240
gagtagtgtg cgtgaatgaa ggaaggaaaa agtttcgtgt gcttcgagat acccctcatc 6300
agctctggaa caacgacatc tgttggtgct gtctttgtcg ttaatttttt cctttagtgt 6360
cttccatcat ttttttgtca ttgcggatat ggtgagacaa caacgggggga gagagaaaag 6420
aaaaaaaaag aaaagaagtt gcatgcgcct attattactt caatagatgg caaatggaaa 6480
aagggtagtg aaacttcgat atgatgatgg ctatcaagtc tagggctaca gtattagttc 6540
gttatgtacc accatcaatg aggcagtgta attggtgtag tcttgtttag cccattatgt 6600
cttgtctggt atctgttcta ttgtatatct cccctccgcc acctacatgt tagggagacc 6660
aacgaaggta ttataggaat cccgatgtat gggtttggtt gccagaaaag aggaagtcca 6720
tattgtacac ccggaaacaa caaaaggatg cgcgcttggc gtaatcatgg tcatagctgt 6780
ttcctgtgtg aaattgttat ccgctcacaa ttccacacaa cataggagcc ggaagcataa 6840
agtgtaaagc ctggggtgcc taatgagtga ggtaactcac attaattgcg ttgcgctcac 6900
tgcccgcttt ccagtcggga aacctgtcgt gccagctgca ttaatgaatc ggccaacgcg 6960
cggggagagg cggtttgcgt attgggcgct cttccgcttc ctcgctcact gactcgctgc 7020
gctcggtcgt tcggctgcgg cgagcggtat cagctcactc aaaggcggta atacggttat 7080
ccacagaatc aggggataac gcaggaaaga acatgtgagc aaaaggccag caaaaggcca 7140
ggaaccgtaa aaaggccgcg ttgctggcgt ttttccatag gctccgcccc cctgacgagc 7200
atcacaaaaa tcgacgctca agtcagaggt ggcgaaaccc gacaggacta taaagatacc 7260

-continued

```
aggcgtttcc ccctggaagc tccctcgtgc gctctcctgt tccgaccctg ccgcttaccg   7320
gatacctgtc cgcctttctc ccttcgggaa gcgtggcgct ttctcatagc tcacgctgta   7380
ggtatctcag ttcggtgtag gtcgttcgct ccaagctggg ctgtgtgcac gaaccccccg   7440
ttcagcccga ccgctgcgcc ttatccggta actatcgtct tgagtccaac ccggtaagac   7500
acgacttatc gccactggca gcagccactg gtaacaggat tagcagagcg aggtatgtag   7560
gcggtgctac agagttcttg aagtggtggc ctaactacgg ctacactaga aggacagtat   7620
ttggtatctg cgctctgctg aagccagtta ccttcggaaa aagagttggt agctcttgat   7680
ccggcaaaca aaccaccgct ggtagcggtg gtttttttgt ttgcaagcag cagattacgc   7740
gcagaaaaaa aggatctcaa gaagatcctt tgatcttttc tacggggtct gacgctcagt   7800
ggaacgaaaa ctcacgttaa gggattttgg tcatgagatt atcaaaaagg atcttcacct   7860
agatcctttt aaattaaaaa tgaagtttta aatcaatcta aagtatatat gagtaaactt   7920
ggtctgacag ttaccaatgc ttaatcagtg aggcacctat ctcagcgatc tgtctatttc   7980
gttcatccat agttgcctga ctccccgtcg tgtagataac tacgatacgg gagggcttac   8040
catctggccc cagtgctgca atgataccgc gagacccacg ctcaccggct ccagatttat   8100
cagcaataaa ccagccagcc ggaagggccg agcgcagaag tggtcctgca actttatccg   8160
cctccatcca gtctattaat tgttgccggg aagctagagt aagtagttcg ccagttaata   8220
gtttgcgcaa cgttgttgcc attgctacag gcatcgtggt gtcacgctcg tcgtttggta   8280
tggcttcatt cagctccggt tcccaacgat caaggcgagt tacatgatcc cccatgttgt   8340
gcaaaaaagc ggttagctcc ttcggtcctc cgatcgttgt cagaagtaag ttggccgcag   8400
tgttatcact catggttatg gcagcactgc ataattctct tactgtcatg ccatccgtaa   8460
gatgcttttc tgtgactggt gagtactcaa ccaagtcatt ctgagaatag tgtatgcggc   8520
gaccgagttg ctcttgcccg gcgtcaatac gggataatac cgcgccacat agcagaactt   8580
taaaagtgct catcattgga aaacgttctt cggggcgaaa actctcaagg atcttaccgc   8640
tgttgagatc cagttcgatg taacccactc gtgcacccaa ctgatcttca gcatctttta   8700
ctttcaccag cgtttctggg tgagcaaaaa caggaaggca aaatgccgca aaaaagggaa   8760
taagggcgac acggaaatgt tgaatactca tactcttcct ttttcaatat tattgaagca   8820
tttatcaggg ttattgtctc atgagcggat acatatttga atgtatttag aaaaataaac   8880
aaataggggt tccgcgcaca tttccccgaa aagtgccacc tgggtccttt tcatcacgtg   8940
ctataaaaat aattataatt taaatttttt aatataaata tataaattaa aaatagaaag   9000
taaaaaaaga aattaaagaa aaaatagttt ttgttttccg aagatgtaaa agactctagg   9060
gggatcgcca acaaatacta ccttttatct tgctcttcct gctctcaggt attaatgccg   9120
aattgtttca tcttgtctgt gtagaagacc acacacgaaa atcctgtgat tttacatttt   9180
acttatcgtt aatcgaatgt atatctattt aatctgcttt tcttgtctaa taaatatata   9240
tgtaaagtac gctttttgtt gaaatttttt aaacctttgt ttattttttt ttcttcattc   9300
cgtaactctt ctaccttctt tatttacttt ctaaaatcca aatacaaaac ataaaaataa   9360
ataaacacag agtaaattcc caaattattc catcattaaa agatacgagg cgcgtgtaag   9420
ttacaggcaa gcgatccgtc ctaagaaacc attattatca tgacattaac ctataaaaat   9480
aggcgtatca cgaggccctt tcgtc                                         9505
```

<210> SEQ ID NO 5
<211> LENGTH: 8696

-continued

<212> TYPE: DNA
<213> ORGANISM: Artificial Sequence
<220> FEATURE:
<223> OTHER INFORMATION: Codon Optimized

<400> SEQUENCE: 5
tcgcgcgttt cggtgatgac ggtgaaaacc tctgacacat gcagctcccg gagacggtca 60
cagcttgtct gtaagcggat gccgggagca gacaagcccg tcagggcgcg tcagcgcgtg 120
ttggcgggtg tcggggctgg cttaactatg cggcatcaga gcagattgta ctgagagtgc 180
accataaatt cccgttttaa gagcttggtg agcgctagga gtcactgcca ggtatcgttt 240
gaacacggca ttagtcaggg aagtcataac acagtccttt cccgcaattt tctttttcta 300
ttactcttgg cctcctaact gtgggaatac tcaggtatcg taagatgcaa gagttcgaat 360
ctcttagcaa ccattatttt tttcctcaac ataacgagaa cacacagggg cgctatcgca 420
cagaatcaaa ttcgatgact ggaaattttt tgttaatttc agaggtcgcc tgacgcatat 480 accttttca actgaaaaat tgggagaaaa aggaaaggtg agaggccgga accggctttt 540
catatagaat agagaagcgt tcatgactaa atgcttgcat cacaatactt gaagttgaca 600
atattattta aggacctatt gtttttcca ataggtggtt agcaatcgtc ttactttcta 660
acttttctta ccttttacat ttcagcaata tatatatata tttcaaggat ataccattct 720
aatgtctgcc cctatgtctg cccctaagaa gatcgtcgtt ttgccaggtg accacgttgg 780
tcaagaaatc acagccgaag ccattaaggt tcttaaagct atttctgatg ttcgttccaa 840
tgtcaagttc gatttcgaaa atcatttaat tggtggtgct gctatcgatg ctacaggtgt 900
cccacttcca gatgaggcgc tggaagcctc caagaaggtt gatgccgttt tgttaggtgc 960
tgtgggtggt cctaaatggg gtaccggtag tgttagacct gaacaaggtt tactaaaaat 1020
ccgtaaagaa cttcaattgt acgccaactt aagaccatgt aactttgcat ccgactctct 1080
tttagactta tctccaatca agccacaatt tgctaaaggt actgacttcg ttgttgtcag 1140
agaattagtg ggaggtattt actttggtaa gagaaaggaa gacgatggtg atggtgtcgc 1200
ttgggatagt gaacaataca ccgttccaga agtgcaaaga atcacaagaa tggccgcttt 1260
catggcccta caacatgagc caccattgcc tatttggtcc ttggataaag ctaatgtttt 1320
ggcctcttca agattatgga gaaaaactgt ggaggaaacc atcaagaacg aattccctac 1380
attgaaggtt caacatcaat tgattgattc tgccgccatg atcctagtta agaacccaac 1440
ccacctaaat ggtattataa tcaccagcaa catgtttggt gatatcatct ccgatgaagc 1500
ctccgttatc ccaggttcct tgggtttgtt gccatctgcg tccttggcct ctttgccaga 1560
caagaacacc gcatttggtt tgtacgaacc atgccacggt tctgctccag atttgccaaa 1620
gaataaggtt gaccctatcg ccactatctt gtctgctgca atgatgttga aattgtcatt 1680
gaacttgcct gaagaaggta aggccattga agatgcagtt aaaaaggttt tggatgcagg 1740
tatcagaact ggtgatttag gtggttccaa cagtaccacc gaagtcggtg atgctgtcgc 1800
cgaagaagtt aagaaaatcc ttgcttaatg acaccgatta tttaaagctg cagcatacga 1860
tatatataca tgtgtatata tgtataccta tgaatgtcag taagtatgta tacgaacagt 1920
atgatactga agatgacaag gtaatgcatc attctatacg tgtcattctg aacgaggcgc 1980
gctttccttt tttctttttg ctttttcttt ttttttctct tgaactcgac ggatctatgc 2040
ggtgtgaaat accgcacaga tgcgtaagga gaaaataccg catcaggaaa ttgtaaacgt 2100
taatattttg ttaaaattcg cgttaaattt ttgttaaatc agctcatttt ttaaccaata 2160

-continued

```
ggccgaaatc ggcaaaatcc cttataaatc aaaagaatag accgagatag ggttgagtgt   2220
tgttccagtt tggaacaaga gtccactatt aaagaacgtg gactccaacg tcaaagggcg   2280
aaaaaccgtc tatcagggcg atggcccact acgtgaacca tcaccctaat caagtttttt   2340
ggggtcgagg tgccgtaaag cactaaatcg gaaccctaaa gggagccccc gatttagagc   2400
ttgacgggga aagccggcga acgtggcgag aaaggaaggg aagaaagcga aaggagcggg   2460
cgctagggcg ctggcaagtg tagcggtcac gctgcgcgta accaccacac ccgccgcgct   2520
taatgcgccg ctacagggcg cgtcgcgcca ttcgccattc aggctgcgca actgttggga   2580
agggcgatcg gtgcgggcct cttcgctatt acgccagctg gcgaaagggg gatgtgctgc   2640
aaggcgatta agttgggtaa cgccagggtt ttcccagtca cgacgttgta aaacgacggc   2700
cagtgagcgc gcgtaatacg actcactata gggcgaattg ggtaccggcc gcaaattaaa   2760
gccttcgagc gtcccaaaac cttctcaagc aaggttttca gtataatgtt acatgcgtac   2820
acgcgtctgt acagaaaaaa aagaaaaatt tgaaatataa ataacgttct taatactaac   2880
ataactataa aaaaataaat agggacctag acttcaggtt gtctaactcc ttcctttttcg   2940
gttagagcgg atgtgggggg agggcgtgaa tgtaagcgtg acataactaa ttacatgact   3000
cgaggtcgac ttatgcatag tctggaacat cgtaagggta ctttcttggg gtgtaatcga   3060
agatcaacaa tttttcccag aaggatctgt aaacgtcacc aaaaccaacg tgagctggat   3120
gaatgatgta atcttggata gtttcaactg attcgaaggt tacttcgaca atgtgtgtat   3180
aaccttcttc tttcttttgt gtaacgtctt taccccagta tacatctttc atagcaggta   3240
taatgttgac caaattaacg taggtcttga aaaattcttc cttttgagct tctgtgattt   3300
catctttaaa cttcaatact atcaaatgct tgacggccat aggacctggg ttttcttcaa   3360
cgtcaccaca agttaacaag gaacctctac cttcatattt aattggtact gatctgacaa   3420
ctactctttc gacggtcaaa ccaggaccga aaccaaataa gacaccccat tcaaaaccgt   3480
caccagtagt agatttaccc tcttctaatg atctctttct caattcatcc attacgaaca   3540
agacagtgga tgaagacatg ttaccgtgtt cagataaaac atgtctacta tctacaaact   3600
tttctttctt caaatccaat ttttcttcaa ccttatccaa aatggcttta ccacctggat   3660
gtgttatcca gaaaatagag ttccaatctg agatacctat aggagtgaat gcttctatca   3720
aacacttttc tatgttgtta gagattaaca ttggaacgtc tttgtgcaaa tcgaagatca   3780
aacctgcttc tcttatatga ccaccaattg taccttcaga attaggcaag atggtttgac   3840
ctgtactgac taattcaaat attggtcttt caccaacaga ttcgtcaggt tctgcaccaa   3900
caataacagc agcagcaccg tcaccgaaga tagcttgacc aactaacaat tccaagtcag   3960
aatcacttgg acctctaaac aagcaagcca taatgtcgca acaaacagct aatactctgg   4020
caccccttgtt gttttctgca atatccttag cgattctcaa aacagtacca ccaccgtagc   4080
aacctaattg atacatcatg actctcttaa cggatggtga caaacctaac aatttggcac   4140
agtggtagtc tgcaccaggc atatctgtag tagatgcact tgtaaaaatc aaatgagtga   4200
tctttgactt tggttgaccc cattccttaa tggcttttgc acaagcatct ttacccaatt   4260
taggaacttc gacaactaac atgtcttgtc tggcatccaa tgtttgcatt tcgtgttcta   4320
ccaatcttgg attttgcttc aaatgttctt cgttcaagaa gcagtttctc tttctgatca   4380
tagacttatc acatattttt ctaaactttt ccttcaattg agtcatgtgt tcactcttgg   4440
taactctgaa gtaataatca ggaaattcat cttggatcaa tatgttttct gggttggctg   4500
tacctatggc taatacggag gcaggacctt cggctctcaa atggttcata ctagttctag   4560
```

-continued

```
atccgtcgaa actaagttct tggtgtttta aaactaaaaa aaagactaac tataaaagta   4620
gaatttaaga agtttaagaa atagatttac agaattacaa tcaataccta ccgtctttat   4680
atacttatta gtcaagtagg ggaataattt cagggaactg gtttaaacct tttttttcag   4740
ctttttccaa atcagagaga gcagaaggta atagaaggtg taagaaaatg agatagatac   4800
atgcgtgggt caattgcctt gtgtcatcat ttactccagg caggttgcat cactccattg   4860
aggttgtgcc cgttttttgc ctgtttgtgc cctgttctct gtagttgcgc taagagaatg   4920
gacctatgaa ctgatggttg gtgaagaaaa caatattttg gtgctgggat tctttttttt   4980
tctggatgcc agcttaaaaa gcgggctcca ttatatttag tggatgccag gaataaacct   5040
gttcacccaa gcaccatcag tgttatatat tctgtgtaac ccgcccccta ttttggcatg   5100
tacgggttac agcagaatta aaaggctaat tttttgacta aataaagtta ggaaaatcac   5160
tactattaat tatttacgta ttctttgaaa tggcagtatt gataatgata aactcgagag   5220
ctccagcttt tgttcagttg attgtatgct tggtatagct tgaaatattg tgcagaaaaa   5280
gaaacaagga agaaagggaa cgagaacaat gacgaggaaa caaaagatta ataattgcag   5340
gtctatttat acttgatagc aagacagcaa actttttttt atttcaaatt caagtaactg   5400
gaaggaaggc cgtataccgt tgctcattag agagtagtgt gcgtgaatga aggaaggaaa   5460
aagtttcgtg tgcttcgaga taccccctcat cagctctgga acaacgacat ctgttggtgc   5520
tgtctttgtc gttaattttt tcctttagtg tcttccatca ttttttttgtc attgcggata   5580
tggtgagaca acaacggggg agagagaaaa gaaaaaaaaa gaaaagaagt tgcatgcgcc   5640
tattattact tcaatagatg gcaaatggaa aaagggtagt gaaacttcga tatgatgatg   5700
gctatcaagt ctagggctac agtattagtt cgttatgtac caccatcaat gaggcagtgt   5760
aattggtgta gtcttgttta gcccattatg tcttgtctgg tatctgttct attgtatatc   5820
tcccctccgc cacctacatg ttagggagac caacgaaggt attataggaa tcccgatgta   5880
tgggtttggt tgccagaaaa gaggaagtcc atattgtaca cccggaaaca acaaaaggat   5940
gcgcgcttgg cgtaatcatg gtcatagctg tttcctgtgt gaaattgtta tccgctcaca   6000
attccacaca acataggagc cggaagcata aagtgtaaag cctggggtgc ctaatgagtg   6060
aggtaactca cattaattgc gttgcgctca ctgcccgctt tccagtcggg aaacctgtcg   6120
tgccagctgc attaatgaat cggccaacgc gcggggagag gcggtttgcg tattgggcgc   6180
tcttccgctt cctcgctcac tgactcgctg cgctcggtcg ttcggctgcg gcgagcggta   6240
tcagctcact caaaggcggt aatacggtta tccacagaat caggggataa cgcaggaaag   6300
aacatgtgag caaaaggcca gcaaaaggcc aggaaccgta aaaaggccgc gttgctggcg   6360
tttttccata ggctccgccc ccctgacgag catcacaaaa atcgacgctc aagtcagagg   6420
tggcgaaacc cgacaggact ataaagatac caggcgtttc cccctggaag ctccctcgtg   6480
cgctctcctg ttccgaccct gccgcttacc ggatacctgt ccgcctttct cccttcggga   6540
agcgtggcgc tttctcatag ctcacgctgt aggtatctca gttcggtgta ggtcgttcgc   6600
tccaagctgg gctgtgtgca cgaacccccc gttcagcccg accgctgcgc cttatccggt   6660
aactatcgtc ttgagtccaa cccggtaaga cacgacttat cgccactggc agcagccact   6720
ggtaacagga ttagcagagc gaggtatgta ggcggtgcta cagagttctt gaagtggtgg   6780
cctaactacg gctacactag aaggacagta tttggtatct gcgctctgct gaagccagtt   6840
accttcggaa aaagagttgg tagctcttga tccggcaaac aaaccaccgc tggtagcggt   6900
```

ggttttttg tttgcaagca gcagattacg cgcagaaaaa aaggatctca agaagatcct 6960
ttgatctttt ctacggggtc tgacgctcag tggaacgaaa actcacgtta agggattttg 7020
gtcatgagat tatcaaaaag gatcttcacc tagatccttt taaattaaaa atgaagtttt 7080
aaatcaatct aaagtatata tgagtaaact tggtctgaca gttaccaatg cttaatcagt 7140
gaggcaccta tctcagcgat ctgtctattt cgttcatcca tagttgcctg actccccgtc 7200
gtgtagataa ctacgatacg ggagggctta ccatctggcc ccagtgctgc aatgataccg 7260
cgagacccac gctcaccggc tccagattta tcagcaataa accagccagc cggaagggcc 7320
gagcgcagaa gtggtcctgc aactttatcc gcctccatcc agtctattaa ttgttgccgg 7380
gaagctagag taagtagttc gccagttaat agtttgcgca acgttgttgc cattgctaca 7440
ggcatcgtgg tgtcacgctc gtcgtttggt atggcttcat tcagctccgg ttcccaacga 7500
tcaaggcgag ttacatgatc ccccatgttg tgcaaaaaag cggttagctc cttcggtcct 7560
ccgatcgttg tcagaagtaa gttggccgca gtgttatcac tcatggttat ggcagcactg 7620
cataattctc ttactgtcat gccatccgta agatgctttt ctgtgactgg tgagtactca 7680
accaagtcat tctgagaata gtgtatgcgg cgaccgagtt gctcttgccc ggcgtcaata 7740
cgggataata ccgcgccaca tagcagaact ttaaaagtgc tcatcattgg aaaacgttct 7800
tcggggcgaa aactctcaag gatcttaccg ctgttgagat ccagttcgat gtaacccact 7860
cgtgcaccca actgatcttc agcatctttt actttcacca gcgtttctgg gtgagcaaaa 7920
acaggaaggc aaaatgccgc aaaaaaggga ataagggcga cacggaaatg ttgaatactc 7980
atactcttcc tttttcaata ttattgaagc atttatcagg gttattgtct catgagcgga 8040
tacatatttg aatgtattta gaaaaataaa caaatagggg ttccgcgcac atttccccga 8100
aaagtgccac ctgggtcctt ttcatcacgt gctataaaaa taattataat ttaaattttt 8160
taatataaat atataaatta aaaatagaaa gtaaaaaaag aaattaaaga aaaaatagtt 8220
tttgttttcc gaagatgtaa aagactctag ggggatcgcc aacaaatact accttttatc 8280
ttgctcttcc tgctctcagg tattaatgcc gaattgtttc atcttgtctg tgtagaagac 8340
cacacacgaa aatcctgtga ttttacattt tacttatcgt taatcgaatg tatatctatt 8400
taatctgctt ttcttgtcta ataaatatat atgtaaagta cgctttttgt tgaaattttt 8460
taaacctttg tttatttttt tttcttcatt ccgtaactct tctaccttct ttatttactt 8520
tctaaaatcc aaatacaaaa cataaaaata aataaacaca gagtaaattc ccaaattatt 8580
ccatcattaa aagatacgag gcgcgtgtaa gttacaggca agcgatccgt cctaagaaac 8640
cattattatc atgacattaa cctataaaaa taggcgtatc acgaggccct ttcgtc 8696

<210> SEQ ID NO 6
<211> LENGTH: 4322
<212> TYPE: DNA
<213> ORGANISM: Artificial Sequence
<220> FEATURE:
<223> OTHER INFORMATION: Codon Optimized

<400> SEQUENCE: 6
aggaaacgaa gataaatctc gagtttatca ttatcaatac tgccatttca aagaatacgt 60
aaataattaa tagtagtgat tttcctaact ttatttagtc aaaaaattag ccttttaatt 120
ctgctgtaac ccgtacatgc caaaataggg ggcgggttac acagaatata taacactgat 180
ggtgcttggg tgaacaggtt tattcctggc atccactaaa tataatggag cccgcttttt 240
aagctggcat ccagaaaaaa aaagaatccc agcaccaaaa tattgttttc ttcaccaacc 300

-continued

```
atcagttcat aggtccattc tcttagcgca actacagaga acagggcaca aacaggcaaa    360
aaacgggcac aacctcaatg gagtgatgca acctgcctgg agtaaatgat gacacaaggc    420
aattgaccca cgcatgtatc tatctcattt tcttacacct tctattacct tctgctctct    480
ctgatttgga aaaagctgaa aaaaaaggtt taaaccagtt ccctgaaatt attcccctac    540
ttgactaata agtatataaa gacggtaggt attgattgta attctgtaaa tctatttctt    600
aaacttctta aattctactt ttatagttag tctttttttt agttttaaaa caccaagaac    660
ttagtttcga cggatctaga actagtatgg gtaaaaacta taagtccttg gattcagtcg    720
ttgcctcaga tttcatcgca ttgggtatca cctcagaagt agcagaaaca ttacatggta    780
gattggcaga aatcgtttgt aattatggtg ctgcaacccc tcaaacttgg atcaacatcg    840
ctaaccatat cttgtcacca gatttgcctt tctccttaca ccaaatgttg ttttatggtt    900
gctacaagga tttcggtcca gccccacctg cttggattcc agaccctgaa aaagtcaagt    960
caactaattt gggtgctttg ttggaaaaga gaggtaaaga atttttgggt gtaaagtaca   1020
aagatccaat ttcttctttt tctcacttcc aagaattttc tgttagaaac cctgaagtct   1080
attggagaac agtattgatg gatgaaatga aaattagttt ctctaaggac ccagaatgta   1140
tcttgagaag agatgacatc aacaacccag gtggttctga atggttacct ggtggttact   1200
tgaactcagc taaaaattgc ttgaacgtaa actccaataa gaaattgaac gatactatga   1260
tcgtttggag agacgagggt aacgatgact tgcctttgaa taagttgaca ttagatcaat   1320
tgagaaagag agtttggttg gttggttatg cattggaaga aatgggttta gaaaaaggtt   1380
gtgcaatagc catcgatatg ccaatgcatg ttgatgctgt tgttatatat ttggccatag   1440
tattggctgg ttacgtagtt gtctctatag cagattcatt ttccgcccct gaaatctcaa   1500
ctagattgag attatccaaa gctaaggcaa ttttcacaca agatcacatc atcagaggta   1560
aaaagagaat accattgtat tcaagagtag ttgaagctaa atccccaatg gcaatagtta   1620
tcccttgtag tggttctaac attggtgcag aattgagaga tggtgacata tcttgggatt   1680
actttttaga aagagccaag gagtttaaaa actgcgagtt tactgccaga gaacaacctg   1740
ttgatgctta tactaacatc ttattctcca gtggtactac aggtgaacca aaagcaattc   1800
cttggacaca agccacccca ttgaaggctg ctgctgatgg ttggtctcat ttggatatta   1860
gaaaaggtga cgttatagta tggccaacta atttgggttg gatgatgggt ccttggttgg   1920
tttatgctag tttgttaaat ggtgcatcta ttgccttgta caacggtagt cctttagtct   1980
ctggtttcgc taaatttgtt caagatgcaa aggtcacaat gttgggtgtc gtaccatcta   2040
ttgtaagatc atggaaatcc acaaattgtg tttcaggtta cgattggtcc accataagat   2100
gcttttcttc atccggtgaa gcctctaatg tagacgaata tttgtggtta atgggtagag   2160
ctaactacaa gccagttata gaaatgtgtg gtggtacaga aatcggtggt gctttttctg   2220
ctggttcatt tttgcaagct caatctttaa gttctttttc atcccaatgt atgggttgca   2280
ccttgtacat attagataag aacggttacc caatgcctaa aaataagcca ggtatcggtg   2340
aattggcatt aggtcctgtt atgtttggtg cctcaaaaac attgttaaac ggtaatcatc   2400
acgatgtcta tttcaagggt atgccaacct tgaatggtga agtattgaga agacatggtg   2460
acattttcga attgacctct aacggttact accatgcaca cggtagagcc gatgacacta   2520
tgaacatcgg tggtatcaaa attagttcta tcgaaatcga aagagtctgt aatgaagtag   2580
atgacagagt ttttgaaacc actgctattg gtgttccacc tttgggtggt ggtccagaac   2640
```

-continued

```
aattggtcat atttttcgta ttgaaggatt caaacgacac aaccattgat ttgaaccaat   2700
tgagattatc ctttaacttg ggtttgcaaa agaaattgaa cccattattc aaagttacta   2760
gagttgtccc attgtcatcc ttacctagaa ctgcaacaaa caagatcatg agaagagttt   2820
tgagacaaca attcagtcat ttcgaagaag gtagaggttc tttgttaaca tgtggtgacg   2880
ttgaagaaaa tccaggtcct atggcttcag aaaaggaaat aagaagagaa agattcttga   2940
acgtattccc aaagttagtt gaagaattga acgctagttt gttagcttat ggtatgccta   3000
aagaagcctg cgattggtat gctcactctt taaactacaa tactccaggt ggtaaattga   3060
atagaggttt gagtgtagtt gatacttatg ctatcttgtc taacaaaacc gttgaacaat   3120
taggtcaaga agaatacgaa aaggtcgcta tcttgggttg gtgtattgaa ttgttgcaag   3180
catacttttt ggttgccgat gacatgatgg ataagtctat aacaagaaga ggtcaaccat   3240
gctggtacaa agttccagaa gttggtgaaa tagccataaa tgatgctttt atgttggaag   3300
ccgctatcta taaattgttg aagtcacatt tcagaaacga aaagtactac atcgatatta   3360
ccgaattatt ccacgaagtt actttccaaa cagaattggg tcaattgatg gatttgataa   3420
ctgcacctga agataaagtt gacttgtcaa agttttcctt gaagaaacat tcattcatcg   3480
tcacctttga aactgcttat tactccttct atttgccagt cgccttggct atgtacgtag   3540
ctggtattac tgatgaaaaa gacttgaagc aagcaagaga tgttttgata cctttgggtg   3600
aatacttcca aatccaagat gactacttag actgtttcgg tactccagaa caaataggta   3660
aaatcggtac agatattcaa gacaataagt gcagttgggt tattaacaag gctttggaat   3720
tagcatctgc cgaacaaaga aagactttgg atgaaaacta cggtaaaaag gactcagttg   3780
ctgaagcaaa gtgtaagaaa atttttaatg atttgaagat tgaacaattg taccatgaat   3840
acgaagaatc catcgctaaa gacttaaagg caaagattag tcaagttgat gaatcaagag   3900
gttttaaagc cgacgttttg acagctttct tgaataaggt ctacaagaga tcaaaggatt   3960
acaaggatca tgacggtgac tataaagacc acgatattga ctacaaagat gacgatgaca   4020
agtaagtcga cctcgagtca tgtaattagt tatgtcacgc ttacattcac gccctccccc   4080
cacatccgct ctaaccgaaa aggaaggagt tagacaacct gaagtctagg tccctattta   4140
tttttttata gttatgttag tattaagaac gttatttata tttcaaattt ttcttttttt   4200
tctgtacaga cgcgtgtacg catgtaacat tatactgaaa accttgcttg agaaggtttt   4260
gggacgctcg aaggctttaa tttgcgtgac ataactaatt acatgacttg actgattttt   4320
cc                                                                  4322
```

<210> SEQ ID NO 7
<211> LENGTH: 2522
<212> TYPE: DNA
<213> ORGANISM: Artificial Sequence
<220> FEATURE:
<223> OTHER INFORMATION: Codon Optimized

<400> SEQUENCE: 7

```
aggaaacgaa gataaatctc gagtttatca ttatcaatac tgccatttca aagaatacgt     60
aaataattaa tagtagtgat tttcctaact ttatttagtc aaaaaattag ccttttaatt    120
ctgctgtaac ccgtacatgc caaaataggg ggcgggttac acagaatata taacactgat    180
ggtgcttggg tgaacaggtt tattcctggc atccactaaa tataatggag cccgcttttt    240
aagctggcat ccagaaaaaa aaagaatccc agcaccaaaa tattgttttc ttcaccaacc    300
atcagttcat aggtccattc tcttagcgca actacagaga acagggcaca aacaggcaaa    360
```

-continued

```
aaacgggcac aacctcaatg gagtgatgca acctgcctgg agtaaatgat gacacaaggc    420
aattgaccca cgcatgtatc tatctcattt tcttacacct tctattacct tctgctctct    480
ctgatttgga aaaagctgaa aaaaaaggtt taaaccagtt ccctgaaatt attcccctac    540
ttgactaata agtatataaa gacggtaggt attgattgta attctgtaaa tctatttctt    600
aaacttctta aattctactt ttatagttag tctttttttt agttttaaaa caccaagaac    660
ttagtttcga cggatctaga actagtatga accatttgag agccgaaggt cctgcctccg    720
tattagccat aggtacagcc aacccagaaa acatattgat ccaagatgaa tttcctgatt    780
attacttcag agttaccaag agtgaacaca tgactcaatt gaaggaaaag tttagaaaaa    840
tatgtgataa gtctatgatc agaaagagaa actgcttctt gaacgaagaa catttgaagc    900
aaaatccaag attggtagaa cacgaaatgc aaacattgga tgccagacaa gacatgttag    960
ttgtcgaagt tcctaaattg ggtaaagatg cttgtgcaaa agccattaag gaatggggtc   1020
aaccaaagtc aaagatcact catttgattt ttacaagtgc atctactaca gatatgcctg   1080
gtgcagacta ccactgtgcc aaattgttag gtttgtcacc atccgttaag agagtcatga   1140
tgtatcaatt aggttgctac ggtggtggta ctgttttgag aatcgctaag gatattgcag   1200
aaaacaacaa gggtgccaga gtattagctg tttgttgcga cattatggct tgcttgttta   1260
gaggtccaag tgattctgac ttggaattgt tagttggtca agctatcttc ggtgacggtg   1320
ctgctgctgt tattgttggt gcagaacctg acgaatctgt tggtgaaaga ccaatatttg   1380
aattagtcag tacaggtcaa accatcttgc ctaattctga aggtacaatt ggtggtcata   1440
taagagaagc aggtttgatc ttcgatttgc acaaagacgt tccaatgtta atctctaaca   1500
acatagaaaa gtgtttgata gaagcattca ctcctatagg tatctcagat tggaactcta   1560
ttttctggat aacacatcca ggtggtaaag ccattttgga taaggttgaa gaaaaattgg   1620
atttgaagaa agaaaagttt gtagatagta gacatgtttt atctgaacac ggtaacatgt   1680
cttcatccac tgtcttgttc gtaatggatg aattgagaaa gagatcatta gaagagggta   1740
aatctactac tggtgacggt tttgaatggg gtgtcttatt tggtttcggt cctggtttga   1800
ccgtcgaaag agtagttgtc agatcagtac caattaaata tgaaggtaga ggttccttgt   1860
taacttgtgg tgacgttgaa gaaaacccag gtcctatggc cgtcaagcat ttgatagtat   1920
tgaagtttaa agatgaaatc acagaagctc aaaaggaaga atttttcaag acctacgtta   1980
atttggtcaa cattatacct gctatgaaag atgtatactg gggtaaagac gttacacaaa   2040
agaaagaaga aggttataca cacattgtcg aagtaacctt cgaatcagtt gaaactatcc   2100
aagattacat cattcatcca gctcacgttg gttttggtga cgtttacaga tccttctggg   2160
aaaaattgtt gatcttcgat tacaccccaa gaaagtaccc ttacgatgtt ccagactatg   2220
cataagtcga cctcgagtca tgtaattagt tatgtcacgc ttacattcac gccctccccc   2280
cacatccgct ctaaccgaaa aggaaggagt tagacaacct gaagtctagg tccctattta   2340
ttttttata gttatgttag tattaagaac gttatttata tttcaaattt ttcttttttt    2400
tctgtacaga cgcgtgtacg catgtaacat tatactgaaa accttgcttg agaaggtttt   2460
gggacgctcg aaggctttaa tttgcgtgac ataactaatt acatgacttg actgattttt   2520
cc                                                                  2522
```

<210> SEQ ID NO 8
<211> LENGTH: 3887
<212> TYPE: DNA

-continued

<213> ORGANISM: Artificial Sequence
<220> FEATURE:
<223> OTHER INFORMATION: Codon Optimized

<400> SEQUENCE: 8
aggaaacgaa gataaatctc gagtttatca ttatcaatac tgccatttca aagaatacgt 60
aaataattaa tagtagtgat tttcctaact ttatttagtc aaaaaattag ccttttaatt 120
ctgctgtaac ccgtacatgc caaaataggg ggcgggttac acagaatata taacactgat 180
ggtgcttggg tgaacaggtt tattcctggc atccactaaa tataatggag cccgcttttt 240
aagctggcat ccagaaaaaa aaagaatccc agcaccaaaa tattgttttc ttcaccaacc 300
atcagttcat aggtccattc tcttagcgca actacagaga acagggcaca aacaggcaaa 360
aaacgggcac aacctcaatg gagtgatgca acctgcctgg agtaaatgat gacacaaggc 420
aattgaccca cgcatgtatc tatctcattt tcttacacct tctattacct tctgctctct 480
ctgatttgga aaaagctgaa aaaaaaggtt taaaccagtt ccctgaaatt attcccctac 540
ttgactaata agtatataaa gacggtaggt attgattgta attctgtaaa tctatttctt 600
aaacttctta aattctactt ttatagttag tctttttttt agttttaaaa caccaagaac 660
ttagtttcga cggatctaga actagtatgg gtttatcatc cgtctgtact ttctccttcc 720
aaactaacta tcatacctta ttgaatcctc acaacaacaa tccaaaaaca tcattgttgt 780
gttacagaca tccaaagaca cctattaagt actcttacaa caactttcca tcaaaacatt 840
gttcaaccaa gtccttccac ttacaaaata agtgctccga aagtttgtct atagctaaga 900
actctatcag agctgcaact acaaatcaaa ctgaaccacc tgaaagtgat aatcactctg 960
ttgccacaaa aattttgaac ttcggtaaag catgttggaa gttgcaaaga ccatacacca 1020
taatcgcttt tacttcttgt gcatgcggtt tattcggtaa agaattgttg cataacacta 1080
acttaatttc atggtccttg atgttcaagg catttttctt tttagttgcc atcttgtgca 1140
tcgcttcatt caccactaca attaatcaaa tatacgattt gcacatcgac agaattaaca 1200
aaccagattt gcctttggct tcaggtgaaa tatccgtcaa tactgcatgg atcatgtcta 1260
tcatagtagc cttgttcggt ttgatcatca caattaaaat gaagggtggt ccattgtaca 1320
tcttcggtta ctgtttcggt atcttcggtg gtattgtcta ttccgtacca cctttagat 1380 ggaaacaaaa ccctagtact gcctttttgt tgaatttctt agctcatatc atcacaaact 1440
tcaccttcta ctacgcttca agagctgctt taggtttgcc attcgaattg agaccttcat 1500
tcacattttt gttggcattc atgaaaagta tgggttctgc attagccttg atcaaggatg 1560
cctctgacgt tgaaggtgac acaaagttcg gtattagtac cttggcttct aagtacggtt 1620
caagaaattt gactttgttc tgctccggta tcgttttgtt aagttacgtc gcagccattt 1680
tggcaggtat catttggcca caagccttta attctaacgt tatgttgttg tcacatgcca 1740
tcttggcttt ctggttgatc ttgcaaacta gagatttcgc tttgacaaat tatgaccctg 1800
aagcaggtag aagattctac gagtttatgt ggaaattgta ctacgctgaa tatttggtat 1860
acgtttttat tgaaggtaga ggttctttgt tgacctgtgg tgacgttgaa gaaaatccag 1920
gtcctatgaa atgttcaact ttctcctttt ggttcgtatg caagatcatc ttcttttct 1980 tttcctttaa catccaaaca agtatcgcaa acccaagaga aaactttttg aagtgcttct 2040
cacaatacat acctaataac gccaccaatt tgaagttggt ttacactcaa aacaacccat 2100
tgtacatgtc cgtcttgaac agtacaatcc ataatttgag attcacttct gataccactc 2160
caaaaccttt ggtcattgta acccctagtc atgtatctca catccaaggt actatcttat 2220

```
gttctaaaaa ggttggtttg caaattagaa ctagatccgg tggtcatgat agtgaaggca   2280

tgtcatacat ctcccaagtt ccattcgtta tcgttgattt gagaaacatg agatcaatta   2340

aaatagacgt acactcacaa actgcttggg ttgaagctgg tgcaacattg ggtgaagtat   2400

actactgggt taacgaaaag aatgaaaact tatcattggc tgctggttac tgtccaacag   2460

tttgcgcagg tggtcatttt ggtggtggtg gttatggtcc tttaatgaga aactacggtt   2520

tggccgctga taacataatc gacgctcatt tggtaaatgt tcacggtaaa gttttggata   2580

gaaagtctat gggtgaagac ttattttggg ctttgagagg tggtggtgca gaatcattcg   2640

gtatcatagt tgcttggaag ataagattag tcgcagtacc aaagtctact atgttctcag   2700

tcaaaaagat aatggaaatc catgaattag ttaaattggt caataagtgg caaaacatcg   2760

catacaagta cgataaggac ttgttgttga tgactcattt catcacaaga aacatcaccg   2820

ataaccaagg taaaaataag actgctatcc acacatactt ttcttcagtt ttcttgggtg   2880

gtgtcgattc cttagtagac ttgatgaata agtcttttcc agaattaggt attaagaaaa   2940

ctgattgtag acaattgtct tggatcgaca ccatcatctt ttattcaggt gttgtcaact   3000

acgatacaga caacttcaac aaagaaatat tattggatag atccgcaggt caaaacggtg   3060

cctttaaaat taagttagac tacgttaaaa agccaatacc tgaatcagtt ttcgtccaaa   3120

tcttagaaaa attgtacgaa gaagatattg gtgcaggcat gtacgccttg tatccatacg   3180

gtggtataat ggacgaaatc agtgaatctg ccattccatt tcctcataga gctggtatct   3240

tatacgaatt gtggtacatt tgttcatggg aaaagcaaga agataacgaa aagcacttaa   3300

actggattag aaacatctat aacttcatga ctccatacgt ttctaaaaac cctagattgg   3360

catatttgaa ctacagagat ttggacatcg gtattaacga tccaaagaat cctaacaact   3420

atacccaagc tagaatttgg ggtgaaaaat acttcggtaa aaatttcgat agattagtaa   3480

aggttaagac attggttgac ccaaacaact tctttagaaa cgaacaatcc attccacctt   3540

tacctagaca tagacacgaa caaaaattaa taagtgaaga agatttgtaa gtcgacctcg   3600

agtcatgtaa ttagttatgt cacgcttaca ttcacgccct ccccccacat ccgctctaac   3660

cgaaaaggaa ggagttagac aacctgaagt ctaggtccct atttattttt ttatagttat   3720

gttagtatta agaacgttat ttatatttca aatttttctt ttttttctgt acagacgcgt   3780

gtacgcatgt aacattatac tgaaaacctt gcttgagaag gttttgggac gctcgaaggc   3840

tttaatttgc gtgacataac taattacatg acttgactga tttttcc                 3887
```

<210> SEQ ID NO 9
<211> LENGTH: 8963
<212> TYPE: DNA
<213> ORGANISM: Artificial Sequence
<220> FEATURE:
<223> OTHER INFORMATION: Codon Optimized

<400> SEQUENCE: 9

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaacg acattactat atatataata taggaagcat ttaatagaca gcatcgtaat    240

atatgtgtac tttgcagtta tgacgccaga tggcagtagt ggaagatatt ctttattgaa    300

aaatagcttg tcaccttacg tacaatcttg atccggagct ttcttttttt tgccgattaa    360
```

-continued

```
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgaggtc   2160
gacttacttg tcatcgtcat ctttgtagtc aatatcgtgg tctttatagt caccgtcatg   2220
atccttgtaa tcctttgatc tcttgtagac cttattcaag aaagctgtca aaacgtcggc   2280
tttaaaacct cttgattcat caacttgact aatctttgcc tttaagtctt tagcgatgga   2340
ttcttcgtat tcatggtaca attgttcaat cttcaaatca ttaaaaattt tcttacactt   2400
tgcttcagca actgagtcct ttttaccgta gttttcatcc aaagtctttc tttgttcggc   2460
agatgctaat tccaaagcct tgttaataac ccaactgcac ttattgtctt gaatatctgt   2520
accgatttta cctatttgtt ctggagtacc gaaacagtct aagtagtcat cttggatttg   2580
gaagtattca cccaaaggta tcaaaacatc tcttgcttgc ttcaagtctt tttcatcagt   2640
aataccagct acgtacatag ccaaggcgac tggcaaatag aaggagtaat aagcagtttc   2700
aaaggtgacg atgaatgaat gtttcttcaa ggaaaacttt gacaagtcaa ctttatcttc   2760
```

```
aggtgcagtt atcaaatcca tcaattgacc caattctgtt tggaaagtaa cttcgtggaa   2820
taattcggta atatcgatgt agtacttttc gtttctgaaa tgtgacttca acaatttata   2880
gatagcggct tccaacataa aagcatcatt tatggctatt tcaccaactt ctggaacttt   2940
gtaccagcat ggttgacctc ttcttgttat agacttatcc atcatgtcat cggcaaccaa   3000
aaagtatgct tgcaacaatt caatacacca acccaagata gcgacctttt cgtattcttc   3060
ttgacctaat tgttcaacgg ttttgttaga caagatagca taagtatcaa ctacactcaa   3120
acctctattc aatttaccac ctggagtatt gtagtttaaa gagtgagcat accaatcgca   3180
ggcttcttta ggcataccat aagctaacaa actagcgttc aattcttcaa ctaactttgg   3240
gaatacgttc aagaatcttt ctcttcttat ttccttttct gaagccatag gacctggatt   3300
ttcttcaacg tcaccacatg ttaacaaaga acctctacct tcttcgaaat gactgaattg   3360
ttgtctcaaa actcttctca tgatcttgtt tgttgcagtt ctaggtaagg atgacaatgg   3420
gacaactcta gtaactttga ataatgggtt caatttcttt tgcaaaccca agttaaagga   3480
taatctcaat tggttcaaat caatggttgt gtcgtttgaa tccttcaata cgaaaaatat   3540
gaccaattgt tctggaccac cacccaaagg tggaacacca atagcagtgg tttcaaaaac   3600
tctgtcatct acttcattac agactctttc gatttcgata gaactaattt tgataccacc   3660
gatgttcata gtgtcatcgg ctctaccgtg tgcatggtag taaccgttag aggtcaattc   3720
gaaaatgtca ccatgtcttc tcaatacttc accattcaag gttggcatac ccttgaaata   3780
gacatcgtga tgattaccgt ttaacaatgt ttttgaggca ccaaacataa caggacctaa   3840
tgccaattca ccgatacctg gcttattttt aggcattggg taaccgttct tatctaatat   3900
gtacaaggtg caacccatac attgggatga aaaagaactt aaagattgag cttgcaaaaa   3960
tgaaccagca gaaaaagcac caccgatttc tgtaccacca cacatttcta taactggctt   4020
gtagttagct ctacccatta accacaaata ttcgtctaca ttagaggctt caccggatga   4080
agaaaagcat cttatggtgg accaatcgta acctgaaaca caatttgtgg atttccatga   4140
tcttacaata gatggtacga cacccaacat tgtgaccttt gcatcttgaa caaatttagc   4200
gaaaccagag actaaaggac taccgttgta caaggcaata gatgcaccat ttaacaaact   4260
agcataaacc aaccaaggac ccatcatcca acccaaatta gttggccata ctataacgtc   4320
accttttcta atatccaaat gagaccaacc atcagcagca gccttcaatg gggtggcttg   4380
tgtccaagga attgcttttg gttcacctgt agtaccactg gagaataaga tgttagtata   4440
agcatcaaca ggttgttctc tggcagtaaa ctcgcagttt ttaaactcct tggctctttc   4500
taaaaagtaa tcccaagata tgtcaccatc tctcaattct gcaccaatgt tagaaccact   4560
acaagggata actattgcca ttggggattt agcttcaact actcttgaat acaatggtat   4620
tctcttttta cctctgatga tgtgatcttg tgtgaaaatt gccttagctt tggataatct   4680
caatctagtt gagatttcag gggcggaaaa tgaatctgct atagagacaa ctacgtaacc   4740
agccaatact atggccaaat atataacaac agcatcaaca tgcattggca tatcgatggc   4800
tattgcacaa ccttttttcta aacccatttc ttccaatgca taaccaacca accaaactct   4860
ctttctcaat tgatctaatg tcaacttatt caaaggcaag tcatcgttac cctcgtctct   4920
ccaaacgatc atagtatcgt tcaatttctt attggagttt acgttcaagc aatttttagc   4980
tgagttcaag taaccaccag gtaaccattc agaaccacct gggttgttga tgtcatctct   5040
tctcaagata cattctgggt ccttagagaa actaattttc atttcatcca tcaatactgt   5100
```

-continued

```
tctccaatag acttcagggt ttctaacaga aaattcttgg aagtgagaaa aagaagaaat   5160
tggatctttg tactttacac ccaaaaattc tttacctctc ttttccaaca aagcacccaa   5220
attagttgac ttgacttttt cagggtctgg aatccaagca ggtggggctg gaccgaaatc   5280
cttgtagcaa ccataaaaca acatttggtg taaggagaaa ggcaaatctg gtgacaagat   5340
atggttagcg atgttgatcc aagtttgagg ggttgcagca ccataattac aaacgatttc   5400
tgccaatcta ccatgtaatg tttctgctac ttctgaggtg atacccaatg cgatgaaatc   5460
tgaggcaacg actgaatcca aggacttata gtttttaccc atactagttc tagatccgtc   5520
gaaactaagt tcttggtgtt ttaaaactaa aaaaaagact aactataaaa gtagaattta   5580
agaagtttaa gaaatagatt tacagaatta caatcaatac ctaccgtctt tatatactta   5640
ttagtcaagt aggggaataa tttcagggaa ctggtttaaa cctttttttt cagctttttc   5700
caaatcagag agagcagaag gtaatagaag gtgtaagaaa atgagataga tacatgcgtg   5760
ggtcaattgc cttgtgtcat catttactcc aggcaggttg catcactcca ttgaggttgt   5820
gcccgttttt tgcctgtttg tgccctgttc tctgtagttg cgctaagaga atggacctat   5880
gaactgatgg ttggtgaaga aaacaatatt ttggtgctgg gattcttttt ttttctggat   5940
gccagcttaa aaagcgggct ccattatatt tagtggatgc caggaataaa cctgttcacc   6000
caagcaccat cagtgttata tattctgtgt aacccgcccc ctattttggc atgtacgggt   6060
tacagcagaa ttaaaaggct aatttttttga ctaaataaag ttaggaaaat cactactatt   6120
aattatttac gtattctttg aaatggcagt attgataatg ataaactcga gagctccagc   6180
ttttgttccc tttagtgagg gttaattgcg cgcttggcgt aatcatggtc atagctgttt   6240
cctgtgtgaa attgttatcc gctcacaatt ccacacaaca taggagccgg aagcataaag   6300
tgtaaagcct ggggtgccta atgagtgagg taactcacat taattgcgtt gcgctcactg   6360
cccgctttcc agtcgggaaa cctgtcgtgc cagctgcatt aatgaatcgg ccaacgcgcg   6420
gggagaggcg gtttgcgtat tgggcgctct tccgcttcct cgctcactga ctcgctgcgc   6480
tcggtcgttc ggctgcggcg agcggtatca gctcactcaa aggcggtaat acggttatcc   6540
acagaatcag gggataacgc aggaaagaac atgtgagcaa aaggccagca aaaggccagg   6600
aaccgtaaaa aggccgcgtt gctggcgttt ttccataggc tccgcccccc tgacgagcat   6660
cacaaaaatc gacgctcaag tcagaggtgg cgaaacccga caggactata aagataccag   6720
gcgtttcccc ctggaagctc cctcgtgcgc tctcctgttc cgaccctgcc gcttaccgga   6780
tacctgtccg cctttctccc ttcgggaagc gtggcgcttt ctcatagctc acgctgtagg   6840
tatctcagtt cggtgtaggt cgttcgctcc aagctgggct gtgtgcacga accccccgtt   6900
cagcccgacc gctgcgcctt atccggtaac tatcgtcttg agtccaaccc ggtaagacac   6960
gacttatcgc cactggcagc agccactggt aacaggatta gcagagcgag gtatgtaggc   7020
ggtgctacag agttcttgaa gtggtggcct aactacggct acactagaag gacagtattt   7080
ggtatctgcg ctctgctgaa gccagttacc ttcggaaaaa gagttggtag ctcttgatcc   7140
ggcaaacaaa ccaccgctgg tagcggtggt ttttttgttt gcaagcagca gattacgcgc   7200
agaaaaaaag gatctcaaga agatcctttg atcttttcta cggggtctga cgctcagtgg   7260
aacgaaaact cacgttaagg gattttggtc atgagattat caaaaaggat cttcacctag   7320
atccttttaa attaaaaatg aagttttaaa tcaatctaaa gtatatatga gtaaacttgg   7380
tctgacagtt accaatgctt aatcagtgag gcacctatct cagcgatctg tctatttcgt   7440
tcatccatag ttgcctgact ccccgtcgtg tagataacta cgatacggga gggcttacca   7500
```

```
tctggcccca gtgctgcaat gataccgcga gacccacgct caccggctcc agatttatca   7560
gcaataaacc agccagccgg aagggccgag cgcagaagtg gtcctgcaac tttatccgcc   7620
tccatccagt ctattaattg ttgccgggaa gctagagtaa gtagttcgcc agttaatagt   7680
ttgcgcaacg ttgttgccat tgctacaggc atcgtggtgt cacgctcgtc gtttggtatg   7740
gcttcattca gctccggttc ccaacgatca aggcgagtta catgatcccc catgttgtgc   7800
aaaaaagcgg ttagctcctt cggtcctccg atcgttgtca gaagtaagtt ggccgcagtg   7860
ttatcactca tggttatggc agcactgcat aattctctta ctgtcatgcc atccgtaaga   7920
tgcttttctg tgactggtga gtactcaacc aagtcattct gagaatagtg tatgcggcga   7980
ccgagttgct cttgcccggc gtcaatacgg gataataccg cgccacatag cagaacttta   8040
aaagtgctca tcattggaaa acgttcttcg gggcgaaaac tctcaaggat cttaccgctg   8100
ttgagatcca gttcgatgta acccactcgt gcacccaact gatcttcagc atcttttact   8160
ttcaccagcg tttctgggtg agcaaaaaca ggaaggcaaa atgccgcaaa aaagggaata   8220
agggcgacac ggaaatgttg aatactcata ctcttccttt ttcaatatta ttgaagcatt   8280
tatcagggtt attgtctcat gagcggatac atatttgaat gtatttagaa aaataaacaa   8340
ataggggttc cgcgcacatt tccccgaaaa gtgccacctg ggtccttttc atcacgtgct   8400
ataaaaataa ttataattta aatttttttaa tataaatata taaattaaaa atagaaagta   8460
aaaaaagaaa ttaaagaaaa aatagttttt gttttccgaa gatgtaaaag actctagggg   8520
gatcgccaac aaatactacc ttttatcttg ctcttcctgc tctcaggtat taatgccgaa   8580
ttgtttcatc ttgtctgtgt agaagaccac acacgaaaat cctgtgattt tacattttac   8640
ttatcgttaa tcgaatgtat atctatttaa tctgcttttc ttgtctaata aatatatatg   8700
taaagtacgc tttttgttga aatttttttaa acctttgttt attttttttt cttcattccg   8760
taactcttct accttcttta tttactttct aaaatccaaa tacaaaacat aaaaataaat   8820
aaacacagag taaattccca aattattcca tcattaaaag atacgaggcg cgtgtaagtt   8880
acaggcaagc gatccgtcct aagaaaccat tattatcatg acattaacct ataaaaatag   8940
gcgtatcacg aggccctttc gtc                                           8963
```

<210> SEQ ID NO 10
<211> LENGTH: 7163
<212> TYPE: DNA
<213> ORGANISM: Artificial Sequence
<220> FEATURE:
<223> OTHER INFORMATION: Codon Optimized

<400> SEQUENCE: 10

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
```

-continued

```
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgaggtc   2160
gacttatgca tagtctggaa catcgtaagg gtactttctt ggggtgtaat cgaagatcaa   2220
caatttttcc cagaaggatc tgtaaacgtc accaaaacca acgtgagctg gatgaatgat   2280
gtaatcttgg atagtttcaa ctgattcgaa ggttacttcg acaatgtgtg tataaccttc   2340
ttctttcttt tgtgtaacgt ctttacccca gtatacatct ttcatagcag gtataatgtt   2400
gaccaaatta acgtaggtct tgaaaaattc ttccttttga gcttctgtga tttcatcttt   2460
aaacttcaat actatcaaat gcttgacggc cataggacct gggttttctt caacgtcacc   2520
acaagttaac aaggaacctc taccttcata tttaattggt actgatctga caactactct   2580
ttcgacggtc aaaccaggac cgaaaccaaa taagacaccc cattcaaaac cgtcaccagt   2640
agtagattta ccctcttcta atgatctctt tctcaattca tccattacga acaagacagt   2700
ggatgaagac atgttaccgt gttcagataa aacatgtcta ctatctacaa acttttcttt   2760
cttcaaatcc aatttttctt caaccttatc caaaatggct ttaccacctg gatgtgttat   2820
ccagaaaata gagttccaat ctgagatacc tataggagtg aatgcttcta tcaaacactt   2880
ttctatgttg ttagagatta acattggaac gtctttgtgc aaatcgaaga tcaaacctgc   2940
```

ttctcttata tgaccaccaa ttgtaccttc agaattaggc aagatggttt gacctgtact 3000
gactaattca aatattggtc tttcaccaac agattcgtca ggttctgcac caacaataac 3060
agcagcagca ccgtcaccga agatagcttg accaactaac aattccaagt cagaatcact 3120
tggacctcta aacaagcaag ccataatgtc gcaacaaaca gctaatactc tggcaccctt 3180
gttgttttct gcaatatcct tagcgattct caaaacagta ccaccaccgt agcaacctaa 3240
ttgatacatc atgactctct taacggatgg tgacaaacct aacaatttgg cacagtggta 3300
gtctgcacca ggcatatctg tagtagatgc acttgtaaaa atcaaatgag tgatctttga 3360
ctttggttga ccccattcct taatggcttt tgcacaagca tctttaccca atttaggaac 3420
ttcgacaact aacatgtctt gtctggcatc caatgtttgc atttcgtgtt ctaccaatct 3480
tggattttgc ttcaaatgtt cttcgttcaa gaagcagttt ctctttctga tcatagactt 3540
atcacatatt tttctaaact tttccttcaa ttgagtcatg tgttcactct tggtaactct 3600
gaagtaataa tcaggaaatt catcttggat caatatgttt tctgggttgg ctgtacctat 3660
ggctaatacg gaggcaggac cttcggctct caaatggttc atactagttc tagatccgtc 3720
gaaactaagt tcttggtgtt ttaaaactaa aaaaaagact aactataaaa gtagaattta 3780
agaagtttaa gaaatagatt tacagaatta caatcaatac ctaccgtctt tatatactta 3840
ttagtcaagt aggggaataa tttcagggaa ctggtttaaa ccttttttt cagcttttc 3900 caaatcagag agagcagaag gtaatagaag gtgtaagaaa atgagataga tacatgcgtg 3960
ggtcaattgc cttgtgtcat catttactcc aggcaggttg catcactcca ttgaggttgt 4020
gcccgttttt tgcctgtttg tgccctgttc tctgtagttg cgctaagaga atggacctat 4080
gaactgatgg ttggtgaaga aaacaatatt ttggtgctgg gattcttttt ttttctggat 4140
gccagcttaa aaagcgggct ccattatatt tagtggatgc caggaataaa cctgttcacc 4200
caagcaccat cagtgttata tattctgtgt aacccgcccc ctatttggc atgtacgggt 4260 tacagcagaa ttaaaaggct aattttttga ctaaataaag ttaggaaaat cactactatt 4320
aattatttac gtattctttg aaatggcagt attgataatg ataaactcga gagctccagc 4380
ttttgttccc tttagtgagg gttaattgcg cgcttggcgt aatcatggtc atagctgttt 4440
cctgtgtgaa attgttatcc gctcacaatt ccacacaaca taggagccgg aagcataaag 4500
tgtaaagcct ggggtgccta atgagtgagg taactcacat taattgcgtt gcgctcactg 4560
cccgctttcc agtcgggaaa cctgtcgtgc cagctgcatt aatgaatcgg ccaacgcgcg 4620
gggagaggcg gtttgcgtat tgggcgctct tccgcttcct cgctcactga ctcgctgcgc 4680
tcggtcgttc ggctgcggcg agcggtatca gctcactcaa aggcggtaat acggttatcc 4740
acagaatcag gggataacgc aggaaagaac atgtgagcaa aaggccagca aaaggccagg 4800
aaccgtaaaa aggccgcgtt gctggcgttt ttccataggc tccgcccccc tgacgagcat 4860
cacaaaaatc gacgctcaag tcagaggtgg cgaaacccga caggactata aagataccag 4920
gcgtttcccc ctggaagctc cctcgtgcgc tctcctgttc cgaccctgcc gcttaccgga 4980
tacctgtccg cctttctccc ttcgggaagc gtggcgcttt ctcatagctc acgctgtagg 5040
tatctcagtt cggtgtaggt cgttcgctcc aagctgggct gtgtgcacga accccccgtt 5100
cagcccgacc gctgcgcctt atccggtaac tatcgtcttg agtccaaccc ggtaagacac 5160
gacttatcgc cactggcagc agccactggt aacaggatta gcagagcgag gtatgtaggc 5220
ggtgctacag agttcttgaa gtggtggcct aactacggct acactagaag gacagtattt 5280

-continued

```
ggtatctgcg ctctgctgaa gccagttacc ttcggaaaaa gagttggtag ctcttgatcc   5340

ggcaaacaaa ccaccgctgg tagcggtggt ttttttgttt gcaagcagca gattacgcgc   5400

agaaaaaaag gatctcaaga agatcctttg atcttttcta cggggtctga cgctcagtgg   5460

aacgaaaact cacgttaagg gattttggtc atgagattat caaaaaggat cttcacctag   5520

atccttttaa attaaaaatg aagttttaaa tcaatctaaa gtatatatga gtaaacttgg   5580

tctgacagtt accaatgctt aatcagtgag gcacctatct cagcgatctg tctatttcgt   5640

tcatccatag ttgcctgact ccccgtcgtg tagataacta cgatacggga gggcttacca   5700

tctggcccca gtgctgcaat gataccgcga gacccacgct caccggctcc agatttatca   5760

gcaataaacc agccagccgg aagggccgag cgcagaagtg gtcctgcaac tttatccgcc   5820

tccatccagt ctattaattg ttgccgggaa gctagagtaa gtagttcgcc agttaatagt   5880

ttgcgcaacg ttgttgccat tgctacaggc atcgtggtgt cacgctcgtc gtttggtatg   5940

gcttcattca gctccggttc ccaacgatca aggcgagtta catgatcccc catgttgtgc   6000

aaaaaagcgg ttagctcctt cggtcctccg atcgttgtca gaagtaagtt ggccgcagtg   6060

ttatcactca tggttatggc agcactgcat aattctctta ctgtcatgcc atccgtaaga   6120

tgcttttctg tgactggtga gtactcaacc aagtcattct gagaatagtg tatgcggcga   6180

ccgagttgct cttgcccggc gtcaatacgg gataataccg cgccacatag cagaacttta   6240

aaagtgctca tcattggaaa acgttcttcg gggcgaaaac tctcaaggat cttaccgctg   6300

ttgagatcca gttcgatgta acccactcgt gcacccaact gatcttcagc atcttttact   6360

ttcaccagcg tttctgggtg agcaaaaaca ggaaggcaaa atgccgcaaa aaagggaata   6420

agggcgacac ggaaatgttg aatactcata ctcttccttt ttcaatatta ttgaagcatt   6480

tatcagggtt attgtctcat gagcggatac atatttgaat gtatttagaa aaataaacaa   6540

ataggggttc cgcgcacatt tccccgaaaa gtgccacctg ggtccttttc atcacgtgct   6600

ataaaaataa ttataattta aatttttttaa tataaatata taaattaaaa atagaaagta   6660

aaaaaagaaa ttaaagaaaa aatagttttt gttttccgaa gatgtaaaag actctagggg   6720

gatcgccaac aaatactacc ttttatcttg ctcttcctgc tctcaggtat taatgccgaa   6780

ttgtttcatc ttgtctgtgt agaagaccac acacgaaaat cctgtgattt tacattttac   6840

ttatcgttaa tcgaatgtat atctatttaa tctgcttttc ttgtctaata aatatatatg   6900

taaagtacgc tttttgttga aattttttaa acctttgttt attttttttt cttcattccg   6960

taactcttct accttcttta tttactttct aaaatccaaa tacaaaacat aaaaataaat   7020

aaacacagag taaattccca aattattcca tcattaaaag atacgaggcg cgtgtaagtt   7080

acaggcaagc gatccgtcct aagaaaccat tattatcatg acattaacct ataaaaatag   7140

gcgtatcacg aggccctttc gtc                                           7163
```

```
<210> SEQ ID NO 11
<211> LENGTH: 8710
<212> TYPE: DNA
<213> ORGANISM: Artificial Sequence
<220> FEATURE:
<223> OTHER INFORMATION: Codon Optimized

<400> SEQUENCE: 11

tcgcgcgttt cggtgatgac ggtgaaaacc tctgacacat gcagctcccg gagacggtca     60

cagcttgtct gtaagcggat gccgggagca gacaagcccg tcagggcgcg tcagcgcgtg    120

ttggcgggtg tcggggctgg cttaactatg cggcatcaga gcagattgta ctgagagtgc    180
```

-continued

```
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctctag tacactctat atttttttat gcctcggtaa tgattttcat    360
ttttttttt ccccctagcgg atgactcttt ttttttctta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
ccttttttct ttttgctttt tcttttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggggatgt gctgcaaggc   1980
gattaagttg ggtaacgcca gggttttccc agtcacgacg ttgtaaaacg acggccagtg   2040
agcgcgcgta atacgactca ctatagggcg aattgggtac cggccgcaaa ttaaagcctt   2100
cgagcgtccc aaaaccttct caagcaaggt tttcagtata atgttacatg cgtacacgcg   2160
tctgtacaga aaaaaaagaa aaatttgaaa tataaataac gttcttaata ctaacataac   2220
tataaaaaaa taaataggga cctagacttc aggttgtcta actccttcct tttcggttag   2280
agcggatgtg gggggagggc gtgaatgtaa gcgtgacata actaattaca tgactcgagg   2340
tcgacttaca aatcttcttc acttattaat ttttgttcgt gtctatgtct aggtaaaggt   2400
ggaatggatt gttcgtttct aaagaagttg tttgggtcaa ccaatgtctt aacctttact   2460
aatctatcga aatttttacc gaagtatttt tcaccccaaa ttctagcttg ggtatagttg   2520
```

-continued ttaggattct ttggatcgtt aataccgatg tccaaatctc tgtagttcaa atatgccaat 2580
ctagggtttt tagaaacgta tggagtcatg aagttataga tgtttctaat ccagtttaag 2640
tgcttttcgt tatcttcttg cttttcccat gaacaaatgt accacaattc gtataagata 2700
ccagctctat gaggaaatgg aatggcagat tcactgattt cgtccattat accaccgtat 2760
ggatacaagg cgtacatgcc tgcaccaata tcttcttcgt acaatttttc taagatttgg 2820
acgaaaactg attcaggtat tggcttttta acgtagtcta acttaatttt aaaggcaccg 2880
ttttgacctg cggatctatc caataatatt tctttgttga agttgtctgt atcgtagttg 2940
acaacacctg aataaaagat gatggtgtcg atccaagaca attgtctaca atcagttttc 3000
ttaataccta attctggaaa agacttattc atcaagtcta ctaaggaatc gacaccaccc 3060
aagaaaactg aagaaaagta tgtgtggata gcagtcttat ttttaccttg gttatcggtg 3120
atgtttcttg tgatgaaatg agtcatcaac aacaagtcct tatcgtactt gtatgcgatg 3180
ttttgccact tattgaccaa tttaactaat tcatggattt ccattatctt tttgactgag 3240
aacatagtag actttggtac tgcgactaat cttatcttcc aagcaactat gataccgaat 3300
gattctgcac caccacctct caaagcccaa aataagtctt cacccataga ctttctatcc 3360
aaaactttac cgtgaacatt taccaaatga gcgtcgatta tgttatcagc ggccaaaccg 3420
tagtttctca ttaaaggacc ataaccacca ccaccaaaat gaccacctgc gcaaactgtt 3480
ggacagtaac cagcagccaa tgataagttt tcattctttt cgttaaccca gtagtatact 3540
tcacccaatg ttgcaccagc ttcaacccaa gcagtttgtg agtgtacgtc tattttaatt 3600
gatctcatgt ttctcaaatc aacgataacg aatggaactt gggagatgta tgacatgcct 3660
tcactatcat gaccaccgga tctagttcta atttgcaaac caaccttttt agaacataag 3720
atagtacctt ggatgtgaga tacatgacta ggggttacaa tgaccaaagg ttttggagtg 3780
gtatcagaag tgaatctcaa attatggatt gtactgttca agacggacat gtacaatggg 3840
ttgttttgag tgtaaaccaa cttcaaattg gtggcgttat taggtatgta ttgtgagaag 3900
cacttcaaaa agttttctct tgggtttgcg atacttgttt ggatgttaaa ggaaaagaaa 3960
aagaagatga tcttgcatac gaaccaaaag gagaaagttg aacatttcat aggacctgga 4020
ttttcttcaa cgtcaccaca ggtcaacaaa gaacctctac cttcaataaa aacgtatacc 4080
aaatattcag cgtagtacaa tttccacata aactcgtaga atcttctacc tgcttcaggg 4140
tcataatttg tcaaagcgaa atctctagtt tgcaagatca accagaaagc caagatggca 4200
tgtgacaaca acataacgtt agaattaaag gcttgtggcc aaatgatacc tgccaaaatg 4260
gctgcgacgt aacttaacaa aacgataccg gagcagaaca aagtcaaatt tcttgaaccg 4320
tacttagaag ccaaggtact aataccgaac tttgtgtcac cttcaacgtc agaggcatcc 4380
ttgatcaagg ctaatgcaga acccatactt ttcatgaatg ccaacaaaaa tgtgaatgaa 4440
ggtctcaatt cgaatggcaa acctaaagca gctcttgaag cgtagtagaa ggtgaagttt 4500
gtgatgatat gagctaagaa attcaacaaa aaggcagtac tagggttttg tttccatcta 4560
aaaggtggta cggaatagac aataccaccg aagataccga aacagtaacc gaagatgtac 4620
aatggaccac ccttcatttt aattgtgatg atcaaaccga acaaggctac tatgatagac 4680
atgatccatg cagtattgac ggatatttca cctgaagcca aaggcaaatc tggtttgtta 4740
attctgtcga tgtgcaaatc gtatatttga ttaattgtag tggtgaatga agcgatgcac 4800
aagatggcaa ctaaaaagaa aaatgccttg aacatcaagg accatgaaat taagttagtg 4860
ttatgcaaca attctttacc gaataaaccg catgcacaag aagtaaaagc gattatggtg 4920

```
tatggtcttt gcaacttcca acatgcttta ccgaagttca aaatttttgt ggcaacagag   4980
tgattatcac tttcaggtgg ttcagtttga tttgtagttg cagctctgat agagttctta   5040
gctatagaca aactttcgga gcacttattt tgtaagtgga aggacttggt tgaacaatgt   5100
tttgatggaa agttgttgta agagtactta ataggtgtct ttggatgtct gtaacacaac   5160
aatgatgttt ttggattgtt gttgtgagga ttcaataagg tatgatagtt agtttggaag   5220
gagaaagtac agacggatga taaacccata ctagttctag atccgtcgaa actaagttct   5280
tggtgtttta aaactaaaaa aaagactaac tataaaagta gaatttaaga agtttaagaa   5340
atagatttac agaattacaa tcaataccta ccgtctttat atacttatta gtcaagtagg   5400
ggaataattt cagggaactg gtttaaacct tttttttcag ctttttccaa atcagagaga   5460
gcagaaggta atagaaggtg taagaaaatg agatagatac atgcgtgggt caattgcctt   5520
gtgtcatcat ttactccagg caggttgcat cactccattg aggttgtgcc cgtttttttgc   5580
ctgtttgtgc cctgttctct gtagttgcgc taagagaatg gacctatgaa ctgatggttg   5640
gtgaagaaaa caatatttttg gtgctgggat tcttttttttt tctggatgcc agcttaaaaa   5700
gcgggctcca ttatatttag tggatgccag gaataaacct gttcacccaa gcaccatcag   5760
tgttatatat tctgtgtaac ccgcccccta ttttggcatg tacgggttac agcagaatta   5820
aaaggctaat tttttgacta aataaagtta ggaaaatcac tactattaat tatttacgta   5880
ttctttgaaa tggcagtatt gataatgata aactcgagag ctccagcttt tgttcccttt   5940
agtgagggtt aattgcgcgc ttggcgtaat catggtcata gctgtttcct gtgtgaaatt   6000
gttatccgct cacaattcca cacaacatag gagccggaag cataaagtgt aaagcctggg   6060
gtgcctaatg agtgaggtaa ctcacattaa ttgcgttgcg ctcactgccc gctttccagt   6120
cgggaaacct gtcgtgccag ctgcattaat gaatcggcca acgcgcgggg agaggcggtt   6180
tgcgtattgg gcgctcttcc gcttcctcgc tcactgactc gctgcgctcg gtcgttcggc   6240
tgcggcgagc ggtatcagct cactcaaagg cggtaatacg gttatccaca gaatcagggg   6300
ataacgcagg aaagaacatg tgagcaaaag gccagcaaaa ggccaggaac cgtaaaaagg   6360
ccgcgttgct ggcgtttttc cataggctcc gcccccctga cgagcatcac aaaaatcgac   6420
gctcaagtca gaggtggcga aacccgacag gactataaag ataccaggcg tttccccctg   6480
gaagctccct cgtgcgctct cctgttccga ccctgccgct taccggatac ctgtccgcct   6540
ttctcccttc gggaagcgtg gcgctttctc atagctcacg ctgtaggtat ctcagttcgg   6600
tgtaggtcgt tcgctccaag ctgggctgtg tgcacgaacc ccccgttcag cccgaccgct   6660
gcgccttatc cggtaactat cgtcttgagt ccaacccggt aagacacgac ttatcgccac   6720
tggcagcagc cactggtaac aggattagca gagcgaggta tgtaggcggt gctacagagt   6780
tcttgaagtg gtggcctaac tacggctaca ctagaaggac agtatttggt atctgcgctc   6840
tgctgaagcc agttaccttc ggaaaaagag ttggtagctc ttgatccggc aaacaaacca   6900
ccgctggtag cggtggtttt tttgtttgca agcagcagat tacgcgcaga aaaaaaggat   6960
ctcaagaaga tcctttgatc ttttctacgg ggtctgacgc tcagtggaac gaaaactcac   7020
gttaagggat tttggtcatg agattatcaa aaaggatctt cacctagatc cttttaaatt   7080
aaaaatgaag ttttaaatca atctaaagta tatatgagta aacttggtct gacagttacc   7140
aatgcttaat cagtgaggca cctatctcag cgatctgtct atttcgttca tccatagttg   7200
cctgactccc cgtcgtgtag ataactacga tacgggaggg cttaccatct ggccccagtg   7260
```

-continued

```
ctgcaatgat accgcgagac ccacgctcac cggctccaga tttatcagca ataaaccagc   7320

cagccggaag ggccgagcgc agaagtggtc ctgcaacttt atccgcctcc atccagtcta   7380

ttaattgttg ccgggaagct agagtaagta gttcgccagt taatagtttg cgcaacgttg   7440

ttgccattgc tacaggcatc gtggtgtcac gctcgtcgtt tggtatggct tcattcagct   7500

ccggttccca acgatcaagg cgagttacat gatcccccat gttgtgcaaa aaagcggtta   7560

gctccttcgg tcctccgatc gttgtcagaa gtaagttggc cgcagtgtta tcactcatgg   7620

ttatggcagc actgcataat tctcttactg tcatgccatc cgtaagatgc ttttctgtga   7680

ctggtgagta ctcaaccaag tcattctgag aatagtgtat gcggcgaccg agttgctctt   7740

gcccggcgtc aatacgggat aataccgcgc cacatagcag aactttaaaa gtgctcatca   7800

ttggaaaacg ttcttcgggg cgaaaactct caaggatctt accgctgttg agatccagtt   7860

cgatgtaacc cactcgtgca cccaactgat cttcagcatc ttttactttc accagcgttt   7920

ctgggtgagc aaaaacagga aggcaaaatg ccgcaaaaaa gggaataagg gcgacacgga   7980

aatgttgaat actcatactc ttcctttttc aatattattg aagcatttat cagggttatt   8040

gtctcatgag cggatacata tttgaatgta tttagaaaaa taaacaaata ggggttccgc   8100

gcacatttcc ccgaaaagtg ccacctgggt cctttttcatc acgtgctata aaaataatta   8160

taatttaaat tttttaatat aaatatataa attaaaaata gaaagtaaaa aaagaaatta   8220

aagaaaaaat agtttttgtt ttccgaagat gtaaaagact ctagggggat cgccaacaaa   8280

tactaccttt tatcttgctc ttcctgctct caggtattaa tgccgaattg tttcatcttg   8340

tctgtgtaga agaccacaca cgaaaatcct gtgattttac attttactta tcgttaatcg   8400

aatgtatatc tatttaatct gcttttcttg tctaataaat atatatgtaa agtacgcttt   8460

ttgttgaaat tttttaaacc tttgtttatt tttttttctt cattccgtaa ctcttctacc   8520

ttctttattt actttctaaa atccaaatac aaaacataaa aataaataaa cacagagtaa   8580

attcccaaat tattccatca ttaaaagata cgaggcgcgt gtaagttaca ggcaagcgat   8640

ccgtcctaag aaaccattat tatcatgaca ttaacctata aaaataggcg tatcacgagg   8700

ccctttcgtc                                                          8710
```

<210> SEQ ID NO 12
<211> LENGTH: 9617
<212> TYPE: DNA
<213> ORGANISM: Artificial Sequence
<220> FEATURE:
<223> OTHER INFORMATION: Codon Optimized

<400> SEQUENCE: 12

```
ttatcatgac attaacctat aaaaataggc gtatcacgag gccctttcgt ctcgcgcgtt     60

tcggtgatga cggtgaaaac ctctgacaca tgcagctccc ggagacggtc acagcttgtc    120

tgtaagcgga tgccgggagc agacaagccc gtcagggcgc gtcagcgggt gttggcgggt    180

gtcggggctg gcttaactat gcggcatcag agcagattgt actgagagtg caccacgctt    240

ttcaattcaa ttcatcattt ttttttattt cttttttttg atttcggttt ctttgaaatt    300

tttttgattc ggtaatctcc gaacagaagg aagaacgaag gaaggagcac agacttagat    360

tggtatatat acgcatatgt agtgttgaag aaacatgaaa ttgcccagta ttcttaaccc    420

aactgcacag aacaaaaacc tgcaggaaac gaagataaat catgtcgaaa gctacatata    480

aggaacgtgc tgctactcat cctagtcctg ttgctgccaa gctatttaat atcatgcacg    540

aaaagcaaac aaacttgtgt gcttcattgg atgttcgtac caccaaggaa ttactggagt    600
```

-continued

```
tagttgaagc attaggtccc aaaatttgtt tactaaaaac acatgtggat atcttgactg    660
atttttccat ggagggcaca gttaagccgc taaaggcatt atccgccaag tacaattttt    720
tactcttcga agacagaaaa tttgctgaca ttggtaatac agtcaaattg cagtactctg    780
cgggtgtata cagaatagca gaatgggcag acattacgaa tgcacacggt gtggtgggcc    840
caggtattgt tagcggtttg aagcaggcgg cagaagaagt aacaaaggaa cctagaggcc    900
ttttgatgtt agcagaattg tcatgcaagg gctccctatc tactggagaa tatactaagg    960
gtactgttga cattgcgaag agcgacaaag attttgttat cggctttatt gctcaaagag   1020
acatgggtgg aagagatgaa ggttacgatt ggttgattat gacacccggt gtgggtttag   1080
atgacaaggg agacgcattg ggtcaacagt atagaaccgt ggatgatgtg gtctctacag   1140
gatctgacat tattattgtt ggaagaggac tatttgcaaa gggaagggat gctaaggtag   1200
agggtgaacg ttacagaaaa gcaggctggg aagcatattt gagaagatgc ggccagcaaa   1260
actaaaaaac tgtattataa gtaaatgcat gtatactaaa ctcacaaatt agagcttcaa   1320
tttaattata tcagttatta ccctgcggtg tgaaataccg cacagatgcg taaggagaaa   1380
ataccgcatc aggaaattgt aaacgttaat attttgttaa aattcgcgtt aaatttttgt   1440
taaatcagct cattttttaa ccaataggcc gaaatcggca aaatccctta taaatcaaaa   1500
gaatagaccg agatagggtt gagtgttgtt ccagtttgga acaagagtcc actattaaag   1560
aacgtggact ccaacgtcaa agggcgaaaa accgtctatc agggcgatgg cccactacgt   1620
gaaccatcac cctaatcaag ttttttgggg tcgaggtgcc gtaaagcact aaatcggaac   1680
cctaaaggga gcccccgatt tagagcttga cggggaaagc cggcgaacgt ggcgagaaag   1740
gaagggaaga aagcgaaagg agcgggcgct agggcgctgg caagtgtagc ggtcacgctg   1800
cgcgtaacca ccacacccgc cgcgcttaat gcgccgctac agggcgcgtc gcgccattcg   1860
ccattcaggc tgcgcaactg ttgggaaggg cgatcggtgc gggcctcttc gctattacgc   1920
cagctggcga aggggggatg tgctgcaagg cgattaagtt gggtaacgcc agggttttcc   1980
cagtcacgac gttgtaaaac gacggccagt gaattgtaat acgactcact atagggcgaa   2040
ttggagctct agtacggatt agaagccgcc gagcgggcga cagccctccg acggaagact   2100
ctcctccgtg cgtcctcgtc ttcaccggtc gcgttcctga aacgcagatg tgcctcgcgc   2160
cgcactgctc cgaacaataa agattctaca atactagctt ttatggttat gaagaggaaa   2220
aattggcagt aacctggccc cacaaacctt caaattaacg aatcaaatta acaaccatag   2280
gatgataatg cgattagttt tttagcctta tttctggggt aattaatcag cgaagcgatg   2340
atttttgatc tattaacaga tatataaatg gaaaagctgc ataaccactt taactaatac   2400
tttcaacatt ttcagtttgt attacttctt attcaaatgt cataaaagta tcaacaaaaa   2460
attgttaata tacctctata ctttaacgtc aaggagaaaa aaccccggat tctagaacta   2520
gtggatcccc catcatgaac catttgagag ccgaaggtcc tgcctccgta ttagccatag   2580
gtacagccaa cccagaaaac atattgatcc aagatgaatt tcctgattat tacttcagag   2640
ttaccaagag tgaacacatg actcaattga aggaaaagtt tagaaaaata tgtgataagt   2700
ctatgatcag aaagagaaac tgcttcttga acgaagaaca tttgaagcaa aatccaagat   2760
tggtagaaca cgaaatgcaa acattggatg ccagacaaga catgttagtt gtcgaagttc   2820
ctaaattggg taaagatgct tgtgcaaaag ccattaagga atggggtcaa ccaaagtcaa   2880
agatcactca tttgattttt acaagtgcat ctactacaga tatgcctggt gcagactacc   2940
```

-continued

```
actgtgccaa attgttaggt ttgtcaccat ccgttaagag agtcatgatg tatcaattag   3000
gttgctacgg tggtggtact gttttgagaa tcgctaagga tattgcagaa aacaacaagg   3060
gtgccagagt attagctgtt tgttgcgaca ttatggcttg cttgtttaga ggtccaagtg   3120
attctgactt ggaattgtta gttggtcaag ctatcttcgg tgacggtgct gctgctgtta   3180
ttgttggtgc agaacctgac gaatctgttg gtgaaagacc aatatttgaa ttagtcagta   3240
caggtcaaac catcttgcct aattctgaag gtacaattgg tggtcatata agagaagcag   3300
gtttgatctt cgatttgcac aaagacgttc caatgttaat ctctaacaac atagaaaagt   3360
gtttgataga agcattcact cctataggta tctcagattg gaactctatt ttctggataa   3420
cacatccagg tggtaaagcc attttggata aggttgaaga aaaattggat ttgaagaaag   3480
aaaagtttgt agatagtaga catgttttat ctgaacacgg taacatgtct tcatccactg   3540
tcttgttcgt aatggatgaa ttgagaaaga gatcattaga agagggtaaa tctactactg   3600
gtgacggttt tgaatggggt gtcttatttg gtttcggtcc tggtttgacc gtcgaaagag   3660
tagttgtcag atcagtacca attaaatatg aaggtagagg ttccttgtta acttgtggtg   3720
acgttgaaga aaacccaggt cctatggccg tcaagcattt gatagtattg aagtttaaag   3780
atgaaatcac agaagctcaa aaggaagaat ttttcaagac ctacgttaat ttggtcaaca   3840
ttatacctgc tatgaaagat gtatactggg gtaaagacgt tacacaaaag aaagaagaag   3900
gttatacaca cattgtcgaa gtaaccttcg aatcagttga aactatccaa gattacatca   3960
ttcatccagc tcacgttggt tttggtgacg tttacagatc cttctgggaa aaattgttga   4020
tcttcgatta caccccaaga aagttaaagc caaaataatg ataacgagaa taatatcaag   4080
aataccttag aacaacatcg acaacaacaa caggcatttt cggatatgag tcacgtggag   4140
tattccagaa ttacaaaatt ttttcaagaa caaccactgg agggatatac ccttttctct   4200
cacaggtctg cgccatgggt ttatcatccg tctgtacttt ctccttccaa actaactatc   4260
ataccttatt gaatcctcac aacaacaatc caaaaacatc attgttgtgt tacagacatc   4320
caaagacacc tattaagtac tcttacaaca actttccatc aaaacattgt tcaaccaagt   4380
ccttccactt acaaaataag tgctccgaaa gtttgtctat agctaagaac tctatcagag   4440
ctgcaactac aaatcaaact gaaccacctg aaagtgataa tcactctgtt gccacaaaaa   4500
ttttgaactt cggtaaagca tgttggaagt tgcaaagacc atacaccata atcgctttta   4560
cttcttgtgc atgcggttta ttcggtaaag aattgttgca taacactaac ttaatttcat   4620
ggtccttgat gttcaaggca tttttctttt tagttgccat cttgtgcatc gcttcattca   4680
ccactacaat taatcaaata tacgatttgc acatcgacag aattaacaaa ccagatttgc   4740
ctttggcttc aggtgaaata tccgtcaata ctgcatggat catgtctatc atagtagcct   4800
tgttcggttt gatcatcaca attaaaatga agggtggtcc attgtacatc ttcggttact   4860
gtttcggtat cttcggtggt attgtctatt ccgtaccacc ttttagatgg aaacaaaacc   4920
ctagtactgc ctttttgttg aatttcttag ctcatatcat cacaaacttc accttctact   4980
acgcttcaag agctgcttta ggtttgccat tcgaattgag accttcattc acatttttgt   5040
tggcattcat gaaaagtatg ggttctgcat tagccttgat caaggatgcc tctgacgttg   5100
aaggtgacac aaagttcggt attagtacct tggcttctaa gtacggttca agaaatttga   5160
ctttgttctg ctccggtatc gttttgttaa gttacgtcgc agccattttg gcaggtatca   5220
tttggccaca agcctttaat tctaacgtta tgttgttgtc acatgccatc ttggctttct   5280
ggttgatctt gcaaactaga gatttcgctt tgacaaatta tgaccctgaa gcaggtagaa   5340
```

```
gattctacga gtttatgtgg aaattgtact acgctgaata tttggtatac gtttttattg   5400
aaggtagagg ttctttgttg acctgtggtg acgttgaaga aaatccaggt cctatgaaat   5460
gttcaacttt ctccttttgg ttcgtatgca agatcatctt ctttttcttt tcctttaaca   5520
tccaaacaag tatcgcaaac ccaagagaaa actttttgaa gtgcttctca caatacatac   5580
ctaataacgc caccaatttg aagttggttt acactcaaaa caacccattg tacatgtccg   5640
tcttgaacag tacaatccat aatttgagat tcacttctga taccactcca aaacctttgg   5700
tcattgtaac ccctagtcat gtatctcaca tccaaggtac tatcttatgt tctaaaaagg   5760
ttggtttgca aattagaact agatccggtg gtcatgatag tgaaggcatg tcatacatct   5820
cccaagttcc attcgttatc gttgatttga gaaacatgag atcaattaaa atagacgtac   5880
actcacaaac tgcttgggtt gaagctggtg caacattggg tgaagtatac tactgggtta   5940
acgaaaagaa tgaaaactta tcattggctg ctggttactg tccaacagtt tgcgcaggtg   6000
gtcattttgg tggtggtggt tatggtcctt taatgagaaa ctacggtttg gccgctgata   6060
acataatcga cgctcatttg gtaaatgttc acggtaaagt tttggataga aagtctatgg   6120
gtgaagactt attttgggct ttgagaggtg gtggtgcaga atcattcggt atcatagttg   6180
cttggaagat aagattagtc gcagtaccaa agtctactat gttctcagtc aaaaagataa   6240
tggaaatcca tgaattagtt aaattggtca ataagtggca aaacatcgca tacaagtacg   6300
ataaggactt gttgttgatg actcatttca tcacaagaaa catcaccgat aaccaaggta   6360
aaaataagac tgctatccac acatactttt cttcagtttt cttgggtggt gtcgattcct   6420
tagtagactt gatgaataag tcttttccag aattaggtat taagaaaact gattgtagac   6480
aattgtcttg gatcgacacc atcatctttt attcaggtgt tgtcaactac gatacagaca   6540
acttcaacaa agaaaatatta ttggatagat ccgcaggtca aaacggtgcc tttaaaatta   6600
agttagacta cgttaaaaag ccaatacctg aatcagtttt cgtccaaatc ttagaaaaat   6660
tgtacgaaga agatattggt gcaggcatgt acgccttgta tccatacggt ggtataatgg   6720
acgaaatcag tgaatctgcc attccatttc ctcatagagc tggtatctta tacgaattgt   6780
ggtacatttg ttcatgggaa aagcaagaag ataacgaaaa gcacttaaac tggattagaa   6840
acatctataa cttcatgact ccatacgttt ctaaaaaccc tagattggca tatttgaact   6900
acagagattt ggacatcggt attaacgatc caaagaatcc taacaactat acccaagcta   6960
gaatttgggg tgaaaaatac ttcggtaaaa atttcgatag attagtaaag gttaagacat   7020
tggttgaccc aaacaacttc tttagaaacg aacaatccat tccaccttta cctagacata   7080
gacactgatg ggctgcagga attcgatatc aagcttatcg ataccgtcga cctcgagtca   7140
tgtaattagt tatgtcacgc ttacattcac gccctccccc cacatccgct ctaaccgaaa   7200
aggaaggagt tagacaacct gaagtctagg tccctattta tttttttata gttatgttag   7260
tattaagaac gttatttata tttcaaattt ttcttttttt tctgtacaga cgcgtgtacg   7320
catgtaacat tatactgaaa accttgcttg agaaggtttt gggacgctcg aaggctttaa   7380
tttgcggccg gtacccagct tttgttccct ttagtgaggg ttaattccga gcttggcgta   7440
atcatggtca tagctgtttc ctgtgtgaaa ttgttatccg ctcacaattc cacacaacat   7500
aggagccgga agcataaagt gtaaagcctg gggtgcctaa tgagtgaggt aactcacatt   7560
aattgcgttg cgctcactgc ccgctttcca gtcgggaaac ctgtcgtgcc agctgcatta   7620
atgaatcggc caacgcgcgg ggagaggcgg tttgcgtatt gggcgctctt ccgcttcctc   7680
```

gctcactgac tcgctgcgct cggtcgttcg gctgcggcga gcggtatcag ctcactcaaa 7740
ggcggtaata cggttatcca cagaatcagg ggataacgca ggaaagaaca tgtgagcaaa 7800
aggccagcaa aaggccagga accgtaaaaa ggccgcgttg ctggcgtttt tccataggct 7860
cggcccccct gacgagcatc acaaaaatcg acgctcaagt cagaggtggc gaaacccgac 7920
aggactataa agataccagg cgtttccccc tggaagctcc ctcgtgcgct ctcctgttcc 7980
gaccctgccg cttaccggat acctgtccgc ctttctccct tcgggaagcg tggcgctttc 8040
tcaatgctca cgctgtaggt atctcagttc ggtgtaggtc gttcgctcca agctgggctg 8100
tgtgcacgaa ccccccgttc agcccgaccg ctgcgcctta tccggtaact atcgtcttga 8160
gtccaacccg gtaagacacg acttatcgcc actggcagca gccactggta acaggattag 8220
cagagcgagg tatgtaggcg gtgctacaga gttcttgaag tggtggccta actacggcta 8280
cactagaagg acagtatttg gtatctgcgc tctgctgaag ccagttacct tcggaaaaag 8340
agttggtagc tcttgatccg gcaaacaaac caccgctggt agcggtggtt tttttgtttg 8400
caagcagcag attacgcgca gaaaaaaagg atctcaagaa gatcctttga tcttttctac 8460
ggggtctgac gctcagtgga acgaaaactc acgttaaggg attttggtca tgagattatc 8520
aaaaaggatc ttcacctaga tccttttaaa ttaaaaatga agttttaaat caatctaaag 8580
tatatatgag taaacttggt ctgacagtta ccaatgctta atcagtgagg cacctatctc 8640
agcgatctgt ctatttcgtt catccatagt tgcctgactg cccgtcgtgt agataactac 8700
gatacgggag ggcttaccat ctggccccag tgctgcaatg ataccgcgag acccacgctc 8760
accggctcca gatttatcag caataaacca gccagccgga agggccgagc gcagaagtgg 8820
tcctgcaact ttatccgcct ccatccagtc tattaattgt tgccgggaag ctagagtaag 8880
tagttcgcca gttaatagtt tgcgcaacgt tgttgccatt gctacaggca tcgtggtgtc 8940
acgctcgtcg tttggtatgg cttcattcag ctccggttcc caacgatcaa ggcgagttac 9000
atgatccccc atgttgtgaa aaaaagcggt tagctccttc ggtcctccga tcgttgtcag 9060
aagtaagttg gccgcagtgt tatcactcat ggttatggca gcactgcata attctcttac 9120
tgtcatgcca tccgtaagat gcttttctgt gactggtgag tactcaacca agtcattctg 9180
agaatagtgt atgcggcgac cgagttgctc ttgcccggcg tcaatacggg ataataccgc 9240
gccacatagc agaactttaa aagtgctcat cattggaaaa cgttcttcgg ggcgaaaact 9300
ctcaaggatc ttaccgctgt tgagatccag ttcgatgtaa cccactcgtg cacccaactg 9360
atcttcagca tcttttactt tcaccagcgt ttctgggtga gcaaaaacag gaaggcaaaa 9420
tgccgcaaaa aagggaataa gggcgacacg gaaatgttga atactcatac tcttcctttt 9480
tcaatattat tgaagcattt atcagggtta ttgtctcatg agcggataca tatttgaatg 9540
tatttagaaa aataaacaaa taggggttcc gcgcacattt ccccgaaaag tgccacctga 9600
cgtctaagaa accatta 9617

<210> SEQ ID NO 13
<211> LENGTH: 7879
<212> TYPE: DNA
<213> ORGANISM: Artificial Sequence
<220> FEATURE:
<223> OTHER INFORMATION: Codon Optimized

<400> SEQUENCE: 13
aacctataaa aataggcgta tcacgaggcc ctttcgtctc gcgcgtttcg gtgatgacgg 60
tgaaaacctc tgacacatgc agctcccgga gacggtcaca gcttgtctgt aagcggatgc 120

```
cgggagcaga caagcccgtc agggcgcgtc agcgggtgtt ggcgggtgtc ggggctggct    180
taactatgcg gcatcagagc agattgtact gagagtgcac cacgcttttc aattcaattc    240
atcatttttt ttttattctt ttttttgatt tcggtttctt tgaaattttt ttgattcggt    300
aatctccgaa cagaaggaag aacgaaggaa ggagcacaga cttagattgg tatatatacg    360
catatgtagt gttgaagaaa catgaaattg cccagtattc ttaacccaac tgcacagaac    420
aaaaacctgc aggaaacgaa gataaatcat gtcgaaagct acatataagg aacgtgctgc    480
tactcatcct agtcctgttg ctgccaagct atttaatatc atgcacgaaa agcaaacaaa    540
cttgtgtgct tcattggatg ttcgtaccac caaggaatta ctggagttag ttgaagcatt    600
aggtcccaaa atttgtttac taaaaacaca tgtggatatc ttgactgatt tttccatgga    660
gggcacagtt aagccgctaa aggcattatc cgccaagtac aatttttttac tcttcgaaga    720
cagaaaattt gctgacattg gtaatacagt caaattgcag tactctgcgg gtgtatacag    780
aatagcagaa tgggcagaca ttacgaatgc acacggtgtg gtgggcccag gtattgttag    840
cggtttgaag caggcggcag aagaagtaac aaaggaacct agaggccttt tgatgttagc    900
agaattgtca tgcaagggct ccctatctac tggagaatat actaagggta ctgttgacat    960
tgcgaagagc gacaaagatt ttgttatcgg ctttattgct caaagagaca tgggtggaag   1020
agatgaaggt tacgattggt tgattatgac acccggtgtg ggtttagatg acaagggaga   1080
cgcattgggt caacagtata gaaccgtgga tgatgtggtc tctacaggat ctgacattat   1140
tattgttgga agaggactat ttgcaaaggg aagggatgct aaggtagagg gtgaacgtta   1200
cagaaaagca ggctgggaag catatttgag aagatgcggc cagcaaaact aaaaaactgt   1260
attataagta aatgcatgta tactaaactc acaaattaga gcttcaattt aattatatca   1320
gttattaccc tgcggtgtga aataccgcac agatgcgtaa ggagaaaata ccgcatcagg   1380
aaattgtaaa cgttaatatt ttgttaaaat tcgcgttaaa tttttgttaa atcagctcat   1440
tttttaacca ataggccgaa atcggcaaaa tcccttataa atcaaaagaa tagaccgaga   1500
tagggttgag tgttgttcca gtttggaaca agagtccact attaaagaac gtggactcca   1560
acgtcaaagg gcgaaaaacc gtctatcagg gcgatggccc actacgtgaa ccatcaccct   1620
aatcaagttt tttggggtcg aggtgccgta aagcactaaa tcggaaccct aaagggagcc   1680
cccgatttag agcttgacgg ggaaagccgg cgaacgtggc gagaaaggaa gggaagaaag   1740
cgaaaggagc gggcgctagg gcgctggcaa gtgtagcggt cacgctgcgc gtaaccacca   1800
cacccgccgc gcttaatgcg ccgctacagg gcgcgtcgcg ccattcgcca ttcaggctgc   1860
gcaactgttg ggaagggcga tcggtgcggg cctcttcgct attacgccag ctggcgaagg   1920
ggggatgtgc tgcaaggcga ttaagttggg taacgccagg gttttcccag tcacgacgtt   1980
gtaaaacgac ggccagtgaa ttgtaatacg actcactata gggcgaattg gagctctagt   2040
acggattaga agccgccgag cgggcgacag ccctccgacg gaagactctc ctccgtgcgt   2100
cctcgtcttc accggtcgcg ttcctgaaac gcagatgtgc ctcgcgccgc actgctccga   2160
acaataaaga ttctacaata ctagctttta tggttatgaa gaggaaaaat tggcagtaac   2220
ctggccccac aaaccttcaa attaacgaat caaattaaca accataggat gataatgcga   2280
ttagtttttt agccttattt ctggggtaat taatcagcga agcgatgatt tttgatctat   2340
taacagatat ataaatggaa aagctgcata accactttaa ctaatacttt caacattttc   2400
agtttgtatt acttcttatt caaatgtcat aaaagtatca acaaaaaatt gttaatatac   2460
```

-continued

```
ctctatactt taacgtcaag gagaaaaaac cccggattct agaactagtg gatcatgaac   2520
catttgagag ccgaaggtcc tgcctccgta ttagccatag gtacagccaa cccagaaaac   2580
atattgatcc aagatgaatt tcctgattat tacttcagag ttaccaagag tgaacacatg   2640
actcaattga aggaaaagtt tagaaaaata tgtgataagt ctatgatcag aaagagaaac   2700
tgcttcttga acgaagaaca tttgaagcaa aatccaagat tggtagaaca cgaaatgcaa   2760
acattggatg ccagacaaga catgttagtt gtcgaagttc ctaaattggg taaagatgct   2820
tgtgcaaaag ccattaagga atggggtcaa ccaaagtcaa agatcactca tttgattttt   2880
acaagtgcat ctactacaga tatgcctggt gcagactacc actgtgccaa attgttaggt   2940
ttgtcaccat ccgttaagag agtcatgatg tatcaattag gttgctacgg tggtggtact   3000
gttttgagaa tcgctaagga tattgcagaa aacaacaagg gtgccagagt attagctgtt   3060
tgttgcgaca ttatggcttg cttgtttaga ggtccaagtg attctgactt ggaattgtta   3120
gttggtcaag ctatcttcgg tgacggtgct gctgctgtta ttgttggtgc agaacctgac   3180
gaatctgttg gtgaaagacc aatatttgaa ttagtcagta caggtcaaac catcttgcct   3240
aattctgaag gtacaattgg tggtcatata agagaagcag gtttgatctt cgatttgcac   3300
aaagacgttc caatgttaat ctctaacaac atagaaaagt gtttgataga agcattcact   3360
cctataggta tctcagattg gaactctatt ttctggataa cacatccagg tggtaaagcc   3420
attttggata aggttgaaga aaaattggat ttgaagaaag aaaagtttgt agatagtaga   3480
catgttttat ctgaacacgg taacatgtct tcatccactg tcttgttcgt aatggatgaa   3540
ttgagaaaga gatcattaga agagggtaaa tctactactg gtgacggttt tgaatggggt   3600
gtcttatttg gtttcggtcc tggtttgacc gtcgaaagag tagttgtcag atcagtacca   3660
attaaatatg aaggtagagg ttccttgtta acttgtggtg acgttgaaga aaacccaggt   3720
cctatggccg tcaagcattt gatagtattg aagtttaaag atgaaatcac agaagctcaa   3780
aaggaagaat tttcaagac ctacgttaat ttggtcaaca ttatacctgc tatgaaagat   3840
gtatactggg gtaaagacgt tacacaaaag aaagaagaag gttatacaca cattgtcgaa   3900
gtaaccttcg aatcagttga aactatccaa gattacatca ttcatccagc tcacgttggt   3960
tttggtgacg tttacagatc cttctgggaa aaattgttga tcttcgatta caccccaaga   4020
aagtgataac gagaataata tcaagaatac cttagaacaa catcgacaac aacaacaggc   4080
attttcggat atgagtcacg tggagtattc cagaattaca aaatttttc aagaacaacc   4140
actggaggga tatacccttt tctctcacag gtctgcgcca tgggtttatc atccgtctgt   4200
actttctcct tccaaactaa ctatcatacc ttattgaatc ctcacaacaa caatccaaaa   4260
acatcattgt tgtgttacag acatccaaag acacctatta agtactctta caacaacttt   4320
ccatcaaaac attgttcaac caagtccttc cacttacaaa ataagtgctc cgaaagtttg   4380
tctatagcta agaactctat cagagctgca actacaaatc aaactgaacc acctgaaagt   4440
gataatcact ctgttgccac aaaaattttg aacttcggta aagcatgttg gaagttgcaa   4500
agaccataca ccataatcgc ttttacttct tgtgcatgcg gtttattcgg taaagaattg   4560
ttgcataaca ctaacttaat ttcatggtcc ttgatgttca aggcattttt ctttttagtt   4620
gccatcttgt gcatcgcttc attcaccact acaattaatc aaatatacga tttgcacatc   4680
gacagaatta acaaaccaga tttgcctttg gcttcaggtg aaatatccgt caatactgca   4740
tggatcatgt ctatcatagt agccttgttc ggtttgatca tcacaattaa aatgaagggt   4800
ggtccattgt acatcttcgg ttactgtttc ggtatcttcg gtggtattgt ctattccgta   4860
```

ccacctttta gatggaaaca aaaccctagt actgcctttt tgttgaattt cttagctcat 4920
atcatcacaa acttcacctt ctactacgct tcaagagctg ctttaggttt gccattcgaa 4980
ttgagacctt cattcacatt tttgttggca ttcatgaaaa gtatgggttc tgcattagcc 5040
ttgatcaagg atgcctctga cgttgaaggt gacacaaagt tcggtattag taccttggct 5100
tctaagtacg gttcaagaaa tttgactttg ttctgctccg gtatcgtttt gttaagttac 5160
gtcgcagcca ttttggcagg tatcatttgg ccacaagcct ttaattctaa cgttatgttg 5220
ttgtcacatg ccatcttggc tttctggttg atcttgcaaa ctagagattt cgctttgaca 5280
aattatgacc ctgaagcagg tagaagattc tacgagttta tgtggaaatt gtactacgct 5340
gaatatttgg tatacgtttt tatttaacga taccgtcgac ctcgagtcat gtaattagtt 5400
atgtcacgct tacattcacg ccctcccccc acatccgctc taaccgaaaa ggaaggagtt 5460
agacaacctg aagtctaggt ccctatttat ttttttatag ttatgttagt attaagaacg 5520
ttatttatat ttcaaatttt tctttttttt ctgtacagac gcgtgtacgc atgtaacatt 5580
atactgaaaa ccttgcttga gaaggttttg ggacgctcga aggctttaat ttgcggccgg 5640
tacccagctt ttgttccctt tagtgagggt taattccgag cttggcgtaa tcatggtcat 5700
agctgtttcc tgtgtgaaat tgttatccgc tcacaattcc acacaacata ggagccggaa 5760
gcataaagtg taaagcctgg ggtgcctaat gagtgaggta actcacatta attgcgttgc 5820
gctcactgcc cgctttccag tcgggaaacc tgtcgtgcca gctgcattaa tgaatcggcc 5880
aacgcgcggg gagaggcggt ttgcgtattg ggcgctcttc cgcttcctcg ctcactgact 5940
cgctgcgctc ggtcgttcgg ctgcggcgag cggtatcagc tcactcaaag gcggtaatac 6000
ggttatccac agaatcaggg gataacgcag gaaagaacat gtgagcaaaa ggccagcaaa 6060
aggccaggaa ccgtaaaaag gccgcgttgc tggcgttttt ccataggctc ggcccccctg 6120
acgagcatca caaaaatcga cgctcaagtc agaggtggcg aaacccgaca ggactataaa 6180
gataccaggc gttcccccct ggaagctccc tcgtgcgctc tcctgttccg accctgccgc 6240
ttaccggata cctgtccgcc tttctccctt cgggaagcgt ggcgctttct caatgctcac 6300
gctgtaggta tctcagttcg gtgtaggtcg ttcgctccaa gctgggctgt gtgcacgaac 6360
cccccgttca gcccgaccgc tgcgccttat ccggtaacta tcgtcttgag tccaacccgg 6420
taagacacga cttatcgcca ctggcagcag ccactggtaa caggattagc agagcgaggt 6480
atgtaggcgg tgctacagag ttcttgaagt ggtggcctaa ctacggctac actagaagga 6540
cagtatttgg tatctgcgct ctgctgaagc cagttacctt cggaaaaaga gttggtagct 6600
cttgatccgg caaacaaacc accgctggta gcggtggttt ttttgtttgc aagcagcaga 6660
ttacgcgcag aaaaaaagga tctcaagaag atcctttgat cttttctacg gggtctgacg 6720
ctcagtggaa cgaaaactca cgttaaggga ttttggtcat gagattatca aaaaggatct 6780
tcacctagat ccttttaaat taaaaatgaa gttttaaatc aatctaaagt atatatgagt 6840
aaacttggtc tgacagttac caatgcttaa tcagtgaggc acctatctca gcgatctgtc 6900
tatttcgttc atccatagtt gcctgactgc ccgtcgtgta gataactacg atacgggagg 6960
gcttaccatc tggccccagt gctgcaatga taccgcgaga cccacgctca ccggctccag 7020
atttatcagc aataaaccag ccagccggaa gggccgagcg cagaagtggt cctgcaactt 7080
tatccgcctc catccagtct attaattgtt gccgggaagc tagagtaagt agttcgccag 7140
ttaatagttt gcgcaacgtt gttgccattg ctacaggcat cgtggtgtca cgctcgtcgt 7200

-continued

```
ttggtatggc ttcattcagc tccggttccc aacgatcaag gcgagttaca tgatccccca   7260

tgttgtgaaa aaaagcggtt agctccttcg gtcctccgat cgttgtcaga agtaagttgg   7320

ccgcagtgtt atcactcatg gttatggcag cactgcataa ttctcttact gtcatgccat   7380

ccgtaagatg cttttctgtg actggtgagt actcaaccaa gtcattctga gaatagtgta   7440

tgcggcgacc gagttgctct tgcccggcgt caatacggga taataccgcg ccacatagca   7500

gaactttaaa agtgctcatc attggaaaac gttcttcggg gcgaaaactc tcaaggatct   7560

taccgctgtt gagatccagt tcgatgtaac ccactcgtgc acccaactga tcttcagcat   7620

cttttacttt caccagcgtt tctgggtgag caaaaacagg aaggcaaaat gccgcaaaaa   7680

agggaataag ggcgacacgg aaatgttgaa tactcatact cttccttttt caatattatt   7740

gaagcattta tcagggttat tgtctcatga gcggatacat atttgaatgt atttagaaaa   7800

ataaacaaat aggggttccg cgcacatttc cccgaaaagt gccacctgac gtctaagaaa   7860

ccattattat catgacatt                                                7879


<210> SEQ ID NO 14
<211> LENGTH: 3353
<212> TYPE: DNA
<213> ORGANISM: Artificial Sequence
<220> FEATURE:
<223> OTHER INFORMATION: Codon Optimized

<400> SEQUENCE: 14

actagtatgg gtaaaaacta taagtccttg gattcagtcg ttgcctcaga tttcatcgca     60

ttgggtatca cctcagaagt agcagaaaca ttacatggta gattggcaga aatcgtttgt    120

aattatggtg ctgcaacccc tcaaacttgg atcaacatcg ctaaccatat cttgtcacca    180

gatttgcctt tctccttaca ccaaatgttg ttttatggtt gctacaagga tttcggtcca    240

gccccacctg cttggattcc agaccctgaa aaagtcaagt caactaattt gggtgctttg    300

ttggaaaaga gaggtaaaga atttttgggt gtaaagtaca aagatccaat ttcttctttt    360

tctcacttcc aagaattttc tgttagaaac cctgaagtct attggagaac agtattgatg    420

gatgaaatga aaattagttt ctctaaggac ccagaatgta tcttgagaag agatgacatc    480

aacaacccag gtggttctga atggttacct ggtggttact tgaactcagc taaaaattgc    540

ttgaacgtaa actccaataa gaaattgaac gatactatga tcgtttggag agacgagggt    600

aacgatgact tgcctttgaa taagttgaca ttagatcaat tgagaaagag agtttggttg    660

gttggttatg cattggaaga aatgggttta gaaaaaggtt gtgcaatagc catcgatatg    720

ccaatgcatg ttgatgctgt tgttatatat ttggccatag tattggctgg ttacgtagtt    780

gtctctatag cagattcatt ttccgcccct gaaatctcaa ctagattgag attatccaaa    840

gctaaggcaa ttttcacaca agatcacatc atcagaggta aaaagagaat accattgtat    900

tcaagagtag ttgaagctaa atccccaatg gcaatagtta tcccttgtag tggttctaac    960

attggtgcag aattgagaga tggtgacata tcttgggatt actttttaga aagagccaag   1020

gagtttaaaa actgcgagtt tactgccaga gaacaacctg ttgatgctta tactaacatc   1080

ttattctcca gtggtactac aggtgaacca aaagcaattc cttggacaca agccacccca   1140

ttgaaggctg ctgctgatgg ttggtctcat ttggatatta gaaaaggtga cgttatagta   1200

tggccaacta atttgggttg gatgatgggt ccttggttgg tttatgctag tttgttaaat   1260

ggtgcatcta ttgccttgta caacggtagt cctttagtct ctggtttcgc taaatttgtt   1320

caagatgcaa aggtcacaat gttgggtgtc gtaccatcta ttgtaagatc atggaaatcc   1380
```

acaaattgtg tttcaggtta cgattggtcc accataagat gcttttcttc atccggtgaa 1440
gcctctaatg tagacgaata tttgtggtta atgggtagag ctaactacaa gccagttata 1500
gaaatgtgtg gtggtacaga aatcggtggt gctttttctg ctggttcatt tttgcaagct 1560
caatctttaa gttctttttc atcccaatgt atgggttgca ccttgtacat attagataag 1620
aacggttacc caatgcctaa aaataagcca ggtatcggtg aattggcatt aggtcctgtt 1680
atgtttggtg cctcaaaaac attgttaaac ggtaatcatc acgatgtcta tttcaagggt 1740
atgccaacct tgaatggtga agtattgaga agacatggtg acattttcga attgacctct 1800
aacggttact accatgcaca cggtagagcc gatgacacta tgaacatcgg tggtatcaaa 1860
attagttcta tcgaaatcga aagagtctgt aatgaagtag atgacagagt tttgaaacc 1920 actgctattg gtgttccacc tttgggtggt ggtccagaac aattggtcat atttttcgta 1980
ttgaaggatt caaacgacac aaccattgat ttgaaccaat tgagattatc ctttaacttg 2040
ggtttgcaaa agaaattgaa cccattattc aaagttacta gagttgtccc attgtcatcc 2100
ttacctagaa ctgcaacaaa caagatcatg agaagagttt tgagacaaca attcagtcat 2160
ttcgaagaag gtagaggttc tttgttaaca tgtggtgacg ttgaagaaaa tccaggtcct 2220
atggcttcag aaaaggaaat aagaagagaa agattcttga acgtattccc aaagttagtt 2280
gaagaattga acgctagttt gttagcttat ggtatgccta aagaagcctg cgattggtat 2340
gctcactctt taaactacaa tactccaggt ggtaaattga atagaggttt gagtgtagtt 2400
gatacttatg ctatcttgtc taacaaaacc gttgaacaat taggtcaaga agaatacgaa 2460
aaggtcgcta tcttgggttg gtgtattgaa ttgttgcaag catacttttt ggttgccgat 2520
gacatgatgg ataagtctat aacaagaaga ggtcaaccat gctggtacaa agttccagaa 2580
gttggtgaaa tagccataaa tgatgctttt atgttggaag ccgctatcta taaattgttg 2640
aagtcacatt tcagaaacga aaagtactac atcgatatta ccgaattatt ccacgaagtt 2700
actttccaaa cagaattggg tcaattgatg gatttgataa ctgcacctga agataaagtt 2760
gacttgtcaa agttttcctt gaagaaacat tcattcatcg tcacctttga aactgcttat 2820
tactccttct atttgccagt cgccttggct atgtacgtag ctggtattac tgatgaaaaa 2880
gacttgaagc aagcaagaga tgttttgata cctttgggtg aatacttcca aatccaagat 2940
gactacttag actgtttcgg tactccagaa caaataggta aaatcggtac agatattcaa 3000
gacaataagt gcagttgggt tattaacaag gctttggaat tagcatctgc cgaacaaaga 3060
aagactttgg atgaaaacta cggtaaaaag gactcagttg ctgaagcaaa gtgtaagaaa 3120
atttttaatg atttgaagat tgaacaattg taccatgaat acgaagaatc catcgctaaa 3180
gacttaaagg caaagattag tcaagttgat gaatcaagag gttttaaagc cgacgttttg 3240
acagctttct tgaataaggt ctacaagaga tcaaaggatt acaaggatca tgacggtgac 3300
tataaagacc acgatattga ctacaaagat gacgatgaca agtaagcggc cgc 3353

<210> SEQ ID NO 15
<211> LENGTH: 1553
<212> TYPE: DNA
<213> ORGANISM: Artificial Sequence
<220> FEATURE:
<223> OTHER INFORMATION: Codon Optimized

<400> SEQUENCE: 15
actagtatga accatttgag agccgaaggt cctgcctccg tattagccat aggtacagcc 60
aacccagaaa acatattgat ccaagatgaa tttcctgatt attacttcag agttaccaag 120
agtgaacaca tgactcaatt gaaggaaaag tttagaaaaa tatgtgataa gtctatgatc 180
agaaagagaa actgcttctt gaacgaagaa catttgaagc aaaatccaag attggtagaa 240
cacgaaatgc aaacattgga tgccagacaa gacatgttag ttgtcgaagt tcctaaattg 300
ggtaaagatg cttgtgcaaa agccattaag gaatggggtc aaccaaagtc aaagatcact 360
catttgattt ttacaagtgc atctactaca gatatgcctg gtgcagacta ccactgtgcc 420
aaattgttag gtttgtcacc atccgttaag agagtcatga tgtatcaatt aggttgctac 480
ggtggtggta ctgttttgag aatcgctaag gatattgcag aaaacaacaa gggtgccaga 540
gtattagctg tttgttgcga cattatggct tgcttgttta gaggtccaag tgattctgac 600
ttggaattgt tagttggtca agctatcttc ggtgacggtg ctgctgctgt tattgttggt 660
gcagaacctg acgaatctgt tggtgaaaga ccaatatttg aattagtcag tacaggtcaa 720
accatcttgc ctaattctga aggtacaatt ggtggtcata taagagaagc aggtttgatc 780
ttcgatttgc acaaagacgt tccaatgtta atctctaaca acatagaaaa gtgtttgata 840
gaagcattca ctcctatagg tatctcagat tggaactcta ttttctggat aacacatcca 900
ggtggtaaag ccattttgga taaggttgaa gaaaaattgg atttgaagaa agaaaagttt 960
gtagatagta gacatgtttt atctgaacac ggtaacatgt cttcatccac tgtcttgttc 1020
gtaatggatg aattgagaaa gagatcatta gaagagggta aatctactac tggtgacggt 1080
tttgaatggg gtgtcttatt tggtttcggt cctggtttga ccgtcgaaag agtagttgtc 1140
agatcagtac caattaaata tgaaggtaga ggttccttgt taacttgtgg tgacgttgaa 1200
gaaaacccag gtcctatggc cgtcaagcat ttgatagtat tgaagtttaa agatgaaatc 1260
acagaagctc aaaaggaaga atttttcaag acctacgtta atttggtcaa cattatacct 1320
gctatgaaag atgtatactg ggtaaagac gttacacaaa agaaagaaga aggttataca 1380
cacattgtcg aagtaacctt cgaatcagtt gaaactatcc aagattacat cattcatcca 1440
gctcacgttg gttttggtga cgtttacaga tccttctggg aaaaattgtt gatcttcgat 1500
tacaccccaa gaaagtaccc ttacgatgtt ccagactatg cataagcggc cgc 1553

<210> SEQ ID NO 16
<211> LENGTH: 2918
<212> TYPE: DNA
<213> ORGANISM: Artificial Sequence
<220> FEATURE:
<223> OTHER INFORMATION: Codon Optimized

<400> SEQUENCE: 16
actagtatgg gtttatcatc cgtctgtact ttctccttcc aaactaacta tcatacctta 60
ttgaatcctc acaacaacaa tccaaaaaca tcattgttgt gttacagaca tccaaagaca 120
cctattaagt actcttacaa caactttcca tcaaaacatt gttcaaccaa gtccttccac 180
ttacaaaata agtgctccga aagtttgtct atagctaaga actctatcag agctgcaact 240
acaaatcaaa ctgaaccacc tgaaagtgat aatcactctg ttgccacaaa aattttgaac 300
ttcggtaaag catgttggaa gttgcaaaga ccatacacca taatcgcttt tacttcttgt 360
gcatgcggtt tattcggtaa agaattgttg cataacacta acttaatttc atggtccttg 420

```
atgttcaagg cattttctt tttagttgcc atcttgtgca tcgcttcatt caccactaca    480

attaatcaaa tatacgattt gcacatcgac agaattaaca aaccagattt gcctttggct    540

tcaggtgaaa tatccgtcaa tactgcatgg atcatgtcta tcatagtagc cttgttcggt    600

ttgatcatca caattaaaat gaagggtggt ccattgtaca tcttcggtta ctgtttcggt    660

atcttcggtg gtattgtcta ttccgtacca ccttttagat ggaaacaaaa ccctagtact    720

gccttttgt tgaatttctt agctcatatc atcacaaact tcaccttcta ctacgcttca    780

agagctgctt taggtttgcc attcgaattg agaccttcat tcacattttt gttggcattc    840

atgaaaagta tgggttctgc attagccttg atcaaggatg cctctgacgt tgaaggtgac    900

acaaagttcg gtattagtac cttggcttct aagtacggtt caagaaattt gactttgttc    960

tgctccggta tcgttttgtt aagttacgtc gcagccattt tggcaggtat catttggcca   1020

caagccttta attctaacgt tatgttgttg tcacatgcca tcttggcttt ctggttgatc   1080

ttgcaaacta gagatttcgc tttgacaaat tatgaccctg aagcaggtag aagattctac   1140

gagtttatgt ggaaattgta ctacgctgaa tatttggtat acgttttat tgaaggtaga   1200

ggttctttgt tgacctgtgg tgacgttgaa gaaaatccag gtcctatgaa atgttcaact   1260

ttctcctttt ggttcgtatg caagatcatc ttctttttct tttcctttaa catccaaaca   1320

agtatcgcaa acccaagaga aaacttttg aagtgcttct cacaatacat acctaataac   1380

gccaccaatt tgaagttggt ttacactcaa acaacccat tgtacatgtc cgtcttgaac   1440

agtacaatcc ataatttgag attcacttct gataccactc caaaacccttt ggtcattgta   1500

accctagtc atgtatctca catccaaggt actatcttat gttctaaaaa ggttggtttg   1560

caaattagaa ctagatccgg tggtcatgat agtgaaggca tgtcatacat ctcccaagtt   1620

ccattcgtta tcgttgattt gagaaacatg agatcaatta aaatagacgt acactcacaa   1680

actgcttggg ttgaagctgg tgcaacattg ggtgaagtat actactgggt taacgaaaag   1740

aatgaaaact tatcattggc tgctggttac tgtccaacag tttgcgcagg tggtcattt   1800

ggtggtggtg gttatggtcc tttaatgaga aactacggtt tggccgctga taacataatc   1860

gacgctcatt tggtaaatgt tcacggtaaa gttttggata aaagtctat gggtgaagac   1920

ttattttggg ctttgagagg tggtggtgca gaatcattcg gtatcatagt tgcttggaag   1980

ataagattag tcgcagtacc aaagtctact atgttctcag tcaaaaagat aatgaaaatc   2040

catgaattag ttaaattggt caataagtgg caaaacatcg catacaagta cgataaggac   2100

ttgttgttga tgactcattt catcacaaga aacatcaccg ataaccaagg taaaaataag   2160

actgctatcc acacatactt tcttcagtt ttcttgggtg gtgtcgattc cttagtagac   2220

ttgatgaata agtcttttcc agaattaggt attaagaaaa ctgattgtag acaattgtct   2280

tggatcgaca ccatcatctt ttattcaggt gttgtcaact acgatacaga caacttcaac   2340

aaagaaatat tattggatag atccgcaggt caaaacggtg cctttaaaat taagttagac   2400

tacgttaaaa agccaatacc tgaatcagtt ttcgtccaaa tcttagaaaa attgtacgaa   2460

gaagatattg gtgcaggcat gtacgccttg tatccatacg gtggtataat ggacgaaatc   2520

agtgaatctg ccattccatt tcctcataga gctggtatct tatacgaatt gtggtacatt   2580

tgttcatggg aaaagcaaga agataacgaa aagcacttaa actggattag aaacatctat   2640

aacttcatga ctccatacgt ttctaaaaac cctagattgg catatttgaa ctacagagat   2700

ttggacatcg gtattaacga tccaaagaat cctaacaact atacccaagc tagaatttgg   2760

ggtgaaaaat acttcggtaa aaatttcgat agattagtaa aggttaagac attggttgac   2820
```

ccaaacaact tctttagaaa cgaacaatcc attccacctt tacctagaca tagacacgaa 2880
caaaaattaa taagtgaaga agatttgtaa gcggccgc 2918

<210> SEQ ID NO 17
<211> LENGTH: 167
<212> TYPE: DNA
<213> ORGANISM: Artificial Sequence
<220> FEATURE:
<223> OTHER INFORMATION: Codon Optimized

<400> SEQUENCE: 17
agccaaaata atgataacga gaataatatc aagaatacct tagaacaaca tcgacaacaa 60
caacaggcat tttcggatat gagtcacgtg gagtattcca gaattacaaa attttttcaa 120
gaacaaccac tggagggata taccctttc tctcacaggt ctgcgcc 167

<210> SEQ ID NO 18
<211> LENGTH: 1518
<212> TYPE: DNA
<213> ORGANISM: Artificial Sequence
<220> FEATURE:
<223> OTHER INFORMATION: Codon Optimized

<400> SEQUENCE: 18
atggtttcca atcacttgtt tgacgcaatg agagccgctg cccctggtaa cgcccctttc 60
ataagaatag ataatactag aacttggaca tacgatgacg cctttgcttt atctggtaga 120
atagcatcag ctatggatgc tttgggtatc agaccaggtg acagagtcgc agttcaagta 180
gaaaaatccg ctgaagcatt gatcttgtat ttggcttgtt tgagaagtgg tgcagtttat 240
ttgccattga atactgccta cacattagct gaattggatt acttcatagg tgacgcagaa 300
cctagattgg ttgtagtcgc ctcttcagcc agagctggtg tagaaacaat tgctaaacca 360
agaggtgcaa tagtcgaaac cttagatgct gctggttctg gtagtttgtt agatttggcc 420
agagacgaac ctgctgattt tgttgacgct tcaagatcag ccgatgactt agccgctatt 480
ttgtacacct ctggtactac aggtagatca aagggtgcta tgttgactca tggtaatttg 540
ttgtcaaacg cattaacctt gagagatttc tggagagtta ctgccggtga cagattaatc 600
cacgctttgc caatttttca tactcacggt ttattcgttg ctaccaacgt aactttgtta 660
gcaggtgcct ccatgttctt gttgagtaag ttcgatccag aagaaatatt atctttgatg 720
cctcaagcta ctatgttgat gggtgtccca acattctacg ttagattgtt acaatcacct 780
agattagata agcaagctgt tgcaaacatc agattgttta tatccggtag tgctccattg 840
ttagcagaaa cccatactga atttcaagca agaacaggtc acgccatttt agaaagatac 900
ggtatgacag aaaccaatat gaacacttct aacccttatg aaggtaaaag aatagctggt 960
acagttggtt ttccattgcc tgatgtcaca gttagagtaa ccgacccagc cactggttta 1020
gctttgccac ctgaacaaac tggtatgatc gaaattaaag gtccaaacgt ttttaagggt 1080
tactggagaa tgcctgaaaa gactgctgct gagtttactg ctgatggttt ctttatctct 1140
ggtgacttag gtaaaattga tagagacggt tatgtccata ttgttggtcg tggtaaagat 1200
ttggttatat ccggtggtta taacatctac cctaaggaag tagaaggtga aatagatcaa 1260
atcgaaggtg ttgtagaatc agctgtaata ggtgtcccac atcctgattt tggtgaaggt 1320
gttacagcag tcgttgtaag aaaaccaggt gctgcattag atgaaaaggc aattgtttct 1380
gccttacaag acagattggc tagatacaag caaccaaaga gaataatctt cgcagaagat 1440
ttgcctagaa atactatggg taaagtacaa aagaacatct tgagacaaca atacgccgac 1500
ttatacacca gaacctga 1518

<210> SEQ ID NO 19
<211> LENGTH: 2092
<212> TYPE: DNA
<213> ORGANISM: Artificial Sequence
<220> FEATURE:
<223> OTHER INFORMATION: Codon Optimized

<400> SEQUENCE: 19
actagtatgg gtttatcatc cgtctgtact ttctccttcc aaactaacta tcatacctta 60
ttgaatcctc acaacaacaa tccaaaaaca tcattgttgt gttacagaca tccaaagaca 120
cctattaagt actcttacaa caactttcca tcaaaacatt gttcaaccaa gtccttccac 180
ttacaaaata agtgctccga aagtttgtct atagctaaga actctatcag agctgcaact 240
acaaatcaaa ctgaaccacc tgaaagtgat aatcactctg ttgccacaaa aattttgaac 300
ttcggtaaag catgttggaa gttgcaaaga ccatacacca taatcgcttt tacttcttgt 360
gcatgcggtt tattcggtaa agaattgttg cataacacta acttaatttc atggtcctat 420
gaactgctcc gcattctctt tctggttcgt ctgtaaaata atcttcttct tcttgtcctt 480
caacatccaa atctccatcg caaatccaca agaaaacttt ttgaagtgtt tctccgaata 540
catcccaaac aaccctgcta acccaaagtt tatatatact caacatgatc aattgtacat 600
gtccgttttg aacagtacca tccaaaattt gagattcact tctgacacta caccaaaacc 660
tttagtcatt gttacacctt ccaatgttag tcacattcaa gcttctatat tgtgctctaa 720
gaaagtaggt ttgcaaatca gaactagatc aggtggtcat gatgcagaag gcatgtctta 780
catctcacaa gttccattcg ttgtagtcga tttgagaaat atgcattcca taaagatcga 840
cgttcacagt caaacagcat gggtagaagc aggtgccacc ttgggtgaag tttactactg 900
gatcaacgaa aagaatgaaa acttttcttt ccctggtggt tactgtccaa cagtaggtgt 960
cggtggtcac ttttctggtg gtggttatgg tgcattgatg agaaactacg gtttagctgc 1020
agataatatt atagacgccc atttggttaa cgtagatggt aaagttttgg acagaaagtc 1080
tatgggtgaa gatttgtttt gggccataag aggtggtggt ggtgaaaatt tcggtatcat 1140
tgccgcttgg aaaattaagt tagtcgctgt tccttccaaa agtactattt tctctgtcaa 1200
aaagaacatg gaaatccacg gtttggttaa gttgtttaat aagtggcaaa acatcgctta 1260
caagtacgat aaggacttgg ttttgatgac ccatttcatc actaaaaata ttacagataa 1320
ccatggtaaa aataagacca ctgttcacgg ttatttttct tcaattttcc atggtggtgt 1380
agattctttg gttgatttga tgaataagtc attcccagaa ttgggtatta aaaagacaga 1440
ttgcaaggaa ttttcttgga tagacacaac catcttctat tcaggtgttg taaacttcaa 1500
caccgctaac ttcaaaaagg aaatcttgtt ggatagatcc gctggtaaaa agaccgcttt 1560
ttctattaaa ttggactacg ttaagaaacc aatccctgaa actgcaatgg tcaagatatt 1620
ggaaaagttg tacgaagaag atgtaggtgt cggcatgtac gttttgtatc catacggtgg 1680
tattatggaa gaaatatctg aatcagccat accatttcct cacagagctg gtatcatgta 1740
tgaattatgg tacacagcct catgggaaaa gcaagaagat aacgaaaagc atatcaactg 1800
ggtcagatcc gtttacaact tcactacacc ttacgttagt caaaacccaa gattggcata 1860
tttgaactac agagatttgg acttaggtaa aactaaccct gaatctccaa ataactatac 1920
acaagcaaga atttggggtg aaaagtactt tggtaaaaat ttcaacagat tagttaaagt 1980
aaagactaaa gccgacccta acaacttttt cagaaacgaa caatccatcc cacctttgcc 2040
acctcaccac cacgaacaaa aattaataag tgaagaagat ttgtaagtcg ac 2092

<210> SEQ ID NO 20
<211> LENGTH: 7904
<212> TYPE: DNA
<213> ORGANISM: Artificial Sequence
<220> FEATURE:
<223> OTHER INFORMATION: Codon Optimized

<400> SEQUENCE: 20
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatcga ctacgtcgta aggccgtttc tgacagagta aaattcttga gggaactttc 240
accattatgg gaaatggttc aagaaggtat tgacttaaac tccatcaaat ggtcaggtca 300
ttgagtgttt tttatttgtt gtattttttt tttttagag aaaatcctcc aatatcaaat 360
taggaatcgt agtttcatga ttttctgtta cacctaactt tttgtgtggt gccctcctcc 420
ttgtcaatat taatgttaaa gtgcaattct ttttccttat cacgttgagc cattagtatc 480
aatttgctta cctgtattcc tttactatcc tcctttttct ccttcttgat aaatgtatgt 540
agattgcgta tatagtttcg tctaccctat gaacatattc cattttgtaa tttcgtgtcg 600
tttctattat gaatttcatt tataaagttt atgtacaaat atcataaaaa aagagaatct 660
ttttaagcaa ggattttctt aacttcttcg gcgacagcat caccgacttc ggtggtactg 720
ttggaaccac ctaaatcacc agttctgata cctgcatcca aaaccttttt aactgcatct 780
tcaatggcct taccttcttc aggcaagttc aatgacaatt tcaacatcat tgcagcagac 840
aagatagtgg cgatagggtc aaccttattc tttggcaaat ctggagcaga accgtggcat 900
ggttcgtaca aaccaaatgc ggtgttcttg tctggcaaag aggccaagga cgcagatggc 960
aacaaaccca aggaacctgg gataacggag gcttcatcgg agatgatatc accaaacatg 1020
ttgctggtga ttataatacc atttaggtgg gttgggttct taactaggat catggcggca 1080
gaatcaatca attgatgttg aaccttcaat gtagggaatt cgttcttgat ggtttcctcc 1140
acagtttttc tccataatct tgaagaggcc aaaacattag ctttatccaa ggaccaaata 1200
ggcaatggtg gctcatgttg tagggccatg aaagcggcca ttcttgtgat tctttgcact 1260
tctggaacgg tgtattgttc actatcccaa gcgacaccat caccatcgtc ttcctttctc 1320
ttaccaaagt aaatacctcc cactaattct ctgacaacaa cgaagtcagt acctttagca 1380
aattgtggct tgattggaga taagtctaaa agagagtcgg atgcaaagtt acatggtctt 1440
aagttggcgt acaattgaag ttctttacgg atttttagta aaccttgttc aggtctaaca 1500
ctaccggtac cccatttagg accacccaca gcacctaaca aaacggcatc aaccttcttg 1560
gaggcttcca gcgcctcatc tggaagtggg acacctgtag catcgatagc agcaccacca 1620
attaaatgat tttcgaaatc gaacttgaca ttggaacgaa catcagaaat agctttaaga 1680
accttaatgg cttcggctgt gatttcttga ccaacgtggt cacctggcaa aacgacgatc 1740
ttcttagggg cagacatagg ggcagacatt agaatggtat atccttgaaa tatatatata 1800
tattgctgaa atgtaaaagg taagaaaagt tagaaagtaa gacgattgct aaccacctat 1860
tggaaaaaac aataggtcct taaataatat tgtcaacttc aagtattgtg atgcaagcat 1920

-continued

```
ttagtcatga acgcttctct attctatatg aaaagccggt tccggcctct cacctttcct   1980
ttttctccca atttttcagt tgaaaaaggt atatgcgtca ggcgacctct gaaattaaca   2040
aaaaatttcc agtcatcgaa tttgattctg tgcgatagcg cccctgtgtg ttctcgttat   2100
gttgaggaaa aaaataatgg ttgctaagag attcgaactc ttgcatctta cgatacctga   2160
gtattcccac agttaactgc ggtcaagata tttcttgaat caggcgcctt agaccgctcg   2220
gccaaacaac caattacttg ttgagaaata gagtataatt atcctataaa tataacgttt   2280
ttgaacacac atgaacaagg aagtacagga caattgattt tgaagagaat gtggattttg   2340
atgtaattgt tgggattcca tttttaataa ggcaataata ttaggtatgt ggatatacta   2400
gaagttctcc tcgagggtcg atatgcggtg tgaaataccg cacagatgcg taaggagaaa   2460
ataccgcatc aggaaattgt aaacgttaat attttgttaa aattcgcgtt aaatttttgt   2520
taaatcagct cattttttaa ccaataggcc gaaatcggca aaatccctta taaatcaaaa   2580
gaatagaccg agatagggtt gagtgttgtt ccagtttgga acaagagtcc actattaaag   2640
aacgtggact ccaacgtcaa agggcgaaaa accgtctatc agggcgatgg cccactacgt   2700
gaaccatcac cctaatcaag ttttttgggg tcgaggtgcc gtaaagcact aaatcggaac   2760
cctaaaggga gcccccgatt tagagcttga cggggaaagc cggcgaacgt ggcgagaaag   2820
gaagggaaga aagcgaaagg agcgggcgct agggcgctgg caagtgtagc ggtcacgctg   2880
cgcgtaacca ccacacccgc cgcgcttaat gcgccgctac agggcgcgtc gcgccattcg   2940
ccattcaggc tgcgcaactg ttgggaaggg cgatcggtgc gggcctcttc gctattacgc   3000
cagctggcga aggggggatg tgctgcaagg cgattaagtt gggtaacgcc agggttttcc   3060
cagtcacgac gttgtaaaac gacggccagt gaattgtaat acgactcact atagggcgaa   3120
ttggagctct agtacggatt agaagccgcc gagcgggcga cagccctccg acggaagact   3180
ctcctccgtg cgtcctcgtc ttcaccggtc gcgttcctga aacgcagatg tgcctcgcgc   3240
cgcactgctc cgaacaataa agattctaca atactagctt ttatggttat gaagaggaaa   3300
aattggcagt aacctggccc cacaaacctt caaattaacg aatcaaatta acaaccatag   3360
gatgataatg cgattagttt tttagcctta tttctggggt aattaatcag cgaagcgatg   3420
atttttgatc tattaacaga tatataaatg gaaaagctgc ataaccactt taactaatac   3480
tttcaacatt ttcagtttgt attacttctt attcaaatgt cataaaagta tcaacaaaaa   3540
attgttaata tacctctata ctttaacgtc aaggagaaaa aaccccggat tctagaacta   3600
gtggatcccc catcacaagt ttgtacaaaa aagctgaacg agaaacgtaa aatgatataa   3660
atatcaatat attaaattag attttgcata aaaaacagac tacataatac tgtaaaacac   3720
aacatatcca gtcactatgg cggccgcatt aggcacccca ggctttacac tttatgcttc   3780
cggctcgtat aatgtgtgga ttttgagtta ggatccgtcg agattttcag gagctaagga   3840
agctaaaatg gagaaaaaaa tcactggata taccaccgtt gatatatccc aatggcatcg   3900
taaagaacat tttgaggcat ttcagtcagt tgctcaatgt acctataacc agaccgttca   3960
gctggatatt acggcctttt taaagaccgt aaagaaaaat aagcacaagt tttatccggc   4020
ctttattcac attcttgccc gcctgatgaa tgctcatccg gaattccgta tggcaatgaa   4080
agacggtgag ctggtgatat gggatagtgt tcacccttgt tacaccgttt tccatgagca   4140
aactgaaacg ttttcatcgc tctggagtga ataccacgac gatttccggc agtttctaca   4200
catatattcg caagatgtgg cgtgttacgg tgaaaacctg gcctatttcc ctaaagggtt   4260
tattgagaat atgtttttcg tctcagccaa tccctgggtg agtttcacca gttttgattt   4320
```

-continued aaacgtggcc aatatggaca acttcttcgc ccccgttttc accatgggca aatattatac 4380
gcaaggcgac aaggtgctga tgccgctggc gattcaggtt catcatgccg tctgtgatgg 4440
cttccatgtc ggcagaatgc ttaatgaatt acaacagtac tgcgatgagt ggcagggcgg 4500
ggcgtaaacg ccgcgtggat ccggcttact aaaagccaga taacagtatg cgtatttgcg 4560
cgctgatttt tgcggtataa gaatatatac tgatatgtat acccgaagta tgtcaaaaag 4620
aggtatgcta tgaagcagcg tattacagtg acagttgaca gcgacagcta tcagttgctc 4680
aaggcatata tgatgtcaat atctccggtc tggtaagcac aaccatgcag aatgaagccc 4740
gtcgtctgcg tgccgaacgc tggaaagcgg aaaatcagga agggatggct gaggtcgccc 4800
ggtttattga aatgaacggc tcttttgctg acgagaacag gggctggtga aatgcagttt 4860
aaggtttaca cctataaaag agagagccgt tatcgtctgt ttgtggatgt acagagtgat 4920
attattgaca cgcccgggcg acggatggtg atccccctgg ccagtgcacg tctgctgtca 4980
gataaagtct cccgtgaact ttacccggtg gtgcatatcg gggatgaaag ctggcgcatg 5040
atgaccaccg atatggccag tgtgccggtc tccgttatcg gggaagaagt ggctgatctc 5100
agccaccgcg aaaatgacat caaaaacgcc attaacctga tgttctgggg aatataaatg 5160
tcaggctccc ttatacacag ccagtctgca ggtcgaccat agtgactgga tatgttgtgt 5220
tttacagtat tatgtagtct gtttttttatg caaaatctaa tttaatatat tgatatttat 5280
atcattttac gtttctcgtt cagctttctt gtacaaagtg gtgatgggct gcaggaattc 5340
gatatcaagc ttatcgatac cgtcgacctc gagtcatgta attagttatg tcacgcttac 5400
attcacgccc tccccccaca tccgctctaa ccgaaaagga aggagttaga caacctgaag 5460
tctaggtccc tatttatttt tttatagtta tgttagtatt aagaacgtta tttatatttc 5520
aaatttttct ttttttttctg tacagacgcg tgtacgcatg taacattata ctgaaaacct 5580
tgcttgagaa ggttttggga cgctcgaagg ctttaatttg cggccggtac ccagcttttg 5640
ttccctttag tgagggttaa ttccgagctt ggcgtaatca tggtcatagc tgtttcctgt 5700
gtgaaattgt tatccgctca caattccaca caacatagga gccggaagca taaagtgtaa 5760
agcctggggt gcctaatgag tgaggtaact cacattaatt gcgttgcgct cactgcccgc 5820
tttccagtcg ggaaacctgt cgtgccagct gcattaatga atcggccaac gcgcggggag 5880
aggcggtttg cgtattgggc gctcttccgc ttcctcgctc actgactcgc tgcgctcggt 5940
cgttcggctg cggcgagcgg tatcagctca ctcaaaggcg gtaatacggt tatccacaga 6000
atcaggggat aacgcaggaa agaacatgtg agcaaaaggc cagcaaaagg ccaggaaccg 6060
taaaaaggcc gcgttgctgg cgtttttcca taggctcggc ccccctgacg agcatcacaa 6120
aaatcgacgc tcaagtcaga ggtggcgaaa cccgacagga ctataaagat accaggcgtt 6180 ccccccctgga agctccctcg tgcgctctcc tgttccgacc ctgccgctta ccggatacct 6240
gtccgccttt ctcccttcgg gaagcgtggc gctttctcaa tgctcacgct gtaggtatct 6300
cagttcggtg taggtcgttc gctccaagct gggctgtgtg cacgaacccc ccgttcagcc 6360
cgaccgctgc gccttatccg gtaactatcg tcttgagtcc aacccggtaa gacacgactt 6420
atcgccactg gcagcagcca ctggtaacag gattagcaga gcgaggtatg taggcggtgc 6480
tacagagttc ttgaagtggt ggcctaacta cggctacact agaaggacag tatttggtat 6540
ctgcgctctg ctgaagccag ttaccttcgg aaaaagagtt ggtagctctt gatccggcaa 6600
acaaaccacc gctggtagcg gtggtttttt tgtttgcaag cagcagatta cgcgcagaaa 6660

-continued

```
aaaaggatct caagaagatc ctttgatctt ttctacgggg tctgacgctc agtggaacga   6720

aaactcacgt taagggattt tggtcatgag attatcaaaa aggatcttca cctagatcct   6780

tttaaattaa aaatgaagtt ttaaatcaat ctaaagtata tatgagtaaa cttggtctga   6840

cagttaccaa tgcttaatca gtgaggcacc tatctcagcg atctgtctat ttcgttcatc   6900

catagttgcc tgactgcccg tcgtgtagat aactacgata cgggagggct taccatctgg   6960

ccccagtgct gcaatgatac cgcgagaccc acgctcaccg gctccagatt tatcagcaat   7020

aaaccagcca gccggaaggg ccgagcgcag aagtggtcct gcaactttat ccgcctccat   7080

ccagtctatt aattgttgcc gggaagctag agtaagtagt tcgccagtta atagtttgcg   7140

caacgttgtt gccattgcta caggcatcgt ggtgtcacgc tcgtcgtttg gtatggcttc   7200

attcagctcc ggttcccaac gatcaaggcg agttacatga tcccccatgt tgtgaaaaaa   7260

agcggttagc tccttcggtc ctccgatcgt tgtcagaagt aagttggccg cagtgttatc   7320

actcatggtt atggcagcac tgcataattc tcttactgtc atgccatccg taagatgctt   7380

ttctgtgact ggtgagtact caaccaagtc attctgagaa tagtgtatgc ggcgaccgag   7440

ttgctcttgc ccggcgtcaa tacgggataa taccgcgcca catagcagaa ctttaaaagt   7500

gctcatcatt ggaaaacgtt cttcggggcg aaaactctca aggatcttac cgctgttgag   7560

atccagttcg atgtaaccca ctcgtgcacc caactgatct tcagcatctt ttactttcac   7620

cagcgtttct gggtgagcaa aaacaggaag gcaaaatgcc gcaaaaaagg gaataagggc   7680

gacacggaaa tgttgaatac tcatactctt cctttttcaa tattattgaa gcatttatca   7740

gggttattgt ctcatgagcg gatacatatt tgaatgtatt tagaaaaata aacaaatagg   7800

ggttccgcgc acatttcccc gaaaagtgcc acctgacgtc taagaaacca ttattatcat   7860

gacattaacc tataaaaata ggcgtatcac gaggcccttt cgtc                    7904
```

<210> SEQ ID NO 21
<211> LENGTH: 6773
<212> TYPE: DNA
<213> ORGANISM: Artificial Sequence
<220> FEATURE:
<223> OTHER INFORMATION: Codon Optimized

<400> SEQUENCE: 21

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accacgcttt tcaattcaat tcatcatttt tttttattc ttttttttga tttcggtttc    240

tttgaaattt ttttgattcg gtaatctccg aacagaagga agaacgaagg aaggagcaca    300

gacttagatt ggtatatata cgcatatgta gtgttgaaga aacatgaaat tgcccagtat    360

tcttaaccca actgcacaga acaaaaacct gcaggaaacg aagataaatc atgtcgaaag    420

ctacatataa ggaacgtgct gctactcatc ctagtcctgt tgctgccaag ctatttaata    480

tcatgcacga aaagcaaaca aacttgtgtg cttcattgga tgttcgtacc accaaggaat    540

tactggagtt agttgaagca ttaggtccca aaatttgttt actaaaaaca catgtggata    600

tcttgactga tttttccatg gagggcacag ttaagccgct aaaggcatta tccgccaagt    660

acaatttttt actcttcgaa gacagaaaat ttgctgacat tggtaataca gtcaaattgc    720

agtactctgc gggtgtatac agaatagcag aatgggcaga cattacgaat gcacacggtg    780

tggtgggccc aggtattgtt agcggtttga agcaggcggc agaagaagta acaaaggaac    840
```

-continued

```
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aatttttgtt aaatcagctc atttttaac caataggccg aaatcggcaa aatcccttat    1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcacaagtt tgtacaaaaa agctgaacga gaaacgtaaa   2520
atgatataaa tatcaatata ttaaattaga ttttgcataa aaaacagact acataatact   2580
gtaaaacaca acatatccag tcactatggc ggccgcatta ggcaccccag gctttacact   2640
ttatgcttcc ggctcgtata atgtgtggat tttgagttag gatccgtcga gattttcagg   2700
agctaaggaa gctaaaatgg agaaaaaaat cactggatat accaccgttg atatatccca   2760
atggcatcgt aaagaacatt ttgaggcatt tcagtcagtt gctcaatgta cctataacca   2820
gaccgttcag ctggatatta cggccttttt aaagaccgta aagaaaaata agcacaagtt   2880
ttatccggcc tttattcaca ttcttgcccg cctgatgaat gctcatccgg aattccgtat   2940
ggcaatgaaa gacggtgagc tggtgatatg ggatagtgtt cacccttgtt acaccgtttt   3000
ccatgagcaa actgaaacgt tttcatcgct ctggagtgaa taccacgacg atttccggca   3060
gtttctacac atatattcgc aagatgtggc gtgttacggt gaaaacctgg cctatttccc   3120
taaagggttt attgagaata tgtttttcgt ctcagccaat ccctgggtga gtttcaccag   3180
```

-continued

```
ttttgattta aacgtggcca atatggacaa cttcttcgcc cccgttttca ccatgggcaa   3240
atattatacg caaggcgaca aggtgctgat gccgctggcg attcaggttc atcatgccgt   3300
ctgtgatggc ttccatgtcg gcagaatgct taatgaatta caacagtact gcgatgagtg   3360
gcagggcggg gcgtaaacgc cgcgtggatc cggcttacta aaagccagat aacagtatgc   3420
gtatttgcgc gctgattttt gcggtataag aatatatact gatatgtata cccgaagtat   3480
gtcaaaaaga ggtatgctat gaagcagcgt attacagtga cagttgacag cgacagctat   3540
cagttgctca aggcatatat gatgtcaata tctccggtct ggtaagcaca accatgcaga   3600
atgaagcccg tcgtctgcgt gccgaacgct ggaaagcgga aaatcaggaa gggatggctg   3660
aggtcgcccg gtttattgaa atgaacggct cttttgctga cgagaacagg ggctggtgaa   3720
atgcagttta aggtttacac ctataaaaga gagagccgtt atcgtctgtt tgtggatgta   3780
cagagtgata ttattgacac gcccgggcga cggatggtga tccccctggc cagtgcacgt   3840
ctgctgtcag ataaagtctc ccgtgaactt tacccggtgg tgcatatcgg ggatgaaagc   3900
tggcgcatga tgaccaccga tatggccagt gtgccggtct ccgttatcgg ggaagaagtg   3960
gctgatctca gccaccgcga aaatgacatc aaaaacgcca ttaacctgat gttctgggga   4020
atataaatgt caggctccct tatacacagc cagtctgcag gtcgaccata gtgactggat   4080
atgttgtgtt ttacagtatt atgtagtctg tttttttatgc aaaatctaat ttaatatatt   4140
gatatttata tcattttacg tttctcgttc agctttcttg tacaaagtgg tgatgggctg   4200
caggaattcg atatcaagct tatcgatacc gtcgacctcg agtcatgtaa ttagttatgt   4260
cacgcttaca ttcacgccct ccccccacat ccgctctaac cgaaaaggaa ggagttagac   4320
aacctgaagt ctaggtccct atttattttt ttatagttat gttagtatta agaacgttat   4380
ttatatttca aatttttctt ttttttctgt acagacgcgt gtacgcatgt aacattatac   4440
tgaaaacctt gcttgagaag gttttgggac gctcgaaggc tttaatttgc ggccggtacc   4500
cagcttttgt tccctttagt gagggttaat tccgagcttg gcgtaatcat ggtcatagct   4560
gtttcctgtg tgaaattgtt atccgctcac aattccacac aacataggag ccggaagcat   4620
aaagtgtaaa gcctggggtg cctaatgagt gaggtaactc acattaattg cgttgcgctc   4680
actgcccgct ttccagtcgg gaaacctgtc gtgccagctg cattaatgaa tcggccaacg   4740
cgcggggaga ggcggtttgc gtattgggcg ctcttccgct tcctcgctca ctgactcgct   4800
gcgctcggtc gttcggctgc ggcgagcggt atcagctcac tcaaaggcgg taatacggtt   4860
atccacagaa tcaggggata acgcaggaaa gaacatgtga gcaaaaggcc agcaaaaggc   4920
caggaaccgt aaaaaggccg cgttgctggc gtttttccat aggctcggcc cccctgacga   4980
gcatcacaaa aatcgacgct caagtcagag gtggcgaaac ccgacaggac tataaagata   5040
ccaggcgttc ccccctggaa gctccctcgt gcgctctcct gttccgaccc tgccgcttac   5100
cggatacctg tccgcctttc tcccttcggg aagcgtggcg ctttctcaat gctcacgctg   5160
taggtatctc agttcggtgt aggtcgttcg ctccaagctg ggctgtgtgc acgaaccccc   5220
cgttcagccc gaccgctgcg ccttatccgg taactatcgt cttgagtcca acccggtaag   5280
acacgactta tcgccactgg cagcagccac tggtaacagg attagcagag cgaggtatgt   5340
aggcggtgct acagagttct tgaagtggtg gcctaactac ggctacacta gaaggacagt   5400
atttggtatc tgcgctctgc tgaagccagt taccttcgga aaaagagttg gtagctcttg   5460
atccggcaaa caaaccaccg ctggtagcgg tggttttttt gtttgcaagc agcagattac   5520
gcgcagaaaa aaaggatctc aagaagatcc tttgatcttt tctacggggt ctgacgctca   5580
```

gtggaacgaa aactcacgtt aagggatttt ggtcatgaga ttatcaaaaa ggatcttcac 5640
ctagatcctt ttaaattaaa aatgaagttt taaatcaatc taaagtatat atgagtaaac 5700
ttggtctgac agttaccaat gcttaatcag tgaggcacct atctcagcga tctgtctatt 5760
tcgttcatcc atagttgcct gactgcccgt cgtgtagata actacgatac gggagggctt 5820
accatctggc cccagtgctg caatgatacc gcgagaccca cgctcaccgg ctccagattt 5880
atcagcaata aaccagccag ccggaagggc cgagcgcaga agtggtcctg caactttatc 5940
cgcctccatc cagtctatta attgttgccg ggaagctaga gtaagtagtt cgccagttaa 6000
tagtttgcgc aacgttgttg ccattgctac aggcatcgtg gtgtcacgct cgtcgtttgg 6060
tatggcttca ttcagctccg gttcccaacg atcaaggcga gttacatgat cccccatgtt 6120
gtgaaaaaaa gcggttagct ccttcggtcc tccgatcgtt gtcagaagta agttggccgc 6180
agtgttatca ctcatggtta tggcagcact gcataattct cttactgtca tgccatccgt 6240
aagatgcttt tctgtgactg gtgagtactc aaccaagtca ttctgagaat agtgtatgcg 6300
gcgaccgagt tgctcttgcc cggcgtcaat acgggataat accgcgccac atagcagaac 6360
tttaaaagtg ctcatcattg gaaaacgttc ttcggggcga aaactctcaa ggatcttacc 6420
gctgttgaga tccagttcga tgtaacccac tcgtgcaccc aactgatctt cagcatcttt 6480
tactttcacc agcgtttctg ggtgagcaaa aacaggaagg caaaatgccg caaaaaaggg 6540
aataagggcg acacggaaat gttgaatact catactcttc ctttttcaat attattgaag 6600
catttatcag ggttattgtc tcatgagcgg atacatattt gaatgtattt agaaaaataa 6660
acaaataggg gttccgcgca catttccccg aaaagtgcca cctgacgtct aagaaaccat 6720
tattatcatg acattaacct ataaaaatag gcgtatcacg aggccctttc gtc 6773

<210> SEQ ID NO 22
<211> LENGTH: 7690
<212> TYPE: DNA
<213> ORGANISM: Artificial Sequence
<220> FEATURE:
<223> OTHER INFORMATION: Codon Optimized

<400> SEQUENCE: 22
ttatcatgac attaacctat aaaaataggc gtatcacgag gccctttcgt ctcgcgcgtt 60
tcggtgatga cggtgaaaac ctctgacaca tgcagctccc ggagacggtc acagcttgtc 120
tgtaagcgga tgccgggagc agacaagccc gtcagggcgc gtcagcgggt gttggcgggt 180
gtcggggctg gcttaactat gcggcatcag agcagattgt actgagagtg caccacgctt 240
ttcaattcaa ttcatcattt ttttttattc ttttttttg atttcggttt ctttgaaatt 300
tttttgattc ggtaatctcc gaacagaagg aagaacgaag gaaggagcac agacttagat 360
tggtatatat acgcatatgt agtgttgaag aaacatgaaa ttgcccagta ttcttaaccc 420
aactgcacag aacaaaaacc tgcaggaaac gaagataaat catgtcgaaa gctacatata 480
aggaacgtgc tgctactcat cctagtcctg ttgctgccaa gctatttaat atcatgcacg 540
aaaagcaaac aaacttgtgt gcttcattgg atgttcgtac caccaaggaa ttactggagt 600
tagttgaagc attaggtccc aaaatttgtt tactaaaaac acatgtggat atcttgactg 660
atttttccat ggagggcaca gttaagccgc taaaggcatt atccgccaag tacaattttt 720
tactcttcga agacagaaaa tttgctgaca ttggtaatac agtcaaattg cagtactctg 780
cgggtgtata cagaatagca gaatgggcag acattacgaa tgcacacggt gtggtgggcc 840

-continued

```
caggtattgt tagcggtttg aagcaggcgg cagaagaagt aacaaaggaa cctagaggcc    900
ttttgatgtt agcagaattg tcatgcaagg gctccctatc tactggagaa tatactaagg    960
gtactgttga cattgcgaag agcgacaaag attttgttat cggctttatt gctcaaagag   1020
acatgggtgg aagagatgaa ggttacgatt ggttgattat gacacccggt gtgggtttag   1080
atgacaaggg agacgcattg ggtcaacagt atagaaccgt ggatgatgtg gtctctacag   1140
gatctgacat tattattgtt ggaagaggac tatttgcaaa gggaagggat gctaaggtag   1200
agggtgaacg ttacagaaaa gcaggctggg aagcatattt gagaagatgc ggccagcaaa   1260
actaaaaaac tgtattataa gtaaatgcat gtatactaaa ctcacaaatt agagcttcaa   1320
tttaattata tcagttatta ccctgcggtg tgaaataccg cacagatgcg taaggagaaa   1380
ataccgcatc aggaaattgt aaacgttaat attttgttaa aattcgcgtt aaatttttgt   1440
taaatcagct catttttaa ccaataggcc gaaatcggca aaatccctta taaatcaaaa    1500
gaatagaccg agatagggtt gagtgttgtt ccagtttgga acaagagtcc actattaaag   1560
aacgtggact ccaacgtcaa agggcgaaaa accgtctatc agggcgatgg cccactacgt   1620
gaaccatcac cctaatcaag ttttttgggg tcgaggtgcc gtaaagcact aaatcggaac   1680
cctaaaggga gcccccgatt tagagcttga cggggaaagc cggcgaacgt ggcgagaaag   1740
gaagggaaga aagcgaaagg agcgggcgct agggcgctgg caagtgtagc ggtcacgctg   1800
cgcgtaacca ccacacccgc cgcgcttaat gcgccgctac agggcgcgtc gcgccattcg   1860
ccattcaggc tgcgcaactg ttgggaaggg cgatcggtgc gggcctcttc gctattacgc   1920
cagctggcga aggggggatg tgctgcaagg cgattaagtt gggtaacgcc agggttttcc   1980
cagtcacgac gttgtaaaac gacggccagt gaattgtaat acgactcact atagggcgaa   2040
ttggagctct agtacggatt agaagccgcc gagcgggcga cagccctccg acggaagact   2100
ctcctccgtg cgtcctcgtc ttcaccggtc gcgttcctga aacgcagatg tgcctcgcgc   2160
cgcactgctc cgaacaataa agattctaca atactagctt ttatggttat gaagaggaaa   2220
aattggcagt aacctggccc cacaaacctt caaattaacg aatcaaatta acaaccatag   2280
gatgataatg cgattagttt tttagcctta tttctggggt aattaatcag cgaagcgatg   2340
atttttgatc tattaacaga tatataaatg gaaaagctgc ataaccactt taactaatac   2400
tttcaacatt ttcagtttgt attacttctt attcaaatgt cataaaagta tcaacaaaaa   2460
attgttaata tacctctata ctttaacgtc aaggagaaaa aaccccggat tctagaacta   2520
gtggatcccc catcatggtt tccaatcact tgtttgacgc aatgagagcc gctgcccctg   2580
gtaacgcccc tttcataaga atagataata ctagaacttg gacatacgat gacgcctttg   2640
ctttatctgg tagaatagca tcagctatgg atgctttggg tatcagacca ggtgacagag   2700
tcgcagttca agtagaaaaa tccgctgaag cattgatctt gtatttggct tgtttgagaa   2760
gtggtgcagt ttatttgcca ttgaatactg cctacacatt agctgaattg gattacttca   2820
taggtgacgc agaacctaga ttggttgtag tcgcctcttc agccagagct ggtgtagaaa   2880
caattgctaa accaagaggt gcaatagtcg aaaccttaga tgctgctggt tctggtagtt   2940
tgttagattt ggccagagac gaacctgctg attttgttga cgcttcaaga tcagccgatg   3000
acttagccgc tattttgtac acctctggta ctacaggtag atcaaagggt gctatgttga   3060
ctcatggtaa tttgttgtca aacgcattaa ccttgagaga tttctggaga gttactgccg   3120
gtgacagatt aatccacgct ttgccaattt ttcatactca cggtttattc gttgctacca   3180
acgtaacttt gttagcaggt gcctccatgt tcttgttgag taagttcgat ccagaagaaa   3240
```

-continued

```
tattatcttt gatgcctcaa gctactatgt tgatgggtgt cccaacattc tacgttagat   3300
tgttacaatc acctagatta gataagcaag ctgttgcaaa catcagattg tttatatccg   3360
gtagtgctcc attgttagca gaaacccata ctgaatttca agcaagaaca ggtcacgcca   3420
ttttagaaag atacggtatg acagaaacca atatgaacac ttctaaccct tatgaaggta   3480
aaagaatagc tggtacagtt ggttttccat tgcctgatgt cacagttaga gtaaccgacc   3540
cagccactgg tttagctttg ccacctgaac aaactggtat gatcgaaatt aaaggtccaa   3600
acgtttttaa gggttactgg agaatgcctg aaaagactgc tgctgagttt actgctgatg   3660
gtttctttat ctctggtgac ttaggtaaaa ttgatagaga cggttatgtc catattgttg   3720
gtcgtggtaa agatttggtt atatccggtg gttataacat ctaccctaag gaagtagaag   3780
gtgaaataga tcaaatcgaa ggtgttgtag aatcagctgt aataggtgtc ccacatcctg   3840
attttggtga aggtgttaca gcagtcgttg taagaaaacc aggtgctgca ttagatgaaa   3900
aggcaattgt ttctgcctta caagacagat tggctagata caagcaacca aagagaataa   3960
tcttcgcaga agatttgcct agaaatacta tgggtaaagt acaaaagaac atcttgagac   4020
aacaatacgc cgacttatac accagaaccg aaggtagagg ttctttgtta acatgtggtg   4080
acgttgaaga aaatccaggt cctatggctt cagaaaagga aataagaaga gaaagattct   4140
tgaacgtatt cccaaagtta gttgaagaat tgaacgctag tttgttagct tatggtatgc   4200
ctaaagaagc ctgcgattgg tatgctcact ctttaaacta caatactcca ggtggtaaat   4260
tgaatagagg tttgagtgta gttgatactt atgctatctt gtctaacaaa accgttgaac   4320
aattaggtca agaagaatac gaaaaggtcg ctatcttggg ttggtgtatt gaattgttgc   4380
aagcatactt tttggttgcc gatgacatga tggataagtc tataacaaga agaggtcaac   4440
catgctggta caaagttcca gaagttggtg aaatagccat aaatgatgct tttatgttgg   4500
aagccgctat ctataaattg ttgaagtcac atttcagaaa cgaaaagtac tacatcgata   4560
ttaccgaatt attccacgaa gttactttcc aaacagaatt gggtcaattg atggatttga   4620
taactgcacc tgaagataaa gttgacttgt caaagttttc cttgaagaaa cattcattca   4680
tcgtcacctt tgaaactgct tattactcct tctatttgcc agtcgccttg gctatgtacg   4740
tagctggtat tactgatgaa aaagacttga agcaagcaag agatgttttg atacctttgg   4800
gtgaatactt ccaaatccaa gatgactact tagactgttt cggtactcca gaacaaatag   4860
gtaaaatcgg tacagatatt caagacaata agtgcagttg ggttattaac aaggctttgg   4920
aattagcatc tgccgaacaa agaaagactt tggatgaaaa ctacggtaaa aaggactcag   4980
ttgctgaagc aaagtgtaag aaaattttta atgatttgaa gattgaacaa ttgtaccatg   5040
aatacgaaga atccatcgct aaagacttaa aggcaaagat tagtcaagtt gatgaatcaa   5100
gaggttttaa agccgacgtt ttgacagctt tcttgaataa ggtctacaag agatcaaagt   5160
gatgggctgc aggaattcga tatcaagctt atcgataccg tcgacctcga gtcatgtaat   5220
tagttatgtc acgcttacat tcacgccctc cccccacatc cgctctaacc gaaaaggaag   5280
gagttagaca acctgaagtc taggtcccta tttatttttt tatagttatg ttagtattaa   5340
gaacgttatt tatatttcaa atttttcttt tttttctgta cagacgcgtg tacgcatgta   5400
acattatact gaaaaccttg cttgagaagg ttttgggacg ctcgaaggct ttaatttgcg   5460
gccggtaccc agcttttgtt ccctttagtg agggttaatt ccgagcttgg cgtaatcatg   5520
gtcatagctg tttcctgtgt gaaattgtta tccgctcaca attccacaca acataggagc   5580
```

```
cggaagcata aagtgtaaag cctggggtgc ctaatgagtg aggtaactca cattaattgc   5640
gttgcgctca ctgcccgctt tccagtcggg aaacctgtcg tgccagctgc attaatgaat   5700
cggccaacgc gcggggagag gcggtttgcg tattgggcgc tcttccgctt cctcgctcac   5760
tgactcgctg cgctcggtcg ttcggctgcg gcgagcggta tcagctcact caaaggcggt   5820
aatacggtta tccacagaat caggggataa cgcaggaaag aacatgtgag caaaaggcca   5880
gcaaaaggcc aggaaccgta aaaaggccgc gttgctggcg tttttccata ggctcggccc   5940
ccctgacgag catcacaaaa atcgacgctc aagtcagagg tggcgaaacc cgacaggact   6000
ataaagatac caggcgttcc cccctggaag ctccctcgtg cgctctcctg ttccgaccct   6060
gccgcttacc ggatacctgt ccgcctttct cccttcggga agcgtggcgc tttctcaatg   6120
ctcacgctgt aggtatctca gttcggtgta ggtcgttcgc tccaagctgg gctgtgtgca   6180
cgaacccccc gttcagcccg accgctgcgc cttatccggt aactatcgtc ttgagtccaa   6240
cccggtaaga cacgacttat cgccactggc agcagccact ggtaacagga ttagcagagc   6300
gaggtatgta ggcggtgcta cagagttctt gaagtggtgg cctaactacg gctacactag   6360
aaggacagta tttggtatct gcgctctgct gaagccagtt accttcggaa aaagagttgg   6420
tagctcttga tccggcaaac aaaccaccgc tggtagcggt ggtttttttg tttgcaagca   6480
gcagattacg cgcagaaaaa aaggatctca agaagatcct ttgatctttt ctacggggtc   6540
tgacgctcag tggaacgaaa actcacgtta agggattttg gtcatgagat tatcaaaaag   6600
gatcttcacc tagatccttt taaattaaaa atgaagtttt aaatcaatct aaagtatata   6660
tgagtaaact tggtctgaca gttaccaatg cttaatcagt gaggcaccta tctcagcgat   6720
ctgtctattt cgttcatcca tagttgcctg actgcccgtc gtgtagataa ctacgatacg   6780
ggagggctta ccatctggcc ccagtgctgc aatgataccg cgagacccac gctcaccggc   6840
tccagattta tcagcaataa accagccagc cggaagggcc gagcgcagaa gtggtcctgc   6900
aactttatcc gcctccatcc agtctattaa ttgttgccgg gaagctagag taagtagttc   6960
gccagttaat agtttgcgca acgttgttgc cattgctaca ggcatcgtgg tgtcacgctc   7020
gtcgtttggt atggcttcat tcagctccgg ttcccaacga tcaaggcgag ttacatgatc   7080
ccccatgttg tgaaaaaaag cggttagctc cttcggtcct ccgatcgttg tcagaagtaa   7140
gttggccgca gtgttatcac tcatggttat ggcagcactg cataattctc ttactgtcat   7200
gccatccgta agatgctttt ctgtgactgg tgagtactca accaagtcat tctgagaata   7260
gtgtatgcgg cgaccgagtt gctcttgccc ggcgtcaata cgggataata ccgcgccaca   7320
tagcagaact ttaaaagtgc tcatcattgg aaaacgttct tcggggcgaa aactctcaag   7380
gatcttaccg ctgttgagat ccagttcgat gtaacccact cgtgcaccca actgatcttc   7440
agcatctttt actttcacca gcgtttctgg gtgagcaaaa acaggaaggc aaaatgccgc   7500
aaaaaaggga ataagggcga cacggaaatg ttgaatactc atactcttcc tttttcaata   7560
ttattgaagc atttatcagg gttattgtct catgagcgga tacatatttg aatgtattta   7620
gaaaaataaa caaatagggg ttccgcgcac atttccccga aaagtgccac ctgacgtcta   7680
agaaaccatt                                                          7690
```

<210> SEQ ID NO 23
<211> LENGTH: 2163
<212> TYPE: DNA
<213> ORGANISM: Artificial Sequence
<220> FEATURE:
<223> OTHER INFORMATION: Codon Optimized

<400> SEQUENCE: 23
atgggtaaaa actataagtc cttggattca gtcgttgcct cagatttcat cgcattgggt 60
atcacctcag aagtagcaga aacattacat ggtagattgg cagaaatcgt ttgtaattat 120
ggtgctgcaa cccctcaaac ttggatcaac atcgctaacc atatcttgtc accagatttg 180
cctttctcct tacaccaaat gttgttttat ggttgctaca aggatttcgg tccagcccca 240
cctgcttgga ttccagaccc tgaaaaagtc aagtcaacta atttgggtgc tttgttggaa 300
aagagaggta aagaattttt gggtgtaaag tacaaagatc caatttcttc tttttctcac 360
ttccaagaat tttctgttag aaaccctgaa gtctattgga gaacagtatt gatggatgaa 420
atgaaaatta gtttctctaa ggacccagaa tgtatcttga gaagagatga catcaacaac 480
ccaggtggtt ctgaatggtt acctggtggt tacttgaact cagctaaaaa ttgcttgaac 540
gtaaactcca ataagaaatt gaacgatact atgatcgttt ggagagacga gggtaacgat 600
gacttgcctt tgaataagtt gacattagat caattgagaa agagagtttg gttggttggt 660
tatgcattgg aagaaatggg tttagaaaaa ggttgtgcaa tagccatcga tatgccaatg 720
catgttgatg ctgttgttat atatttggcc atagtattgg ctggttacgt agttgtctct 780
atagcagatt cattttccgc ccctgaaatc tcaactagat tgagattatc caaagctaag 840
gcaattttca cacaagatca catcatcaga ggtaaaaaga gaataccatt gtattcaaga 900
gtagttgaag ctaaatcccc aatggcaata gttatccctt gtagtggttc taacattggt 960
gcagaattga gagatggtga catatcttgg gattactttt tagaaagagc caaggagttt 1020
aaaaactgcg agtttactgc cagagaacaa cctgttgatg cttatactaa catcttattc 1080
tccagtggta ctacaggtga accaaaagca attccttgga cacaagccac cccattgaag 1140
gctgctgctg atggttggtc tcatttggat attagaaaag gtgacgttat agtatggcca 1200
actaatttgg gttggatgat gggtccttgg ttggtttatg ctagtttgtt aaatggtgca 1260
tctattgcct tgtacaacgg tagtccttta gtctctggtt tcgctaaatt tgttcaagat 1320
gcaaaggtca caatgttggg tgtcgtacca tctattgtaa gatcatggaa atccacaaat 1380
tgtgtttcag gttacgattg gtccaccata agatgctttt cttcatccgg tgaagcctct 1440
aatgtagacg aatatttgtg gttaatgggt agagctaact acaagccagt tatagaaatg 1500
tgtggtggta cagaaatcgg tggtgctttt tctgctggtt catttttgca agctcaatct 1560
ttaagttctt tttcatccca atgtatgggt tgcaccttgt acatattaga taagaacggt 1620
tacccaatgc ctaaaaataa gccaggtatc ggtgaattgg cattaggtcc tgttatgttt 1680
ggtgcctcaa aacattgtt aaacggtaat catcacgatg tctatttcaa gggtatgcca 1740
accttgaatg gtgaagtatt gagaagacat ggtgacattt tcgaattgac ctctaacggt 1800
tactaccatg cacacggtag agccgatgac actatgaaca tcggtggtat caaaattagt 1860
tctatcgaaa tcgaaagagt ctgtaatgaa gtagatgaca gagtttttga aaccactgct 1920
attggtgttc cacctttggg tggtggtcca gaacaattgg tcatattttt cgtattgaag 1980
gattcaaacg acacaaccat tgatttgaac caattgagat tatcctttaa cttgggtttg 2040
caaaagaaat tgaacccatt attcaaagtt actagagttg tcccattgtc atccttacct 2100
agaactgcaa caaacaagat catgagaaga gttttgagac aacaattcag tcatttcgaa 2160
tga 2163

<210> SEQ ID NO 24

<211> LENGTH: 1059
<212> TYPE: DNA
<213> ORGANISM: Artificial Sequence
<220> FEATURE:
<223> OTHER INFORMATION: Codon Optimized

<400> SEQUENCE: 24
atggcttcag aaaaggaaat aagaagagaa agattcttga acgtattccc aaagttagtt 60
gaagaattga acgctagttt gttagcttat ggtatgccta aagaagcctg cgattggtat 120
gctcactctt taaactacaa tactccaggt ggtaaattga atagaggttt gagtgtagtt 180
gatacttatg ctatcttgtc taacaaaacc gttgaacaat taggtcaaga agaatacgaa 240
aaggtcgcta tcttgggttg gtgtattgaa ttgttgcaag catacttttt ggttgccgat 300
gacatgatgg ataagtctat aacaagaaga ggtcaaccat gctggtacaa agttccagaa 360
gttggtgaaa tagccataaa tgatgctttt atgttggaag ccgctatcta taaattgttg 420
aagtcacatt tcagaaacga aaagtactac atcgatatta ccgaattatt ccacgaagtt 480
actttccaaa cagaattggg tcaattgatg gatttgataa ctgcacctga agataaagtt 540
gacttgtcaa agttttcctt gaagaaacat tcattcatcg tcacctttga aactgcttat 600
tactccttct atttgccagt cgccttggct atgtacgtag ctggtattac tgatgaaaaa 660
gacttgaagc aagcaagaga tgttttgata cctttgggtg aatacttcca aatccaagat 720
gactacttag actgtttcgg tactccagaa caaataggta aaatcggtac agatattcaa 780
gacaataagt gcagttgggt tattaacaag gctttggaat tagcatctgc cgaacaaaga 840
aagactttgg atgaaaacta cggtaaaaag gactcagttg ctgaagcaaa gtgtaagaaa 900
atttttaatg atttgaagat tgaacaattg taccatgaat acgaagaatc catcgctaaa 960
gacttaaagg caaagattag tcaagttgat gaatcaagag gttttaaagc cgacgttttg 1020
acagctttct tgaataaggt ctacaagaga tcaaagtag 1059

<210> SEQ ID NO 25
<211> LENGTH: 1158
<212> TYPE: DNA
<213> ORGANISM: Artificial Sequence
<220> FEATURE:
<223> OTHER INFORMATION: Codon Optimized

<400> SEQUENCE: 25
atgaaccatt tgagagccga aggtcctgcc tccgtattag ccataggtac agccaaccca 60
gaaaacatat tgatccaaga tgaatttcct gattattact tcagagttac caagagtgaa 120
cacatgactc aattgaagga aaagtttaga aaaatatgtg ataagtctat gatcagaaag 180
agaaactgct tcttgaacga agaacatttg aagcaaaatc caagattggt agaacacgaa 240
atgcaaacat tggatgccag acaagacatg ttagttgtcg aagttcctaa attgggtaaa 300
gatgcttgtg caaaagccat taaggaatgg ggtcaaccaa agtcaaagat cactcatttg 360
atttttacaa gtgcatctac tacagatatg cctggtgcag actaccactg tgccaaattg 420
ttaggtttgt caccatccgt taagagagtc atgatgtatc aattaggttg ctacggtggt 480
ggtactgttt tgagaatcgc taaggatatt gcagaaaaca acaagggtgc cagagtatta 540
gctgtttgtt gcgacattat ggcttgcttg tttagaggtc caagtgattc tgacttggaa 600
ttgttagttg gtcaagctat cttcggtgac ggtgctgctg ctgttattgt tggtgcagaa 660
cctgacgaat ctgttggtga aagaccaata tttgaattag tcagtacagg tcaaaccatc 720
ttgcctaatt ctgaaggtac aattggtggt catataagag aagcaggttt gatcttcgat 780
ttgcacaaag acgttccaat gttaatctct aacaacatag aaaagtgttt gatagaagca 840
ttcactccta taggtatctc agattggaac tctattttct ggataacaca tccaggtggt 900
aaagccattt tggataaggt tgaagaaaaa ttggatttga agaaagaaaa gtttgtagat 960
agtagacatg ttttatctga acacggtaac atgtcttcat ccactgtctt gttcgtaatg 1020
gatgaattga gaaagagatc attagaagag ggtaaatcta ctactggtga cggttttgaa 1080
tggggtgtct tatttggttt cggtcctggt ttgaccgtcg aaagagtagt tgtcagatca 1140
gtaccaatta aatattag 1158

<210> SEQ ID NO 26
<211> LENGTH: 315
<212> TYPE: DNA
<213> ORGANISM: Artificial Sequence
<220> FEATURE:
<223> OTHER INFORMATION: Codon Optimized

<400> SEQUENCE: 26
atggccgtca agcatttgat agtattgaag tttaaagatg aaatcacaga agctcaaaag 60
gaagaatttt tcaagaccta cgttaatttg gtcaacatta tacctgctat gaaagatgta 120
tactggggta aagacgttac acaaaagaaa gaagaaggtt atacacacat tgtcgaagta 180
accttcgaat cagttgaaac tatccaagat tacatcattc atccagctca cgttggtttt 240
ggtgacgttt acagatcctt ctgggaaaaa ttgttgatct tcgattacac cccaagaaag 300
ttaaagccaa aataa 315

<210> SEQ ID NO 27
<211> LENGTH: 1188
<212> TYPE: DNA
<213> ORGANISM: Artificial Sequence
<220> FEATURE:
<223> OTHER INFORMATION: Codon Optimized

<400> SEQUENCE: 27
atgggtttat catccgtctg tactttctcc ttccaaacta actatcatac cttattgaat 60
cctcacaaca acaatccaaa aacatcattg ttgtgttaca gacatccaaa gacacctatt 120
aagtactctt acaacaactt tccatcaaaa cattgttcaa ccaagtcctt ccacttacaa 180
aataagtgct ccgaaagttt gtctatagct aagaactcta tcagagctgc aactacaaat 240
caaactgaac cacctgaaag tgataatcac tctgttgcca caaaaatttt gaacttcggt 300
aaagcatgtt ggaagttgca aagaccatac accataatcg cttttacttc ttgtgcatgc 360
ggtttattcg gtaaagaatt gttgcataac actaacttaa tttcatggtc cttgatgttc 420
aaggcatttt tctttttagt tgccatcttg tgcatcgctt cattcaccac tacaattaat 480
caaatatacg atttgcacat cgacagaatt aacaaaccag atttgccttt ggcttcaggt 540
gaaatatccg tcaatactgc atggatcatg tctatcatag tagccttgtt cggtttgatc 600
atcacaatta aaatgaaggg tggtccattg tacatcttcg gttactgttt cggtatcttc 660
ggtggtattg tctattccgt accacctttt agatggaaac aaaaccctag tactgccttt 720
ttgttgaatt tcttagctca tatcatcaca aacttcacct tctactacgc ttcaagagct 780
gctttaggtt tgccattcga attgagacct tcattcacat tttgttggc attcatgaaa 840 agtatgggtt ctgcattagc cttgatcaag gatgcctctg acgttgaagg tgacacaaag 900
ttcggtatta gtaccttggc ttctaagtac ggttcaagaa atttgacttt gttctgctcc 960

-continued

```
ggtatcgttt tgttaagtta cgtcgcagcc attttggcag gtatcatttg gccacaagcc   1020

tttaattcta acgttatgtt gttgtcacat gccatcttgg ctttctggtt gatcttgcaa   1080

actagagatt tcgctttgac aaattatgac cctgaagcag gtagaagatt ctacgagttt   1140

atgtggaaat tgtactacgc tgaatatttg gtatacgttt ttatttag                1188
```

<210> SEQ ID NO 28
<211> LENGTH: 1635
<212> TYPE: DNA
<213> ORGANISM: Artificial Sequence
<220> FEATURE:
<223> OTHER INFORMATION: Codon Optimized

<400> SEQUENCE: 28

```
atgaaatgtt caactttctc cttttggttc gtatgcaaga tcatcttctt tttcttttcc     60

tttaacatcc aaacaagtat cgcaaaccca agagaaaact tttgaagtg cttctcacaa    120

tacataccta ataacgccac caatttgaag ttggtttaca ctcaaaacaa cccattgtac    180

atgtccgtct tgaacagtac aatccataat ttgagattca cttctgatac cactccaaaa    240

cctttggtca ttgtaacccc tagtcatgta tctcacatcc aaggtactat cttatgttct    300

aaaaaggttg gtttgcaaat tagaactaga tccggtggtc atgatagtga aggcatgtca    360

tacatctccc aagttccatt cgttatcgtt gatttgagaa acatgagatc aattaaaata    420

gacgtacact cacaaactgc ttgggttgaa gctggtgcaa cattgggtga agtatactac    480

tgggttaacg aaaagaatga aaacttatca ttggctgctg gttactgtcc aacagtttgc    540

gcaggtggtc attttggtgg tggtggttat ggtcctttaa tgagaaacta cggtttggcc    600

gctgataaca taatcgacgc tcatttggta aatgttcacg gtaaagtttt ggatagaaag    660

tctatgggtg aagacttatt ttgggctttg agaggtggtg gtgcagaatc attcggtatc    720

atagttgctt ggaagataag attagtcgca gtaccaaagt ctactatgtt ctcagtcaaa    780

aagataatgg aaatccatga attagttaaa ttggtcaata agtggcaaaa catcgcatac    840

aagtacgata aggacttgtt gttgatgact catttcatca caagaaacat caccgataac    900

caaggtaaaa ataagactgc tatccacaca tacttttctt cagttttctt gggtggtgtc    960

gattccttag tagacttgat gaataagtct tttccagaat taggtattaa gaaaactgat   1020

tgtagacaat tgtcttggat cgacaccatc atcttttatt caggtgttgt caactacgat   1080

acagacaact tcaacaaaga aatattattg gatagatccg caggtcaaaa cggtgccttt   1140

aaaattaagt tagactacgt taaaaagcca atacctgaat cagttttcgt ccaaatctta   1200

gaaaaattgt acgaagaaga tattggtgca ggcatgtacg ccttgtatcc atacggtggt   1260

ataatggacg aaatcagtga atctgccatt ccatttcctc atagagctgg tatcttatac   1320

gaattgtggt acatttgttc atgggaaaag caagaagata acgaaaagca cttaaactgg   1380

attagaaaca tctataactt catgactcca tacgtttcta aaaaccctag attggcatat   1440

ttgaactaca gagatttgga catcggtatt aacgatccaa agaatcctaa caactatacc   1500

caagctagaa tttggggtga aaaatacttc ggtaaaaatt tcgatagatt agtaaaggtt   1560

aagacattgg ttgacccaaa caacttcttt agaaacgaac aatccattcc acctttacct   1620

agacatagac actga                                                    1635
```

<210> SEQ ID NO 29
<211> LENGTH: 1638
<212> TYPE: DNA
<213> ORGANISM: Artificial Sequence
<220> FEATURE:
<223> OTHER INFORMATION: Codon Optimized

<400> SEQUENCE: 29
atgaactgct ccgcattctc tttctggttc gtctgtaaaa taatcttctt cttcttgtcc 60
ttcaacatcc aaatctccat cgcaaatcca caagaaaact ttttgaagtg tttctccgaa 120
tacatcccaa acaaccctgc taacccaaag tttatatata ctcaacatga tcaattgtac 180
atgtccgttt tgaacagtac catccaaaat ttgagattca cttctgacac tacaccaaaa 240
cctttagtca ttgttacacc ttccaatgtt agtcacattc aagcttctat attgtgctct 300
aagaaagtag gtttgcaaat cagaactaga tcaggtggtc atgatgcaga aggcatgtct 360
tacatctcac aagttccatt cgttgtagtc gatttgagaa atatgcattc cataaagatc 420
gacgttcaca gtcaaacagc atgggtagaa gcaggtgcca ccttgggtga agtttactac 480
tggatcaacg aaaagaatga aaacttttct ttccctggtg gttactgtcc aacagtaggt 540
gtcggtggtc acttttctgg tggtggttat ggtgcattga tgagaaacta cggtttagct 600
gcagataata ttatagacgc ccatttggtt aacgtagatg gtaaagtttt ggacagaaag 660
tctatgggtg aagatttgtt ttgggccata agaggtggtg gtggtgaaaa tttcggtatc 720
attgccgctt ggaaaattaa gttagtcgct gttccttcca aagtactat tttctctgtc 780 aaaaagaaca tggaaatcca cggtttggtt aagttgttta ataagtggca aaacatcgct 840
tacaagtacg ataaggactt ggttttgatg acccatttca tcactaaaaa tattacagat 900
aaccatggta aaaataagac cactgttcac ggttattttt cttcaatttt ccatggtggt 960
gtagattctt tggttgattt gatgaataag tcattcccag aattgggtat taaaaagaca 1020
gattgcaagg aattttcttg gatagacaca accatcttct attcaggtgt tgtaaacttc 1080
aacaccgcta acttcaaaaa ggaaatcttg ttggatagat ccgctggtaa aaagaccgct 1140
ttttctatta aattggacta cgttaagaaa ccaatccctg aaactgcaat ggtcaagata 1200
ttggaaaagt tgtacgaaga agatgtaggt gtcggcatgt acgttttgta tccatacggt 1260
ggtattatgg aagaaatatc tgaatcagcc ataccatttc ctcacagagc tggtatcatg 1320
tatgaattat ggtacacagc ctcatgggaa aagcaagaag ataacgaaaa gcatatcaac 1380
tgggtcagat ccgtttacaa cttcactaca ccttacgtta gtcaaaaccc aagattggca 1440
tatttgaact acagagattt ggacttaggt aaaactaacc ctgaatctcc aaataactat 1500
acacaagcaa gaatttgggg tgaaaagtac tttggtaaaa atttcaacag attagttaaa 1560
gtaaagacta aagccgaccc taacaacttt ttcagaaacg aacaatccat cccacctttg 1620
ccacctcacc accactaa 1638

<210> SEQ ID NO 30
<211> LENGTH: 960
<212> TYPE: DNA
<213> ORGANISM: Artificial Sequence
<220> FEATURE:
<223> OTHER INFORMATION: Codon Optimized

<400> SEQUENCE: 30
atggctaatc aaacagaacc tccagaatct aatacgaaat atagtgtagt taccaaaatc 60
ctaagttttg gccacacttg ttggaaattg cagagaccgt atactttcat tggagtgatt 120
agttgcgcct gtggattgtt cggtagagag ttattccata atactaattt gctatcatgg 180
tctctgatgt tgaaagcttt cagctcattg atggtaatac tgtcagtgaa tctatgtacc 240
aatatcataa accagatcac tgacctggac atagacagaa tcaataagcc ggacttgcca 300
ttggcgagcg gggaaatgtc cattgaaaca gcatggatta tgagtattat agttgcacta 360
actggattga tacttacgat aaagcttaat tgcggccctt tgtttatatc tctatattgt 420
gtcagcatac tagtcggggc actatattca gtaccgccat tcagatggaa gcaaaatccc 480
aataccgcat tctcaagtta ttttatggga ctggtgatcg tcaattttac ctgctattac 540
gcaagcaggg ccgcctttgg actgccattc gagatgtcac ccccgttcac attcattctt 600
gcctttgtca agtcaatggg tagcgcactt tttttgtgta aagatgtctc tgacattgaa 660
ggagattcta agcacggtat atctaccctt gcgacgaggt atggagcaaa aaacattact 720
ttcctttgct caggaatcgt actgctaacc tacgtaagcg cgatattggc tgcgattatt 780
tggccacaag ccttcaagtc caacgtgatg ctgttgagtc acgcaaccct ggccttttgg 840
cttatctttc agactagaga gttcgcgtta actaattaca atccagaggc agggaggaag 900
ttttacgagt tcatgtggaa gctgcactac gctgaatact tagtctatgt atttatatag 960

<210> SEQ ID NO 31
<211> LENGTH: 960
<212> TYPE: DNA
<213> ORGANISM: Artificial Sequence
<220> FEATURE:
<223> OTHER INFORMATION: Codon Optimized

<400> SEQUENCE: 31
atggctaatc aaacagaacc tccagaatct aatacgaaat atagtgtagt taccaaaatc 60
ctaagttttg gccacacttg ttggaaattg cagagaccgt atactttcat tggagtgatt 120
agttgcgcct gtggattgtt cggtagagag ttattccata atactaattt gctatcatgg 180
tctctgatgt tgaaagcttt cagctcattg atggtaatac tgtcagtgaa tctatgtacc 240
aatatcataa accagatcac tgacctggac atagacagaa tcaataagcc ggacttgcca 300
ttggcgagcg gggaaatgtc cattgaaaca gcatggatta tgagtattat agttgcacta 360
actggattga tacttacgat aaagcttaat tgcggccctt tgtttatatc tctatattgt 420
gtcagcatac tagtcggggc actatattca gtaccgccat tcagatggaa gcaaaatccc 480
aataccgcat tctcaagtta ttttatggga ctggtgatcg tcaattttac ctgctattac 540
gcaagcaggg ccgcctttgg actgccattc gagatgtcac ccccgttcac attcattctt 600
gcctttgtca agtcaatggg tagcgcactt tttttgtgta aagatgtctc tgacattgaa 660
ggagattcta agcacggtat atctaccctt gcgacgaggt atggagcaaa aaacattact 720
ttcctttgct caggaatcgt actgctaacc tacgtaagcg cgatattggc tgcgattatt 780
tggccacaag ccttcaagtc caacgtgatg ctgttgagtc acgcaaccct ggccttttgg 840
cttatctttc agactagaga gttcgcgtta actaattaca atccagaggc agggaggaag 900
ttttacgagt tcatgtggaa gctgcactac gctgaatact tagtctatgt atttatatag 960

<210> SEQ ID NO 32
<211> LENGTH: 1023
<212> TYPE: DNA
<213> ORGANISM: Artificial Sequence
<220> FEATURE:
<223> OTHER INFORMATION: Codon Optimized

<400> SEQUENCE: 32
atgagattcc catctatttt cactgctgtt ttgttcgctg cttcttctgc tttggctgct 60
ccagttgcta atcaaacaga acctccagaa tctaatacga aatatagtgt agttaccaaa 120
atcctaagtt ttggccacac ttgttggaaa ttgcagagac cgtatacttt cattggagtg 180
attagttgcg cctgtggatt gttcggtaga gagttattcc ataatactaa tttgctatca 240
tggtctctga tgttgaaagc tttcagctca ttgatggtaa tactgtcagt gaatctatgt 300
accaatatca taaaccagat cactgacctg gacatagaca gaatcaataa gccggacttg 360
ccattggcga gcggggaaat gtccattgaa acagcatgga ttatgagtat tatagttgca 420
ctaactggat tgatacttac gataaagctt aattgcggcc ctttgtttat atctctatat 480
tgtgtcagca tactagtcgg ggcactatat tcagtaccgc cattcagatg gaagcaaaat 540
cccaataccg cattctcaag ttattttatg ggactggtga tcgtcaattt tacctgctat 600
tacgcaagca gggccgcctt tggactgcca ttcgagatgt cacccccgtt cacattcatt 660
cttgcctttg tcaagtcaat gggtagcgca cttttttttgt gtaaagatgt ctctgacatt 720
gaaggagatt ctaagcacgg tatatctacc cttgcgacga ggtatggagc aaaaaacatt 780
actttccttt gctcaggaat cgtactgcta acctacgtaa gcgcgatatt ggctgcgatt 840
atttggccac aagccttcaa gtccaacgtg atgctgttga gtcacgcaac cctggccttt 900
tggcttatct ttcagactag agagttcgcg ttaactaatt acaatccaga ggcagggagg 960
aagttttacg agttcatgtg gaagctgcac tacgctgaat acttagtcta tgtatttata 1020
tag 1023

<210> SEQ ID NO 33
<211> LENGTH: 6025
<212> TYPE: DNA
<213> ORGANISM: Artificial Sequence
<220> FEATURE:
<223> OTHER INFORMATION: Codon Optimized

<400> SEQUENCE: 33
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc tttttttga tttcggtttc 240 tttgaaattt ttttgattcg gtaatctccg aacagaagga agaacgaagg aaggagcaca 300
gacttagatt ggtatatata cgcatatgta gtgttgaaga aacatgaaat tgcccagtat 360
tcttaaccca actgcacaga acaaaaacct gcaggaaacg aagataaatc atgtcgaaag 420
ctacatataa ggaacgtgct gctactcatc ctagtcctgt tgctgccaag ctatttaata 480
tcatgcacga aaagcaaaca aacttgtgtg cttcattgga tgttcgtacc accaaggaat 540
tactggagtt agttgaagca ttaggtccca aaatttgttt actaaaaaca catgtggata 600
tcttgactga tttttccatg gagggcacag ttaagccgct aaaggcatta tccgccaagt 660
acaatttttt actcttcgaa gacagaaaat ttgctgacat tggtaataca gtcaaattgc 720
agtactctgc gggtgtatac agaatagcag aatgggcaga cattacgaat gcacacggtg 780
tggtgggccc aggtattgtt agcggtttga agcaggcggc agaagaagta acaaaggaac 840
ctagaggcct tttgatgtta gcagaattgt catgcaaggg ctccctatct actggagaat 900
atactaaggg tactgttgac attgcgaaga gcgacaaaga ttttgttatc ggctttattg 960
ctcaaagaga catgggtgga agagatgaag gttacgattg gttgattatg acacccggtg 1020
tgggtttaga tgacaaggga gacgcattgg gtcaacagta tagaaccgtg gatgatgtgg 1080

-continued tctctacagg atctgacatt attattgttg gaagaggact atttgcaaag ggaagggatg 1140
ctaaggtaga gggtgaacgt tacagaaaag caggctggga agcatatttg agaagatgcg 1200
gccagcaaaa ctaaaaaact gtattataag taaatgcatg tatactaaac tcacaaatta 1260
gagcttcaat ttaattatat cagttattac cctgcggtgt gaaataccgc acagatgcgt 1320
aaggagaaaa taccgcatca ggaaattgta aacgttaata ttttgttaaa attcgcgtta 1380
aatttttgtt aaatcagctc attttttaac caataggccg aaatcggcaa aatcccttat 1440
aaatcaaaag aatagaccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc ctaatcaagt tttttggggt cgaggtgccg taaagcacta 1620
aatcggaacc ctaaagggag cccccgattt agagcttgac ggggaaagcc ggcgaacgtg 1680
gcgagaaagg aagggaagaa agcgaaagga gcgggcgcta gggcgctggc aagtgtagcg 1740
gtcacgctgc gcgtaaccac cacacccgcc gcgcttaatg cgccgctaca gggcgcgtcg 1800
cgccattcgc cattcaggct gcgcaactgt tgggaagggc gatcggtgcg ggcctcttcg 1860
ctattacgcc agctggcgaa agggggatgt gctgcaaggc gattaagttg ggtaacgcca 1920
gggttttccc agtcacgacg ttgtaaaacg acggccagtg aattgtaata cgactcacta 1980
tagggcgaat tggagctcta gtacggatta gaagccgccg agcgggcgac agccctccga 2040
cggaagactc tcctccgtgc gtcctcgtct tcaccggtcg cgttcctgaa acgcagatgt 2100
gcctcgcgcc gcactgctcc gaacaataaa gattctacaa tactagcttt tatggttatg 2160
aagaggaaaa attggcagta acctggcccc acaaaccttc aaattaacga atcaaattaa 2220
caaccatagg atgataatgc gattagtttt ttagccttat ttctggggta attaatcagc 2280
gaagcgatga tttttgatct attaacagat atataaatgg aaaagctgca taaccacttt 2340
aactaatact ttcaacattt tcagtttgta ttacttctta ttcaaatgtc ataaaagtat 2400
caacaaaaaa ttgttaatat acctctatac tttaacgtca aggagaaaaa accccggatt 2460
ctagaactag tggatccccc atcatggcta atcaaacaga acctccagaa tctaatacga 2520
aatatagtgt agttaccaaa atcctaagtt ttggccacac ttgttggaaa ttgcagagac 2580
cgtatacttt cattggagtg attagttgcg cctgtggatt gttcggtaga gagttattcc 2640
ataatactaa tttgctatca tggtctctga tgttgaaagc tttcagctca ttgatggtaa 2700
tactgtcagt gaatctatgt accaatatca taaaccagat cactgacctg gacatagaca 2760
gaatcaataa gccggacttg ccattggcga gcggggaaat gtccattgaa acagcatgga 2820
ttatgagtat tatagttgca ctaactggat tgatacttac gataaagctt aattgcggcc 2880
ctttgtttat atctctatat tgtgtcagca tactagtcgg ggcactatat tcagtaccgc 2940
cattcagatg gaagcaaaat cccaataccg cattctcaag ttattttatg ggactggtga 3000
tcgtcaattt tacctgctat tacgcaagca gggccgcctt tggactgcca ttcgagatgt 3060
cacccccgtt cacattcatt cttgcctttg tcaagtcaat gggtagcgca cttttttttgt 3120 gtaaagatgt ctctgacatt gaaggagatt ctaagcacgg tatatctacc cttgcgacga 3180
ggtatggagc aaaaaacatt actttccttt gctcaggaat cgtactgcta acctacgtaa 3240
gcgcgatatt ggctgcgatt atttggccac aagccttcaa gtccaacgtg atgctgttga 3300
gtcacgcaac cctggccttt tggcttatct ttcagactag agagttcgcg ttaactaatt 3360
acaatccaga ggcagggagg aagttttacg agttcatgtg gaagctgcac tacgctgaat 3420
acttagtcta tgtatttata taggatgggc tgcaggaatt cgatatcaag cttatcgata 3480

```
ccgtcgacct cgagtcatgt aattagttat gtcacgctta cattcacgcc ctccccccac   3540
atccgctcta accgaaaagg aaggagttag acaacctgaa gtctaggtcc ctatttattt   3600
ttttatagtt atgttagtat taagaacgtt atttatattt caaatttttc ttttttttct   3660
gtacagacgc gtgtacgcat gtaacattat actgaaaacc ttgcttgaga aggttttggg   3720
acgctcgaag gctttaattt gcggccggta cccagctttt gttcccttta gtgagggtta   3780
attccgagct tggcgtaatc atggtcatag ctgtttcctg tgtgaaattg ttatccgctc   3840
acaattccac acaacatagg agccggaagc ataaagtgta aagcctgggg tgcctaatga   3900
gtgaggtaac tcacattaat tgcgttgcgc tcactgcccg ctttccagtc gggaaacctg   3960
tcgtgccagc tgcattaatg aatcggccaa cgcgcgggga gaggcggttt gcgtattggg   4020
cgctcttccg cttcctcgct cactgactcg ctgcgctcgg tcgttcggct gcggcgagcg   4080
gtatcagctc actcaaaggc ggtaatacgg ttatccacag aatcagggga taacgcagga   4140
aagaacatgt gagcaaaagg ccagcaaaag gccaggaacc gtaaaaaggc cgcgttgctg   4200
gcgtttttcc ataggctcgg cccccctgac gagcatcaca aaaatcgacg ctcaagtcag   4260
aggtggcgaa acccgacagg actataaaga taccaggcgt ttccccctgg aagctccctc   4320
gtgcgctctc ctgttccgac cctgccgctt accggatacc tgtccgcctt tctcccttcg   4380
ggaagcgtgg cgctttctca atgctcacgc tgtaggtatc tcagttcggt gtaggtcgtt   4440
cgctccaagc tgggctgtgt gcacgaaccc cccgttcagc ccgaccgctg cgccttatcc   4500
ggtaactatc gtcttgagtc caacccggta agacacgact tatcgccact ggcagcagcc   4560
actggtaaca ggattagcag agcgaggtat gtaggcggtg ctacagagtt cttgaagtgg   4620
tggcctaact acggctacac tagaaggaca gtatttggta tctgcgctct gctgaagcca   4680
gttaccttcg gaaaaagagt tggtagctct tgatccggca aacaaaccac cgctggtagc   4740
ggtggttttt ttgtttgcaa gcagcagatt acgcgcagaa aaaaaggatc tcaagaagat   4800
cctttgatct tttctacggg gtctgacgct cagtggaacg aaaactcacg ttaagggatt   4860
ttggtcatga gattatcaaa aaggatcttc acctagatcc ttttaaatta aaaatgaagt   4920
tttaaatcaa tctaaagtat atatgagtaa acttggtctg acagttacca atgcttaatc   4980
agtgaggcac ctatctcagc gatctgtcta tttcgttcat ccatagttgc ctgactgccc   5040
gtcgtgtaga taactacgat acgggagggc ttaccatctg gccccagtgc tgcaatgata   5100
ccgcgagacc cacgctcacc ggctccagat ttatcagcaa taaaccagcc agccggaagg   5160
gccgagcgca gaagtggtcc tgcaacttta tccgcctcca tccagtctat taattgttgc   5220
cgggaagcta gagtaagtag ttcgccagtt aatagtttgc gcaacgttgt tgccattgct   5280
acaggcatcg tggtgtcacg ctcgtcgttt ggtatggctt cattcagctc cggttcccaa   5340
cgatcaaggc gagttacatg atcccccatg ttgtgaaaaa aagcggttag ctccttcggt   5400
cctccgatcg ttgtcagaag taagttggcc gcagtgttat cactcatggt tatggcagca   5460
ctgcataatt ctcttactgt catgccatcc gtaagatgct tttctgtgac tggtgagtac   5520
tcaaccaagt cattctgaga atagtgtatg cggcgaccga gttgctcttg cccggcgtca   5580
atacgggata ataccgcgcc acatagcaga actttaaaag tgctcatcat tggaaaacgt   5640
tcttcggggc gaaaactctc aaggatctta ccgctgttga gatccagttc gatgtaaccc   5700
actcgtgcac ccaactgatc ttcagcatct tttactttca ccagcgtttc tgggtgagca   5760
aaaacaggaa ggcaaaatgc cgcaaaaaag ggaataaggg cgacacggaa atgttgaata   5820
```

-continued

```
ctcatactct tcctttttca atattattga agcatttatc agggttattg tctcatgagc   5880

ggatacatat ttgaatgtat ttagaaaaat aaacaaatag gggttccgcg cacatttccc   5940

cgaaaagtgc cacctgacgt ctaagaaacc attattatca tgacattaac ctataaaaat   6000

aggcgtatca cgaggccctt tcgtc                                         6025
```

<210> SEQ ID NO 34
<211> LENGTH: 6025
<212> TYPE: DNA
<213> ORGANISM: Artificial Sequence
<220> FEATURE:
<223> OTHER INFORMATION: Codon Optimized

<400> SEQUENCE: 34

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accacgcttt tcaattcaat tcatcatttt tttttattc tttttttga tttcggtttc     240

tttgaaattt ttttgattcg gtaatctccg aacagaagga agaacgaagg aaggagcaca    300

gacttagatt ggtatatata cgcatatgta gtgttgaaga aacatgaaat tgcccagtat    360

tcttaaccca actgcacaga acaaaaacct gcaggaaacg aagataaatc atgtcgaaag    420

ctacatataa ggaacgtgct gctactcatc ctagtcctgt tgctgccaag ctatttaata    480

tcatgcacga aaagcaaaca aacttgtgtg cttcattgga tgttcgtacc accaaggaat    540

tactggagtt agttgaagca ttaggtccca aaatttgttt actaaaaaca catgtggata    600

tcttgactga tttttccatg gagggcacag ttaagccgct aaaggcatta tccgccaagt    660

acaatttttt actcttcgaa gacagaaaat ttgctgacat tggtaataca gtcaaattgc    720

agtactctgc gggtgtatac agaatagcag aatgggcaga cattacgaat gcacacggtg    780

tggtgggccc aggtattgtt agcggtttga agcaggcggc agaagaagta acaaaggaac    840

ctagaggcct tttgatgtta gcagaattgt catgcaaggg ctccctatct actggagaat    900

atactaaggg tactgttgac attgcgaaga gcgacaaaga ttttgttatc ggctttattg    960

ctcaaagaga catgggtgga agagatgaag gttacgattg gttgattatg acacccggtg   1020

tgggtttaga tgacaaggga gacgcattgg gtcaacagta tagaaccgtg gatgatgtgg   1080

tctctacagg atctgacatt attattgttg gaagaggact atttgcaaag ggaagggatg   1140

ctaaggtaga gggtgaacgt tacagaaaag caggctggga agcatatttg agaagatgcg   1200

gccagcaaaa ctaaaaaact gtattataag taaatgcatg tatactaaac tcacaaatta   1260

gagcttcaat ttaattatat cagttattac cctgcggtgt gaaataccgc acagatgcgt   1320

aaggagaaaa taccgcatca ggaaattgta aacgttaata ttttgttaaa attcgcgtta   1380

aatttttgtt aaatcagctc atttttaac caataggccg aaatcggcaa aatcccttat    1440

aaatcaaaag aatagaccga gatagggttg agtgttgttc cagtttggaa caagagtcca   1500

ctattaaaga acgtggactc caacgtcaaa gggcgaaaaa ccgtctatca gggcgatggc   1560

ccactacgtg aaccatcacc ctaatcaagt tttttggggt cgaggtgccg taaagcacta   1620

aatcggaacc ctaaagggag cccccgattt agagcttgac ggggaaagcc ggcgaacgtg   1680

gcgagaaagg aagggaagaa agcgaaagga gcgggcgcta gggcgctggc aagtgtagcg   1740

gtcacgctgc gcgtaaccac cacacccgcc gcgcttaatg cgccgctaca gggcgcgtcg   1800

cgccattcgc cattcaggct gcgcaactgt tgggaagggc gatcggtgcg ggcctcttcg   1860
```

ctattacgcc agctggcgaa gggggggatgt gctgcaaggc gattaagttg ggtaacgcca 1920
gggttttccc agtcacgacg ttgtaaaacg acggccagtg aattgtaata cgactcacta 1980
tagggcgaat tggagctcta gtacggatta gaagccgccg agcgggcgac agccctccga 2040
cggaagactc tcctccgtgc gtcctcgtct tcaccggtcg cgttcctgaa acgcagatgt 2100
gcctcgcgcc gcactgctcc gaacaataaa gattctacaa tactagcttt tatggttatg 2160
aagaggaaaa attggcagta acctggcccc acaaaccttc aaattaacga atcaaattaa 2220
caaccatagg atgataatgc gattagtttt ttagccttat ttctggggta attaatcagc 2280
gaagcgatga tttttgatct attaacagat atataaatgg aaaagctgca taaccacttt 2340
aactaatact ttcaacattt tcagtttgta ttacttctta ttcaaatgtc ataaaagtat 2400
caacaaaaaa ttgttaatat acctctatac tttaacgtca aggagaaaaa accccggatt 2460
ctagaactag tggatccccc atcatggcta atcaaacaga acctccagaa tctaatacga 2520
aatatagtgt agttaccaaa atcctaagtt ttggccacac ttgttggaaa ttgcagagac 2580
cgtatacttt cattggagtg attagttgcg cctgtggatt gttcggtaga gagttattcc 2640
ataatactaa tttgctatca tggtctctga tgttgaaagc tttcagctca ttgatggtaa 2700
tactgtcagt gaatctatgt accaatatca taaaccagat cactgacctg gacatagaca 2760
gaatcaataa gccggacttg ccattggcga gcggggaaat gtccattgaa acagcatgga 2820
ttatgagtat tatagttgca ctaactggat tgatacttac gataaagctt aattgcggcc 2880
ctttgtttat atctctatat tgtgtcagca tactagtcgg ggcactatat tcagtaccgc 2940
cattcagatg gaagcaaaat cccaataccg cattctcaag ttattttatg ggactggtga 3000
tcgtcaattt tacctgctat tacgcaagca gggccgcctt tggactgcca ttcgagatgt 3060
cacccccgtt cacattcatt cttgcctttg tcaagtcaat gggtagcgca cttttttttgt 3120 gtaaagatgt ctctgacatt gaaggagatt ctaagcacgg tatatctacc cttgcgacga 3180
ggtatggagc aaaaaacatt actttccttt gctcaggaat cgtactgcta acctacgtaa 3240
gcgcgatatt ggctgcgatt atttggccac aagccttcaa gtccaacgtg atgctgttga 3300
gtcacgcaac cctggccttt tggcttatct ttcagactag agagttcgcg ttaactaatt 3360
acaatccaga ggcagggagg aagttttacg agttcatgtg gaagctgcac tacgctgaat 3420
acttagtcta tgtatttata taggatgggc tgcaggaatt cgatatcaag cttatcgata 3480
ccgtcgacct cgagtcatgt aattagttat gtcacgctta cattcacgcc ctccccccac 3540
atccgctcta accgaaaagg aaggagttag acaacctgaa gtctaggtcc ctatttattt 3600
ttttatagtt atgttagtat taagaacgtt atttatattt caaatttttc ttttttttct 3660
gtacagacgc gtgtacgcat gtaacattat actgaaaacc ttgcttgaga aggttttggg 3720
acgctcgaag gctttaattt gcggccggta cccagctttt gttcccttta gtgagggtta 3780
attccgagct tggcgtaatc atggtcatag ctgtttcctg tgtgaaattg ttatccgctc 3840
acaattccac acaacatagg agccggaagc ataaagtgta aagcctgggg tgcctaatga 3900
gtgaggtaac tcacattaat tgcgttgcgc tcactgcccg ctttccagtc gggaaacctg 3960
tcgtgccagc tgcattaatg aatcggccaa cgcgcgggga gaggcggttt gcgtattggg 4020
cgctcttccg cttcctcgct cactgactcg ctgcgctcgg tcgttcggct gcggcgagcg 4080
gtatcagctc actcaaaggc ggtaatacgg ttatccacag aatcagggga taacgcagga 4140
aagaacatgt gagcaaaagg ccagcaaaag gccaggaacc gtaaaaaggc cgcgttgctg 4200

-continued

```
gcgtttttcc ataggctcgg ccccccctgac gagcatcaca aaaatcgacg ctcaagtcag   4260

aggtggcgaa acccgacagg actataaaga taccaggcgt tccccccctgg aagctccctc   4320

gtgcgctctc ctgttccgac cctgccgctt accggatacc tgtccgcctt tctcccttcg   4380

ggaagcgtgg cgctttctca atgctcacgc tgtaggtatc tcagttcggt gtaggtcgtt   4440

cgctccaagc tgggctgtgt gcacgaaccc cccgttcagc ccgaccgctg cgccttatcc   4500

ggtaactatc gtcttgagtc caacccggta agacacgact tatcgccact ggcagcagcc   4560

actggtaaca ggattagcag agcgaggtat gtaggcggtg ctacagagtt cttgaagtgg   4620

tggcctaact acggctacac tagaaggaca gtatttggta tctgcgctct gctgaagcca   4680

gttaccttcg gaaaaagagt tggtagctct tgatccggca aacaaaccac cgctggtagc   4740

ggtggttttt ttgtttgcaa gcagcagatt acgcgcagaa aaaaaggatc tcaagaagat   4800

cctttgatct tttctacggg gtctgacgct cagtggaacg aaaactcacg ttaagggatt   4860

ttggtcatga gattatcaaa aaggatcttc acctagatcc ttttaaatta aaaatgaagt   4920

tttaaatcaa tctaaagtat atatgagtaa acttggtctg acagttacca atgcttaatc   4980

agtgaggcac ctatctcagc gatctgtcta tttcgttcat ccatagttgc ctgactgccc   5040

gtcgtgtaga taactacgat acgggagggc ttaccatctg gccccagtgc tgcaatgata   5100

ccgcgagacc cacgctcacc ggctccagat ttatcagcaa taaaccagcc agccggaagg   5160

gccgagcgca gaagtggtcc tgcaacttta tccgcctcca tccagtctat taattgttgc   5220

cgggaagcta gagtaagtag ttcgccagtt aatagtttgc gcaacgttgt tgccattgct   5280

acaggcatcg tggtgtcacg ctcgtcgttt ggtatggctt cattcagctc cggttcccaa   5340

cgatcaaggc gagttacatg atcccccatg ttgtgaaaaa aagcggttag ctccttcggt   5400

cctccgatcg ttgtcagaag taagttggcc gcagtgttat cactcatggt tatggcagca   5460

ctgcataatt ctcttactgt catgccatcc gtaagatgct tttctgtgac tggtgagtac   5520

tcaaccaagt cattctgaga atagtgtatg cggcgaccga gttgctcttg cccggcgtca   5580

atacgggata ataccgcgcc acatagcaga actttaaaag tgctcatcat tggaaaacgt   5640

tcttcggggc gaaaactctc aaggatctta ccgctgttga gatccagttc gatgtaaccc   5700

actcgtgcac ccaactgatc ttcagcatct tttactttca ccagcgtttc tgggtgagca   5760

aaaacaggaa ggcaaaatgc cgcaaaaaag ggaataaggg cgacacggaa atgttgaata   5820

ctcatactct tcctttttca atattattga agcatttatc agggttattg tctcatgagc   5880

ggatacatat ttgaatgtat ttagaaaaat aaacaaatag gggttccgcg cacatttccc   5940

cgaaaagtgc cacctgacgt ctaagaaacc attattatca tgacattaac ctataaaaat   6000

aggcgtatca cgaggccctt tcgtc                                         6025
```

<210> SEQ ID NO 35
<211> LENGTH: 6088
<212> TYPE: DNA
<213> ORGANISM: Artificial Sequence
<220> FEATURE:
<223> OTHER INFORMATION: Codon Optimized

<400> SEQUENCE: 35

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accacgcttt tcaattcaat tcatcatttt tttttattc tttttttga tttcggtttc    240
```

-continued

```
tttgaaattt ttttgattcg gtaatctccg aacagaagga agaacgaagg aaggagcaca    300
gacttagatt ggtatatata cgcatatgta gtgttgaaga aacatgaaat tgcccagtat    360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga tttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aatttttgtt aaatcagctc attttttaac caataggccg aaatcggcaa aatcccttat   1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa gggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatgagat tcccatctat tttcactgct gttttgttcg   2520
ctgcttcttc tgctttggct gctccagttg ctaatcaaac agaacctcca gaatctaata   2580
```

-continued

```
cgaaatatag tgtagttacc aaaatcctaa gttttggcca cacttgttgg aaattgcaga   2640
gaccgtatac tttcattgga gtgattagtt gcgcctgtgg attgttcggt agagagttat   2700
tccataatac taatttgcta tcatggtctc tgatgttgaa agctttcagc tcattgatgg   2760
taatactgtc agtgaatcta tgtaccaata tcataaacca gatcactgac ctggacatag   2820
acagaatcaa taagccggac ttgccattgg cgagcgggga aatgtccatt gaaacagcat   2880
ggattatgag tattatagtt gcactaactg gattgatact tacgataaag cttaattgcg   2940
gccctttgtt tatatctcta tattgtgtca gcatactagt cggggcacta tattcagtac   3000
cgccattcag atggaagcaa aatcccaata ccgcattctc aagttatttt atgggactgg   3060
tgatcgtcaa ttttacctgc tattacgcaa gcagggccgc ctttggactg ccattcgaga   3120
tgtcaccccc gttcacattc attcttgcct ttgtcaagtc aatgggtagc gcactttttt   3180
tgtgtaaaga tgtctctgac attgaaggag attctaagca cggtatatct acccttgcga   3240
cgaggtatgg agcaaaaaac attactttcc tttgctcagg aatcgtactg ctaacctacg   3300
taagcgcgat attggctgcg attatttggc cacaagcctt caagtccaac gtgatgctgt   3360
tgagtcacgc aaccctggcc ttttggctta tctttcagac tagagagttc gcgttaacta   3420
attacaatcc agaggcaggg aggaagtttt acgagttcat gtggaagctg cactacgctg   3480
aatacttagt ctatgtattt atataggatg ggctgcagga attcgatatc aagcttatcg   3540
ataccgtcga cctcgagtca tgtaattagt tatgtcacgc ttacattcac gccctccccc   3600
cacatccgct ctaaccgaaa aggaaggagt tagacaacct gaagtctagg tccctattta   3660
tttttttata gttatgttag tattaagaac gttatttata tttcaaattt ttcttttttt   3720
tctgtacaga cgcgtgtacg catgtaacat tatactgaaa accttgcttg agaaggtttt   3780
gggacgctcg aaggctttaa tttgcggccg gtacccagct tttgttccct ttagtgaggg   3840
ttaattccga gcttggcgta atcatggtca tagctgtttc ctgtgtgaaa ttgttatccg   3900
ctcacaattc cacacaacat aggagccgga agcataaagt gtaaagcctg gggtgcctaa   3960
tgagtgaggt aactcacatt aattgcgttg cgctcactgc ccgctttcca gtcgggaaac   4020
ctgtcgtgcc agctgcatta atgaatcggc caacgcgcgg ggagaggcgg tttgcgtatt   4080
gggcgctctt ccgcttcctc gctcactgac tcgctgcgct cggtcgttcg gctgcggcga   4140
gcggtatcag ctcactcaaa ggcggtaata cggttatcca cagaatcagg ggataacgca   4200
ggaaagaaca tgtgagcaaa aggccagcaa aaggccagga accgtaaaaa ggccgcgttg   4260
ctggcgtttt tccataggct ccgcccccct gacgagcatc acaaaaatcg acgctcaagt   4320
cagaggtggc gaaacccgac aggactataa agataccagg cgtttccccc tggaagctcc   4380
ctcgtgcgct ctcctgttcc gaccctgccg cttaccggat acctgtccgc ctttctccct   4440
tcgggaagcg tggcgctttc tcaatgctca cgctgtaggt atctcagttc ggtgtaggtc   4500
gttcgctcca agctgggctg tgtgcacgaa ccccccgttc agcccgaccg ctgcgcctta   4560
tccggtaact atcgtcttga gtccaacccg gtaagacacg acttatcgcc actggcagca   4620
gccactggta acaggattag cagagcgagg tatgtaggcg gtgctacaga gttcttgaag   4680
tggtggccta actacggcta cactagaagg acagtatttg gtatctgcgc tctgctgaag   4740
ccagttacct tcggaaaaag agttggtagc tcttgatccg gcaaacaaac caccgctggt   4800
agcggtggtt tttttgtttg caagcagcag attacgcgca gaaaaaaagg atctcaagaa   4860
gatcctttga tcttttctac ggggtctgac gctcagtgga acgaaaactc acgttaaggg   4920
attttggtca tgagattatc aaaaaggatc ttcacctaga tccttttaaa ttaaaaatga   4980
```

agttttaaat caatctaaag tatatatgag taaacttggt ctgacagtta ccaatgctta 5040
atcagtgagg cacctatctc agcgatctgt ctatttcgtt catccatagt tgcctgactg 5100
cccgtcgtgt agataactac gatacgggag ggcttaccat ctggccccag tgctgcaatg 5160
ataccgcgag acccacgctc accggctcca gatttatcag caataaacca gccagccgga 5220
agggccgagc gcagaagtgg tcctgcaact ttatccgcct ccatccagtc tattaattgt 5280
tgccgggaag ctagagtaag tagttcgcca gttaatagtt tgcgcaacgt tgttgccatt 5340
gctacaggca tcgtggtgtc acgctcgtcg tttggtatgg cttcattcag ctccggttcc 5400
caacgatcaa ggcgagttac atgatccccc atgttgtgaa aaaaagcggt tagctccttc 5460
ggtcctccga tcgttgtcag aagtaagttg gccgcagtgt tatcactcat ggttatggca 5520
gcactgcata attctcttac tgtcatgcca tccgtaagat gcttttctgt gactggtgag 5580
tactcaacca agtcattctg agaatagtgt atgcggcgac cgagttgctc ttgcccggcg 5640
tcaatacggg ataataccgc gccacatagc agaactttaa aagtgctcat cattggaaaa 5700
cgttcttcgg ggcgaaaact ctcaaggatc ttaccgctgt tgagatccag ttcgatgtaa 5760
cccactcgtg cacccaactg atcttcagca tcttttactt tcaccagcgt ttctgggtga 5820
gcaaaaacag gaaggcaaaa tgccgcaaaa aagggaataa gggcgacacg gaaatgttga 5880
atactcatac tcttcctttt tcaatattat tgaagcattt atcagggtta ttgtctcatg 5940
agcggataca tatttgaatg tatttagaaa aataaacaaa taggggttcc gcgcacattt 6000
ccccgaaaag tgccacctga cgtctaagaa accattatta tcatgacatt aacctataaa 6060
aataggcgta tcacgaggcc ctttcgtc 6088

<210> SEQ ID NO 36
<211> LENGTH: 1197
<212> TYPE: DNA
<213> ORGANISM: Artificial Sequence
<220> FEATURE:
<223> OTHER INFORMATION: Codon Optimized

<400> SEQUENCE: 36
atgggcctta gtctagtttg tacgttttct tttcagacga actaccacac gttgctgaat 60
ccgcacaata agaacccaaa aaactctcta ttgagctatc agcatcctaa gaccccgata 120
ataaagtctt cttacgataa ctttccttct aaatactgtt taacaaagaa ctttcattta 180
ctgggactga actctcataa ccgtataagt agccaatcca ggagcattcg tgcgggctca 240
gatcagattg aaggttcccc ccaccacgaa agtgacaact ccatagcgac caaaattctt 300
aattttgggc acacttgttg gaagttacaa agaccctacg tagtgaaagg tatgatatcc 360
atagcgtgtg gtctgtttgg ccgtgaattg tttaataaca gacacttatt cagttggggg 420
ttaatgtgga aggctttttt tgctctagtt cccatcttga gttttaactt cttcgcggct 480
ataatgaacc aaatctacga cgtcgacatc gacaggatta ataaaccgga tcttccactt 540
gtgtccggag aaatgtccat tgaaacggct tggatcctta gtattattgt tgcccttact 600
ggtcttattg tgaccattaa gctaaaatca gccccacttt ttgtttttat ctatatattt 660
ggcatctttg ccggattcgc gtattcagtt ccccctatcc gttggaaaca ataccccttt 720
acgaacttcc ttataacaat ttcctcccat gttgggttgg ccttcacatc atactcagcg 780
acaacttcag cactaggatt gcccttcgtg tggaggcccg catttagctt tatcattgct 840
tttatgacgg ttatgggcat gacaatagca ttcgccaaag acattagtga tattgaaggt 900

```
gatgcaaaat acggtgtgtc aacggtcgcc actaagttag gagcaagaaa tatgacattc    960

gtggtgtcag gtgttttatt gcttaattat cttgtgtcca ttagcatcgg tataatctgg   1020

cctcaggttt tcaaatcaaa tatcatgatc ctatctcacg caattctagc tttctgcttg   1080

atctttcaga cgagagaatt ggctctagcc aactacgcat cagcacctag taggcagttc   1140

ttcgaattta tttggctatt gtattacgca gagtatttcg tgtatgtgtt catttaa      1197
```

<210> SEQ ID NO 37
<211> LENGTH: 969
<212> TYPE: DNA
<213> ORGANISM: Artificial Sequence
<220> FEATURE:
<223> OTHER INFORMATION: Codon Optimized

<400> SEQUENCE: 37

```
atggcgggct cagatcagat tgaaggttcc ccccaccacg aaagtgacaa ctccatagcg     60

accaaaattc ttaattttgg gcacacttgt tggaagttac aaagacccta cgtagtgaaa    120

ggtatgatat ccatagcgtg tggtctgttt ggccgtgaat tgtttaataa cagacactta    180

ttcagttggg ggttaatgtg gaaggctttt tttgctctag ttcccatctt gagttttaac    240

ttcttcgcgg ctataatgaa ccaaatctac gacgtcgaca tcgacaggat taataaaccg    300

gatcttccac ttgtgtccgg agaaatgtcc attgaaacgg cttggatcct tagtattatt    360

gttgccctta ctggtcttat tgtgaccatt aagctaaaat cagcccccact ttttgttttt    420

atctatatat ttggcatctt tgccggattc gcgtattcag ttcccccctat ccgttggaaa    480

caatacccct ttacgaactt ccttataaca atttcctccc atgttgggtt ggccttcaca    540

tcatactcag cgacaacttc agcactagga ttgcccttcg tgtggaggcc cgcatttagc    600

tttatcattg cttttatgac ggttatgggc atgacaatag cattcgccaa agacattagt    660

gatattgaag gtgatgcaaa atacggtgtg tcaacggtcg ccactaagtt aggagcaaga    720

aatatgacat tcgtggtgtc aggtgtttta ttgcttaatt atcttgtgtc cattagcatc    780

ggtataatct ggcctcaggt tttcaaatca aatatcatga tcctatctca cgcaattcta    840

gctttctgct tgatctttca gacgagagaa ttggctctag ccaactacgc atcagcacct    900

agtaggcagt tcttcgaatt tatttggcta ttgtattacg cagagtattt cgtgtatgtg    960

ttcatttaa                                                            969
```

<210> SEQ ID NO 38
<211> LENGTH: 1032
<212> TYPE: DNA
<213> ORGANISM: Artificial Sequence
<220> FEATURE:
<223> OTHER INFORMATION: Codon Optimized

<400> SEQUENCE: 38

```
atgagattcc catctatttt cactgctgtt ttgttcgctg cttcttctgc tttggctgct     60

ccagttgcgg gctcagatca gattgaaggt tccccccacc acgaaagtga caactccata    120

gcgaccaaaa ttcttaattt tgggcacact tgttggaagt tacaaagacc ctacgtagtg    180

aaaggtatga tatccatagc gtgtggtctg tttggccgtg aattgtttaa taacagacac    240

ttattcagtt gggggttaat gtggaaggct ttttttgctc tagttcccat cttgagtttt    300

aacttcttcg cggctataat gaaccaaatc tacgacgtcg acatcgacag gattaataaa    360

ccggatcttc cacttgtgtc cggagaaatg tccattgaaa cggcttggat ccttagtatt    420

attgttgccc ttactggtct tattgtgacc attaagctaa aatcagcccc actttttgtt    480
```

```
tttatctata tatttggcat ctttgccgga ttcgcgtatt cagttccccc tatccgttgg    540
aaacaatacc cctttacgaa cttccttata acaatttcct cccatgttgg gttggccttc    600
acatcatact cagcgacaac ttcagcacta ggattgccct tcgtgtggag gcccgcattt    660
agctttatca ttgcttttat gacggttatg ggcatgacaa tagcattcgc caaagacatt    720
agtgatattg aaggtgatgc aaaatacggt gtgtcaacgg tcgccactaa gttaggagca    780
agaaatatga cattcgtggt gtcaggtgtt ttattgctta attatcttgt gtccattagc    840
atcggtataa tctggcctca ggttttcaaa tcaaatatca tgatcctatc tcacgcaatt    900
ctagctttct gcttgatctt tcagacgaga gaattggctc tagccaacta cgcatcagca    960
cctagtaggc agttcttcga atttatttgg ctattgtatt acgcagagta tttcgtgtat   1020
gtgttcattt aa                                                       1032
```

```
<210> SEQ ID NO 39
<211> LENGTH: 6262
<212> TYPE: DNA
<213> ORGANISM: Artificial Sequence
<220> FEATURE:
<223> OTHER INFORMATION: Codon Optimized

<400> SEQUENCE: 39

tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accacgcttt tcaattcaat tcatcatttt tttttattc ttttttttga tttcggtttc    240
tttgaaattt ttttgattcg gtaatctccg aacagaagga agaacgaagg aaggagcaca    300
gacttagatt ggtatatata cgcatatgta gtgttgaaga aacatgaaat tgcccagtat    360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga tttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aatttttgtt aaatcagctc atttttaac caataggccg aaatcggcaa aatcccttat   1440
```

-continued

```
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa gggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatgggcc ttagtctagt ttgtacgttt tcttttcaga   2520
cgaactacca cacgttgctg aatccgcaca ataagaaccc aaaaaactct ctattgagct   2580
atcagcatcc taagaccccg ataataaagt cttcttacga taactttcct tctaaatact   2640
gtttaacaaa gaactttcat ttactgggac tgaactctca taaccgtata agtagccaat   2700
ccaggagcat tcgtgcgggc tcagatcaga ttgaaggttc cccccaccac gaaagtgaca   2760
actccatagc gaccaaaatt cttaattttg ggcacacttg ttggaagtta caaagaccct   2820
acgtagtgaa aggtatgata tccatagcgt gtggtctgtt tggccgtgaa ttgtttaata   2880
acagacactt attcagttgg gggttaatgt ggaaggcttt ttttgctcta gttcccatct   2940
tgagttttaa cttcttcgcg gctataatga accaaatcta cgacgtcgac atcgacagga   3000
ttaataaacc ggatcttcca cttgtgtccg gagaaatgtc cattgaaacg gcttggatcc   3060
ttagtattat tgttgccctt actggtctta ttgtgaccat taagctaaaa tcagccccac   3120
tttttgtttt tatctatata tttggcatct ttgccggatt cgcgtattca gttcccccta   3180
tccgttggaa acaatacccc tttacgaact tccttataac aatttcctcc catgttgggt   3240
tggccttcac atcatactca gcgacaactt cagcactagg attgcccttc gtgtggaggc   3300
ccgcatttag ctttatcatt gcttttatga cggttatggg catgacaata gcattcgcca   3360
aagacattag tgatattgaa ggtgatgcaa aatacggtgt gtcaacggtc gccactaagt   3420
taggagcaag aaatatgaca ttcgtggtgt caggtgtttt attgcttaat tatcttgtgt   3480
ccattagcat cggtataatc tggcctcagg ttttcaaatc aaatatcatg atcctatctc   3540
acgcaattct agctttctgc ttgatctttc agacgagaga attggctcta gccaactacg   3600
catcagcacc tagtaggcag ttcttcgaat ttatttggct attgtattac gcagagtatt   3660
tcgtgtatgt gttcatttaa gatgggctgc aggaattcga tatcaagctt atcgataccg   3720
tcgacctcga gtcatgtaat tagttatgtc acgcttacat tcacgccctc cccccacatc   3780
cgctctaacc gaaaaggaag gagttagaca acctgaagtc taggtcccta tttatttttt   3840
```

tatagttatg ttagtattaa gaacgttatt tatatttcaa atttttcttt tttttctgta 3900
cagacgcgtg tacgcatgta acattatact gaaaaccttg cttgagaagg ttttgggacg 3960
ctcgaaggct ttaatttgcg gccggtaccc agcttttgtt ccctttagtg agggttaatt 4020
ccgagcttgg cgtaatcatg gtcatagctg tttcctgtgt gaaattgtta tccgctcaca 4080
attccacaca acataggagc cggaagcata aagtgtaaag cctggggtgc ctaatgagtg 4140
aggtaactca cattaattgc gttgcgctca ctgcccgctt tccagtcggg aaacctgtcg 4200
tgccagctgc attaatgaat cggccaacgc gcggggagag gcggtttgcg tattgggcgc 4260
tcttccgctt cctcgctcac tgactcgctg cgctcggtcg ttcggctgcg gcgagcggta 4320
tcagctcact caaaggcggt aatacggtta tccacagaat caggggataa cgcaggaaag 4380
aacatgtgag caaaaggcca gcaaaaggcc aggaaccgta aaaaggccgc gttgctggcg 4440
tttttccata ggctcggccc ccctgacgag catcacaaaa atcgacgctc aagtcagagg 4500
tggcgaaacc cgacaggact ataaagatac caggcgttcc ccctggaag ctccctcgtg 4560 cgctctcctg ttccgaccct gccgcttacc ggatacctgt ccgcctttct cccttcggga 4620
agcgtggcgc tttctcaatg ctcacgctgt aggtatctca gttcggtgta ggtcgttcgc 4680
tccaagctgg gctgtgtgca cgaacccccc gttcagcccg accgctgcgc cttatccggt 4740
aactatcgtc ttgagtccaa cccggtaaga cacgacttat cgccactggc agcagccact 4800
ggtaacagga ttagcagagc gaggtatgta ggcggtgcta cagagttctt gaagtggtgg 4860
cctaactacg gctacactag aaggacagta tttggtatct gcgctctgct gaagccagtt 4920
accttcggaa aaagagttgg tagctcttga tccggcaaac aaaccaccgc tggtagcggt 4980
ggtttttttg tttgcaagca gcagattacg cgcagaaaaa aaggatctca agaagatcct 5040
ttgatctttt ctacggggtc tgacgctcag tggaacgaaa actcacgtta agggattttg 5100
gtcatgagat tatcaaaaag gatcttcacc tagatccttt taaattaaaa atgaagtttt 5160
aaatcaatct aaagtatata tgagtaaact tggtctgaca gttaccaatg cttaatcagt 5220
gaggcaccta tctcagcgat ctgtctattt cgttcatcca tagttgcctg actgcccgtc 5280
gtgtagataa ctacgatacg ggagggctta ccatctggcc ccagtgctgc aatgataccg 5340
cgagacccac gctcaccggc tccagattta tcagcaataa accagccagc cggaagggcc 5400
gagcgcagaa gtggtcctgc aactttatcc gcctccatcc agtctattaa ttgttgccgg 5460
gaagctagag taagtagttc gccagttaat agtttgcgca acgttgttgc cattgctaca 5520
ggcatcgtgg tgtcacgctc gtcgtttggt atggcttcat tcagctccgg ttcccaacga 5580
tcaaggcgag ttacatgatc ccccatgttg tgaaaaaaag cggttagctc cttcggtcct 5640
ccgatcgttg tcagaagtaa gttggccgca gtgttatcac tcatggttat ggcagcactg 5700
cataattctc ttactgtcat gccatccgta agatgctttt ctgtgactgg tgagtactca 5760
accaagtcat tctgagaata gtgtatgcgg cgaccgagtt gctcttgccc ggcgtcaata 5820
cgggataata ccgcgccaca tagcagaact ttaaaagtgc tcatcattgg aaaacgttct 5880
tcggggcgaa aactctcaag gatcttaccg ctgttgagat ccagttcgat gtaacccact 5940
cgtgcaccca actgatcttc agcatctttt actttcacca gcgtttctgg gtgagcaaaa 6000
acaggaaggc aaaatgccgc aaaaaaggga ataagggcga cacggaaatg ttgaatactc 6060
atactcttcc tttttcaata ttattgaagc atttatcagg gttattgtct catgagcgga 6120
tacatatttg aatgtattta gaaaaataaa caaatagggg ttccgcgcac atttccccga 6180
aaagtgccac ctgacgtcta agaaaccatt attatcatga cattaaccta taaaaatagg 6240
cgtatcacga ggccctttcg tc 6262

<210> SEQ ID NO 40
<211> LENGTH: 6034
<212> TYPE: DNA
<213> ORGANISM: Artificial Sequence
<220> FEATURE:
<223> OTHER INFORMATION: Codon Optimized

<400> SEQUENCE: 40
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc tttttttga tttcggtttc 240 tttgaaattt ttttgattcg gtaatctccg aacagaagga agaacgaagg aaggagcaca 300
gacttagatt ggtatatata cgcatatgta gtgttgaaga aacatgaaat tgcccagtat 360
tcttaaccca actgcacaga acaaaaacct gcaggaaacg aagataaatc atgtcgaaag 420
ctacatataa ggaacgtgct gctactcatc ctagtcctgt tgctgccaag ctatttaata 480
tcatgcacga aaagcaaaca aacttgtgtg cttcattgga tgttcgtacc accaaggaat 540
tactggagtt agttgaagca ttaggtccca aaatttgttt actaaaaaca catgtggata 600
tcttgactga tttttccatg gagggcacag ttaagccgct aaaggcatta tccgccaagt 660
acaatttttt actcttcgaa gacagaaaat ttgctgacat tggtaataca gtcaaattgc 720
agtactctgc gggtgtatac agaatagcag aatgggcaga cattacgaat gcacacggtg 780
tggtgggccc aggtattgtt agcggtttga agcaggcggc agaagaagta acaaaggaac 840
ctagaggcct tttgatgtta gcagaattgt catgcaaggg ctccctatct actggagaat 900
atactaaggg tactgttgac attgcgaaga gcgacaaaga ttttgttatc ggctttattg 960
ctcaaagaga catgggtgga agagatgaag gttacgattg gttgattatg acacccggtg 1020
tgggtttaga tgacaaggga gacgcattgg gtcaacagta tagaaccgtg gatgatgtgg 1080
tctctacagg atctgacatt attattgttg gaagaggact atttgcaaag ggaagggatg 1140
ctaaggtaga gggtgaacgt tacagaaaag caggctggga agcatatttg agaagatgcg 1200
gccagcaaaa ctaaaaaact gtattataag taaatgcatg tatactaaac tcacaaatta 1260
gagcttcaat ttaattatat cagttattac cctgcggtgt gaaataccgc acagatgcgt 1320
aaggagaaaa taccgcatca ggaaattgta aacgttaata ttttgttaaa attcgcgtta 1380
aatttttgtt aaatcagctc attttttaac caataggccg aaatcggcaa aatcccttat 1440
aaatcaaaag aatagaccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc ctaatcaagt tttttggggt cgaggtgccg taaagcacta 1620
aatcggaacc ctaaagggag cccccgattt agagcttgac ggggaaagcc ggcgaacgtg 1680
gcgagaaagg aagggaagaa agcgaaagga gcgggcgcta gggcgctggc aagtgtagcg 1740
gtcacgctgc gcgtaaccac cacacccgcc gcgcttaatg cgccgctaca gggcgcgtcg 1800
cgccattcgc cattcaggct gcgcaactgt tgggaagggc gatcggtgcg ggcctcttcg 1860
ctattacgcc agctggcgaa gggggatgt gctgcaaggc gattaagttg ggtaacgcca 1920
gggttttccc agtcacgacg ttgtaaaacg acggccagtg aattgtaata cgactcacta 1980
tagggcgaat tggagctcta gtacggatta gaagccgccg agcgggcgac agccctccga 2040
cggaagactc tcctccgtgc gtcctcgtct tcaccggtcg cgttcctgaa acgcagatgt 2100
gcctcgcgcc gcactgctcc gaacaataaa gattctacaa tactagcttt tatggttatg 2160
aagaggaaaa attggcagta acctggcccc acaaaccttc aaattaacga atcaaattaa 2220
caaccatagg atgataatgc gattagtttt ttagccttat ttctggggta attaatcagc 2280
gaagcgatga tttttgatct attaacagat atataaatgg aaaagctgca taaccacttt 2340
aactaatact ttcaacattt tcagtttgta ttacttctta ttcaaatgtc ataaaagtat 2400
caacaaaaaa ttgttaatat acctctatac tttaacgtca aggagaaaaa accccggatt 2460
ctagaactag tggatccccc atcatggcgg gctcagatca gattgaaggt tcccccccacc 2520 acgaaagtga caactccata gcgaccaaaa ttcttaattt tgggcacact tgttggaagt 2580
tacaaagacc ctacgtagtg aaaggtatga tatccatagc gtgtggtctg tttggccgtg 2640
aattgtttaa taacagacac ttattcagtt gggggttaat gtggaaggct ttttttgctc 2700
tagttcccat cttgagtttt aacttcttcg cggctataat gaaccaaatc tacgacgtcg 2760
acatcgacag gattaataaa ccggatcttc cacttgtgtc cggagaaatg tccattgaaa 2820
cggcttggat ccttagtatt attgttgccc ttactggtct tattgtgacc attaagctaa 2880
aatcagcccc actttttgtt tttatctata tatttggcat ctttgccgga ttcgcgtatt 2940
cagttccccc tatccgttgg aaacaatacc cctttacgaa cttccttata acaatttcct 3000
cccatgttgg gttggccttc acatcatact cagcgacaac ttcagcacta ggattgccct 3060
tcgtgtggag gcccgcattt agctttatca ttgcttttat gacggttatg ggcatgacaa 3120
tagcattcgc caaagacatt agtgatattg aaggtgatgc aaaatacggt gtgtcaacgg 3180
tcgccactaa gttaggagca agaaatatga cattcgtggt gtcaggtgtt ttattgctta 3240
attatcttgt gtccattagc atcggtataa tctggcctca ggttttcaaa tcaaatatca 3300
tgatcctatc tcacgcaatt ctagctttct gcttgatctt tcagacgaga gaattggctc 3360
tagccaacta cgcatcagca cctagtaggc agttcttcga atttatttgg ctattgtatt 3420
acgcagagta tttcgtgtat gtgttcattt aagatgggct gcaggaattc gatatcaagc 3480
ttatcgatac cgtcgacctc gagtcatgta attagttatg tcacgcttac attcacgccc 3540
tccccccaca tccgctctaa ccgaaaagga aggagttaga caacctgaag tctaggtccc 3600
tatttatttt tttatagtta tgttagtatt aagaacgtta tttatatttc aaatttttct 3660 ttttttctg tacagacgcg tgtacgcatg taacattata ctgaaaacct tgcttgagaa 3720
ggttttggga cgctcgaagg ctttaatttg cggccggtac ccagcttttg ttccctttag 3780
tgagggttaa ttccgagctt ggcgtaatca tggtcatagc tgtttcctgt gtgaaattgt 3840
tatccgctca caattccaca caacatagga gccggaagca taaagtgtaa agcctggggt 3900
gcctaatgag tgaggtaact cacattaatt gcgttgcgct cactgcccgc tttccagtcg 3960
ggaaacctgt cgtgccagct gcattaatga atcggccaac gcgcggggag aggcggtttg 4020
cgtattgggc gctcttccgc ttcctcgctc actgactcgc tgcgctcggt cgttcggctg 4080
cggcgagcgg tatcagctca ctcaaaggcg gtaatacggt tatccacaga atcaggggat 4140
aacgcaggaa agaacatgtg agcaaaaggc cagcaaaagg ccaggaaccg taaaaaggcc 4200
gcgttgctgg cgtttttcca taggctcggc ccccctgacg agcatcacaa aaatcgacgc 4260
tcaagtcaga ggtggcgaaa cccgacagga ctataaagat accaggcgtt tccccctgga 4320
agctccctcg tgcgctctcc tgttccgacc ctgccgctta ccggatacct gtccgccttt 4380
ctcccttcgg gaagcgtggc gctttctcaa tgctcacgct gtaggtatct cagttcggtg 4440
taggtcgttc gctccaagct gggctgtgtg cacgaacccc ccgttcagcc cgaccgctgc 4500
gccttatccg gtaactatcg tcttgagtcc aacccggtaa gacacgactt atcgccactg 4560
gcagcagcca ctggtaacag gattagcaga gcgaggtatg taggcggtgc tacagagttc 4620
ttgaagtggt ggcctaacta cggctacact agaaggacag tatttggtat ctgcgctctg 4680
ctgaagccag ttaccttcgg aaaaagagtt ggtagctctt gatccggcaa acaaaccacc 4740
gctggtagcg gtggtttttt tgtttgcaag cagcagatta cgcgcagaaa aaaaggatct 4800
caagaagatc ctttgatctt ttctacgggg tctgacgctc agtggaacga aaactcacgt 4860
taagggattt tggtcatgag attatcaaaa aggatcttca cctagatcct tttaaattaa 4920
aaatgaagtt ttaaatcaat ctaaagtata tatgagtaaa cttggtctga cagttaccaa 4980
tgcttaatca gtgaggcacc tatctcagcg atctgtctat ttcgttcatc catagttgcc 5040
tgactgcccg tcgtgtagat aactacgata cgggagggct taccatctgg ccccagtgct 5100
gcaatgatac cgcgagaccc acgctcaccg gctccagatt tatcagcaat aaaccagcca 5160
gccggaaggg ccgagcgcag aagtggtcct gcaactttat ccgcctccat ccagtctatt 5220
aattgttgcc gggaagctag agtaagtagt tcgccagtta atagtttgcg caacgttgtt 5280
gccattgcta caggcatcgt ggtgtcacgc tcgtcgtttg gtatggcttc attcagctcc 5340
ggttcccaac gatcaaggcg agttacatga tcccccatgt tgtgaaaaaa agcggttagc 5400
tccttcggtc ctccgatcgt tgtcagaagt aagttggccg cagtgttatc actcatggtt 5460
atggcagcac tgcataattc tcttactgtc atgccatccg taagatgctt ttctgtgact 5520
ggtgagtact caaccaagtc attctgagaa tagtgtatgc ggcgaccgag ttgctcttgc 5580
ccggcgtcaa tacgggataa taccgcgcca catagcagaa ctttaaaagt gctcatcatt 5640
ggaaaacgtt cttcggggcg aaaactctca aggatcttac cgctgttgag atccagttcg 5700
atgtaaccca ctcgtgcacc caactgatct tcagcatctt ttactttcac cagcgtttct 5760
gggtgagcaa aaacaggaag gcaaaatgcc gcaaaaaagg gaataagggc gacacggaaa 5820
tgttgaatac tcatactctt cctttttcaa tattattgaa gcatttatca gggttattgt 5880
ctcatgagcg gatacatatt tgaatgtatt tagaaaaata aacaaatagg ggttccgcgc 5940
acatttcccc gaaaagtgcc acctgacgtc taagaaacca ttattatcat gacattaacc 6000
tataaaaata ggcgtatcac gaggcccttt cgtc 6034

<210> SEQ ID NO 41
<211> LENGTH: 6088
<212> TYPE: DNA
<213> ORGANISM: Artificial Sequence
<220> FEATURE:
<223> OTHER INFORMATION: Codon Optimized

<400> SEQUENCE: 41
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc tttttttga tttcggtttc 240 tttgaaattt ttttgattcg gtaatctccg aacagaagga agaacgaagg aaggagcaca 300
gacttagatt ggtatatata cgcatatgta gtgttgaaga aacatgaaat tgcccagtat 360

-continued

```
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga tttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aatttttgtt aaatcagctc atttttttaac caataggccg aaatcggcaa aatcccttat   1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa agggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatgagat tcccatctat tttcactgct gttttgttcg   2520
ctgcttcttc tgctttggct gctccagttg ctaatcaaac agaacctcca gaatctaata   2580
cgaaatatag tgtagttacc aaaatcctaa gttttggcca cacttgttgg aaattgcaga   2640
gaccgtatac tttcattgga gtgattagtt gcgcctgtgg attgttcggt agagagttat   2700
```

```
tccataatac taatttgcta tcatggtctc tgatgttgaa agctttcagc tcattgatgg   2760
taatactgtc agtgaatcta tgtaccaata tcataaacca gatcactgac ctggacatag   2820
acagaatcaa taagccggac ttgccattgg cgagcgggga aatgtccatt gaaacagcat   2880
ggattatgag tattatagtt gcactaactg gattgatact tacgataaag cttaattgcg   2940
gccctttgtt tatatctcta tattgtgtca gcatactagt cggggcacta tattcagtac   3000
cgccattcag atggaagcaa aatcccaata ccgcattctc aagttatttt atgggactgg   3060
tgatcgtcaa ttttacctgc tattacgcaa gcagggccgc ctttggactg ccattcgaga   3120
tgtcaccccc gttcacattc attcttgcct ttgtcaagtc aatgggtagc gcactttttt   3180
tgtgtaaaga tgtctctgac attgaaggag attctaagca cggtatatct acccttgcga   3240
cgaggtatgg agcaaaaaac attactttcc tttgctcagg aatcgtactg ctaacctacg   3300
taagcgcgat attggctgcg attatttggc cacaagcctt caagtccaac gtgatgctgt   3360
tgagtcacgc aaccctggcc ttttggctta tctttcagac tagagagttc gcgttaacta   3420
attacaatcc agaggcaggg aggaagtttt acgagttcat gtggaagctg cactacgctg   3480
aatacttagt ctatgtattt atataggatg ggctgcagga attcgatatc aagcttatcg   3540
ataccgtcga cctcgagtca tgtaattagt tatgtcacgc ttacattcac gccctccccc   3600
cacatccgct ctaaccgaaa aggaaggagt tagacaacct gaagtctagg tccctattta   3660
tttttttata gttatgttag tattaagaac gttatttata tttcaaattt ttcttttttt   3720
tctgtacaga cgcgtgtacg catgtaacat tatactgaaa accttgcttg agaaggtttt   3780
gggacgctcg aaggctttaa tttgcggccg gtacccagct tttgttccct ttagtgaggg   3840
ttaattccga gcttggcgta atcatggtca tagctgtttc ctgtgtgaaa ttgttatccg   3900
ctcacaattc cacacaacat aggagccgga agcataaagt gtaaagcctg gggtgcctaa   3960
tgagtgaggt aactcacatt aattgcgttg cgctcactgc ccgctttcca gtcgggaaac   4020
ctgtcgtgcc agctgcatta atgaatcggc caacgcgcgg ggagaggcgg tttgcgtatt   4080
gggcgctctt ccgcttcctc gctcactgac tcgctgcgct cggtcgttcg gctgcggcga   4140
gcggtatcag ctcactcaaa ggcggtaata cggttatcca cagaatcagg ggataacgca   4200
ggaaagaaca tgtgagcaaa aggccagcaa aaggccagga accgtaaaaa ggccgcgttg   4260
ctggcgtttt tccataggct ccgcccccct gacgagcatc acaaaaatcg acgctcaagt   4320
cagaggtggc gaaacccgac aggactataa agataccagg cgtttccccc tggaagctcc   4380
ctcgtgcgct ctcctgttcc gaccctgccg cttaccggat acctgtccgc ctttctccct   4440
tcgggaagcg tggcgctttc tcaatgctca cgctgtaggt atctcagttc ggtgtaggtc   4500
gttcgctcca agctgggctg tgtgcacgaa ccccccgttc agcccgaccg ctgcgcctta   4560
tccggtaact atcgtcttga gtccaacccg gtaagacacg acttatcgcc actggcagca   4620
gccactggta acaggattag cagagcgagg tatgtaggcg gtgctacaga gttcttgaag   4680
tggtggccta actacggcta cactagaagg acagtatttg gtatctgcgc tctgctgaag   4740
ccagttacct tcggaaaaag agttggtagc tcttgatccg gcaaacaaac caccgctggt   4800
agcggtggtt tttttgtttg caagcagcag attacgcgca gaaaaaaagg atctcaagaa   4860
gatcctttga tcttttctac ggggtctgac gctcagtgga acgaaaactc acgttaaggg   4920
attttggtca tgagattatc aaaaaggatc ttcacctaga tccttttaaa ttaaaaatga   4980
agttttaaat caatctaaag tatatatgag taaacttggt ctgacagtta ccaatgctta   5040
atcagtgagg cacctatctc agcgatctgt ctatttcgtt catccatagt tgcctgactg   5100
```

cccgtcgtgt agataactac gatacgggag ggcttaccat ctggccccag tgctgcaatg 5160
ataccgcgag acccacgctc accggctcca gatttatcag caataaacca gccagccgga 5220
agggccgagc gcagaagtgg tcctgcaact ttatccgcct ccatccagtc tattaattgt 5280
tgccgggaag ctagagtaag tagttcgcca gttaatagtt tgcgcaacgt tgttgccatt 5340
gctacaggca tcgtggtgtc acgctcgtcg tttggtatgg cttcattcag ctccggttcc 5400
caacgatcaa ggcgagttac atgatccccc atgttgtgaa aaaaagcggt tagctccttc 5460
ggtcctccga tcgttgtcag aagtaagttg gccgcagtgt tatcactcat ggttatggca 5520
gcactgcata attctcttac tgtcatgcca tccgtaagat gcttttctgt gactggtgag 5580
tactcaacca agtcattctg agaatagtgt atgcggcgac cgagttgctc ttgcccggcg 5640
tcaatacggg ataataccgc gccacatagc agaactttaa aagtgctcat cattggaaaa 5700
cgttcttcgg ggcgaaaact ctcaaggatc ttaccgctgt tgagatccag ttcgatgtaa 5760
cccactcgtg cacccaactg atcttcagca tcttttactt tcaccagcgt ttctgggtga 5820
gcaaaaacag gaaggcaaaa tgccgcaaaa aagggaataa gggcgacacg gaaatgttga 5880
atactcatac tcttcctttt tcaatattat tgaagcattt atcagggtta ttgtctcatg 5940
agcggataca tatttgaatg tatttagaaa aataaacaaa taggggttcc gcgcacattt 6000
ccccgaaaag tgccacctga cgtctaagaa accattatta tcatgacatt aacctataaa 6060
aataggcgta tcacgaggcc ctttcgtc 6088

<210> SEQ ID NO 42
<211> LENGTH: 1203
<212> TYPE: DNA
<213> ORGANISM: Artificial Sequence
<220> FEATURE:
<223> OTHER INFORMATION: Codon Optimized

<400> SEQUENCE: 42
atggtatttt cctcagtgtg tagttttccg tcctctcttg gtacaaactt taagctggtg 60
cctagatcta attttaaggc ttcaagttca cattaccacg aaatcaacaa tttcattaac 120
aacaaaccca ttaaatttag ttatttctct tcaaggttgt attgcagtgc caagccaata 180
gtacacagag aaaacaagtt cacaaaatca ttctcactat cacacttaca acgtaaatct 240
tctatcaagg cccatggaga gatagaggct gatggaagta acgggacttc tgagttcaac 300
gtaatgaagt ccggaaatgc tatctggaga tttgtgaggc cgtatgccgc taaaggtgtc 360
ctgtttaact ccgcggcaat gttcgctaag gaacttgttg gaaatctgaa cttatttagc 420
tggccgttga tgttcaagat cctttcattt actcttgtca ttctgtgtat ctttgtatct 480
acatcaggca taaatcagat atatgatcta gacatcgata gactgaacaa accgaacttg 540
cccgtggcaa gcggggaaat tagcgtagaa ttggcatggt tacttactat agtatgtacg 600
attagtggac ttaccttaac cattataact aatagtggcc cctttttcc gttcctttac 660 tcagcctcca tattctttgg tttcctatac tccgcccccc cgttccgttg gaagaaaaac 720
ccctttaccg cctgcttttg caatgtgatg ttatacgtgg gaaccagtgt tggggtttat 780
tatgcctgca aagccagttt gggccttcct gccaattggt ctccagcatt ctgcctttta 840
ttttggttta ttagtctgct ttccatacct atcagcatag ctaaggattt atctgatatt 900
gaaggtgata ggaagtttgg aatcattact ttctctacta agttcggggc aaaaaccgatc 960 gcgtacatat gtcacgggct tatgcttttg aattacgtga gtgttatggc cgcggccata 1020

-continued atatggcctc aattcttcaa ctcctcagta atactgttat cacatgcctt catggcgatc 1080
tgggttttgt accaagcgtg gatactggag aaaagtaact atgcaacgga aacttgccag 1140
aaatattaca tcttcttatg gataatattc tcccttgagc acgcttttta cctattcatg 1200
tag 1203

<210> SEQ ID NO 43
<211> LENGTH: 1128
<212> TYPE: DNA
<213> ORGANISM: Artificial Sequence
<220> FEATURE:
<223> OTHER INFORMATION: Codon Optimized

<400> SEQUENCE: 43
atggcttcaa gttcacatta ccacgaaatc aacaatttca ttaacaacaa acccattaaa 60
tttagttatt tctcttcaag gttgtattgc agtgccaagc caatagtaca cagagaaaac 120
aagttcacaa aatcattctc actatcacac ttacaacgta aatcttctat caaggcccat 180
ggagagatag aggctgatgg aagtaacggg acttctgagt tcaacgtaat gaagtccgga 240
aatgctatct ggagatttgt gaggccgtat gccgctaaag gtgtcctgtt taactccgcg 300
gcaatgttcg ctaaggaact tgttggaaat ctgaacttat ttagctggcc gttgatgttc 360
aagatccttt catttactct tgtcattctg tgtatctttg tatctacatc aggcataaat 420
cagatatatg atctagacat cgatagactg aacaaaccga acttgcccgt ggcaagcggg 480
gaaattagcg tagaattggc atggttactt actatagtat gtacgattag tggacttacc 540
ttaaccatta taactaatag tggccccttt tttccgttcc tttactcagc ctccatattc 600
tttggtttcc tatactccgc ccccccgttc cgttggaaga aaaacccctt taccgcctgc 660
ttttgcaatg tgatgttata cgtgggaacc agtgttgggg tttattatgc ctgcaaagcc 720
agtttgggcc ttcctgccaa ttggtctcca gcattctgcc ttttattttg gtttattagt 780
ctgctttcca tacctatcag catagctaag gatttatctg atattgaagg tgataggaag 840
tttggaatca ttactttctc tactaagttc ggggcaaaac cgatcgcgta catatgtcac 900
gggcttatgc ttttgaatta cgtgagtgtt atggccgcgg ccataaatatg gcctcaattc 960 ttcaactcct cagtaatact gttatcacat gccttcatgg cgatctgggt tttgtaccaa 1020
gcgtggatac tggagaaaag taactatgca acggaaactt gccagaaata ttacatcttc 1080
ttatggataa tattctccct tgagcacgct ttttacctat tcatgtag 1128

<210> SEQ ID NO 44
<211> LENGTH: 1191
<212> TYPE: DNA
<213> ORGANISM: Artificial Sequence
<220> FEATURE:
<223> OTHER INFORMATION: Codon Optimized

<400> SEQUENCE: 44
atgagattcc catctatttt cactgctgtt ttgttcgctg cttcttctgc tttggctgct 60
ccagttgctt caagttcaca ttaccacgaa atcaacaatt tcattaacaa caaacccatt 120
aaatttagtt atttctcttc aaggttgtat tgcagtgcca agccaatagt acacagagaa 180
aacaagttca caaaatcatt ctcactatca cacttacaac gtaaatcttc tatcaaggcc 240
catggagaga tagaggctga tggaagtaac gggacttctg agttcaacgt aatgaagtcc 300
ggaaatgcta tctggagatt tgtgaggccg tatgccgcta aaggtgtcct gtttaactcc 360
gcggcaatgt tcgctaagga acttgttgga aatctgaact tatttagctg gccgttgatg 420

-continued ttcaagatcc tttcatttac tcttgtcatt ctgtgtatct ttgtatctac atcaggcata 480
aatcagatat atgatctaga catcgataga ctgaacaaac cgaacttgcc cgtggcaagc 540
ggggaaatta gcgtagaatt ggcatggtta cttactatag tatgtacgat tagtggactt 600
accttaacca ttataactaa tagtggcccc ttttttccgt tcctttactc agcctccata 660
ttctttggtt tcctatactc cgcccccccg ttccgttgga agaaaaaccc ctttaccgcc 720
tgcttttgca atgtgatgtt atacgtggga accagtgttg ggtttatta tgcctgcaaa 780 gccagtttgg gccttcctgc caattggtct ccagcattct gccttttatt ttggtttatt 840
agtctgcttt ccatacctat cagcatagct aaggatttat ctgatattga aggtgatagg 900
aagtttggaa tcattacttt ctctactaag ttcggggcaa aaccgatcgc gtacatatgt 960
cacgggctta tgcttttgaa ttacgtgagt gttatggccg cggccataat atggcctcaa 1020
ttcttcaact cctcagtaat actgttatca catgccttca tggcgatctg ggttttgtac 1080
caagcgtgga tactggagaa aagtaactat gcaacggaaa cttgccagaa atattacatc 1140
ttcttatgga taatattctc ccttgagcac gctttttacc tattcatgta g 1191

<210> SEQ ID NO 45
<211> LENGTH: 6268
<212> TYPE: DNA
<213> ORGANISM: Artificial Sequence
<220> FEATURE:
<223> OTHER INFORMATION: Codon Optimized

<400> SEQUENCE: 45
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc ttttttttga tttcggtttc 240
tttgaaattt ttttgattcg gtaatctccg aacagaagga agaacgaagg aaggagcaca 300
gacttagatt ggtatatata cgcatatgta gtgttgaaga aacatgaaat tgcccagtat 360
tcttaaccca actgcacaga acaaaaacct gcaggaaacg aagataaatc atgtcgaaag 420
ctacatataa ggaacgtgct gctactcatc ctagtcctgt tgctgccaag ctatttaata 480
tcatgcacga aaagcaaaca aacttgtgtg cttcattgga tgttcgtacc accaaggaat 540
tactggagtt agttgaagca ttaggtccca aaatttgttt actaaaaaca catgtggata 600
tcttgactga tttttccatg gagggcacag ttaagccgct aaaggcatta tccgccaagt 660
acaatttttt actcttcgaa gacagaaaat ttgctgacat tggtaataca gtcaaattgc 720
agtactctgc gggtgtatac agaatagcag aatgggcaga cattacgaat gcacacggtg 780
tggtgggccc aggtattgtt agcggtttga agcaggcggc agaagaagta acaaaggaac 840
ctagaggcct tttgatgtta gcagaattgt catgcaaggg ctccctatct actggagaat 900
atactaaggg tactgttgac attgcgaaga gcgacaaaga ttttgttatc ggctttattg 960
ctcaaagaga catgggtgga agagatgaag gttacgattg gttgattatg acacccggtg 1020
tgggtttaga tgacaaggga gacgcattgg gtcaacagta tagaaccgtg gatgatgtgg 1080
tctctacagg atctgacatt attattgttg gaagaggact atttgcaaag ggaagggatg 1140
ctaaggtaga gggtgaacgt tacagaaaag caggctggga agcatatttg agaagatgcg 1200
gccagcaaaa ctaaaaaact gtattataag taaatgcatg tatactaaac tcacaaatta 1260

-continued gagcttcaat ttaattatat cagttattac cctgcggtgt gaaataccgc acagatgcgt 1320
aaggagaaaa taccgcatca ggaaattgta aacgttaata ttttgttaaa attcgcgtta 1380
aatttttgtt aaatcagctc atttttttaac caataggccg aaatcggcaa aatcccttat 1440
aaatcaaaag aatagaccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc ctaatcaagt tttttggggt cgaggtgccg taaagcacta 1620
aatcggaacc ctaaagggag cccccgattt agagcttgac ggggaaagcc ggcgaacgtg 1680
gcgagaaagg aagggaagaa agcgaaagga gcgggcgcta gggcgctggc aagtgtagcg 1740
gtcacgctgc gcgtaaccac cacacccgcc gcgcttaatg cgccgctaca gggcgcgtcg 1800
cgccattcgc cattcaggct gcgcaactgt tgggaagggc gatcggtgcg ggcctcttcg 1860
ctattacgcc agctggcgaa gggggggatgt gctgcaaggc gattaagttg ggtaacgcca 1920
gggttttccc agtcacgacg ttgtaaaacg acggccagtg aattgtaata cgactcacta 1980
tagggcgaat tggagctcta gtacggatta gaagccgccg agcgggcgac agccctccga 2040
cggaagactc tcctccgtgc gtcctcgtct tcaccggtcg cgttcctgaa acgcagatgt 2100
gcctcgcgcc gcactgctcc gaacaataaa gattctacaa tactagcttt tatggttatg 2160
aagaggaaaa attggcagta acctggcccc acaaaccttc aaattaacga atcaaattaa 2220
caaccatagg atgataatgc gattagtttt ttagccttat ttctggggta attaatcagc 2280
gaagcgatga tttttgatct attaacagat atataaatgg aaaagctgca taaccacttt 2340
aactaatact ttcaacattt tcagtttgta ttacttctta ttcaaatgtc ataaaagtat 2400
caacaaaaaa ttgttaatat acctctatac tttaacgtca aggagaaaaa accccggatt 2460
ctagaactag tggatccccc atcatggtat tttcctcagt gtgtagtttt ccgtcctctc 2520
ttggtacaaa ctttaagctg gtgcctagat ctaattttaa ggcttcaagt tcacattacc 2580
acgaaatcaa caatttcatt aacaacaaac ccattaaatt tagttatttc tcttcaaggt 2640
tgtattgcag tgccaagcca atagtacaca gagaaaacaa gttcacaaaa tcattctcac 2700
tatcacactt acaacgtaaa tcttctatca aggcccatgg agagatagag gctgatggaa 2760
gtaacgggac ttctgagttc aacgtaatga agtccggaaa tgctatctgg agatttgtga 2820
ggccgtatgc cgctaaaggt gtcctgttta actccgcggc aatgttcgct aaggaacttg 2880
ttggaaatct gaacttattt agctggccgt tgatgttcaa gatcctttca tttactcttg 2940
tcattctgtg tatctttgta tctacatcag gcataaatca gatatatgat ctagacatcg 3000
atagactgaa caaaccgaac ttgcccgtgg caagcgggga aattagcgta gaattggcat 3060
ggttacttac tatagtatgt acgattagtg gacttacctt aaccattata actaatagtg 3120 gcccctttttt tccgttcctt tactcagcct ccatattctt tggtttccta tactccgccc 3180
ccccgttccg ttggaagaaa aacccccttta ccgcctgctt ttgcaatgtg atgttatacg 3240
tgggaaccag tgttggggtt tattatgcct gcaaagccag tttgggcctt cctgccaatt 3300
ggtctccagc attctgcctt ttattttggt ttattagtct gctttccata cctatcagca 3360
tagctaagga tttatctgat attgaaggtg ataggaagtt tggaatcatt actttctcta 3420
ctaagttcgg ggcaaaaccg atcgcgtaca tatgtcacgg gcttatgctt ttgaattacg 3480
tgagtgttat ggccgcggcc ataatatggc ctcaattctt caactcctca gtaatactgt 3540
tatcacatgc cttcatggcg atctgggttt tgtaccaagc gtggatactg gagaaaagta 3600
actatgcaac ggaaacttgc cagaaatatt acatcttctt atggataata ttctcccttg 3660
agcacgcttt ttacctattc atgtaggatg ggctgcagga attcgatatc aagcttatcg 3720
ataccgtcga cctcgagtca tgtaattagt tatgtcacgc ttacattcac gccctccccc 3780
cacatccgct ctaaccgaaa aggaaggagt tagacaacct gaagtctagg tccctattta 3840
tttttttata gttatgttag tattaagaac gttatttata tttcaaattt ttcttttttt 3900
tctgtacaga cgcgtgtacg catgtaacat tatactgaaa accttgcttg agaaggtttt 3960
gggacgctcg aaggctttaa tttgcggccg gtacccagct tttgttccct ttagtgaggg 4020
ttaattccga gcttggcgta atcatggtca tagctgtttc ctgtgtgaaa ttgttatccg 4080
ctcacaattc cacacaacat aggagccgga agcataaagt gtaaagcctg gggtgcctaa 4140
tgagtgaggt aactcacatt aattgcgttg cgctcactgc ccgctttcca gtcgggaaac 4200
ctgtcgtgcc agctgcatta atgaatcggc caacgcgcgg ggagaggcgg tttgcgtatt 4260
gggcgctctt ccgcttcctc gctcactgac tcgctgcgct cggtcgttcg gctgcggcga 4320
gcggtatcag ctcactcaaa ggcggtaata cggttatcca cagaatcagg ggataacgca 4380
ggaaagaaca tgtgagcaaa aggccagcaa aaggccagga accgtaaaaa ggccgcgttg 4440
ctggcgtttt tccataggct cggcccccct gacgagcatc acaaaaatcg acgctcaagt 4500
cagaggtggc gaaacccgac aggactataa agataccagg cgttcccccc tggaagctcc 4560
ctcgtgcgct ctcctgttcc gaccctgccg cttaccggat acctgtccgc ctttctccct 4620
tcgggaagcg tggcgctttc tcaatgctca cgctgtaggt atctcagttc ggtgtaggtc 4680
gttcgctcca agctgggctg tgtgcacgaa ccccccgttc agcccgaccg ctgcgcctta 4740
tccggtaact atcgtcttga gtccaacccg gtaagacacg acttatcgcc actggcagca 4800
gccactggta acaggattag cagagcgagg tatgtaggcg gtgctacaga gttcttgaag 4860
tggtggccta actacggcta cactagaagg acagtatttg gtatctgcgc tctgctgaag 4920
ccagttacct tcggaaaaag agttggtagc tcttgatccg gcaaacaaac caccgctggt 4980
agcggtggtt tttttgtttg caagcagcag attacgcgca gaaaaaaagg atctcaagaa 5040
gatcctttga tcttttctac ggggtctgac gctcagtgga acgaaaactc acgttaaggg 5100
attttggtca tgagattatc aaaaaggatc ttcacctaga tccttttaaa ttaaaaatga 5160
agttttaaat caatctaaag tatatatgag taaacttggt ctgacagtta ccaatgctta 5220
atcagtgagg cacctatctc agcgatctgt ctatttcgtt catccatagt tgcctgactg 5280
cccgtcgtgt agataactac gatacgggag ggcttaccat ctggccccag tgctgcaatg 5340
ataccgcgag acccacgctc accggctcca gatttatcag caataaacca gccagccgga 5400
agggccgagc gcagaagtgg tcctgcaact ttatccgcct ccatccagtc tattaattgt 5460
tgccgggaag ctagagtaag tagttcgcca gttaatagtt tgcgcaacgt tgttgccatt 5520
gctacaggca tcgtggtgtc acgctcgtcg tttggtatgg cttcattcag ctccggttcc 5580
caacgatcaa ggcgagttac atgatccccc atgttgtgaa aaaaagcggt tagctccttc 5640
ggtcctccga tcgttgtcag aagtaagttg gccgcagtgt tatcactcat ggttatggca 5700
gcactgcata attctcttac tgtcatgcca tccgtaagat gcttttctgt gactggtgag 5760
tactcaacca agtcattctg agaatagtgt atgcggcgac cgagttgctc ttgcccggcg 5820
tcaatacggg ataataccgc gccacatagc agaactttaa aagtgctcat cattggaaaa 5880
cgttcttcgg ggcgaaaact ctcaaggatc ttaccgctgt tgagatccag ttcgatgtaa 5940
cccactcgtg cacccaactg atcttcagca tcttttactt tcaccagcgt ttctgggtga 6000
gcaaaaacag gaaggcaaaa tgccgcaaaa aagggaataa gggcgacacg gaaatgttga 6060
atactcatac tcttcctttt tcaatattat tgaagcattt atcagggtta ttgtctcatg 6120
agcggataca tatttgaatg tatttagaaa aataaacaaa taggggttcc gcgcacattt 6180
ccccgaaaag tgccacctga cgtctaagaa accattatta tcatgacatt aacctataaa 6240
aataggcgta tcacgaggcc ctttcgtc 6268

<210> SEQ ID NO 46
<211> LENGTH: 6268
<212> TYPE: DNA
<213> ORGANISM: Artificial Sequence
<220> FEATURE:
<223> OTHER INFORMATION: Codon Optimized

<400> SEQUENCE: 46
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc tttttttga tttcggtttc 240 tttgaaattt ttttgattcg gtaatctccg aacagaagga agaacgaagg aaggagcaca 300
gacttagatt ggtatatata cgcatatgta gtgttgaaga aacatgaaat tgcccagtat 360
tcttaaccca actgcacaga acaaaaacct gcaggaaacg aagataaatc atgtcgaaag 420
ctacatataa ggaacgtgct gctactcatc ctagtcctgt tgctgccaag ctatttaata 480
tcatgcacga aaagcaaaca aacttgtgtg cttcattgga tgttcgtacc accaaggaat 540
tactggagtt agttgaagca ttaggtccca aaatttgttt actaaaaaca catgtggata 600
tcttgactga tttttccatg gagggcacag ttaagccgct aaaggcatta tccgccaagt 660
acaatttttt actcttcgaa gacagaaaat ttgctgacat tggtaataca gtcaaattgc 720
agtactctgc gggtgtatac agaatagcag aatgggcaga cattacgaat gcacacggtg 780
tggtgggccc aggtattgtt agcggtttga agcaggcggc agaagaagta acaaaggaac 840
ctagaggcct tttgatgtta gcagaattgt catgcaaggg ctccctatct actggagaat 900
atactaaggg tactgttgac attgcgaaga gcgacaaaga ttttgttatc ggctttattg 960
ctcaaagaga catgggtgga agagatgaag gttacgattg gttgattatg acacccggtg 1020
tgggtttaga tgacaaggga gacgcattgg gtcaacagta tagaaccgtg gatgatgtgg 1080
tctctacagg atctgacatt attattgttg gaagaggact atttgcaaag ggaagggatg 1140
ctaaggtaga gggtgaacgt tacagaaaag caggctggga agcatatttg agaagatgcg 1200
gccagcaaaa ctaaaaaact gtattataag taaatgcatg tatactaaac tcacaaatta 1260
gagcttcaat ttaattatat cagttattac cctgcggtgt gaaataccgc acagatgcgt 1320
aaggagaaaa taccgcatca ggaaattgta aacgttaata ttttgttaaa attcgcgtta 1380
aatttttgtt aaatcagctc attttttaac caataggccg aaatcggcaa aatcccttat 1440
aaatcaaaag aatagaccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc ctaatcaagt tttttggggt cgaggtgccg taaagcacta 1620
aatcggaacc ctaaagggag cccccgattt agagcttgac ggggaaagcc ggcgaacgtg 1680
gcgagaaagg aagggaagaa agcgaaagga gcgggcgcta gggcgctggc aagtgtagcg 1740
gtcacgctgc gcgtaaccac cacacccgcc gcgcttaatg cgccgctaca gggcgcgtcg 1800

```
cgccattcgc cattcaggct gcgcaactgt tgggaagggc gatcggtgcg ggcctcttcg    1860

ctattacgcc agctggcgaa ggggggatgt gctgcaaggc gattaagttg ggtaacgcca    1920

gggttttccc agtcacgacg ttgtaaaacg acggccagtg aattgtaata cgactcacta    1980

tagggcgaat tggagctcta gtacggatta gaagccgccg agcgggcgac agccctccga    2040

cggaagactc tcctccgtgc gtcctcgtct tcaccggtcg cgttcctgaa acgcagatgt    2100

gcctcgcgcc gcactgctcc gaacaataaa gattctacaa tactagcttt tatggttatg    2160

aagaggaaaa attggcagta acctggcccc acaaaccttc aaattaacga atcaaattaa    2220

caaccatagg atgataatgc gattagtttt ttagccttat ttctggggta attaatcagc    2280

gaagcgatga ttttgatct attaacagat atataaatgg aaaagctgca taaccacttt     2340

aactaatact ttcaacattt tcagtttgta ttacttctta ttcaaatgtc ataaaagtat    2400

caacaaaaaa ttgttaatat acctctatac tttaacgtca aggagaaaaa accccggatt    2460

ctagaactag tggatccccc atcatggtat tttcctcagt gtgtagtttt ccgtcctctc    2520

ttggtacaaa ctttaagctg gtgcctagat ctaattttaa ggcttcaagt tcacattacc    2580

acgaaatcaa caatttcatt aacaacaaac ccattaaatt tagttatttc tcttcaaggt    2640

tgtattgcag tgccaagcca atagtacaca gagaaaacaa gttcacaaaa tcattctcac    2700

tatcacactt acaacgtaaa tcttctatca aggcccatgg agagatagag gctgatggaa    2760

gtaacgggac ttctgagttc aacgtaatga agtccggaaa tgctatctgg agatttgtga    2820

ggccgtatgc cgctaaaggt gtcctgttta actccgcggc aatgttcgct aaggaacttg    2880

ttggaaatct gaacttattt agctggccgt tgatgttcaa gatcctttca tttactcttg    2940

tcattctgtg tatctttgta tctacatcag gcataaatca gatatatgat ctagacatcg    3000

atagactgaa caaaccgaac ttgcccgtgg caagcgggga aattagcgta gaattggcat    3060

ggttacttac tatagtatgt acgattagtg gacttacctt aaccattata actaatagtg    3120

gccccttttt tccgttcctt tactcagcct ccatattctt tggtttccta tactccgccc    3180

ccccgttccg ttggaagaaa aaccccttta ccgcctgctt ttgcaatgtg atgttatacg    3240

tgggaaccag tgttggggtt tattatgcct gcaaagccag tttgggcctt cctgccaatt    3300

ggtctccagc attctgcctt ttattttggt ttattagtct gctttccata cctatcagca    3360

tagctaagga tttatctgat attgaaggtg ataggaagtt tggaatcatt actttctcta    3420

ctaagttcgg ggcaaaaccg atcgcgtaca tatgtcacgg gcttatgctt ttgaattacg    3480

tgagtgttat ggccgcggcc ataatatggc ctcaattctt caactcctca gtaatactgt    3540

tatcacatgc cttcatggcg atctgggttt tgtaccaagc gtggatactg gagaaaagta    3600

actatgcaac ggaaacttgc cagaaatatt acatcttctt atggataata ttctcccttg    3660

agcacgcttt ttacctattc atgtaggatg ggctgcagga attcgatatc aagcttatcg    3720

ataccgtcga cctcgagtca tgtaattagt tatgtcacgc ttacattcac gccctccccc    3780

cacatccgct ctaaccgaaa aggaaggagt tagacaacct gaagtctagg tccctattta    3840

tttttttata gttatgttag tattaagaac gttatttata tttcaaattt ttcttttttt    3900

tctgtacaga cgcgtgtacg catgtaacat tatactgaaa accttgcttg agaaggtttt    3960

gggacgctcg aaggctttaa tttgcggccg gtacccagct tttgttccct ttagtgaggg    4020

ttaattccga gcttggcgta atcatggtca gctgtttcc ctgtgtgaaa ttgttatccg     4080

ctcacaattc cacacaacat aggagccgga agcataaagt gtaaagcctg gggtgcctaa    4140
```

-continued

```
tgagtgaggt aactcacatt aattgcgttg cgctcactgc ccgctttcca gtcgggaaac   4200

ctgtcgtgcc agctgcatta atgaatcggc caacgcgcgg ggagaggcgg tttgcgtatt   4260

gggcgctctt ccgcttcctc gctcactgac tcgctgcgct cggtcgttcg gctgcggcga   4320

gcggtatcag ctcactcaaa ggcggtaata cggttatcca cagaatcagg ggataacgca   4380

ggaaagaaca tgtgagcaaa aggccagcaa aaggccagga accgtaaaaa ggccgcgttg   4440

ctggcgtttt tccataggct cggcccccct gacgagcatc acaaaaatcg acgctcaagt   4500

cagaggtggc gaaacccgac aggactataa agataccagg cgttcccccc tggaagctcc   4560

ctcgtgcgct ctcctgttcc gaccctgccg cttaccggat acctgtccgc ctttctccct   4620

tcgggaagcg tggcgctttc tcaatgctca cgctgtaggt atctcagttc ggtgtaggtc   4680

gttcgctcca agctgggctg tgtgcacgaa ccccccgttc agcccgaccg ctgcgcctta   4740

tccggtaact atcgtcttga gtccaacccg gtaagacacg acttatcgcc actggcagca   4800

gccactggta acaggattag cagagcgagg tatgtaggcg gtgctacaga gttcttgaag   4860

tggtggccta actacggcta cactagaagg acagtatttg gtatctgcgc tctgctgaag   4920

ccagttacct tcggaaaaag agttggtagc tcttgatccg gcaaacaaac caccgctggt   4980

agcggtggtt tttttgtttg caagcagcag attacgcgca gaaaaaaagg atctcaagaa   5040

gatcctttga tcttttctac ggggtctgac gctcagtgga acgaaaactc acgttaaggg   5100

attttggtca tgagattatc aaaaaggatc ttcacctaga tccttttaaa ttaaaaatga   5160

agttttaaat caatctaaag tatatatgag taaacttggt ctgacagtta ccaatgctta   5220

atcagtgagg cacctatctc agcgatctgt ctatttcgtt catccatagt tgcctgactg   5280

cccgtcgtgt agataactac gatacgggag ggcttaccat ctggccccag tgctgcaatg   5340

ataccgcgag acccacgctc accggctcca gatttatcag caataaacca gccagccgga   5400

agggccgagc gcagaagtgg tcctgcaact ttatccgcct ccatccagtc tattaattgt   5460

tgccgggaag ctagagtaag tagttcgcca gttaatagtt tgcgcaacgt tgttgccatt   5520

gctacaggca tcgtggtgtc acgctcgtcg tttggtatgg cttcattcag ctccggttcc   5580

caacgatcaa ggcgagttac atgatccccc atgttgtgaa aaaaagcggt tagctccttc   5640

ggtcctccga tcgttgtcag aagtaagttg gccgcagtgt tatcactcat ggttatggca   5700

gcactgcata attctcttac tgtcatgcca tccgtaagat gcttttctgt gactggtgag   5760

tactcaacca agtcattctg agaatagtgt atgcggcgac cgagttgctc ttgcccggcg   5820

tcaatacggg ataataccgc gccacatagc agaactttaa aagtgctcat cattggaaaa   5880

cgttcttcgg ggcgaaaact ctcaaggatc ttaccgctgt tgagatccag ttcgatgtaa   5940

cccactcgtg cacccaactg atcttcagca tcttttactt tcaccagcgt ttctgggtga   6000

gcaaaaacag gaaggcaaaa tgccgcaaaa aagggaataa gggcgacacg gaaatgttga   6060

atactcatac tcttcctttt tcaatattat tgaagcattt atcagggtta ttgtctcatg   6120

agcggataca tatttgaatg tatttagaaa aataaacaaa taggggttcc gcgcacattt   6180

ccccgaaaag tgccacctga cgtctaagaa accattatta tcatgacatt aacctataaa   6240

aataggcgta tcacgaggcc ctttcgtc                                      6268
```

<210> SEQ ID NO 47
<211> LENGTH: 6256
<212> TYPE: DNA
<213> ORGANISM: Artificial Sequence
<220> FEATURE:
<223> OTHER INFORMATION: Codon Optimized

<400> SEQUENCE: 47
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc tttttttga tttcggtttc 240
tttgaaattt ttttgattcg gtaatctccg aacagaagga agaacgaagg aaggagcaca 300
gacttagatt ggtatatata cgcatatgta gtgttgaaga aacatgaaat tgcccagtat 360
tcttaaccca actgcacaga acaaaaacct gcaggaaacg aagataaatc atgtcgaaag 420
ctacatataa ggaacgtgct gctactcatc ctagtcctgt tgctgccaag ctatttaata 480
tcatgcacga aaagcaaaca aacttgtgtg cttcattgga tgttcgtacc accaaggaat 540
tactggagtt agttgaagca ttaggtccca aaatttgttt actaaaaaca catgtggata 600
tcttgactga tttttccatg gagggcacag ttaagccgct aaaggcatta tccgccaagt 660
acaatttttt actcttcgaa gacagaaaat ttgctgacat tggtaataca gtcaaattgc 720
agtactctgc gggtgtatac agaatagcag aatgggcaga cattacgaat gcacacggtg 780
tggtgggccc aggtattgtt agcggtttga agcaggcggc agaagaagta acaaaggaac 840
ctagaggcct tttgatgtta gcagaattgt catgcaaggg ctccctatct actggagaat 900
atactaaggg tactgttgac attgcgaaga gcgacaaaga ttttgttatc ggctttattg 960
ctcaaagaga catgggtgga agagatgaag gttacgattg gttgattatg acacccggtg 1020
tgggtttaga tgacaaggga gacgcattgg gtcaacagta tagaaccgtg gatgatgtgg 1080
tctctacagg atctgacatt attattgttg gaagaggact atttgcaaag ggaagggatg 1140
ctaaggtaga gggtgaacgt tacagaaaag caggctggga agcatatttg agaagatgcg 1200
gccagcaaaa ctaaaaaact gtattataag taaatgcatg tatactaaac tcacaaatta 1260
gagcttcaat ttaattatat cagttattac cctgcggtgt gaaataccgc acagatgcgt 1320
aaggagaaaa taccgcatca ggaaattgta aacgttaata ttttgttaaa attcgcgtta 1380
aatttttgtt aaatcagctc atttttaac caataggccg aaatcggcaa aatcccttat 1440
aaatcaaaag aatagaccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc ctaatcaagt tttttggggt cgaggtgccg taaagcacta 1620
aatcggaacc ctaaagggag cccccgattt agagcttgac ggggaaagcc ggcgaacgtg 1680
gcgagaaagg aagggaagaa agcgaaagga gcgggcgcta gggcgctggc aagtgtagcg 1740
gtcacgctgc gcgtaaccac cacacccgcc gcgcttaatg cgccgctaca gggcgcgtcg 1800
cgccattcgc cattcaggct gcgcaactgt tgggaagggc gatcggtgcg ggcctcttcg 1860
ctattacgcc agctggcgaa gggggatgt gctgcaaggc gattaagttg ggtaacgcca 1920
gggttttccc agtcacgacg ttgtaaaacg acggccagtg aattgtaata cgactcacta 1980
tagggcgaat tggagctcta gtacggatta gaagccgccg agcgggcgac agccctccga 2040
cggaagactc tcctccgtgc gtcctcgtct tcaccggtcg cgttcctgaa acgcagatgt 2100
gcctcgcgcc gcactgctcc gaacaataaa gattctacaa tactagcttt tatggttatg 2160
aagaggaaaa attggcagta acctggcccc acaaaccttc aaattaacga atcaaattaa 2220
caaccatagg atgataatgc gattagtttt ttagccttat ttctggggta attaatcagc 2280
gaagcgatga tttttgatct attaacagat atataaatgg aaaagctgca taaccacttt 2340
aactaatact ttcaacattt tcagtttgta ttacttctta ttcaaatgtc ataaaagtat 2400
caacaaaaaa ttgttaatat acctctatac tttaacgtca aggagaaaaa accccggatt 2460
ctagaactag tggatccccc atcatgagat tcccatctat tttcactgct gttttgttcg 2520
ctgcttcttc tgctttggct gctccagttg cttcaagttc acattaccac gaaatcaaca 2580
atttcattaa caacaaaccc attaaattta gttatttctc ttcaaggttg tattgcagtg 2640
ccaagccaat agtacacaga gaaaacaagt tcacaaaatc attctcacta tcacacttac 2700
aacgtaaatc ttctatcaag gcccatggag agatagaggc tgatggaagt aacgggactt 2760
ctgagttcaa cgtaatgaag tccggaaatg ctatctggag atttgtgagg ccgtatgccg 2820
ctaaaggtgt cctgtttaac tccgcggcaa tgttcgctaa ggaacttgtt ggaaatctga 2880
acttatttag ctggccgttg atgttcaaga tcctttcatt tactcttgtc attctgtgta 2940
tctttgtatc tacatcaggc ataaatcaga tatatgatct agacatcgat agactgaaca 3000
aaccgaactt gcccgtggca agcggggaaa ttagcgtaga attggcatgg ttacttacta 3060
tagtatgtac gattagtgga cttaccttaa ccattataac taatagtggc cccttttttc 3120
cgttccttta ctcagcctcc atattctttg gtttcctata ctccgccccc ccgttccgtt 3180
ggaagaaaaa cccctttacc gcctgctttt gcaatgtgat gttatacgtg ggaaccagtg 3240
ttggggttta ttatgcctgc aaagccagtt tgggccttcc tgccaattgg tctccagcat 3300
tctgcctttt attttggttt attagtctgc tttccatacc tatcagcata gctaaggatt 3360
tatctgatat tgaaggtgat aggaagtttg gaatcattac tttctctact aagttcgggg 3420
caaaaccgat cgcgtacata tgtcacgggc ttatgctttt gaattacgtg agtgttatgg 3480
ccgcggccat aatatggcct caattcttca actcctcagt aatactgtta tcacatgcct 3540
tcatggcgat ctgggttttg taccaagcgt ggatactgga gaaaagtaac tatgcaacgg 3600
aaacttgcca gaaatattac atcttcttat ggataatatt ctcccttgag cacgcttttt 3660
acctattcat gtaggatggg ctgcaggaat tcgatatcaa gcttatcgat accgtcgacc 3720
tcgagtcatg taattagtta tgtcacgctt acattcacgc cctcccccca catccgctct 3780
aaccgaaaag gaaggagtta gacaacctga agtctaggtc cctatttatt tttttatagt 3840
tatgttagta ttaagaacgt tatttatatt tcaaattttt cttttttttc tgtacagacg 3900
cgtgtacgca tgtaacatta tactgaaaac cttgcttgag aaggttttgg gacgctcgaa 3960
ggctttaatt tgcggccggt acccagcttt tgttcccttt agtgagggtt aattccgagc 4020
ttggcgtaat catggtcata gctgtttcct gtgtgaaatt gttatccgct cacaattcca 4080
cacaacatag gagccggaag cataaagtgt aaagcctggg gtgcctaatg agtgaggtaa 4140
ctcacattaa ttgcgttgcg ctcactgccc gctttccagt cgggaaacct gtcgtgccag 4200
ctgcattaat gaatcggcca acgcgcgggg agaggcggtt tgcgtattgg gcgctcttcc 4260
gcttcctcgc tcactgactc gctgcgctcg gtcgttcggc tgcggcgagc ggtatcagct 4320
cactcaaagg cggtaatacg gttatccaca gaatcagggg ataacgcagg aaagaacatg 4380
tgagcaaaag gccagcaaaa ggccaggaac cgtaaaaagg ccgcgttgct ggcgtttttc 4440
cataggctcg gcccccctga cgagcatcac aaaaatcgac gctcaagtca gaggtggcga 4500
aacccgacag gactataaag ataccaggcg tttccccctg gaagctccct cgtgcgctct 4560
cctgttccga ccctgccgct taccggatac ctgtccgcct ttctcccttc gggaagcgtg 4620
gcgctttctc aatgctcacg ctgtaggtat ctcagttcgg tgtaggtcgt tcgctccaag 4680
ctgggctgtg tgcacgaacc ccccgttcag cccgaccgct gcgccttatc cggtaactat 4740
cgtcttgagt ccaacccggt aagacacgac ttatcgccac tggcagcagc cactggtaac 4800
aggattagca gagcgaggta tgtaggcggt gctacagagt tcttgaagtg gtggcctaac 4860
tacggctaca ctagaaggac agtatttggt atctgcgctc tgctgaagcc agttaccttc 4920
ggaaaaagag ttggtagctc ttgatccggc aaacaaacca ccgctggtag cggtggtttt 4980
tttgtttgca agcagcagat tacgcgcaga aaaaaaggat ctcaagaaga tcctttgatc 5040
ttttctacgg ggtctgacgc tcagtggaac gaaaactcac gttaagggat tttggtcatg 5100
agattatcaa aaaggatctt cacctagatc cttttaaatt aaaaatgaag ttttaaatca 5160
atctaaagta tatatgagta aacttggtct gacagttacc aatgcttaat cagtgaggca 5220
cctatctcag cgatctgtct atttcgttca tccatagttg cctgactgcc cgtcgtgtag 5280
ataactacga tacgggaggg cttaccatct ggccccagtg ctgcaatgat accgcgagac 5340
ccacgctcac cggctccaga tttatcagca ataaaccagc cagccggaag ggccgagcgc 5400
agaagtggtc ctgcaacttt atccgcctcc atccagtcta ttaattgttg ccgggaagct 5460
agagtaagta gttcgccagt taatagtttg cgcaacgttg ttgccattgc tacaggcatc 5520
gtggtgtcac gctcgtcgtt tggtatggct tcattcagct ccggttccca acgatcaagg 5580
cgagttacat gatcccccat gttgtgaaaa aaagcggtta gctccttcgg tcctccgatc 5640
gttgtcagaa gtaagttggc cgcagtgtta tcactcatgg ttatggcagc actgcataat 5700
tctcttactg tcatgccatc cgtaagatgc ttttctgtga ctggtgagta ctcaaccaag 5760
tcattctgag aatagtgtat gcggcgaccg agttgctctt gcccggcgtc aatacgggat 5820
aataccgcgc cacatagcag aactttaaaa gtgctcatca ttggaaaacg ttcttcgggg 5880
cgaaaactct caaggatctt accgctgttg agatccagtt cgatgtaacc cactcgtgca 5940
cccaactgat cttcagcatc ttttactttc accagcgttt ctgggtgagc aaaaacagga 6000
aggcaaaatg ccgcaaaaaa gggaataagg gcgacacgga aatgttgaat actcatactc 6060
ttcctttttc aatattattg aagcatttat cagggttatt gtctcatgag cggatacata 6120
tttgaatgta tttagaaaaa taaacaaata ggggttccgc gcacatttcc ccgaaaagtg 6180
ccacctgacg tctaagaaac cattattatc atgacattaa cctataaaaa taggcgtatc 6240
acgaggccct ttcgtc 6256

<210> SEQ ID NO 48
<211> LENGTH: 648
<212> TYPE: DNA
<213> ORGANISM: Artificial Sequence
<220> FEATURE:
<223> OTHER INFORMATION: Codon Optimized

<400> SEQUENCE: 48
atgagcatcg aaatggcctg ggtcctgacc atattctgtg ctatcagtgg gttaatactt 60
acaatcacta tgaacagcgg ccctctattt ccattcttgt actgtggatc tatatttgtt 120
gctggctttc tatatagtgc tccgcccttc agatttaaga ataaccactt cactgccctg 180
ctgtgtaatt acgtaatgtt tgtcagcaca acccttcaga tatactgcgc atacaaggcg 240
ggccttggcc ttccactgaa ttggagcccc gcgttctgcc tattagtgtg gttcttgtca 300
ttaatcgctg tcactatatg tattggcaaa gatttgtcag acattgaagg cgatagaaag 360
ttcggcgtaa caaccttccc gacagaatac ggggcaaagc ccatagcgct aatttgccac 420

-continued

```
ggcctgattc tattagacta cgtgggtctg atggcagccg ccataatctg gccgcagtta    480

ttcaactcta agctaatcct actgtctcat gcgtttatgg ccgtgtgggt cgtttatcag    540

gcttggattt tggaaaagag caattatacg accgaggcat gtcaaaagta ctatatgtac    600

ttatggacga tctattctgt cgagcacatc ttatatctgt tcatgtag                 648


<210> SEQ ID NO 49
<211> LENGTH: 423
<212> TYPE: DNA
<213> ORGANISM: Artificial Sequence
<220> FEATURE:
<223> OTHER INFORMATION: Codon Optimized

<400> SEQUENCE: 49

atggcataca aggcgggcct tggccttcca ctgaattgga gccccgcgtt ctgcctatta     60

gtgtggttct tgtcattaat cgctgtcact atatgtattg gcaaagattt gtcagacatt    120

gaaggcgata gaaagttcgg cgtaacaacc ttcccgacag aatacggggc aaagcccata    180

gcgctaattt gccacggcct gattctatta gactacgtgg gtctgatggc agccgccata    240

atctggccgc agttattcaa ctctaagcta atcctactgt ctcatgcgtt tatggccgtg    300

tgggtcgttt atcaggcttg gattttggaa aagagcaatt atacgaccga ggcatgtcaa    360

aagtactata tgtacttatg gacgatctat tctgtcgagc acatcttata tctgttcatg    420

tag                                                                  423


<210> SEQ ID NO 50
<211> LENGTH: 485
<212> TYPE: DNA
<213> ORGANISM: Artificial Sequence
<220> FEATURE:
<223> OTHER INFORMATION: Codon Optimized

<400> SEQUENCE: 50

atgagattcc catctatttt cactgctgtt ttgttcgctg cttcttctgc tttggctgct     60

ccagttcata caaggcgggc cttggccttc cactgaattg gagccccgcg ttctgcctat    120

tagtgtggtt cttgtcatta atcgctgtca ctatatgtat tggcaaagat ttgtcagaca    180

ttgaaggcga tagaaagttc ggcgtaacaa ccttcccgac agaatacggg gcaaagccca    240

tagcgctaat ttgccacggc ctgattctat tagactacgt gggtctgatg gcagccgcca    300

taatctggcc gcagttattc aactctaagc taatcctact gtctcatgcg tttatggccg    360

tgtgggtcgt ttatcaggct tggattttgg aaaagagcaa ttatacgacc gaggcatgtc    420

aaaagtacta tatgtactta tggacgatct attctgtcga gcacatctta tatctgttca    480

tgtag                                                                485


<210> SEQ ID NO 51
<211> LENGTH: 5713
<212> TYPE: DNA
<213> ORGANISM: Artificial Sequence
<220> FEATURE:
<223> OTHER INFORMATION: Codon Optimized

<400> SEQUENCE: 51

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accacgcttt tcaattcaat tcatcatttt tttttattc tttttttga tttcggtttc     240
```

-continued

```
tttgaaattt ttttgattcg gtaatctccg aacagaagga agaacgaagg aaggagcaca    300
gacttagatt ggtatatata cgcatatgta gtgttgaaga aacatgaaat tgcccagtat    360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga tttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aatttttgtt aaatcagctc attttttaac caataggccg aaatcggcaa aatcccttat   1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatgagca tcgaaatggc ctgggtcctg accatattct   2520
gtgctatcag tgggttaata cttacaatca ctatgaacag cggccctcta tttccattct   2580
```

-continued

```
tgtactgtgg atctatattt gttgctggct ttctatatag tgctccgccc ttcagattta   2640
agaataacca cttcactgcc ctgctgtgta attacgtaat gtttgtcagc acaacccttc   2700
agatatactg cgcatacaag gcgggccttg gccttccact gaattggagc cccgcgttct   2760
gcctattagt gtggttcttg tcattaatcg ctgtcactat atgtattggc aaagatttgt   2820
cagacattga aggcgataga aagttcggcg taacaacctt cccgacagaa tacggggcaa   2880
agcccatagc gctaatttgc cacggcctga ttctattaga ctacgtgggt ctgatggcag   2940
ccgccataat ctggccgcag ttattcaact ctaagctaat cctactgtct catgcgttta   3000
tggccgtgtg ggtcgtttat caggcttgga ttttggaaaa gagcaattat acgaccgagg   3060
catgtcaaaa gtactatatg tacttatgga cgatctattc tgtcgagcac atcttatatc   3120
tgttcatgta ggatgggctg caggaattcg atatcaagct tatcgatacc gtcgacctcg   3180
agtcatgtaa ttagttatgt cacgcttaca ttcacgccct ccccccacat ccgctctaac   3240
cgaaaaggaa ggagttagac aacctgaagt ctaggtccct atttattttt ttatagttat   3300
gttagtatta agaacgttat ttatatttca aatttttctt ttttttctgt acagacgcgt   3360
gtacgcatgt aacattatac tgaaaacctt gcttgagaag gttttgggac gctcgaaggc   3420
tttaatttgc ggccggtacc cagcttttgt tccctttagt gagggttaat tccgagcttg   3480
gcgtaatcat ggtcatagct gtttcctgtg tgaaattgtt atccgctcac aattccacac   3540
aacataggag ccggaagcat aaagtgtaaa gcctggggtg cctaatgagt gaggtaactc   3600
acattaattg cgttgcgctc actgcccgct ttccagtcgg gaaacctgtc gtgccagctg   3660
cattaatgaa tcggccaacg cgcggggaga ggcggtttgc gtattgggcg ctcttccgct   3720
tcctcgctca ctgactcgct gcgctcggtc gttcggctgc ggcgagcggt atcagctcac   3780
tcaaaggcgg taatacggtt atccacagaa tcaggggata acgcaggaaa gaacatgtga   3840
gcaaaaggcc agcaaaaggc caggaaccgt aaaaaggccg cgttgctggc gtttttccat   3900
aggctcggcc cccctgacga gcatcacaaa aatcgacgct caagtcagag gtggcgaaac   3960
ccgacaggac tataaagata ccaggcgttc cccccctggaa gctccctcgt gcgctctcct   4020
gttccgaccc tgccgcttac cggatacctg tccgcctttc tcccttcggg aagcgtggcg   4080
ctttctcaat gctcacgctg taggtatctc agttcggtgt aggtcgttcg ctccaagctg   4140
ggctgtgtgc acgaaccccc cgttcagccc gaccgctgcg ccttatccgg taactatcgt   4200
cttgagtcca acccggtaag acacgactta tcgccactgg cagcagccac tggtaacagg   4260
attagcagag cgaggtatgt aggcggtgct acagagttct tgaagtggtg gcctaactac   4320
ggctacacta gaaggacagt atttggtatc tgcgctctgc tgaagccagt taccttcgga   4380
aaaagagttg gtagctcttg atccggcaaa caaaccaccg ctggtagcgg tggttttttt   4440
gtttgcaagc agcagattac gcgcagaaaa aaaggatctc aagaagatcc tttgatcttt   4500
tctacggggt ctgacgctca gtggaacgaa aactcacgtt aagggatttt ggtcatgaga   4560
ttatcaaaaa ggatcttcac ctagatcctt ttaaattaaa aatgaagttt taaatcaatc   4620
taaagtatat atgagtaaac ttggtctgac agttaccaat gcttaatcag tgaggcacct   4680
atctcagcga tctgtctatt tcgttcatcc atagttgcct gactgcccgt cgtgtagata   4740
actacgatac gggagggctt accatctggc cccagtgctg caatgatacc gcgagaccca   4800
cgctcaccgg ctccagattt atcagcaata aaccagccag ccggaagggc cgagcgcaga   4860
agtggtcctg caactttatc cgcctccatc cagtctatta attgttgccg ggaagctaga   4920
gtaagtagtt cgccagttaa tagtttgcgc aacgttgttg ccattgctac aggcatcgtg   4980
```

gtgtcacgct cgtcgtttgg tatggcttca ttcagctccg gttcccaacg atcaaggcga 5040
gttacatgat cccccatgtt gtgaaaaaaa gcggttagct ccttcggtcc tccgatcgtt 5100
gtcagaagta agttggccgc agtgttatca ctcatggtta tggcagcact gcataattct 5160
cttactgtca tgccatccgt aagatgcttt tctgtgactg gtgagtactc aaccaagtca 5220
ttctgagaat agtgtatgcg gcgaccgagt tgctcttgcc cggcgtcaat acgggataat 5280
accgcgccac atagcagaac tttaaaagtg ctcatcattg gaaaacgttc ttcggggcga 5340
aaactctcaa ggatcttacc gctgttgaga tccagttcga tgtaacccac tcgtgcaccc 5400
aactgatctt cagcatcttt tactttcacc agcgtttctg ggtgagcaaa aacaggaagg 5460
caaaatgccg caaaaaaggg aataagggcg acacggaaat gttgaatact catactcttc 5520
ctttttcaat attattgaag catttatcag ggttattgtc tcatgagcgg atacatattt 5580
gaatgtattt agaaaaataa acaaataggg gttccgcgca catttccccg aaaagtgcca 5640
cctgacgtct aagaaaccat tattatcatg acattaacct ataaaaatag gcgtatcacg 5700
aggccctttc gtc 5713

<210> SEQ ID NO 52
<211> LENGTH: 5488
<212> TYPE: DNA
<213> ORGANISM: Artificial Sequence
<220> FEATURE:
<223> OTHER INFORMATION: Codon Optimized

<400> SEQUENCE: 52
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc ttttttttga tttcggtttc 240
tttgaaattt ttttgattcg gtaatctccg aacagaagga agaacgaagg aaggagcaca 300
gacttagatt ggtatatata cgcatatgta gtgttgaaga aacatgaaat tgcccagtat 360
tcttaaccca actgcacaga acaaaaacct gcaggaaacg aagataaatc atgtcgaaag 420
ctacatataa ggaacgtgct gctactcatc ctagtcctgt tgctgccaag ctatttaata 480
tcatgcacga aaagcaaaca aacttgtgtg cttcattgga tgttcgtacc accaaggaat 540
tactggagtt agttgaagca ttaggtccca aaatttgttt actaaaaaca catgtggata 600
tcttgactga tttttccatg gagggcacag ttaagccgct aaaggcatta tccgccaagt 660
acaatttttt actcttcgaa gacagaaaat ttgctgacat tggtaataca gtcaaattgc 720
agtactctgc gggtgtatac agaatagcag aatgggcaga cattacgaat gcacacggtg 780
tggtgggccc aggtattgtt agcggtttga agcaggcggc agaagaagta acaaaggaac 840
ctagaggcct tttgatgtta gcagaattgt catgcaaggg ctccctatct actggagaat 900
atactaaggg tactgttgac attgcgaaga gcgacaaaga ttttgttatc ggctttattg 960
ctcaaagaga catgggtgga agagatgaag gttacgattg gttgattatg acacccggtg 1020
tgggtttaga tgacaaggga gacgcattgg gtcaacagta tagaaccgtg gatgatgtgg 1080
tctctacagg atctgacatt attattgttg gaagaggact atttgcaaag ggaagggatg 1140
ctaaggtaga gggtgaacgt tacagaaaag caggctggga agcatatttg agaagatgcg 1200
gccagcaaaa ctaaaaaact gtattataag taaatgcatg tatactaaac tcacaaatta 1260

-continued gagcttcaat ttaattatat cagttattac cctgcggtgt gaaataccgc acagatgcgt 1320
aaggagaaaa taccgcatca ggaaattgta aacgttaata ttttgttaaa attcgcgtta 1380
aatttttgtt aaatcagctc attttttaac caataggccg aaatcggcaa aatcccttat 1440
aaatcaaaag aatagaccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc ctaatcaagt tttttggggt cgaggtgccg taaagcacta 1620
aatcggaacc ctaaagggag cccccgattt agagcttgac ggggaaagcc ggcgaacgtg 1680
gcgagaaagg aagggaagaa agcgaaagga gcgggcgcta gggcgctggc aagtgtagcg 1740
gtcacgctgc gcgtaaccac cacacccgcc gcgcttaatg cgccgctaca gggcgcgtcg 1800
cgccattcgc cattcaggct gcgcaactgt tgggaagggc gatcggtgcg ggcctcttcg 1860
ctattacgcc agctggcgaa gggggatgt gctgcaaggc gattaagttg ggtaacgcca 1920
gggttttccc agtcacgacg ttgtaaaacg acggccagtg aattgtaata cgactcacta 1980
tagggcgaat tggagctcta gtacggatta gaagccgccg agcgggcgac agccctccga 2040
cggaagactc tcctccgtgc gtcctcgtct tcaccggtcg cgttcctgaa acgcagatgt 2100
gcctcgcgcc gcactgctcc gaacaataaa gattctacaa tactagcttt tatggttatg 2160
aagaggaaaa attggcagta acctggcccc acaaaccttc aaattaacga atcaaattaa 2220
caaccatagg atgataatgc gattagtttt ttagccttat ttctggggta attaatcagc 2280
gaagcgatga tttttgatct attaacagat atataaatgg aaaagctgca taaccacttt 2340
aactaatact ttcaacattt tcagtttgta ttacttctta ttcaaatgtc ataaaagtat 2400
caacaaaaaa ttgttaatat acctctatac tttaacgtca aggagaaaaa accccggatt 2460
ctagaactag tggatccccc atcatggcat acaaggcggg ccttggcctt ccactgaatt 2520
ggagccccgc gttctgccta ttagtgtggt tcttgtcatt aatcgctgtc actatatgta 2580
ttggcaaaga tttgtcagac attgaaggcg atagaaagtt cggcgtaaca accttcccga 2640
cagaatacgg ggcaaagccc atagcgctaa tttgccacgg cctgattcta ttagactacg 2700
tgggtctgat ggcagccgcc ataatctggc cgcagttatt caactctaag ctaatcctac 2760
tgtctcatgc gtttatggcc gtgtgggtcg tttatcaggc ttggattttg gaaaagagca 2820
attatacgac cgaggcatgt caaaagtact atatgtactt atggacgatc tattctgtcg 2880
agcacatctt atatctgttc atgtaggatg ggctgcagga attcgatatc aagcttatcg 2940
ataccgtcga cctcgagtca tgtaattagt tatgtcacgc ttacattcac gccctccccc 3000
cacatccgct ctaaccgaaa aggaaggagt tagacaacct gaagtctagg tccctattta 3060
tttttttata gttatgttag tattaagaac gttatttata tttcaaattt ttcttttttt 3120
tctgtacaga cgcgtgtacg catgtaacat tatactgaaa accttgcttg agaaggtttt 3180
gggacgctcg aaggctttaa tttgcggccg gtacccagct tttgttccct ttagtgaggg 3240
ttaattccga gcttggcgta atcatggtca tagctgtttc ctgtgtgaaa ttgttatccg 3300
ctcacaattc cacacaacat aggagccgga agcataaagt gtaaagcctg gggtgcctaa 3360
tgagtgaggt aactcacatt aattgcgttg cgctcactgc ccgctttcca gtcgggaaac 3420
ctgtcgtgcc agctgcatta atgaatcggc caacgcgcgg ggagaggcgg tttgcgtatt 3480
gggcgctctt ccgcttcctc gctcactgac tcgctgcgct cggtcgttcg gctgcggcga 3540
gcggtatcag ctcactcaaa ggcggtaata cggttatcca cagaatcagg ggataacgca 3600
ggaaagaaca tgtgagcaaa aggccagcaa aaggccagga accgtaaaaa ggccgcgttg 3660
ctggcgtttt tccataggct cggcccccct gacgagcatc acaaaaatcg acgctcaagt 3720
cagaggtggc gaaacccgac aggactataa agataccagg cgttcccccc tggaagctcc 3780
ctcgtgcgct ctcctgttcc gaccctgccg cttaccggat acctgtccgc ctttctccct 3840
tcgggaagcg tggcgctttc tcaatgctca cgctgtaggt atctcagttc ggtgtaggtc 3900
gttcgctcca agctgggctg tgtgcacgaa ccccccgttc agcccgaccg ctgcgcctta 3960
tccggtaact atcgtcttga gtccaacccg gtaagacacg acttatcgcc actggcagca 4020
gccactggta acaggattag cagagcgagg tatgtaggcg gtgctacaga gttcttgaag 4080
tggtggccta actacggcta cactagaagg acagtatttg gtatctgcgc tctgctgaag 4140
ccagttacct tcggaaaaag agttggtagc tcttgatccg gcaaacaaac caccgctggt 4200
agcggtggtt tttttgtttg caagcagcag attacgcgca gaaaaaaagg atctcaagaa 4260
gatcctttga tcttttctac ggggtctgac gctcagtgga acgaaaactc acgttaaggg 4320
attttggtca tgagattatc aaaaaggatc ttcacctaga tccttttaaa ttaaaaatga 4380
agttttaaat caatctaaag tatatatgag taaacttggt ctgacagtta ccaatgctta 4440
atcagtgagg cacctatctc agcgatctgt ctatttcgtt catccatagt tgcctgactg 4500
cccgtcgtgt agataactac gatacgggag ggcttaccat ctggccccag tgctgcaatg 4560
ataccgcgag acccacgctc accggctcca gatttatcag caataaacca gccagccgga 4620
agggccgagc gcagaagtgg tcctgcaact ttatccgcct ccatccagtc tattaattgt 4680
tgccgggaag ctagagtaag tagttcgcca gttaatagtt tgcgcaacgt tgttgccatt 4740
gctacaggca tcgtggtgtc acgctcgtcg tttggtatgg cttcattcag ctccggttcc 4800
caacgatcaa ggcgagttac atgatccccc atgttgtgaa aaaaagcggt tagctccttc 4860
ggtcctccga tcgttgtcag aagtaagttg gccgcagtgt tatcactcat ggttatggca 4920
gcactgcata attctcttac tgtcatgcca tccgtaagat gcttttctgt gactggtgag 4980
tactcaacca agtcattctg agaatagtgt atgcggcgac cgagttgctc ttgcccggcg 5040
tcaatacggg ataataccgc gccacatagc agaactttaa aagtgctcat cattggaaaa 5100
cgttcttcgg ggcgaaaact ctcaaggatc ttaccgctgt tgagatccag ttcgatgtaa 5160
cccactcgtg cacccaactg atcttcagca tcttttactt tcaccagcgt ttctgggtga 5220
gcaaaaacag gaaggcaaaa tgccgcaaaa aagggaataa gggcgacacg gaaatgttga 5280
atactcatac tcttcctttt tcaatattat tgaagcattt atcagggtta ttgtctcatg 5340
agcggataca tatttgaatg tatttagaaa aataaacaaa taggggttcc gcgcacattt 5400
ccccgaaaag tgccacctga cgtctaagaa accattatta tcatgacatt aacctataaa 5460
aataggcgta tcacgaggcc ctttcgtc 5488

<210> SEQ ID NO 53
<211> LENGTH: 5550
<212> TYPE: DNA
<213> ORGANISM: Artificial Sequence
<220> FEATURE:
<223> OTHER INFORMATION: Codon Optimized

<400> SEQUENCE: 53
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180

-continued

```
accacgcttt tcaattcaat tcatcatttt ttttttattc ttttttttga tttcggtttc    240
tttgaaattt ttttgattcg gtaatctccg aacagaagga agaacgaagg aaggagcaca    300
gacttagatt ggtatatata cgcatatgta gtgttgaaga aacatgaaat tgcccagtat    360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga tttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aatttttgtt aaatcagctc attttttaac caataggccg aaatcggcaa aatcccttat   1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa agggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatgagat tcccatctat tttcactgct gttttgttcg   2520
ctgcttcttc tgctttggct gctccagttc atacaaggcg ggccttggcc ttccactgaa   2580
```

ttggagcccc gcgttctgcc tattagtgtg gttcttgtca ttaatcgctg tcactatatg 2640
tattggcaaa gatttgtcag acattgaagg cgatagaaag ttcggcgtaa caaccttccc 2700
gacagaatac ggggcaaagc ccatagcgct aatttgccac ggcctgattc tattagacta 2760
cgtgggtctg atggcagccg ccataatctg gccgcagtta ttcaactcta agctaatcct 2820
actgtctcat gcgtttatgg ccgtgtgggt cgtttatcag gcttggattt tggaaaagag 2880
caattatacg accgaggcat gtcaaaagta ctatatgtac ttatggacga tctattctgt 2940
cgagcacatc ttatatctgt tcatgtagga tgggctgcag gaattcgata tcaagcttat 3000
cgataccgtc gacctcgagt catgtaatta gttatgtcac gcttacattc acgccctccc 3060
cccacatccg ctctaaccga aaaggaagga gttagacaac ctgaagtcta ggtccctatt 3120
tattttttta tagttatgtt agtattaaga acgttattta tatttcaaat ttttcttttt 3180
tttctgtaca gacgcgtgta cgcatgtaac attatactga aaaccttgct tgagaaggtt 3240
ttgggacgct cgaaggcttt aatttgcggc cggtacccag cttttgttcc ctttagtgag 3300
ggttaattcc gagcttggcg taatcatggt catagctgtt tcctgtgtga aattgttatc 3360
cgctcacaat tccacacaac ataggagccg gaagcataaa gtgtaaagcc tggggtgcct 3420
aatgagtgag gtaactcaca ttaattgcgt tgcgctcact gcccgctttc cagtcgggaa 3480
acctgtcgtg ccagctgcat taatgaatcg gccaacgcgc ggggagaggc ggtttgcgta 3540
ttgggcgctc ttccgcttcc tcgctcactg actcgctgcg ctcggtcgtt cggctgcggc 3600
gagcggtatc agctcactca aaggcggtaa tacggttatc cacagaatca ggggataacg 3660
caggaaagaa catgtgagca aaaggccagc aaaaggccag gaaccgtaaa aaggccgcgt 3720
tgctggcgtt tttccatagg ctcggccccc ctgacgagca tcacaaaaat cgacgctcaa 3780
gtcagaggtg gcgaaacccg acaggactat aaagatacca ggcgttcccc cctggaagct 3840
ccctcgtgcg ctctcctgtt ccgaccctgc cgcttaccgg atacctgtcc gcctttctcc 3900
cttcgggaag cgtggcgctt tctcaatgct cacgctgtag gtatctcagt tcggtgtagg 3960
tcgttcgctc caagctgggc tgtgtgcacg aaccccccgt tcagcccgac cgctgcgcct 4020
tatccggtaa ctatcgtctt gagtccaacc cggtaagaca cgacttatcg ccactggcag 4080
cagccactgg taacaggatt agcagagcga ggtatgtagg cggtgctaca gagttcttga 4140
agtggtggcc taactacggc tacactagaa ggacagtatt tggtatctgc gctctgctga 4200
agccagttac cttcggaaaa agagttggta gctcttgatc cggcaaacaa accaccgctg 4260
gtagcggtgg tttttttgtt tgcaagcagc agattacgcg cagaaaaaaa ggatctcaag 4320
aagatccttt gatcttttct acggggtctg acgctcagtg gaacgaaaac tcacgttaag 4380
ggattttggt catgagatta tcaaaaagga tcttcaccta gatcctttta aattaaaaat 4440
gaagttttaa atcaatctaa agtatatatg agtaaacttg gtctgacagt taccaatgct 4500
taatcagtga ggcacctatc tcagcgatct gtctatttcg ttcatccata gttgcctgac 4560
tgcccgtcgt gtagataact acgatacggg agggcttacc atctggcccc agtgctgcaa 4620
tgataccgcg agacccacgc tcaccggctc cagatttatc agcaataaac cagccagccg 4680
gaagggccga gcgcagaagt ggtcctgcaa ctttatccgc ctccatccag tctattaatt 4740
gttgccggga agctagagta agtagttcgc cagttaatag tttgcgcaac gttgttgcca 4800
ttgctacagg catcgtggtg tcacgctcgt cgtttggtat ggcttcattc agctccggtt 4860
cccaacgatc aaggcgagtt acatgatccc ccatgttgtg aaaaaaagcg gttagctcct 4920

```
tcggtcctcc gatcgttgtc agaagtaagt tggccgcagt gttatcactc atggttatgg   4980

cagcactgca taattctctt actgtcatgc catccgtaag atgcttttct gtgactggtg   5040

agtactcaac caagtcattc tgagaatagt gtatgcggcg accgagttgc tcttgcccgg   5100

cgtcaatacg ggataatacc gcgccacata gcagaacttt aaaagtgctc atcattggaa   5160

aacgttcttc ggggcgaaaa ctctcaagga tcttaccgct gttgagatcc agttcgatgt   5220

aacccactcg tgcacccaac tgatcttcag catcttttac tttcaccagc gtttctgggt   5280

gagcaaaaac aggaaggcaa aatgccgcaa aaaagggaat aagggcgaca cggaaatgtt   5340

gaatactcat actcttcctt tttcaatatt attgaagcat ttatcagggt tattgtctca   5400

tgagcggata catatttgaa tgtatttaga aaaataaaca aataggggtt ccgcgcacat   5460

ttccccgaaa agtgccacct gacgtctaag aaaccattat tatcatgaca ttaacctata   5520

aaaataggcg tatcacgagg ccctttcgtc                                    5550
```

<210> SEQ ID NO 54
<211> LENGTH: 1155
<212> TYPE: DNA
<213> ORGANISM: Artificial Sequence
<220> FEATURE:
<223> OTHER INFORMATION: Codon Optimized

<400> SEQUENCE: 54

```
atggaattat cattatctct gggcgggccg acgatattcc ccagatatag agcaagctat     60

acttccacta aactgaccac tcatttctct aattttccgt ccaaattcag cacaaaaaat    120

ttccaccaga cgctatcttt ctacggacca acgagaggca gcaaatcatt gttgaatacc    180

catcagtgga ggaactccat aagagcctgc gccgaggcgg gggctgccgg gtcaaacccg    240

gtgctaaaca aggtctctga ctttagggac gcatgctggc gtttcttaag gccgcatact    300

ataaggggga ccaccctggg tagtatagcc ctagtagcaa gggcgcttat agaaaatccc    360

aacttaatca agtggagtct tttactgaag gctttctctg gcttactagc cttaatttgc    420

gggaacggct acattgtagg aatcaaccaa atctatgaca taggtattga taaggtcaac    480

aaaccgtacc ttcccatagc cgcgggtgat ttgtcagtcc agagtgcttg gtaccttgta    540

atattgtttg ccgttgcggg tctactaact gttggcttca attttgggcc gttcattacg    600

tctctatact gcttaggact tgttctgggg acaatatata gcgttccacc ctttaggatg    660

aaaagatttc cggttgcagc attcttaatc attgcgaccg tgaggggttt tctattaaac    720

tttggtgtat actacgccac aagagctgca ttgggcttaa cctttgaatg gagtagtgcg    780

gttgcgttca ttacgacctt cgttacatta ttcgctttgg tgatagctat aacgaaagat    840

ctgccagacg tggagggaga ccgtaaattt cagatcagca cattcgcaac aaagcttggt    900

gtgagaaaca tcgcgtatct tggatctgga ctattattat taaactacat tggggcaatt    960

gcggcggcca tttatatgcc tcaggctttt aagagaaatt taatgcttcc tatccacacc   1020

atcttggcgt tgagccttgt cttccaggcc tgggtcttgg aacaagcgaa ttacaccaag   1080

gaggctattg ctgggttcta tagattcatt tggaatttgt tctatgtaga atacattata   1140

ttccccttta tatag                                                    1155
```

<210> SEQ ID NO 55
<211> LENGTH: 933
<212> TYPE: DNA
<213> ORGANISM: Artificial Sequence
<220> FEATURE:
<223> OTHER INFORMATION: Codon Optimized

<400> SEQUENCE: 55
atggccgggt caaacccggt gctaaacaag gtctctgact ttagggacgc atgctggcgt 60
ttcttaaggc cgcatactat aagggggacc accctgggta gtatagccct agtagcaagg 120
gcgcttatag aaaatcccaa cttaatcaag tggagtcttt tactgaaggc tttctctggc 180
ttactagcct taatttgcgg gaacggctac attgtaggaa tcaaccaaat ctatgacata 240
ggtattgata aggtcaacaa accgtacctt cccatagccg cgggtgattt gtcagtccag 300
agtgcttggt accttgtaat attgtttgcc gttgcgggtc tactaactgt tggcttcaat 360
tttgggccgt tcattacgtc tctatactgc ttaggacttg ttctggggac aatatatagc 420
gttccaccct ttaggatgaa aagatttccg gttgcagcat tcttaatcat tgcgaccgtg 480
aggggttttc tattaaactt tggtgtatac tacgccacaa gagctgcatt gggcttaacc 540
tttgaatgga gtagtgcggt tgcgttcatt acgaccttcg ttacattatt cgctttggtg 600
atagctataa cgaaagatct gccagacgtg gagggagacc gtaaatttca gatcagcaca 660
ttcgcaacaa agcttggtgt gagaaacatc gcgtatcttg gatctggact attattatta 720
aactacattg gggcaattgc ggcggccatt tatatgcctc aggcttttaa gagaaattta 780
atgcttccta tccacaccat cttggcgttg agccttgtct tccaggcctg ggtcttggaa 840
caagcgaatt acaccaagga ggctattgct gggttctata gattcatttg gaatttgttc 900
tatgtagaat acattatatt ccccttata tag 933

<210> SEQ ID NO 56
<211> LENGTH: 996
<212> TYPE: DNA
<213> ORGANISM: Artificial Sequence
<220> FEATURE:
<223> OTHER INFORMATION: Codon Optimized

<400> SEQUENCE: 56
atgagattcc catctatttt cactgctgtt ttgttcgctg cttcttctgc tttggctgct 60
ccagttgccg ggtcaaaccc ggtgctaaac aaggtctctg actttaggga cgcatgctgg 120
cgtttcttaa ggccgcatac tataaggggg accaccctgg gtagtatagc cctagtagca 180
agggcgctta tagaaaatcc caacttaatc aagtggagtc ttttactgaa ggctttctct 240
ggcttactag ccttaatttg cgggaacggc tacattgtag gaatcaacca aatctatgac 300
ataggtattg ataaggtcaa caaaccgtac cttcccatag ccgcgggtga tttgtcagtc 360
cagagtgctt ggtaccttgt aatattgttt gccgttgcgg gtctactaac tgttggcttc 420
aattttgggc cgttcattac gtctctatac tgcttaggac ttgttctggg gacaatatat 480
agcgttccac cctttaggat gaaaagattt ccggttgcag cattcttaat cattgcgacc 540
gtgaggggtt ttctattaaa ctttggtgta tactacgcca caagagctgc attgggctta 600
acctttgaat ggagtagtgc ggttgcgttc attacgacct tcgttacatt attcgctttg 660
gtgatagcta taacgaaaga tctgccagac gtggagggag accgtaaatt tcagatcagc 720
acattcgcaa caaagcttgg tgtgagaaac atcgcgtatc ttggatctgg actattatta 780
ttaaactaca ttggggcaat tgcggcggcc atttatatgc ctcaggcttt taagagaaat 840
ttaatgcttc ctatccacac catcttggcg ttgagccttg tcttccaggc ctgggtcttg 900
gaacaagcga attacaccaa ggaggctatt gctgggttct atagattcat ttggaatttg 960
ttctatgtag aatacattat attccccttt atatag 996

<210> SEQ ID NO 57
<211> LENGTH: 6220
<212> TYPE: DNA
<213> ORGANISM: Artificial Sequence
<220> FEATURE:
<223> OTHER INFORMATION: Codon Optimized

<400> SEQUENCE: 57
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc ttttttttga tttcggtttc 240
tttgaaattt ttttgattcg gtaatctccg aacagaagga agaacgaagg aaggagcaca 300
gacttagatt ggtatatata cgcatatgta gtgttgaaga aacatgaaat tgcccagtat 360
tcttaaccca actgcacaga acaaaaacct gcaggaaacg aagataaatc atgtcgaaag 420
ctacatataa ggaacgtgct gctactcatc ctagtcctgt tgctgccaag ctatttaata 480
tcatgcacga aaagcaaaca aacttgtgtg cttcattgga tgttcgtacc accaaggaat 540
tactggagtt agttgaagca ttaggtccca aaatttgttt actaaaaaca catgtggata 600
tcttgactga tttttccatg gagggcacag ttaagccgct aaaggcatta tccgccaagt 660
acaatttttt actcttcgaa gacagaaaat ttgctgacat tggtaataca gtcaaattgc 720
agtactctgc gggtgtatac agaatagcag aatgggcaga cattacgaat gcacacggtg 780
tggtgggccc aggtattgtt agcggtttga agcaggcggc agaagaagta acaaaggaac 840
ctagaggcct tttgatgtta gcagaattgt catgcaaggg ctccctatct actggagaat 900
atactaaggg tactgttgac attgcgaaga gcgacaaaga ttttgttatc ggctttattg 960
ctcaaagaga catgggtgga agagatgaag gttacgattg gttgattatg acacccggtg 1020
tgggtttaga tgacaaggga gacgcattgg gtcaacagta tagaaccgtg gatgatgtgg 1080
tctctacagg atctgacatt attattgttg gaagaggact atttgcaaag ggaagggatg 1140
ctaaggtaga gggtgaacgt tacagaaaag caggctggga agcatatttg agaagatgcg 1200
gccagcaaaa ctaaaaaact gtattataag taaatgcatg tatactaaac tcacaaatta 1260
gagcttcaat ttaattatat cagttattac cctgcggtgt gaaataccgc acagatgcgt 1320
aaggagaaaa taccgcatca ggaaattgta aacgttaata ttttgttaaa attcgcgtta 1380
aatttttgtt aaatcagctc attttttaac caataggccg aaatcggcaa aatcccttat 1440
aaatcaaaag aatagaccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc ctaatcaagt tttttggggt cgaggtgccg taaagcacta 1620
aatcggaacc ctaaagggag cccccgattt agagcttgac ggggaaagcc ggcgaacgtg 1680
gcgagaaagg aagggaagaa agcgaaagga gcgggcgcta gggcgctggc aagtgtagcg 1740
gtcacgctgc gcgtaaccac cacacccgcc gcgcttaatg cgccgctaca gggcgcgtcg 1800
cgccattcgc cattcaggct gcgcaactgt tgggaagggc gatcggtgcg ggcctcttcg 1860
ctattacgcc agctggcgaa agggggatgt gctgcaaggc gattaagttg ggtaacgcca 1920
gggttttccc agtcacgacg ttgtaaaacg acggccagtg aattgtaata cgactcacta 1980
tagggcgaat tggagctcta gtacggatta gaagccgccg agcgggcgac agccctccga 2040
cggaagactc tcctccgtgc gtcctcgtct tcaccggtcg cgttcctgaa acgcagatgt 2100

-continued

```
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatggaat tatcattatc tctgggcggg ccgacgatat   2520
tccccagata tagagcaagc tatacttcca ctaaactgac cactcatttc tctaattttc   2580
cgtccaaatt cagcacaaaa aatttccacc agacgctatc tttctacgga ccaacgagag   2640
gcagcaaatc attgttgaat acccatcagt ggaggaactc cataagagcc tgcgccgagg   2700
cgggggctgc cgggtcaaac ccggtgctaa acaaggtctc tgactttagg gacgcatgct   2760
ggcgtttctt aaggccgcat actataaggg ggaccaccct gggtagtata gccctagtag   2820
caagggcgct tatagaaaat cccaacttaa tcaagtggag tcttttactg aaggctttct   2880
ctggcttact agccttaatt tgcgggaacg gctacattgt aggaatcaac caaatctatg   2940
acataggtat tgataaggtc aacaaaccgt accttcccat agccgcgggt gatttgtcag   3000
tccagagtgc ttggtacctt gtaatattgt ttgccgttgc gggtctacta actgttggct   3060
tcaattttgg gccgttcatt acgtctctat actgcttagg acttgttctg ggacaatat    3120
atagcgttcc accctttagg atgaaaagat ttccggttgc agcattctta atcattgcga   3180
ccgtgagggg ttttctatta aactttggtg tatactacgc cacaagagct gcattgggct   3240
taacctttga atggagtagt gcggttgcgt tcattacgac cttcgttaca ttattcgctt   3300
tggtgatagc tataacgaaa gatctgccag acgtggaggg agaccgtaaa tttcagatca   3360
gcacattcgc aacaaagctt ggtgtgagaa acatcgcgta tcttggatct ggactattat   3420
tattaaacta cattggggca attgcggcgg ccatttatat gcctcaggct tttaagagaa   3480
atttaatgct tcctatccac accatcttgg cgttgagcct tgtcttccag gcctgggtct   3540
tggaacaagc gaattacacc aaggaggcta ttgctgggtt ctatagattc atttggaatt   3600
tgttctatgt agaatacatt atattcccct ttatatagga tgggctgcag gaattcgata   3660
tcaagcttat cgataccgtc gacctcgagt catgtaatta gttatgtcac gcttacattc   3720
acgccctccc cccacatccg ctctaaccga aaaggaagga gttagacaac ctgaagtcta   3780
ggtccctatt tattttttta tagttatgtt agtattaaga acgttattta tatttcaaat   3840
ttttcttttt tttctgtaca gacgcgtgta cgcatgtaac attatactga aaaccttgct   3900
tgagaaggtt ttgggacgct cgaaggcttt aatttgcggc cggtacccag cttttgttcc   3960
ctttagtgag ggttaattcc gagcttggcg taatcatggt catagctgtt tcctgtgtga   4020
aattgttatc cgctcacaat tccacacaac ataggagccg gaagcataaa gtgtaaagcc   4080
tggggtgcct aatgagtgag gtaactcaca ttaattgcgt tgcgctcact gcccgctttc   4140
cagtcgggaa acctgtcgtg ccagctgcat taatgaatcg gccaacgcgc ggggagaggc   4200
ggtttgcgta ttgggcgctc ttccgcttcc tcgctcactg actcgctgcg ctcggtcgtt   4260
cggctgcggc gagcggtatc agctcactca aaggcggtaa tacggttatc cacagaatca   4320
ggggataacg caggaaagaa catgtgagca aaaggccagc aaaaggccag gaaccgtaaa   4380
aaggccgcgt tgctggcgtt tttccatagg ctcggccccc ctgacgagca tcacaaaaat   4440
```

cgacgctcaa gtcagaggtg gcgaaacccg acaggactat aaagatacca ggcgttcccc 4500
cctggaagct ccctcgtgcg ctctcctgtt ccgaccctgc cgcttaccgg atacctgtcc 4560
gcctttctcc cttcgggaag cgtggcgctt tctcaatgct cacgctgtag gtatctcagt 4620
tcggtgtagg tcgttcgctc caagctgggc tgtgtgcacg aaccccccgt tcagcccgac 4680
cgctgcgcct tatccggtaa ctatcgtctt gagtccaacc cggtaagaca cgacttatcg 4740
ccactggcag cagccactgg taacaggatt agcagagcga ggtatgtagg cggtgctaca 4800
gagttcttga agtggtggcc taactacggc tacactagaa ggacagtatt tggtatctgc 4860
gctctgctga agccagttac cttcggaaaa agagttggta gctcttgatc cggcaaacaa 4920
accaccgctg gtagcggtgg tttttttgtt tgcaagcagc agattacgcg cagaaaaaaa 4980
ggatctcaag aagatccttt gatcttttct acggggtctg acgctcagtg gaacgaaaac 5040
tcacgttaag ggattttggt catgagatta tcaaaaagga tcttcaccta gatcctttta 5100
aattaaaaat gaagttttaa atcaatctaa agtatatatg agtaaacttg gtctgacagt 5160
taccaatgct taatcagtga ggcacctatc tcagcgatct gtctatttcg ttcatccata 5220
gttgcctgac tgcccgtcgt gtagataact acgatacggg agggcttacc atctggcccc 5280
agtgctgcaa tgataccgcg agacccacgc tcaccggctc cagatttatc agcaataaac 5340
cagccagccg gaagggccga gcgcagaagt ggtcctgcaa ctttatccgc ctccatccag 5400
tctattaatt gttgccggga agctagagta agtagttcgc cagttaatag tttgcgcaac 5460
gttgttgcca ttgctacagg catcgtggtg tcacgctcgt cgtttggtat ggcttcattc 5520
agctccggtt cccaacgatc aaggcgagtt acatgatccc ccatgttgtg aaaaaaagcg 5580
gttagctcct tcggtcctcc gatcgttgtc agaagtaagt tggccgcagt gttatcactc 5640
atggttatgg cagcactgca taattctctt actgtcatgc catccgtaag atgcttttct 5700
gtgactggtg agtactcaac caagtcattc tgagaatagt gtatgcggcg accgagttgc 5760
tcttgcccgg cgtcaatacg ggataatacc gcgccacata gcagaacttt aaaagtgctc 5820
atcattggaa aacgttcttc ggggcgaaaa ctctcaagga tcttaccgct gttgagatcc 5880
agttcgatgt aacccactcg tgcacccaac tgatcttcag catcttttac tttcaccagc 5940
gtttctgggt gagcaaaaac aggaaggcaa aatgccgcaa aaaagggaat aagggcgaca 6000
cggaaatgtt gaatactcat actcttcctt tttcaatatt attgaagcat ttatcagggt 6060
tattgtctca tgagcggata catatttgaa tgtatttaga aaaataaaca aataggggtt 6120
ccgcgcacat ttccccgaaa agtgccacct gacgtctaag aaaccattat tatcatgaca 6180
ttaacctata aaaataggcg tatcacgagg ccctttcgtc 6220

<210> SEQ ID NO 58
<211> LENGTH: 6220
<212> TYPE: DNA
<213> ORGANISM: Artificial Sequence
<220> FEATURE:
<223> OTHER INFORMATION: Codon Optimized

<400> SEQUENCE: 58
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc ttttttttga tttcggtttc 240
tttgaaattt ttttgattcg gtaatctccg aacagaagga agaacgaagg aaggagcaca 300

-continued

```
gacttagatt ggtatatata cgcatatgta gtgttgaaga aacatgaaat tgcccagtat    360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga tttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta aacgttaata ttttgttaaa attcgcgtta   1380
aatttttgtt aaatcagctc attttttaac caataggccg aaatcggcaa aatcccttat   1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa agggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga tttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatggaat tatcattatc tctgggcggg ccgacgatat   2520
tccccagata tagagcaagc tatacttcca ctaaactgac cactcatttc tctaattttc   2580
cgtccaaatt cagcacaaaa aatttccacc agacgctatc tttctacgga ccaacgagag   2640
```

-continued

```
gcagcaaatc attgttgaat acccatcagt ggaggaactc cataagagcc tgcgccgagg   2700
cgggggctgc cgggtcaaac ccggtgctaa acaaggtctc tgactttagg gacgcatgct   2760
ggcgtttctt aaggccgcat actataaggg ggaccaccct gggtagtata gccctagtag   2820
caagggcgct tatagaaaat cccaacttaa tcaagtggag tcttttactg aaggctttct   2880
ctggcttact agccttaatt tgcgggaacg gctacattgt aggaatcaac caaatctatg   2940
acataggtat tgataaggtc aacaaaccgt accttcccat agccgcgggt gatttgtcag   3000
tccagagtgc ttggtacctt gtaatattgt ttgccgttgc gggtctacta actgttggct   3060
tcaattttgg gccgttcatt acgtctctat actgcttagg acttgttctg ggacaatat    3120
atagcgttcc accctttagg atgaaaagat ttccggttgc agcattctta atcattgcga   3180
ccgtgagggg ttttctatta aactttggtg tatactacgc cacaagagct gcattgggct   3240
taacctttga atggagtagt gcggttgcgt tcattacgac cttcgttaca ttattcgctt   3300
tggtgatagc tataacgaaa gatctgccag acgtggaggg agaccgtaaa tttcagatca   3360
gcacattcgc aacaaagctt ggtgtgagaa acatcgcgta tcttggatct ggactattat   3420
tattaaacta cattggggca attgcggcgg ccatttatat gcctcaggct tttaagagaa   3480
atttaatgct tcctatccac accatcttgg cgttgagcct tgtcttccag gcctgggtct   3540
tggaacaagc gaattacacc aaggaggcta ttgctgggtt ctatagattc atttggaatt   3600
tgttctatgt agaatacatt atattcccct ttatatagga tgggctgcag gaattcgata   3660
tcaagcttat cgataccgtc gacctcgagt catgtaatta gttatgtcac gcttacattc   3720
acgccctccc cccacatccg ctctaaccga aaaggaagga gttagacaac ctgaagtcta   3780
ggtccctatt tattttttta tagttatgtt agtattaaga acgttattta tatttcaaat   3840
ttttcttttt tttctgtaca gacgcgtgta cgcatgtaac attatactga aaaccttgct   3900
tgagaaggtt ttgggacgct cgaaggcttt aatttgcggc cggtacccag cttttgttcc   3960
ctttagtgag ggttaattcc gagcttggcg taatcatggt catagctgtt tcctgtgtga   4020
aattgttatc cgctcacaat tccacacaac ataggagccg gaagcataaa gtgtaaagcc   4080
tggggtgcct aatgagtgag gtaactcaca ttaattgcgt tgcgctcact gcccgctttc   4140
cagtcgggaa acctgtcgtg ccagctgcat taatgaatcg gccaacgcgc ggggagaggc   4200
ggtttgcgta ttgggcgctc ttccgcttcc tcgctcactg actcgctgcg ctcggtcgtt   4260
cggctgcggc gagcggtatc agctcactca aaggcggtaa tacggttatc cacagaatca   4320
ggggataacg caggaaagaa catgtgagca aaaggccagc aaaaggccag gaaccgtaaa   4380
aaggccgcgt tgctggcgtt tttccatagg ctcggccccc ctgacgagca tcacaaaaat   4440
cgacgctcaa gtcagaggtg gcgaaacccg acaggactat aaagatacca ggcgttcccc   4500
cctggaagct ccctcgtgcg ctctcctgtt ccgaccctgc cgcttaccgg atacctgtcc   4560
gcctttctcc cttcgggaag cgtggcgctt tctcaatgct cacgctgtag gtatctcagt   4620
tcggtgtagg tcgttcgctc caagctgggc tgtgtgcacg aaccccccgt tcagcccgac   4680
cgctgcgcct tatccggtaa ctatcgtctt gagtccaacc cggtaagaca cgacttatcg   4740
ccactggcag cagccactgg taacaggatt agcagagcga ggtatgtagg cggtgctaca   4800
gagttcttga agtggtggcc taactacggc tacactagaa ggacagtatt tggtatctgc   4860
gctctgctga agccagttac cttcggaaaa agagttggta gctcttgatc cggcaaacaa   4920
accaccgctg gtagcggtgg tttttttgtt tgcaagcagc agattacgcg cagaaaaaaa   4980
ggatctcaag aagatccttt gatcttttct acggggtctg acgctcagtg gaacgaaaac   5040
```

tcacgttaag ggattttggt catgagatta tcaaaaagga tcttcaccta gatcctttta 5100
aattaaaaat gaagttttaa atcaatctaa agtatatatg agtaaacttg gtctgacagt 5160
taccaatgct taatcagtga ggcacctatc tcagcgatct gtctatttcg ttcatccata 5220
gttgcctgac tgcccgtcgt gtagataact acgatacggg agggcttacc atctggcccc 5280
agtgctgcaa tgataccgcg agacccacgc tcaccggctc cagatttatc agcaataaac 5340
cagccagccg gaagggccga gcgcagaagt ggtcctgcaa ctttatccgc ctccatccag 5400
tctattaatt gttgccggga agctagagta agtagttcgc cagttaatag tttgcgcaac 5460
gttgttgcca ttgctacagg catcgtggtg tcacgctcgt cgtttggtat ggcttcattc 5520
agctccggtt cccaacgatc aaggcgagtt acatgatccc ccatgttgtg aaaaaaagcg 5580
gttagctcct tcggtcctcc gatcgttgtc agaagtaagt tggccgcagt gttatcactc 5640
atggttatgg cagcactgca taattctctt actgtcatgc catccgtaag atgcttttct 5700
gtgactggtg agtactcaac caagtcattc tgagaatagt gtatgcggcg accgagttgc 5760
tcttgcccgg cgtcaatacg ggataatacc gcgccacata gcagaacttt aaaagtgctc 5820
atcattggaa aacgttcttc ggggcgaaaa ctctcaagga tcttaccgct gttgagatcc 5880
agttcgatgt aacccactcg tgcacccaac tgatcttcag catcttttac tttcaccagc 5940
gtttctgggt gagcaaaaac aggaaggcaa aatgccgcaa aaaagggaat aagggcgaca 6000
cggaaatgtt gaatactcat actcttcctt tttcaatatt attgaagcat ttatcagggt 6060
tattgtctca tgagcggata catatttgaa tgtatttaga aaaataaaca aataggggtt 6120
ccgcgcacat ttccccgaaa agtgccacct gacgtctaag aaaccattat tatcatgaca 6180
ttaacctata aaaataggcg tatcacgagg ccctttcgtc 6220

<210> SEQ ID NO 59
<211> LENGTH: 6061
<212> TYPE: DNA
<213> ORGANISM: Artificial Sequence
<220> FEATURE:
<223> OTHER INFORMATION: Codon Optimized

<400> SEQUENCE: 59
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accacgcttt tcaattcaat tcatcatttt tttttattc ttttttttga tttcggtttc 240
tttgaaattt ttttgattcg gtaatctccg aacagaagga agaacgaagg aaggagcaca 300
gacttagatt ggtatatata cgcatatgta gtgttgaaga aacatgaaat tgcccagtat 360
tcttaaccca actgcacaga acaaaaacct gcaggaaacg aagataaatc atgtcgaaag 420
ctacatataa ggaacgtgct gctactcatc ctagtcctgt tgctgccaag ctatttaata 480
tcatgcacga aaagcaaaca aacttgtgtg cttcattgga tgttcgtacc accaaggaat 540
tactggagtt agttgaagca ttaggtccca aaatttgttt actaaaaaca catgtggata 600
tcttgactga tttttccatg gagggcacag ttaagccgct aaaggcatta tccgccaagt 660
acaatttttt actcttcgaa gacagaaaat ttgctgacat tggtaataca gtcaaattgc 720
agtactctgc gggtgtatac agaatagcag aatgggcaga cattacgaat gcacacggtg 780
tggtgggccc aggtattgtt agcggtttga agcaggcggc agaagaagta acaaaggaac 840
ctagaggcct tttgatgtta gcagaattgt catgcaaggg ctccctatct actggagaat 900
atactaaggg tactgttgac attgcgaaga gcgacaaaga ttttgttatc ggctttattg 960
ctcaaagaga catgggtgga agagatgaag gttacgattg gttgattatg acacccggtg 1020
tgggtttaga tgacaaggga gacgcattgg gtcaacagta tagaaccgtg gatgatgtgg 1080
tctctacagg atctgacatt attattgttg gaagaggact atttgcaaag ggaagggatg 1140
ctaaggtaga gggtgaacgt tacagaaaag caggctggga agcatatttg agaagatgcg 1200
gccagcaaaa ctaaaaaact gtattataag taaatgcatg tatactaaac tcacaaatta 1260
gagcttcaat ttaattatat cagttattac cctgcggtgt gaaataccgc acagatgcgt 1320
aaggagaaaa taccgcatca ggaaattgta aacgttaata ttttgttaaa attcgcgtta 1380
aatttttgtt aaatcagctc attttttaac caataggccg aaatcggcaa aatcccttat 1440
aaatcaaaag aatagaccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc ctaatcaagt tttttggggt cgaggtgccg taaagcacta 1620
aatcggaacc ctaaagggag cccccgattt agagcttgac ggggaaagcc ggcgaacgtg 1680
gcgagaaagg aagggaagaa agcgaaagga gcgggcgcta gggcgctggc aagtgtagcg 1740
gtcacgctgc gcgtaaccac cacacccgcc gcgcttaatg cgccgctaca gggcgcgtcg 1800
cgccattcgc cattcaggct gcgcaactgt tgggaagggc gatcggtgcg ggcctcttcg 1860
ctattacgcc agctggcgaa ggggggatgt gctgcaaggc gattaagttg ggtaacgcca 1920
gggttttccc agtcacgacg ttgtaaaacg acggccagtg aattgtaata cgactcacta 1980
tagggcgaat tggagctcta gtacggatta gaagccgccg agcgggcgac agccctccga 2040
cggaagactc tcctccgtgc gtcctcgtct tcaccggtcg cgttcctgaa acgcagatgt 2100
gcctcgcgcc gcactgctcc gaacaataaa gattctacaa tactagcttt tatggttatg 2160
aagaggaaaa attggcagta acctggcccc acaaaccttc aaattaacga atcaaattaa 2220
caaccatagg atgataatgc gattagtttt ttagccttat ttctggggta attaatcagc 2280
gaagcgatga tttttgatct attaacagat atataaatgg aaaagctgca taaccacttt 2340
aactaatact ttcaacattt tcagtttgta ttacttctta ttcaaatgtc ataaaagtat 2400
caacaaaaaa ttgttaatat acctctatac tttaacgtca aggagaaaaa accccggatt 2460
ctagaactag tggatccccc atcatgagat tcccatctat tttcactgct gttttgttcg 2520
ctgcttcttc tgctttggct gctccagttg ccgggtcaaa cccggtgcta aacaaggtct 2580
ctgactttag ggacgcatgc tggcgtttct taaggccgca tactataagg gggaccaccc 2640
tgggtagtat agccctagta gcaagggcgc ttatagaaaa tcccaactta atcaagtgga 2700
gtcttttact gaaggctttc tctggcttac tagccttaat ttgcgggaac ggctacattg 2760
taggaatcaa ccaaatctat gacataggta ttgataaggt caacaaaccg taccttccca 2820
tagccgcggg tgatttgtca gtccagagtg cttggtacct tgtaatattg tttgccgttg 2880
cgggtctact aactgttggc ttcaattttg ggccgttcat tacgtctcta tactgcttag 2940
gacttgttct ggggacaata tatagcgttc caccctttag gatgaaaaga tttccggttg 3000
cagcattctt aatcattgcg accgtgaggg gttttctatt aaactttggt gtatactacg 3060
ccacaagagc tgcattgggc ttaacctttg aatggagtag tgcggttgcg ttcattacga 3120
ccttcgttac attattcgct ttggtgatag ctataacgaa agatctgcca gacgtggagg 3180
gagaccgtaa atttcagatc agcacattcg caacaaagct tggtgtgaga aacatcgcgt 3240

-continued

```
atcttggatc tggactatta ttattaaact acattggggc aattgcggcg gccatttata   3300
tgcctcaggc ttttaagaga aatttaatgc ttcctatcca caccatcttg gcgttgagcc   3360
ttgtcttcca ggcctgggtc ttggaacaag cgaattacac caaggaggct attgctgggt   3420
tctatagatt catttggaat ttgttctatg tagaatacat tatattcccc tttatatagg   3480
atgggctgca ggaattcgat atcaagctta tcgataccgt cgacctcgag tcatgtaatt   3540
agttatgtca cgcttacatt cacgccctcc ccccacatcc gctctaaccg aaaaggaagg   3600
agttagacaa cctgaagtct aggtccctat ttattttttt atagttatgt tagtattaag   3660
aacgttattt atatttcaaa tttttctttt ttttctgtac agacgcgtgt acgcatgtaa   3720
cattatactg aaaaccttgc ttgagaaggt tttgggacgc tcgaaggctt taatttgcgg   3780
ccggtaccca gcttttgttc cctttagtga gggttaattc cgagcttggc gtaatcatgg   3840
tcatagctgt ttcctgtgtg aaattgttat ccgctcacaa ttccacacaa cataggagcc   3900
ggaagcataa agtgtaaagc ctggggtgcc taatgagtga ggtaactcac attaattgcg   3960
ttgcgctcac tgcccgcttt ccagtcggga aacctgtcgt gccagctgca ttaatgaatc   4020
ggccaacgcg cggggagagg cggtttgcgt attgggcgct cttccgcttc ctcgctcact   4080
gactcgctgc gctcggtcgt tcggctgcgg cgagcggtat cagctcactc aaaggcggta   4140
atacggttat ccacagaatc aggggataac gcaggaaaga acatgtgagc aaaaggccag   4200
caaaaggcca ggaaccgtaa aaaggccgcg ttgctggcgt ttttccatag gctcggcccc   4260
cctgacgagc atcacaaaaa tcgacgctca agtcagaggt ggcgaaaccc gacaggacta   4320
taaagatacc aggcgttccc cctggaagc tccctcgtgc gctctcctgt tccgaccctg   4380
ccgcttaccg gatacctgtc cgcctttctc ccttcgggaa gcgtggcgct ttctcaatgc   4440
tcacgctgta ggtatctcag ttcggtgtag gtcgttcgct ccaagctggg ctgtgtgcac   4500
gaaccccccg ttcagcccga ccgctgcgcc ttatccggta actatcgtct tgagtccaac   4560
ccggtaagac acgacttatc gccactggca gcagccactg gtaacaggat tagcagagcg   4620
aggtatgtag gcggtgctac agagttcttg aagtggtggc ctaactacgg ctacactaga   4680
aggacagtat ttggtatctg cgctctgctg aagccagtta ccttcggaaa aagagttggt   4740
agctcttgat ccggcaaaca aaccaccgct ggtagcggtg gtttttttgt ttgcaagcag   4800
cagattacgc gcagaaaaaa aggatctcaa gaagatcctt tgatcttttc tacggggtct   4860
gacgctcagt ggaacgaaaa ctcacgttaa gggattttgg tcatgagatt atcaaaaagg   4920
atcttcacct agatcctttt aaattaaaaa tgaagtttta aatcaatcta aagtatatat   4980
gagtaaactt ggtctgacag ttaccaatgc ttaatcagtg aggcacctat ctcagcgatc   5040
tgtctatttc gttcatccat agttgcctga ctgcccgtcg tgtagataac tacgatacgg   5100
gagggcttac catctggccc cagtgctgca atgataccgc gagacccacg ctcaccggct   5160
ccagatttat cagcaataaa ccagccagcc ggaagggccg agcgcagaag tggtcctgca   5220
actttatccg cctccatcca gtctattaat tgttgccggg aagctagagt aagtagttcg   5280
ccagttaata gtttgcgcaa cgttgttgcc attgctacag gcatcgtggt gtcacgctcg   5340
tcgtttggta tggcttcatt cagctccggt tcccaacgat caaggcgagt tacatgatcc   5400
cccatgttgt gaaaaaaagc ggttagctcc ttcggtcctc cgatcgttgt cagaagtaag   5460
ttggccgcag tgttatcact catggttatg gcagcactgc ataattctct tactgtcatg   5520
ccatccgtaa gatgcttttc tgtgactggt gagtactcaa ccaagtcatt ctgagaatag   5580
```

-continued

```
tgtatgcggc gaccgagttg ctcttgcccg gcgtcaatac gggataatac cgcgccacat   5640

agcagaactt taaaagtgct catcattgga aaacgttctt cggggcgaaa actctcaagg   5700

atcttaccgc tgttgagatc cagttcgatg taacccactc gtgcacccaa ctgatcttca   5760

gcatctttta ctttcaccag cgtttctggg tgagcaaaaa caggaaggca aaatgccgca   5820

aaaaagggaa taagggcgac acggaaatgt tgaatactca tactcttcct ttttcaatat   5880

tattgaagca tttatcaggg ttattgtctc atgagcggat acatatttga atgtatttag   5940

aaaaataaac aaataggggt tccgcgcaca tttccccgaa aagtgccacc tgacgtctaa   6000

gaaaccatta ttatcatgac attaacctat aaaaataggc gtatcacgag gccctttcgt   6060

c                                                                   6061
```

<210> SEQ ID NO 60
<211> LENGTH: 1161
<212> TYPE: DNA
<213> ORGANISM: Artificial Sequence
<220> FEATURE:
<223> OTHER INFORMATION: Codon Optimized

<400> SEQUENCE: 60

```
atgaatcatt tgagagctga aggtccagct tctgttttgg ctattggtac tgctaatcca     60

gaaaatattt tgattcaaga tgaatttcca gattattatt ttagagttac taaatctgaa    120

catatgactc aattgaaaga aaaatttaga aaaatttgtg ataaatctat gattagaaaa    180

agaaattgtt ttttgaatga agaacatttg aaacaaaatc caagattggt tgaacatgaa    240

atgcaaactt tggatgctag acaagatatg ttggttgttg aagttccaaa attgggtaaa    300

gatgcttgtg ctaaagctat taaagaatgg ggtcaaccaa aatctaaaat tactcatttg    360

atttttactt ctgcttctac tactgatatg ccaggtgctg attatcattg tgctaaattg    420

ttgggtttgt ctccatctgt taaaagagtt atgatgtatc aattgggttg ttatggtggt    480

ggtactgttt tgagaattgc taaagatatt gctgaaaata ataaaggtgc tagagttttg    540

gctgtttgtt gtgatattat ggcttgtttg tttagaggtc catctgattc tgatttggaa    600

gcttctttgt tggttggtca agctattttt ggtgatggtg ctgctgctgt tattgttggt    660

gctgaaccag atgaatctgt tggtgaaaga ccaatttttg aattggtttc tactggtcaa    720

actattttgc caaattctga aggtactatt ggtggtcata ttagagaagc tggtttgatt    780

tttgatttgc ataaagatgt tccaatgttg atttctaata atattgaaaa atgtttgatt    840

gaagctttta ctccaattgg tatttctgat tggaattcta ttttttggat tactcatcca    900

ggtggtaaag ctattttgga taaagttgaa gaaaaattgg atttgaaaaa agaaaaattt    960

gttgattcta gacatgtttt gtctgaacat ggtaatatgt cttcttctac tgttttgttt   1020

gttatggatg aattgagaaa aagatctttg gaagaaggta aatctactac tggtgatggt   1080

tttgaatggg gtgttttgtt tggttttggt ccaggtttga ctgttgaaag agttgttgtt   1140

agatctgttc caattaaata t                                             1161
```

<210> SEQ ID NO 61
<211> LENGTH: 1155
<212> TYPE: DNA
<213> ORGANISM: Artificial Sequence
<220> FEATURE:
<223> OTHER INFORMATION: Codon Optimized

<400> SEQUENCE: 61
atgaatcatt tgagagctga aggtccagct tctgttttgg ctattggtac tgctaatcca 60
gaaaatattt tgattcaaga tgaatttcca gattattatt ttagagttac taaatctgaa 120
catatgactc aattgaaaga aaaatttaga aaaatttgtg ataaatctat gattagaaaa 180
agaaattgtt ttttgaatga agaacatttg aaacaaaatc caagattggt tgaacatgaa 240
atgcaaactt tggatgctag acaagatatg ttggttgttg aagttccaaa attgggtaaa 300
gatgcttgtg ctaaagctat taaagaatgg ggtcaaccaa aatctaaaat tactcatttg 360
atttttactt ctgcttctac tactgatatg ccaggtgctg attatcattg tgctaaattg 420
ttgggtttgt ctccatctgt taaaagagtt atgatgtatc aattgggttg ttatggtggt 480
ggtactgttt tgagaattgc taaagatatt gctgaaaata ataaaggtgc tagagttttg 540
gctgtttgtt gtgatattat ggcttgtttg tttagaggtc catctgattc tgatttggaa 600
ttgttggttg gtcaagctat ttttggtgat ggtgctgctg ctgttattgt tggtgctgaa 660
ccagatgaat ctgttggtga aagaccaatt tttgaattgg tttctactgg tcaaactatt 720
ttgccaaatt ctgaaggtac tattggtggt catattagag aagctggttt gatttttgat 780
ttgcataaag atgttccaat gttgatttct aataatattg aaaaatgttt gattgaagct 840
tttactccaa ttggtatttc tgattggaat tctatttttt ggattactca tccaggtggt 900
aaagctattt tggataaagt tgaagaaaaa ttgcatttga aatctgataa atttgttgat 960
tctagacatg ttttgtctga acatggtaat atgtcttctt ctactgtttt gtttgttatg 1020
gatgaattga gaaaaagatc tttggaagaa ggtaaatcta ctactggtga tggttttgaa 1080
tggggtgttt tgtttggttt tggtccaggt ttgactgttg aaagagttgt tgttagatct 1140
gttccaatta aatat 1155

<210> SEQ ID NO 62
<211> LENGTH: 1155
<212> TYPE: DNA
<213> ORGANISM: Artificial Sequence
<220> FEATURE:
<223> OTHER INFORMATION: Codon Optimized

<400> SEQUENCE: 62
atgaatcatt tgagagctga aggtccagct tctgttttgg ctattggtac tgctaatcca 60
gaaaatattt tgattcaaga tgaatttcca gattattatt ttagagttac taaatctgaa 120
catatgactc aattgaaaga aaaatttaga aaaatttgtg ataaatctat gattagaaaa 180
agaaattgtt ttttgaatga agaacatttg aaacaaaatc caagattggt tgaacatgaa 240
atgcaaactt tggatgctag acaagatatg ttggttgttg aagttccaaa attgggtaaa 300
gatgcttgtg ctaaagctat taaagaatgg ggtcaaccaa aatctaaaat tactcatttg 360
atttttactt ctgcttctac tactgatatg ccaggtgctg attatcattg tgctaaattg 420
ttgggtttgt ctccatctgt taaaagagtt atgatgtatc aattgggttg ttatggtggt 480
ggtactgttt tgagaattgc taaagatatt gctgaaaata ataaaggtgc tagagttttg 540
gctgtttgtt gtgatattat ggcttgtttg tttagaggtc catctgattc tgatttggaa 600
ttgttggttg gtcaagctat ttttggtgat ggtgctgctg ctgttattgt tggtgctgaa 660
ccagatgaat ctgttggtga aagaccaatt tttgaattgg tttctactgg tcaaactatt 720
ttgccaaatt ctgaaggtac tattggtggt catattagag aagctggttt gatttttgat 780

```
ttgcataaag atgttccaat gttgatttct aataatattg aaaaatgttt gattgaagct    840

tttactccaa ttggtatttc tgattggaat tctatttttt ggattactca tccaggtggt    900

aaagctattt tggataaagt tgaagaaaaa ttgcatttga aaaaagaaaa atttgttgat    960

tctagacatg ttttgtctga acatggtaat atgtcttctt ctactgtttt gtttgttatg   1020

gatgaattga gaaaaagatc tttggaagaa ggtaaatcta ctactggtga tggttttgaa   1080

tggggtgttt tgtttggttt tggtccaggt ttgactgttg aaactgttgt tttgagatct   1140

gttccaatta attat                                                    1155
```

<210> SEQ ID NO 63
<211> LENGTH: 1155
<212> TYPE: DNA
<213> ORGANISM: Artificial Sequence
<220> FEATURE:
<223> OTHER INFORMATION: Codon Optimized

<400> SEQUENCE: 63

```
atgaatcatt tgagagctga aggtccagct tctgttttgg ctattggtac tgctaatcca     60

gaaaatattt tgttgcaaga tgaatttcca gattattatt ttagagttac taaatctgaa    120

catatgactc aattgaaaga aaaatttaga aaaatttgtg ataaatctat gattagaaaa    180

agaaattgtt ttttgaatga agaacatttg aaacaaaatc caagattggt tgaacatgaa    240

atgcaaactt tggatgctag acaagatatg ttggttgttg aagttccaaa attgggtaaa    300

gatgcttgtg ctaaagctat taaagaatgg ggtcaaccaa aatctaaaat tactcatttg    360

atttttactt ctgcttctac tactgatatg ccaggtgctg attatcattg tgctaaattg    420

ttgggtttgt ctccatctgt taaaagagtt atgatgtatc aattgggttg ttatggtggt    480

ggtactgttt tgagaattgc taaagatatt gctgaaaata ataaaggtgc tagagttttg    540

gctgtttgtt gtgatattat ggcttgtttg tttagaggtc catctgaatc tgatttggaa    600

ttgttggttg gtcaagctat ttttggtgat ggtgctgctg ctgttattgt tggtgctgaa    660

ccagatgaat ctgttggtga aagaccaatt tttgaattgg tttctactgg tcaaactatt    720

ttgccaaatt ctgaaggtac tattggtggt catattagag aagctggttt gatttttgat    780

ttgcataaag atgttccaat gttgatttct aataatattg aaaaatgttt gattgaagct    840

tttactccaa ttggtatttc tgattggaat tctatttttt ggattactca tccaggtggt    900

aaagctattt tggataaagt tgaagaaaaa ttgcatttga aatctgataa atttgttgat    960

tctagacatg ttttgtctga acatggtaat atgtcttctt ctactgtttt gtttgttatg   1020

gatgaattga gaaaaagatc tttggaagaa ggtaaatcta ctactggtga tggttttgaa   1080

tggggtgttt tgtttggttt tggtccaggt ttgactgttg aaagagttgt tgttagatct   1140

gttccaatta aatat                                                    1155
```

<210> SEQ ID NO 64
<211> LENGTH: 1155
<212> TYPE: DNA
<213> ORGANISM: Artificial Sequence
<220> FEATURE:
<223> OTHER INFORMATION: Codon Optimized

<400> SEQUENCE: 64

```
atgaatcatt tgagagctga aggtccagct tctgttttgg ctattggtac tgctaatcca     60

gaaaatattt tgattcaaga tgaatttcca gattattatt ttagagttac taaatctgaa    120

catatgactc aattgaaaga aaaatttaga aaaatttgtg ataaatctat gattagaaaa    180
```

```
agaaatattt ttttgaatga agaacatttg aaacaaaatc caaaattggt tgaacatgat    240

gttcaaactt tggatgctag acaagatatg ttggttgttg aagttccaaa attgggtaaa    300

gatgcttgtg ctaaagctat taaagaatgg ggtcaaccaa aatctaaaat tactcatttg    360

atttttactt ctgcttctac tactgatatg ccaggtgctg attatcattg tgctaaattg    420

ttgggtttgt ctccatctgt taaaagagtt atgatgtatc aattgggttg ttatggtggt    480

ggtactgttt tgagaattgc taaagatatt gctgaaaata ataaaggtgc tagagttttg    540

gctgtttgtt gtgatattat ggcttgtttg tttagaggtc catctgattc tgatttggaa    600

ttgttggttg gtcaagctat ttttggtgat ggtgctgctg ctgttattgt tggtgctgaa    660

ccagatgaat ctgttggtga aagaccaatt tttgaattgg tttctactgg tcaaactatt    720

ttgccaaatt ctgaaggtac tattggtggt catattagag aagctggttt gatttttgat    780

ttgcataaag atgttccaat gttgatttct aataatattg aaaaatgttt gattgaagct    840

tttactccaa ttggtatttc tgattggaat tctatttttt ggattactca tccaggtggt    900

aaagctattt tggataaagt tgaagaaaaa ttgcatttga aatctgataa atttgttgat    960

tctagacatg ttttgtctga acatggtaat atgtcttctt ctactgtttt gtttgttatg   1020

gatgaattga gaaaaagatc tttggaagaa ggtaaatcta ctactggtga tggttttgaa   1080

tggggtgttt tgtttggttt tggtccaggt ttgactgttg aaagagttgt tgttagatct   1140

gttccaatta aatat                                                    1155
```

```
<210> SEQ ID NO 65
<211> LENGTH: 1155
<212> TYPE: DNA
<213> ORGANISM: Artificial Sequence
<220> FEATURE:
<223> OTHER INFORMATION: Codon Optimized

<400> SEQUENCE: 65
```

```
atgaatcatt tgagagctga aggtccagct tctgttttgg ctattggtac tgctaatcca     60

gaaaatattt tgattcaaga tgaatttcca gattattatt ttagagttac taaatctgaa    120

catatgactc aattgaaaga aaaatttaga aaaatttgtg ataaatctat gattagaaaa    180

agaaattgtt ttttgaatga agaacatttg aaacaaaatc caagattggt tgaacatgaa    240

atgcaaactt tggatgctag acaagatatg ttggttgttg aagttccaaa attgggtaaa    300

gatgcttgtg ctaaagctat taaagaatgg ggtcaaccaa aatctaaaat tactcatttg    360

atttttactt ctgcttctac tactgatatg ccaggtgctg attatcattg tgctaaattg    420

ttgggtttgt ctccatctgt taaaagagtt atgatgtatc aattgggttg ttatggtggt    480

ggtactgttt tgagaattgc taaagatatt gctgaaaata ataaaggtgc tagagttttg    540

gctgtttgtt gtgatatgac tgcttgtttg tttagaggtc catctgattc taatttggaa    600

ttgttggttg gtcaagctat ttttggtgat ggtgctgctg ctgttattgt tggtgctgaa    660

ccagatgaat ctgttggtga aagaccaatt tttgaattgg tttctactgg tcaaactttt    720

ttgccaaatt ctgaaggtac tattggtggt catattagag aagctggttt gatgtttgat    780

ttgcataaag atgttccaat gttgatttct aataatattg aaaaatgttt gattgaagct    840

tttactccaa ttggtatttc tgattggaat tctatttttt ggattactca tccaggtggt    900

aaagctattt tggataaagt tgaagaaaaa ttgcatttga aatctgataa atttgttgat    960

tctagacatg ttttgtctga acatggtaat atgtcttctt ctactgtttt gtttgttatg   1020
```

gatgaattga gaaaaagatc tttggaagaa ggtaaatcta ctactggtga tggttttgaa 1080
tggggtgttt tgtttggttt tggtccaggt ttgactgttg aaagagttgt tttgagatct 1140
gttccaatta attat 1155

<210> SEQ ID NO 66
<211> LENGTH: 1173
<212> TYPE: DNA
<213> ORGANISM: Artificial Sequence
<220> FEATURE:
<223> OTHER INFORMATION: Codon Optimized

<400> SEQUENCE: 66
atggaagaaa ttaaaggtgt tttgaaagct aaagatgttg gttgtgttgc tactattttg 60
gctattggta ctgctaatcc attgaattgt gttaatcaag atgaattttt gcattcttat 120
tttaaattga ctaataatca taataatact tcttttaaag aattgtttac tagaatttgt 180
aataattcta tgattaaaaa tagatatatg catttgactg aagatatttt gaaagaaaat 240
ccaaatttgt gtgattatgc tgctcaatct ttgaatacta gacaagatat taaaattaaa 300
gaaattccaa aattggctga aagagctgct atggttgcta ttaaagaatg gggtaaacca 360
atttctaatt tgactcatat tatttttcat tcttctactg gtgctgctga tatgccaggt 420
gctgattatc aattggttaa atctttgggt ttgaatagat ctattaaaag aattatgttg 480
tataatttgg gttgttttgc tggtggtact gttttgagag ttgctaaaga tttggttgaa 540
aataatttgg gtgcttctgt tttggctgtt tgtgctgaaa ttacttctgc tgatgctact 600
tttggtagat tgtctgaaga tgataaaggt agattggttg gtcatgctat tttggtgat 660 ggtgctgctg ctttggttat tggtaatgct gatgatccag aaaataaagg tttgtttcaa 720
attgtttcta cttctcaaac tattttgcca aattctgaag gttgtattga aggtcatatt 780
agagaagatg gtgttacttt tactttgtct ccaagagttc caaaattgat tggtgataat 840
attgaaactt gtttgatgga agcttttact ccatttaaaa tttctgattg gaattctttg 900
ttttgggttg ttcatccagg tggtgctgct attttgagag aagttgaatc tagagttggt 960
ttggaacaag aaaaattgag agcttcttgg catgttttga gagaatatgg taatatttct 1020
tctgcttctg ttttgtttat tttggatgaa atgagaaata aatctttgga agaaggtaga 1080
aaaactactg gtgaaggtaa aaattggggt gttttgtttg gttttggtcc aggtttgact 1140
gttgaaactg ttgttttgca ttctattcca att 1173

<210> SEQ ID NO 67
<211> LENGTH: 1155
<212> TYPE: DNA
<213> ORGANISM: Artificial Sequence
<220> FEATURE:
<223> OTHER INFORMATION: Codon Optimized

<400> SEQUENCE: 67
atgaatcatt tgagagctga aggtccagct tctgttttgg ctattggtac tgctaatcca 60
gaaaatattt tgattcaaga tgaatttcca gattattatt ttagagttac taaatctgaa 120
catatgactc aattgaaaga aaaatttaga aaaatttgtg ataaatctat gattagaaaa 180
agaaattgtt ttttgaatga agaacatttg aaacaaaatc caagattggt tgaacatgaa 240
atgcaaactt tggatgctag acaagatatg ttggttgttg aagttccaaa attgggtaaa 300
gatgcttgtg ctaaagctat taaagaatgg ggtcaaccaa aatctaaaat tactcatttg 360
atttttactt ctgcttctac tactgatatg ccaggtgctg attatcattg tgctaaattg 420

```
ttgggtttgt ctccatctgt taaaagagtt atgatgtatc aattgggttg ttatggtggt    480

ggtactgttt tgagaattgc taaagatatt gctgaaaata ataaaggtgc tagagttttg    540

gctgtttgtt gtgatattat ggcttgtttg tttagaggtc catctgattc tgatttggaa    600

ttgttggttg gtcaagctat ttttggtgat ggtgctgctg ctgttattgt tggtgctgaa    660

ccagatgaat ctgttggtga aagaccaatt tttgaattgg tttctactgg tcaaactatt    720

ttgccaaatt ctgaaggtac tattggtggt catattagag aagctggttt gatttttgat    780

ttgcataaag atgttccaat gttgatttct aataatattg aaaaatgttt gattgaagct    840

tttactccaa ttggtatttc tgattggaat tctatttttt ggattactca tccaggtggt    900

aaagctattt tggataaagt tgaagaaaaa ttgcatttga aatctgataa atttgttgat    960

tctagacatg ttttgtctga acatggtaat atgtcttctt ctactgtttt gtttgttatg   1020

gatgaattga gaaaaagatc tttggaagaa ggtaaatcta ctactggtga tggttttgaa   1080

tggggtgttt tgtttggttt tggtccaggt ttgactgttg aaagagttgt tgttagatct   1140

gttccaatta aatat                                                    1155
```

<210> SEQ ID NO 68
<211> LENGTH: 1200
<212> TYPE: DNA
<213> ORGANISM: Artificial Sequence
<220> FEATURE:
<223> OTHER INFORMATION: Codon Optimized

<400> SEQUENCE: 68

```
atgaatcatt tgagagctga aggtccagct tctgttttgg ctattggtac tgctaatcca     60

gaaaatattt tgattcaaga tgaatttcca gattattatt ttagagttac taaatctgaa    120

catatgactc aattgaaaga aaaatttaga aaaatttgtg ataaatctat gattagaaaa    180

agaaattgtt ttttgaatga agaacatttg aaacaaaatc caagattggt tgaacatgaa    240

atgcaaactt tggatgctag acaagatatg ttggttgttg aagttccaaa attgggtaaa    300

gatgcttgtg ctaaagctat taaagaatgg ggtcaaccaa aatctaaaat tactcatttg    360

atttttactt ctgcttctac tactgatatg ccaggtgctg attatcattg tgctaaattg    420

ttgggtttgt ctccatctgt taaaagagtt atgatgtatc aattgggttg ttatggtggt    480

ggtactgttt tgagaattgc taaagatatt gctgaaaata ataaaggtgc tagagttttg    540

gctgtttgtt gtgatattat ggcttgtttg tttagaggtc catctgattc tgatttggaa    600

ttgttggttg gtcaagctat ttttggtgat ggtgctgctg ctgttattgt tggtgctgaa    660

ccagatgaat ctgttggtga aagaccaatt tttgaattgg tttctactgg tcaaactatt    720

ttgccaaatt ctgaaggtac tattggtggt catattagag aagctggttt gatttttgat    780

ttgcataaag atgttccaat gttgatttct aataatattg aaaaatgttt gattgaagct    840

tttactccaa ttggtatttc tgattggaat tctatttttt ggattactca tccaggtggt    900

aaagctattt tggataaagt tgaagaaaaa ttgcatttga aatctgataa atttgttgat    960

tctagacatg ttttgtctga acatggtaat atgtcttctt ctactgtttt gtttgttatg   1020

gatgaattga gaaaaagatc tttggaagaa ggtaaatcta ctactggtga tggttttgaa   1080

tggggtgttt tgtttggttt tggtccaggt ttgactgttg aaagaggtag atggagaaaa   1140

ggtaatttgc cattggaaat ggatttgtct ggtgtttttt ttttgggttt ggatcaagtt   1200
```

<210> SEQ ID NO 69

<211> LENGTH: 1167
<212> TYPE: DNA
<213> ORGANISM: Artificial Sequence
<220> FEATURE:
<223> OTHER INFORMATION: Codon Optimized

<400> SEQUENCE: 69
atggttactg ttgaagaatt tagaaaagct caaagagctg aaggtccagc tactattatg 60
gctattggta ctgctactcc agctaattgt gttttgcaat ctgaatatcc agattattat 120
tttagaatta ctaattctga acataaaact gaattgaaag aaaaatttaa aagaatgtgt 180
gataaatcta tgattagaaa aagatatatg catttgactg aagaaatttt gaaagaaaat 240
ccaaatttgt gtgcttatga agctccatct ttggatgcta gacaagatat ggttgttgtt 300
gaagttccaa aattgggtaa agaagctgct actaaagcta ttaaagaatg gggtcaacca 360
aaatctaaaa ttactcattt ggtttttgt actacttctg gtgttgatat gccaggtgct 420
gattatcaat tgactaaatt gttgggtttg agaccatctg ttaaaagatt gatgatgtat 480
caacaaggtt gttttgctgg tggtactgtt ttgagattgg ctaaagattt ggctgaaaat 540
aataaaggtg ctagagtttt ggttgtttgt tctgaaatta ctgctgttac ttttagaggt 600
ccaaatgata ctcatttgga ttctttggtt ggtcaagctt tgtttggtga tggttctgct 660
gctttgattg ttggttctga tccaattcca gaagttgaaa aaccaatttt tgaattggtt 720
tctgctgctc aaactatttt gccagattct gatggtgcta ttgatggtca tttgagagaa 780
gttggtttga cttttcattt gttgaaagat gttccaggtt tgatttctaa aaatattgaa 840
aaatctttga atgaagcttt taaaccattg ggtatttctg attggaattc tttgttttgg 900
attgctcatc caggtggtcc agctattttg gatcaagttg aatctaaatt ggctttgaaa 960
actgaaaaat tgagagctac tagacatgtt ttgtctgaat atggtaatat gtcttctgct 1020
tgtgttttgt ttattttgga tgaaatgaga agaaaatgtg ttgaagatgg tttgaatact 1080
actggtgaag gtttggaatg ggtgttttg tttggttttg gtccaggttt gactgttgaa 1140
actgttgttt tgcattctgt tgctatt 1167

<210> SEQ ID NO 70
<211> LENGTH: 573
<212> TYPE: DNA
<213> ORGANISM: Artificial Sequence
<220> FEATURE:
<223> OTHER INFORMATION: Codon Optimized

<400> SEQUENCE: 70
atgaatcatt tgagagctga aggtccagct tctgttttgg ctattggtac tgctaatcca 60
gaaaatattt tgattcaaga tgaatttcca gattattatt ttagagttac taaatctgaa 120
catatgactc aattgaaaga aaaatttaga aaaatttgtg ataaatctat gattagaaaa 180
agaaattgtt ttttgaatga agaacatttg aaacaaaatc caagattggc tgaacatgaa 240
atgcaaactt tggatgctag acaagatatg ttggttgttg aagttccaaa attgggtaaa 300
gatgcttgtg ctaaagctat taaagaatgg ggtcaaccaa aatctaaaat tactcatttg 360
atttttactt ctgcttctac tactgatatg ccaggtgctg attatcattg tgctaaattg 420
ttgggtttgt ctccatctgt taaaagagtt atgatgtatc aattgggttg ttatggtggt 480
ggtactgttt tgagaattgc taaagatatt gctgaaaata ataaaggtgc tagagttttg 540
gctgtttgtt gtgatattat ggcttttttt ttt 573

<210> SEQ ID NO 71
<211> LENGTH: 597
<212> TYPE: DNA
<213> ORGANISM: Artificial Sequence
<220> FEATURE:
<223> OTHER INFORMATION: Codon Optimized

<400> SEQUENCE: 71

```
atggcttgtt tgtttagagg tccatctgaa tctgatttgg aattgttggt tggtcaagct     60

atttttggtg atggtgctgc tgctgttatt gttggtgctg aaccagatga atctgttggt    120

gaaagaccaa tttttgaatt ggtttctact ggtcaaacta ttttgccaaa ttctgaaggt    180

actattggtg gtcatattag agaagctggt ttgatttttg atttgcataa agatgttcca    240

atgttgattt ctaataatat tgaaaaatgt ttgattgaag cttttactcc aattggtatt    300

tctgattgga attctatttt ttggattact catccaggtg gtaaagctat tttggataaa    360

gttgaagaaa aattgcattt gaaatctgat aaatttgttg attctagaca tgttttgtct    420

gaacatggta atatgtcttc ttctactgtt ttgtttgtta tggatgaatt gagaaaaaga    480

tctttggaag aaggtaaatc tactactggt gatggttttg aatggggtgt tttgtttggt    540

tttggtccag gtttgactgt tgaaagagtt gttgttagat ctgttccaat taaatat        597
```

<210> SEQ ID NO 72
<211> LENGTH: 936
<212> TYPE: DNA
<213> ORGANISM: Artificial Sequence
<220> FEATURE:
<223> OTHER INFORMATION: Codon Optimized

<400> SEQUENCE: 72

```
atgaatttgg aaaatattga taaagttaat tctccaggta ctgaagataa agattttgat     60

tctagagctt ctggttctaa aactaatggt tgtgaatctt ctgataatga agttgaatct    120

tctattaatg ctaatccaaa ttctatttct ggttcttctt ctggttttgg taatggtaaa    180

agagaaggtg ttaaaagagc tgctccaggt gatattgctc caacttctag acattataga    240

tctttgtcta tggattctta tatgggttct ttgcaatttg atgatgaatc tttgaaattg    300

ttgccattgg gtactggtgt tggtttgcaa tctccaaatt ctttggctga tggtaattct    360

actaaatttg gtatggaatt tccaaatggt gaatttaatg ctgttgaatt gaaaaaaatt    420

atggaatctg aaaaattgac tgaaattgct ttgtctgatc caaaaagagc taaaagaatt    480

ttggctaata gacaatctgc tgctagatct aaagaaagaa gatctagata tatttctgaa    540

ttggaacata aagttcaaac tttgcaaact gaagctacta ctttgtctgc tcaagttact    600

aaattgcaaa gagattctgt tggtttgact tctcaaaatt ctgaattgaa atttagagtt    660

caagctatgg aacaacaagc tcaattgaaa gatgctttga atgatgcttt gagagctgaa    720

gttcaaagat tgaaattgac tgctgctgaa ttgtctggtg aagctcattt gtctaattgt    780

atggctcaac aattgtctat taatcaacaa atgtatcaaa tgcaacatag acaaactgtt    840

caattgaatt tgtatcaaat gcaacaacaa caacaacata atgaaatgtc ttctcaacca    900

tgttctggtg aagttactga acatgaatct tctaaa                              936
```

<210> SEQ ID NO 73
<211> LENGTH: 10349
<212> TYPE: DNA
<213> ORGANISM: Artificial Sequence
<220> FEATURE:
<223> OTHER INFORMATION: Codon Optimized

<400> SEQUENCE: 73

```
attcagctcc ggttcccaac gatcaaggcg agttacatga tcccccatgt tgtgaaaaaa     60
agcggttagc tccttcggtc ctccgatcgt tgtcagaagt aagttggccg cagtgttatc    120
actcatggtt atggcagcac tgcataattc tcttactgtc atgccatccg taagatgctt    180
ttctgtgact ggtgagtact caaccaagtc attctgagaa tagtgtatgc ggcgaccgag    240
ttgctcttgc ccggcgtcaa tacgggataa taccgcgcca catagcagaa ctttaaaagt    300
gctcatcatt ggaaaacgtt cttcggggcg aaaactctca aggatcttac cgctgttgag    360
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt cctttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gtttttttatt   1020
tgttgtattt tttttttttt agagaaaatc ctccaatatc aaattaggaa tcgtagtttc   1080
atgattttct gttacaccta actttttgtg tggtgccctc ctccttgtca atattaatgt   1140
taaagtgcaa ttctttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaaagaga atctttttaa gcaaggattt   1380
tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca aagtaaatac   2040
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
```

aatcgaactt gacattggaa cgaacatcag aaatagcttt aagaacctta atggcttcgg 2400
ctgtgatttc ttgaccaacg tggtcacctg gcaaaacgac gatcttctta ggggcagaca 2460
taggggcaga cattagaatg gtatatcctt gaaatatata tatatattgc tgaaatgtaa 2520
aaggtaagaa aagttagaaa gtaagacgat tgctaaccac ctattggaaa aaacaatagg 2580
tccttaaata atattgtcaa cttcaagtat tgtgatgcaa gcatttagtc atgaacgctt 2640
ctctattcta tatgaaaagc cggttccggc ctctcacctt tcctttttct cccaattttt 2700
cagttgaaaa aggtatatgc gtcaggcgac ctctgaaatt aacaaaaaat ttccagtcat 2760
cgaatttgat tctgtgcgat agcgcccctg tgtgttctcg ttatgttgag gaaaaaaata 2820
atggttgcta agagattcga actcttgcat cttacgatac ctgagtattc ccacagttaa 2880
ctgcggtcaa gatatttctt gaatcaggcg ccttagaccg ctcggccaaa caaccaatta 2940
cttgttgaga aatagagtat aattatccta taaatataac gtttttgaac acacatgaac 3000
aaggaagtac aggacaattg attttgaaga gaatgtggat tttgatgtaa ttgttgggat 3060
tccattttta ataaggcaat aatattaggt atgtggatat actagaagtt ctcctcgagg 3120
gtcgatatgc ggtgtgaaat accgcacaga tgcgtaagga gaaaataccg catcaggaaa 3180
ttgtaaacgt taatattttg ttaaaattcg cgttaaattt ttgttaaatc agctcatttt 3240
ttaaccaata ggccgaaatc ggcaaaatcc cttataaatc aaaagaatag accgagatag 3300
ggttgagtgt tgttccagtt tggaacaaga gtccactatt aaagaacgtg gactccaacg 3360
tcaaagggcg aaaaaccgtc tatcagggcg atggcccact acgtgaacca tcaccctaat 3420
caagtttttt ggggtcgagg tgccgtaaag cactaaatcg gaaccctaaa gggagccccc 3480
gatttagagc ttgacgggga aagccggcga acgtggcgag aaaggaaggg aagaaagcga 3540
aaggagcggg cgctagggcg ctggcaagtg tagcggtcac gctgcgcgta accaccacac 3600
ccgccgcgct taatgcgccg ctacagggcg cgtcgcgcca ttcgccattc aggctgcgca 3660
actgttggga agggcgatcg gtgcgggcct cttcgctatt acgccagctg gcgaaggggg 3720
gatgtgctgc aaggcgatta agttgggtaa cgccagggtt ttcccagtca cgacgttgta 3780
aaacgacggc cagtgaattg taatacgact cactataggg cgaattggag ctctagtcgc 3840
aaattaaagc cttcgagcgt cccaaaacct tctcaagcaa ggttttcagt ataatgttac 3900
atgcgtacac gcgtctgtac agaaaaaaaa gaaaaatttg aaatataaat aacgttctta 3960
atactaacat aactataaaa aaataaatag ggacctagac ttcaggttgt ctaactcctt 4020
ccttttcggt tagagcggat gtgggggagg ggcgtgaatg taagcgtgac ataactaatt 4080
acatgatcat tcgaaatgac tgaattgttg tctcaaaact cttctcatga tcttgtttgt 4140
tgcagttcta ggtaaggatg acaatgggac aactctagta actttgaata atgggttcaa 4200
tttcttttgc aaacccaagt taaaggataa tctcaattgg ttcaaatcaa tggttgtgtc 4260
gtttgaatcc ttcaatacga aaaatatgac caattgttct ggaccaccac ccaaaggtgg 4320
aacaccaata gcagtggttt caaaaactct gtcatctact tcattacaga ctctttcgat 4380
ttcgatagaa ctaattttga taccaccgat gttcatagtg tcatcggctc taccgtgtgc 4440
atggtagtaa ccgttagagg tcaattcgaa aatgtcacca tgtcttctca atacttcacc 4500
attcaaggtt ggcataccct tgaaatagac atcgtgatga ttaccgttta acaatgtttt 4560
tgaggcacca aacataacag gacctaatgc caattcaccg atacctggct tatttttagg 4620
cattgggtaa ccgttcttat ctaatatgta caaggtgcaa cccatacatt gggatgaaaa 4680
agaacttaaa gattgagctt gcaaaaatga accagcagaa aaagcaccac cgatttctgt 4740
accaccacac atttctataa ctggcttgta gttagctcta cccattaacc acaaatattc 4800
gtctacatta gaggcttcac cggatgaaga aaagcatctt atggtggacc aatcgtaacc 4860
tgaaacacaa tttgtggatt tccatgatct tacaatagat ggtacgacac ccaacattgt 4920
gacctttgca tcttgaacaa atttagcgaa accagagact aaaggactac cgttgtacaa 4980
ggcaatagat gcaccattta acaaactagc ataaaccaac caaggaccca tcatccaacc 5040
caaattagtt ggccatacta taacgtcacc ttttctaata tccaaatgag accaaccatc 5100
agcagcagcc ttcaatgggg tggcttgtgt ccaaggaatt gcttttggtt cacctgtagt 5160
accactggag aataagatgt tagtataagc atcaacaggt tgttctctgg cagtaaactc 5220
gcagttttta aactccttgg ctctttctaa aaagtaatcc caagatatgt caccatctct 5280
caattctgca ccaatgttag aaccactaca agggataact attgccattg gggatttagc 5340
ttcaactact cttgaataca atggtattct ctttttacct ctgatgatgt gatcttgtgt 5400
gaaaattgcc ttagctttgg ataatctcaa tctagttgag atttcagggg cggaaaatga 5460
atctgctata gagacaacta cgtaaccagc caatactatg gccaaatata taacaacagc 5520
atcaacatgc attggcatat cgatggctat tgcacaacct ttttctaaac ccatttcttc 5580
caatgcataa ccaaccaacc aaactctctt tctcaattga tctaatgtca acttattcaa 5640
aggcaagtca tcgttaccct cgtctctcca aacgatcata gtatcgttca atttcttatt 5700
ggagtttacg ttcaagcaat ttttagctga gttcaagtaa ccaccaggta accattcaga 5760
accacctggg ttgttgatgt catctcttct caagatacat tctgggtcct tagagaaact 5820
aattttcatt tcatccatca atactgttct ccaatagact tcagggtttc taacagaaaa 5880
ttcttggaag tgagaaaaag aagaaattgg atctttgtac tttacaccca aaaattcttt 5940
acctctcttt tccaacaaag cacccaaatt agttgacttg actttttcag ggtctggaat 6000
ccaagcaggt ggggctggac cgaaatcctt gtagcaacca taaaacaaca tttggtgtaa 6060
ggagaaaggc aaatctggtg acaagatatg gttagcgatg ttgatccaag tttgaggggt 6120
tgcagcacca taattacaaa cgatttctgc caatctacca tgtaatgttt ctgctacttc 6180
tgaggtgata cccaatgcga tgaaatctga ggcaacgact gaatccaagg acttatagtt 6240
tttacccatt cttttaatcg tggatccttc aaaaattctt actttttttt tggatggacg 6300
caaagaagtt taataatcat attacatggc attaccacca tatacatatc catatacata 6360
tccatatcta atcttactta tatgttgtgg aaatgtaaag agccccatta tcttagccta 6420
aaaaaacctt ctctttggaa ctttcagtaa tacgcttaac tgctcattgc tatattgaag 6480
tacggattag aagccgccga gcgggtgaca gccctccgaa ggaagactct cctccgtgcg 6540
tcctcgtctt caccggtcgc gttcctgaaa cgcagatgtg cctcgcgccg cactgctccg 6600
aacaataaag attctacaat actagctttt atggttatga agaggaaaaa ttggcagtaa 6660
cctggcccca caaaccttca aatgaacgaa tcaaattaac aaccatagga tgataatgcg 6720
attagttttt tagccttatt tctggggtaa ttaatcagcg aagcgatgat ttttgatcta 6780
ttaacagata tataaatgca aaaactgcat aaccacttta actaatactt tcaacatttt 6840
cggtttgtat tacttcttat tcaaatgtaa taaaagtatc aacaaaaaat tgttaatata 6900
cctctatact ttaacgtcaa ggagaaaaaa ccccggatcc gtaatacgac tcactataat 6960
gaatcatttg agagctgaag gtccagcttc tgttttggct attggtactg ctaatccaga 7020
aaatatttg attcaagatg aatttccaga ttattatttt agagttacta aatctgaaca 7080

```
tatgactcaa ttgaaagaaa aatttagaaa aatttgtgat aaatctatga ttagaaaaag   7140
aaattgtttt ttgaatgaag aacatttgaa acaaaatcca agattggttg aacatgaaat   7200
gcaaactttg gatgctagac aagatatgtt ggttgttgaa gttccaaaat tgggtaaaga   7260
tgcttgtgct aaagctatta aagaatgggg tcaaccaaaa tctaaaatta ctcatttgat   7320
ttttacttct gcttctacta ctgatatgcc aggtgctgat tatcattgtg ctaaattgtt   7380
gggtttgtct ccatctgtta aaagagttat gatgtatcaa ttgggttgtt atggtggtgg   7440
tactgttttg agaattgcta aagatattgc tgaaaataat aaaggtgcta gagttttggc   7500
tgtttgttgt gatattatgg cttgtttgtt tagaggtcca tctgattctg atttggaatt   7560
gttggttggt caagctattt ttggtgatgg tgctgctgct gttattgttg gtgctgaacc   7620
agatgaatct gttggtgaaa gaccaatttt tgaattggtt tctactggtc aaactatttt   7680
gccaaattct gaaggtacta ttggtggtca tattagagaa gctggtttga tttttgattt   7740
gcataaagat gttccaatgt tgatttctaa taatattgaa aaatgtttga ttgaagcttt   7800
tactccaatt ggtatttctg attggaattc tatttttggg attactcatc caggtggtaa   7860
agctattttg gataaagttg aagaaaaatt gcatttgaaa tctgataaat ttgttgattc   7920
tagacatgtt ttgtctgaac atggtaatat gtcttcttct actgttttgt ttgttatgga   7980
tgaattgaga aaaagatctt tggaagaagg taaatctact actggtgatg gttttgaatg   8040
gggtgttttg tttggttttg gtccaggttt gactgttgaa agagttgttg ttagatctgt   8100
tccaattaaa tatgaaggta gaggttcctt gttaacttgt ggtgacgttg aagaaaaccc   8160
aggtcctatg gccgtcaagc atttgatagt attgaagttt aaagatgaaa tcacagaagc   8220
tcaaaaggaa gaatttttca agacctacgt taatttggtc aacattatac ctgctatgaa   8280
agatgtatac tggggtaaag acgttacaca aaagaaagaa gaaggttata cacacattgt   8340
cgaagtaacc ttcgaatcag ttgaaactat ccaagattac atcattcatc cagctcacgt   8400
tggttttggt gacgtttaca gatccttctg ggaaaaattg ttgatcttcg attacacccc   8460
aagaaagtga tgatgggctg caggaattcg atatcaagct tatcgatacc gtcgacctcg   8520
agtcatgtaa ttagttatgt cacgcttaca ttcacgccct ccccccacat ccgctctaac   8580
cgaaaaggaa ggagttagac aacctgaagt ctaggtccct atttattttt ttatagttat   8640
gttagtatta agaacgttat ttatatttca aatttttctt ttttttctgt acagacgcgt   8700
gtacgcatgt aacattatac tgaaaacctt gcttgagaag gttttgggac gctcgaaggc   8760
tttaatttgc ggccggtacc cagcttttgt tccctttagt gagggttaat tccgagcttg   8820
gcgtaatcat ggtcatagct gtttcctgtg tgaaattgtt atccgctcac aattccacac   8880
aacataggag ccggaagcat aaagtgtaaa gcctggggtg cctaatgagt gaggtaactc   8940
acattaattg cgttgcgctc actgcccgct ttccagtcgg gaaacctgtc gtgccagctg   9000
cattaatgaa tcggccaacg cgcggggaga ggcggtttgc gtattgggcg ctcttccgct   9060
tcctcgctca ctgactcgct gcgctcggtc gttcggctgc ggcgagcggt atcagctcac   9120
tcaaaggcgg taatacggtt atccacagaa tcaggggata acgcaggaaa gaacatgtga   9180
gcaaaaggcc agcaaaaggc caggaaccgt aaaaaggccg cgttgctggc gtttttccat   9240
aggctcggcc cccctgacga gcatcacaaa aatcgacgct caagtcagag gtggcgaaac   9300
ccgacaggac tataaagata ccaggcgttc ccccctggaa gctccctcgt gcgctctcct   9360
gttccgaccc tgccgcttac cggatacctg tccgcctttc tcccttcggg aagcgtggcg   9420
```

```
ctttctcaat gctcacgctg taggtatctc agttcggtgt aggtcgttcg ctccaagctg   9480
ggctgtgtgc acgaaccccc cgttcagccc gaccgctgcg ccttatccgg taactatcgt   9540
cttgagtcca acccggtaag acacgactta tcgccactgg cagcagccac tggtaacagg   9600
attagcagag cgaggtatgt aggcggtgct acagagttct tgaagtggtg gcctaactac   9660
ggctacacta gaaggacagt atttggtatc tgcgctctgc tgaagccagt taccttcgga   9720
aaaagagttg gtagctcttg atccggcaaa caaaccaccg ctggtagcgg tggttttttt   9780
gtttgcaagc agcagattac gcgcagaaaa aaaggatctc aagaagatcc tttgatcttt   9840
tctacggggt ctgacgctca gtggaacgaa aactcacgtt aagggatttt ggtcatgaga   9900
ttatcaaaaa ggatcttcac ctagatcctt ttaaattaaa aatgaagttt taaatcaatc   9960
taaagtatat atgagtaaac ttggtctgac agttaccaat gcttaatcag tgaggcacct  10020
atctcagcga tctgtctatt tcgttcatcc atagttgcct gactgcccgt cgtgtagata  10080
actacgatac gggagggctt accatctggc cccagtgctg caatgatacc gcgagaccca  10140
cgctcaccgg ctccagattt atcagcaata aaccagccag ccggaagggc cgagcgcaga  10200
agtggtcctg caactttatc cgcctccatc cagtctatta attgttgccg ggaagctaga  10260
gtaagtagtt cgccagttaa tagtttgcgc aacgttgttg ccattgctac aggcatcgtg  10320
gtgtcacgct cgtcgtttgg tatggcttc                                    10349
```

<210> SEQ ID NO 74
<211> LENGTH: 10349
<212> TYPE: DNA
<213> ORGANISM: Artificial Sequence
<220> FEATURE:
<223> OTHER INFORMATION: Codon Optimized

<400> SEQUENCE: 74

```
attcagctcc ggttcccaac gatcaaggcg agttacatga tcccccatgt tgtgaaaaaa     60
agcggttagc tccttcggtc ctccgatcgt tgtcagaagt aagttggccg cagtgttatc    120
actcatggtt atggcagcac tgcataattc tcttactgtc atgccatccg taagatgctt    180
ttctgtgact ggtgagtact caaccaagtc attctgagaa tagtgtatgc ggcgaccgag    240
ttgctcttgc ccggcgtcaa tacgggataa taccgcgcca catagcagaa ctttaaaagt    300
gctcatcatt ggaaaacgtt cttcggggcg aaaactctca aggatcttac cgctgttgag    360
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt cctttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gttttttatt   1020
tgttgtattt tttttttttt agagaaaatc ctccaatatc aaattaggaa tcgtagtttc   1080
atgattttct gttacaccta actttttgtg tggtgccctc ctccttgtca atattaatgt   1140
```

taaagtgcaa ttctttttcc ttatcacgtt gagccattag tatcaatttg cttacctgta 1200
ttcctttact atcctccttt ttctccttct tgataaatgt atgtagattg cgtatatagt 1260
ttcgtctacc ctatgaacat attccatttt gtaatttcgt gtcgtttcta ttatgaattt 1320
catttataaa gtttatgtac aaatatcata aaaaaagaga atctttttaa gcaaggattt 1380
tcttaacttc ttcggcgaca gcatcaccga cttcggtggt actgttggaa ccacctaaat 1440
caccagttct gatacctgca tccaaaacct ttttaactgc atcttcaatg gccttacctt 1500
cttcaggcaa gttcaatgac aatttcaaca tcattgcagc agacaagata gtggcgatag 1560
ggtcaacctt attctttggc aaatctggag cagaaccgtg gcatggttcg tacaaaccaa 1620
atgcggtgtt cttgtctggc aaagaggcca aggacgcaga tggcaacaaa cccaaggaac 1680
ctgggataac ggaggcttca tcggagatga tatcaccaaa catgttgctg gtgattataa 1740
taccatttag gtgggttggg ttcttaacta ggatcatggc ggcagaatca atcaattgat 1800
gttgaacctt caatgtaggg aattcgttct tgatggtttc ctccacagtt tttctccata 1860
atcttgaaga ggccaaaaca ttagctttat ccaaggacca aataggcaat ggtggctcat 1920
gttgtagggc catgaaagcg gccattcttg tgattctttg cacttctgga acggtgtatt 1980
gttcactatc ccaagcgaca ccatcaccat cgtcttcctt tctcttacca aagtaaatac 2040
ctcccactaa ttctctgaca acaacgaagt cagtaccttt agcaaattgt ggcttgattg 2100
gagataagtc taaaagagag tcggatgcaa agttacatgg tcttaagttg gcgtacaatt 2160
gaagttcttt acggattttt agtaaacctt gttcaggtct aacactaccg gtaccccatt 2220
taggaccacc cacagcacct aacaaaacgg catcaacctt cttggaggct tccagcgcct 2280
catctggaag tgggacacct gtagcatcga tagcagcacc accaattaaa tgattttcga 2340
aatcgaactt gacattggaa cgaacatcag aaatagcttt aagaacctta atggcttcgg 2400
ctgtgatttc ttgaccaacg tggtcacctg gcaaaacgac gatcttctta ggggcagaca 2460
taggggcaga cattagaatg gtatatcctt gaaatatata tatatattgc tgaaatgtaa 2520
aaggtaagaa aagttagaaa gtaagacgat tgctaaccac ctattggaaa aaacaatagg 2580
tccttaaata atattgtcaa cttcaagtat tgtgatgcaa gcatttagtc atgaacgctt 2640
ctctattcta tatgaaaagc cggttccggc ctctcacctt tcctttttct cccaattttt 2700
cagttgaaaa aggtatatgc gtcaggcgac ctctgaaatt aacaaaaaat ttccagtcat 2760
cgaatttgat tctgtgcgat agcgcccctg tgtgttctcg ttatgttgag gaaaaaaata 2820
atggttgcta agagattcga actcttgcat cttacgatac ctgagtattc ccacagttaa 2880
ctgcggtcaa gatatttctt gaatcaggcg ccttagaccg ctcggccaaa caaccaatta 2940
cttgttgaga aatagagtat aattatccta taaatataac gtttttgaac acacatgaac 3000
aaggaagtac aggacaattg attttgaaga gaatgtggat tttgatgtaa ttgttgggat 3060
tccattttta ataaggcaat aatattaggt atgtggatat actagaagtt ctcctcgagg 3120
gtcgatatgc ggtgtgaaat accgcacaga tgcgtaagga gaaaataccg catcaggaaa 3180
ttgtaaacgt taatattttg ttaaaattcg cgttaaattt ttgttaaatc agctcatttt 3240
ttaaccaata ggccgaaatc ggcaaaatcc cttataaatc aaaagaatag accgagatag 3300
ggttgagtgt tgttccagtt tggaacaaga gtccactatt aaagaacgtg gactccaacg 3360
tcaaagggcg aaaaaccgtc tatcagggcg atggcccact acgtgaacca tcaccctaat 3420
caagtttttt ggggtcgagg tgccgtaaag cactaaatcg gaaccctaaa gggagccccc 3480

-continued

```
gatttagagc ttgacgggga aagccggcga acgtggcgag aaaggaaggg aagaaagcga   3540
aaggagcggg cgctagggcg ctggcaagtg tagcggtcac gctgcgcgta accaccacac   3600
ccgccgcgct taatgcgccg ctacagggcg cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccagggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
atactaacat aactataaaa aaataaatag ggacctagac ttcaggttgt ctaactcctt   4020
ccttttcggt tagagcggat gtgggggag ggcgtgaatg taagcgtgac ataactaatt   4080
acatgatcat tcgaaatgac tgaattgttg tctcaaaact cttctcatga tcttgtttgt   4140
tgcagttcta ggtaaggatg acaatgggac aactctagta actttgaata atgggttcaa   4200
tttcttttgc aaacccaagt taaaggataa tctcaattgg ttcaaatcaa tggttgtgtc   4260
gtttgaatcc ttcaatacga aaaatatgac caattgttct ggaccaccac ccaaaggtgg   4320
aacaccaata gcagtggttt caaaaactct gtcatctact tcattacaga ctctttcgat   4380
ttcgatagaa ctaattttga taccaccgat gttcatagtg tcatcggctc taccgtgtgc   4440
atggtagtaa ccgttagagg tcaattcgaa aatgtcacca tgtcttctca atacttcacc   4500
attcaaggtt ggcataccct tgaaatagac atcgtgatga ttaccgttta acaatgtttt   4560
tgaggcacca aacataacag gacctaatgc caattcaccg atacctggct tatttttagg   4620
cattgggtaa ccgttcttat ctaatatgta caaggtgcaa cccatacatt gggatgaaaa   4680
agaacttaaa gattgagctt gcaaaaatga accagcagaa aaagcaccac cgatttctgt   4740
accaccacac atttctataa ctggcttgta gttagctcta cccattaacc acaaatattc   4800
gtctacatta gaggcttcac cggatgaaga aaagcatctt atggtggacc aatcgtaacc   4860
tgaaacacaa tttgtggatt tccatgatct tacaatagat ggtacgacac ccaacattgt   4920
gacctttgca tcttgaacaa atttagcgaa accagagact aaaggactac cgttgtacaa   4980
ggcaatagat gcaccattta acaaactagc ataaaccaac caaggaccca tcatccaacc   5040
caaattagtt ggccatacta taacgtcacc ttttctaata tccaaatgag accaaccatc   5100
agcagcagcc ttcaatgggg tggcttgtgt ccaaggaatt gcttttggtt cacctgtagt   5160
accactggag aataagatgt tagtataagc atcaacaggt tgttctctgg cagtaaactc   5220
gcagttttta aactccttgg ctctttctaa aaagtaatcc caagatatgt caccatctct   5280
caattctgca ccaatgttag aaccactaca agggataact attgccattg gggatttagc   5340
ttcaactact cttgaataca atggtattct ctttttacct ctgatgatgt gatcttgtgt   5400
gaaaattgcc ttagctttgg ataatctcaa tctagttgag atttcagggg cggaaaatga   5460
atctgctata gagacaacta cgtaaccagc caatactatg gccaaatata taacaacagc   5520
atcaacatgc attggcatat cgatggctat tgcacaacct ttttctaaac ccatttcttc   5580
caatgcataa ccaaccaacc aaactctctt tctcaattga tctaatgtca acttattcaa   5640
aggcaagtca tcgttaccct cgtctctcca aacgatcata gtatcgttca atttcttatt   5700
ggagtttacg ttcaagcaat ttttagctga gttcaagtaa ccaccaggta accattcaga   5760
accacctggg ttgttgatgt catctcttct caagatacat tctgggtcct tagagaaact   5820
aattttcatt tcatccatca atactgttct ccaatagact tcagggtttc taacagaaaa   5880
```

ttcttggaag tgagaaaaag aagaaattgg atctttgtac tttacaccca aaaattcttt 5940
acctctcttt tccaacaaag cacccaaatt agttgacttg actttttcag ggtctggaat 6000
ccaagcaggt ggggctggac cgaaatcctt gtagcaacca taaaacaaca tttggtgtaa 6060
ggagaaaggc aaatctggtg acaagatatg gttagcgatg ttgatccaag tttgaggggt 6120
tgcagcacca taattacaaa cgatttctgc caatctacca tgtaatgttt ctgctacttc 6180
tgaggtgata cccaatgcga tgaaatctga ggcaacgact gaatccaagg acttatagtt 6240
tttacccatt cttttaatcg tggatccttc aaaaattctt actttttttt tggatggacg 6300
caaagaagtt taataatcat attacatggc attaccacca tatacatatc catatacata 6360
tccatatcta atcttactta tatgttgtgg aaatgtaaag agccccatta tcttagccta 6420
aaaaaacctt ctctttggaa ctttcagtaa tacgcttaac tgctcattgc tatattgaag 6480
tacggattag aagccgccga gcgggtgaca gccctccgaa ggaagactct cctccgtgcg 6540
tcctcgtctt caccggtcgc gttcctgaaa cgcagatgtg cctcgcgccg cactgctccg 6600
aacaataaag attctacaat actagctttt atggttatga agaggaaaaa ttggcagtaa 6660
cctggcccca caaaccttca aatgaacgaa tcaaattaac aaccatagga tgataatgcg 6720
attagttttt tagccttatt tctggggtaa ttaatcagcg aagcgatgat ttttgatcta 6780
ttaacagata tataaatgca aaaactgcat aaccacttta actaatactt tcaacatttt 6840
cggtttgtat tacttcttat tcaaatgtaa taaaagtatc aacaaaaaat tgttaatata 6900
cctctatact ttaacgtcaa ggagaaaaaa ccccggatcc gtaatacgac tcactataat 6960
gaatcatttg agagctgaag gtccagcttc tgttttggct attggtactg ctaatccaga 7020
aaatattttg attcaagatg aatttccaga ttattatttt agagttacta aatctgaaca 7080
tatgactcaa ttgaaagaaa aatttagaaa aatttgtgat aaatctatga ttagaaaaag 7140
aaattgtttt ttgaatgaag aacatttgaa acaaaatcca agattggttg aacatgaaat 7200
gcaaactttg gatgctagac aagatatgtt ggttgttgaa gttccaaaat tgggtaaaga 7260
tgcttgtgct aaagctatta aagaatgggg tcaaccaaaa tctaaaatta ctcatttgat 7320
ttttacttct gcttctacta ctgatatgcc aggtgctgat tatcattgtg ctaaattgtt 7380
gggtttgtct ccatctgtta aaagagttat gatgtatcaa ttgggttgtt atggtggtgg 7440
tactgttttg agaattgcta aagatattgc tgaaaataat aaaggtgcta gagttttggc 7500
tgtttgttgt gatattatgg cttgtttgtt tagaggtcca tctgattctg atttggaatt 7560
gttggttggt caagctattt ttggtgatgg tgctgctgct gttattgttg gtgctgaacc 7620
agatgaatct gttggtgaaa gaccaatttt tgaattggtt tctactggtc aaactatttt 7680
gccaaattct gaaggtacta ttggtggtca tattagagaa gctggtttga tttttgattt 7740
gcataaagat gttccaatgt tgatttctaa taatattgaa aaatgtttga ttgaagcttt 7800
tactccaatt ggtatttctg attggaattc tattttttgg attactcatc caggtggtaa 7860
agctattttg gataaagttg aagaaaaatt gcatttgaaa aaagaaaaat ttgttgattc 7920
tagacatgtt ttgtctgaac atggtaatat gtcttcttct actgttttgt ttgttatgga 7980
tgaattgaga aaaagatctt tggaagaagg taaatctact actggtgatg gttttgaatg 8040
ggtgttttg tttggttttg gtccaggttt gactgttgaa actgttgttt tgagatctgt 8100
tccaattaat tatgaaggta gaggttcctt gttaacttgt ggtgacgttg aagaaaaccc 8160
aggtcctatg gccgtcaagc atttgatagt attgaagttt aaagatgaaa tcacagaagc 8220

-continued

```
tcaaaaggaa gaatttttca agacctacgt taatttggtc aacattatac ctgctatgaa   8280

agatgtatac tggggtaaag acgttacaca aaagaaagaa gaaggttata cacacattgt   8340

cgaagtaacc ttcgaatcag ttgaaactat ccaagattac atcattcatc cagctcacgt   8400

tggttttggt gacgtttaca gatccttctg ggaaaaattg ttgatcttcg attacacccc   8460

aagaaagtga tgatgggctg caggaattcg atatcaagct tatcgatacc gtcgacctcg   8520

agtcatgtaa ttagttatgt cacgcttaca ttcacgccct ccccccacat ccgctctaac   8580

cgaaaaggaa ggagttagac aacctgaagt ctaggtccct atttattttt ttatagttat   8640

gttagtatta agaacgttat ttatatttca aatttttctt ttttttctgt acagacgcgt   8700

gtacgcatgt aacattatac tgaaaacctt gcttgagaag gttttgggac gctcgaaggc   8760

tttaatttgc ggccggtacc cagcttttgt tccctttagt gagggttaat tccgagcttg   8820

gcgtaatcat ggtcatagct gtttcctgtg tgaaattgtt atccgctcac aattccacac   8880

aacataggag ccggaagcat aaagtgtaaa gcctggggtg cctaatgagt gaggtaactc   8940

acattaattg cgttgcgctc actgcccgct ttccagtcgg gaaacctgtc gtgccagctg   9000

cattaatgaa tcggccaacg cgcggggaga ggcggtttgc gtattgggcg ctcttccgct   9060

tcctcgctca ctgactcgct gcgctcggtc gttcggctgc ggcgagcggt atcagctcac   9120

tcaaaggcgg taatacggtt atccacagaa tcaggggata acgcaggaaa gaacatgtga   9180

gcaaaaggcc agcaaaaggc caggaaccgt aaaaaggccg cgttgctggc gtttttccat   9240

aggctcggcc cccctgacga gcatcacaaa aatcgacgct caagtcagag gtggcgaaac   9300

ccgacaggac tataaagata ccaggcgttc cccccctggaa gctccctcgt gcgctctcct   9360

gttccgaccc tgccgcttac cggatacctg tccgcctttc tcccttcggg aagcgtggcg   9420

ctttctcaat gctcacgctg taggtatctc agttcggtgt aggtcgttcg ctccaagctg   9480

ggctgtgtgc acgaaccccc cgttcagccc gaccgctgcg ccttatccgg taactatcgt   9540

cttgagtcca acccggtaag acacgactta tcgccactgg cagcagccac tggtaacagg   9600

attagcagag cgaggtatgt aggcggtgct acagagttct tgaagtggtg gcctaactac   9660

ggctacacta gaaggacagt atttggtatc tgcgctctgc tgaagccagt taccttcgga   9720

aaaagagttg gtagctcttg atccggcaaa caaaccaccg ctggtagcgg tggttttttt   9780

gtttgcaagc agcagattac gcgcagaaaa aaaggatctc aagaagatcc tttgatcttt   9840

tctacggggt ctgacgctca gtggaacgaa aactcacgtt aagggatttt ggtcatgaga   9900

ttatcaaaaa ggatcttcac ctagatcctt ttaaattaaa aatgaagttt taaatcaatc   9960

taaagtatat atgagtaaac ttggtctgac agttaccaat gcttaatcag tgaggcacct  10020

atctcagcga tctgtctatt tcgttcatcc atagttgcct gactgcccgt cgtgtagata  10080

actacgatac gggagggctt accatctggc cccagtgctg caatgatacc gcgagaccca  10140

cgctcaccgg ctccagattt atcagcaata aaccagccag ccggaagggc cgagcgcaga  10200

agtggtcctg caactttatc cgcctccatc cagtctatta attgttgccg ggaagctaga  10260

gtaagtagtt cgccagttaa tagtttgcgc aacgttgttg ccattgctac aggcatcgtg  10320

gtgtcacgct cgtcgtttgg tatggcttc                                   10349
```

<210> SEQ ID NO 75
<211> LENGTH: 10349
<212> TYPE: DNA
<213> ORGANISM: Artificial Sequence
<220> FEATURE:
<223> OTHER INFORMATION: Codon Optimized -continued

<400> SEQUENCE: 75

```
attcagctcc ggttcccaac gatcaaggcg agttacatga tcccccatgt tgtgaaaaaa     60
agcggttagc tccttcggtc ctccgatcgt tgtcagaagt aagttggccg cagtgttatc    120
actcatggtt atggcagcac tgcataattc tcttactgtc atgccatccg taagatgctt    180
ttctgtgact ggtgagtact caaccaagtc attctgagaa tagtgtatgc ggcgaccgag    240
ttgctcttgc ccggcgtcaa tacgggataa taccgcgcca catagcagaa ctttaaaagt    300
gctcatcatt ggaaaacgtt cttcggggcg aaaactctca aggatcttac cgctgttgag    360
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt cctttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gtttttttatt   1020
tgttgtattt tttttttttt agagaaaatc ctccaatatc aaattaggaa tcgtagtttc   1080
atgattttct gttacaccta actttttgtg tggtgccctc ctccttgtca atattaatgt   1140
taaagtgcaa ttcttttttcc ttatcacgtt gagccattag tatcaatttg cttacctgta  1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaaagaga atctttttaa gcaaggattt   1380
tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca aagtaaatac   2040
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
```

-continued

```
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tcctttttct cccaattttt   2700
cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaaata   2820
atggttgcta agagattcga actcttgcat cttacgatac ctgagtattc ccacagttaa   2880
ctgcggtcaa gatatttctt gaatcaggcg ccttagaccg ctcggccaaa caaccaatta   2940
cttgttgaga aatagagtat aattatccta taaatataac gtttttgaac acacatgaac   3000
aaggaagtac aggacaattg attttgaaga gaatgtggat tttgatgtaa ttgttgggat   3060
tccattttta ataaggcaat aatattaggt atgtggatat actagaagtt ctcctcgagg   3120
gtcgatatgc ggtgtgaaat accgcacaga tgcgtaagga gaaaataccg catcaggaaa   3180
ttgtaaacgt taatattttg ttaaaattcg cgttaaattt ttgttaaatc agctcatttt   3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420
caagtttttt ggggtcgagg tgccgtaaag cactaaatcg gaaccctaaa gggagccccc   3480
gatttagagc ttgacgggga aagccggcga acgtggcgag aaaggaaggg aagaaagcga   3540
aaggagcggg cgctagggcg ctggcaagtg tagcggtcac gctgcgcgta accaccacac   3600
ccgccgcgct taatgcgccg ctacagggcg cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccagggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
atactaacat aactataaaa aaataaatag ggacctagac ttcaggttgt ctaactcctt   4020
ccttttcggt tagagcggat gtggggggag ggcgtgaatg taagcgtgac ataactaatt   4080
acatgatcat tcgaaatgac tgaattgttg tctcaaaact cttctcatga tcttgtttgt   4140
tgcagttcta ggtaaggatg acaatgggac aactctagta actttgaata atgggttcaa   4200
tttcttttgc aaacccaagt taaaggataa tctcaattgg ttcaaatcaa tggttgtgtc   4260
gtttgaatcc ttcaatacga aaaatatgac caattgttct ggaccaccac ccaaaggtgg   4320
aacaccaata gcagtggttt caaaaactct gtcatctact tcattacaga ctctttcgat   4380
ttcgatagaa ctaattttga taccaccgat gttcatagtg tcatcggctc taccgtgtgc   4440
atggtagtaa ccgttagagg tcaattcgaa aatgtcacca tgtcttctca atacttcacc   4500
attcaaggtt ggcataccct tgaaatagac atcgtgatga ttaccgttta acaatgtttt   4560
tgaggcacca aacataacag gacctaatgc caattcaccg atacctggct tatttttagg   4620
cattgggtaa ccgttcttat ctaatatgta caaggtgcaa cccatacatt gggatgaaaa   4680
```

-continued

```
agaacttaaa gattgagctt gcaaaaatga accagcagaa aaagcaccac cgatttctgt   4740
accaccacac atttctataa ctggcttgta gttagctcta cccattaacc acaaatattc   4800
gtctacatta gaggcttcac cggatgaaga aaagcatctt atggtggacc aatcgtaacc   4860
tgaaacacaa tttgtggatt tccatgatct tacaatagat ggtacgacac ccaacattgt   4920
gacctttgca tcttgaacaa atttagcgaa accagagact aaaggactac cgttgtacaa   4980
ggcaatagat gcaccattta acaaactagc ataaaccaac caaggaccca tcatccaacc   5040
caaattagtt ggccatacta taacgtcacc ttttctaata tccaaatgag accaaccatc   5100
agcagcagcc ttcaatgggg tggcttgtgt ccaaggaatt gcttttggtt cacctgtagt   5160
accactggag aataagatgt tagtataagc atcaacaggt tgttctctgg cagtaaactc   5220
gcagttttta aactccttgg ctctttctaa aaagtaatcc caagatatgt caccatctct   5280
caattctgca ccaatgttag aaccactaca agggataact attgccattg gggatttagc   5340
ttcaactact cttgaataca atggtattct ctttttacct ctgatgatgt gatcttgtgt   5400
gaaaattgcc ttagctttgg ataatctcaa tctagttgag atttcagggg cggaaaatga   5460
atctgctata gagacaacta cgtaaccagc caatactatg gccaaatata taacaacagc   5520
atcaacatgc attggcatat cgatggctat tgcacaacct ttttctaaac ccatttcttc   5580
caatgcataa ccaaccaacc aaactctctt tctcaattga tctaatgtca acttattcaa   5640
aggcaagtca tcgttaccct cgtctctcca aacgatcata gtatcgttca atttcttatt   5700
ggagtttacg ttcaagcaat ttttagctga gttcaagtaa ccaccaggta accattcaga   5760
accacctggg ttgttgatgt catctcttct caagatacat tctgggtcct tagagaaact   5820
aattttcatt tcatccatca atactgttct ccaatagact tcagggtttc taacagaaaa   5880
ttcttggaag tgagaaaaag aagaaattgg atctttgtac tttacaccca aaaattcttt   5940
acctctcttt tccaacaaag cacccaaatt agttgacttg actttttcag ggtctggaat   6000
ccaagcaggt ggggctggac cgaaatcctt gtagcaacca taaaacaaca tttggtgtaa   6060
ggagaaaggc aaatctggtg acaagatatg gttagcgatg ttgatccaag tttgaggggt   6120
tgcagcacca taattacaaa cgatttctgc caatctacca tgtaatgttt ctgctacttc   6180
tgaggtgata cccaatgcga tgaaatctga ggcaacgact gaatccaagg acttatagtt   6240
tttacccatt cttttaatcg tggatccttc aaaaattctt actttttttt tggatggacg   6300
caaagaagtt taataatcat attacatggc attaccacca tatacatatc catatacata   6360
tccatatcta atcttactta tatgttgtgg aaatgtaaag agccccatta tcttagccta   6420
aaaaaacctt ctctttggaa ctttcagtaa tacgcttaac tgctcattgc tatattgaag   6480
tacggattag aagccgccga gcgggtgaca gccctccgaa ggaagactct cctccgtgcg   6540
tcctcgtctt caccggtcgc gttcctgaaa cgcagatgtg cctcgcgccg cactgctccg   6600
aacaataaag attctacaat actagctttt atggttatga agaggaaaaa ttggcagtaa   6660
cctggcccca caaaccttca aatgaacgaa tcaaattaac aaccatagga tgataatgcg   6720
attagttttt tagccttatt tctggggtaa ttaatcagcg aagcgatgat ttttgatcta   6780
ttaacagata tataaatgca aaaactgcat aaccacttta actaatactt tcaacatttt   6840
cggtttgtat tacttcttat tcaaatgtaa taaaagtatc aacaaaaaat tgttaatata   6900
cctctatact ttaacgtcaa ggagaaaaaa ccccggatcc gtaatacgac tcactataat   6960
gaatcatttg agagctgaag gtccagcttc tgttttggct attggtactg ctaatccaga   7020
```

-continued

```
aaatatttg ttgcaagatg aatttccaga ttattatttt agagttacta aatctgaaca   7080
tatgactcaa ttgaaagaaa aatttagaaa aatttgtgat aaatctatga ttagaaaaag   7140
aaattgtttt ttgaatgaag aacatttgaa acaaaatcca agattggttg aacatgaaat   7200
gcaaactttg gatgctagac aagatatgtt ggttgttgaa gttccaaaat tgggtaaaga   7260
tgcttgtgct aaagctatta aagaatgggg tcaaccaaaa tctaaaatta ctcatttgat   7320
ttttacttct gcttctacta ctgatatgcc aggtgctgat tatcattgtg ctaaattgtt   7380
gggtttgtct ccatctgtta aaagagttat gatgtatcaa ttgggttgtt atggtggtgg   7440
tactgttttg agaattgcta aagatattgc tgaaaataat aaaggtgcta gagttttggc   7500
tgtttgttgt gatattatgg cttgtttgtt tagaggtcca tctgaatctg atttggaatt   7560
gttggttggt caagctattt ttggtgatgg tgctgctgct gttattgttg gtgctgaacc   7620
agatgaatct gttggtgaaa gaccaatttt tgaattggtt tctactggtc aaactatttt   7680
gccaaattct gaaggtacta ttggtggtca tattagagaa gctggtttga tttttgattt   7740
gcataaagat gttccaatgt tgatttctaa taatattgaa aaatgtttga ttgaagcttt   7800
tactccaatt ggtatttctg attggaattc tatttttgg attactcatc caggtggtaa   7860
agctattttg gataaagttg aagaaaaatt gcatttgaaa tctgataaat ttgttgattc   7920
tagacatgtt ttgtctgaac atggtaatat gtcttcttct actgttttgt ttgttatgga   7980
tgaattgaga aaaagatctt tggaagaagg taaatctact actggtgatg gttttgaatg   8040
gggtgttttg tttggttttg gtccaggttt gactgttgaa agagttgttg ttagatctgt   8100
tccaattaaa tatgaaggta gaggttcctt gttaacttgt ggtgacgttg aagaaaaccc   8160
aggtcctatg gccgtcaagc atttgatagt attgaagttt aaagatgaaa tcacagaagc   8220
tcaaaaggaa gaatttttca agacctacgt taatttggtc aacattatac ctgctatgaa   8280
agatgtatac tggggtaaag acgttacaca aaagaaagaa gaaggttata cacacattgt   8340
cgaagtaacc ttcgaatcag ttgaaactat ccaagattac atcattcatc cagctcacgt   8400
tggttttggt gacgtttaca gatccttctg ggaaaaattg ttgatcttcg attacacccc   8460
aagaaagtga tgatgggctg caggaattcg atatcaagct tatcgatacc gtcgacctcg   8520
agtcatgtaa ttagttatgt cacgcttaca ttcacgccct ccccccacat ccgctctaac   8580
cgaaaaggaa ggagttagac aacctgaagt ctaggtccct atttattttt ttatagttat   8640
gttagtatta agaacgttat ttatatttca aatttttctt ttttttctgt acagacgcgt   8700
gtacgcatgt aacattatac tgaaaacctt gcttgagaag gttttgggac gctcgaaggc   8760
tttaatttgc ggccggtacc cagcttttgt tccctttagt gagggttaat tccgagcttg   8820
gcgtaatcat ggtcatagct gtttcctgtg tgaaattgtt atccgctcac aattccacac   8880
aacataggag ccggaagcat aaagtgtaaa gcctggggtg cctaatgagt gaggtaactc   8940
acattaattg cgttgcgctc actgcccgct ttccagtcgg gaaacctgtc gtgccagctg   9000
cattaatgaa tcggccaacg cgcggggaga ggcggtttgc gtattgggcg ctcttccgct   9060
tcctcgctca ctgactcgct gcgctcggtc gttcggctgc ggcgagcggt atcagctcac   9120
tcaaaggcgg taatacggtt atccacagaa tcaggggata acgcaggaaa gaacatgtga   9180
gcaaaaggcc agcaaaaggc caggaaccgt aaaaaggccg cgttgctggc gtttttccat   9240
aggctcggcc cccctgacga gcatcacaaa aatcgacgct caagtcagag gtggcgaaac   9300
ccgacaggac tataaagata ccaggcgttc ccccctggaa gctccctcgt gcgctctcct   9360
gttccgaccc tgccgcttac cggatacctg tccgcctttc tcccttcggg aagcgtggcg   9420
```

```
ctttctcaat gctcacgctg taggtatctc agttcggtgt aggtcgttcg ctccaagctg   9480

ggctgtgtgc acgaaccccc cgttcagccc gaccgctgcg ccttatccgg taactatcgt   9540

cttgagtcca acccggtaag acacgactta tcgccactgg cagcagccac tggtaacagg   9600

attagcagag cgaggtatgt aggcggtgct acagagttct tgaagtggtg gcctaactac   9660

ggctacacta gaaggacagt atttggtatc tgcgctctgc tgaagccagt taccttcgga   9720

aaaagagttg gtagctcttg atccggcaaa caaaccaccg ctggtagcgg tggttttttt   9780

gtttgcaagc agcagattac gcgcagaaaa aaaggatctc aagaagatcc tttgatcttt   9840

tctacggggt ctgacgctca gtggaacgaa aactcacgtt aagggatttt ggtcatgaga   9900

ttatcaaaaa ggatcttcac ctagatcctt ttaaattaaa aatgaagttt taaatcaatc   9960

taaagtatat atgagtaaac ttggtctgac agttaccaat gcttaatcag tgaggcacct  10020

atctcagcga tctgtctatt tcgttcatcc atagttgcct gactgcccgt cgtgtagata  10080

actacgatac gggagggctt accatctggc cccagtgctg caatgatacc gcgagaccca  10140

cgctcaccgg ctccagattt atcagcaata aaccagccag ccggaagggc cgagcgcaga  10200

agtggtcctg caactttatc cgcctccatc cagtctatta attgttgccg ggaagctaga  10260

gtaagtagtt cgccagttaa tagtttgcgc aacgttgttg ccattgctac aggcatcgtg  10320

gtgtcacgct cgtcgtttgg tatggcttc                                   10349
```

<210> SEQ ID NO 76
<211> LENGTH: 10349
<212> TYPE: DNA
<213> ORGANISM: Artificial Sequence
<220> FEATURE:
<223> OTHER INFORMATION: Codon Optimized

<400> SEQUENCE: 76

```
attcagctcc ggttcccaac gatcaaggcg agttacatga tcccccatgt tgtgaaaaaa     60

agcggttagc tccttcggtc ctccgatcgt tgtcagaagt aagttggccg cagtgttatc    120

actcatggtt atggcagcac tgcataattc tcttactgtc atgccatccg taagatgctt    180

ttctgtgact ggtgagtact caaccaagtc attctgagaa tagtgtatgc ggcgaccgag    240

ttgctcttgc ccggcgtcaa tacgggataa taccgcgcca catagcagaa ctttaaaagt    300

gctcatcatt ggaaaacgtt cttcggggcg aaaactctca aggatcttac cgctgttgag    360

atccagttcg atgtaaccca ctcgtgcacc caactgatct tcagcatctt ttactttcac    420

cagcgtttct gggtgagcaa aaacaggaag gcaaaatgcc gcaaaaaagg gaataagggc    480

gacacggaaa tgttgaatac tcatactctt cctttttcaa tattattgaa gcatttatca    540

gggttattgt ctcatgagcg gatacatatt tgaatgtatt tagaaaaata aacaaatagg    600

ggttccgcgc acatttcccc gaaaagtgcc acctgacgtc taagaaacca ttattatcat    660

gacattaacc tataaaaata ggcgtatcac gaggcccttt cgtctcgcgc gtttcggtga    720

tgacggtgaa aacctctgac acatgcagct cccggagacg gtcacagctt gtctgtaagc    780

ggatgccggg agcagacaag cccgtcaggg cgcgtcagcg ggtgttggcg ggtgtcgggg    840

ctggcttaac tatgcggcat cagagcagat tgtactgaga gtgcaccata tcgactacgt    900

cgtaaggccg tttctgacag agtaaaattc ttgagggaac tttcaccatt atgggaaatg    960

gttcaagaag gtattgactt aaactccatc aaatggtcag gtcattgagt gttttttatt   1020

tgttgtattt ttttttttt agagaaaatc ctccaatatc aaattaggaa tcgtagtttc   1080
```

-continued

```
atgattttct gttacaccta actttttgtg tggtgccctc ctccttgtca atattaatgt   1140
taaagtgcaa ttctttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaaagaga atctttttaa gcaaggattt   1380
tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca aagtaaatac   2040
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tccttttttct cccaattttt   2700
cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaaata   2820
atggttgcta agagattcga actcttgcat cttacgatac ctgagtattc ccacagttaa   2880
ctgcggtcaa gatatttctt gaatcaggcg ccttagaccg ctcggccaaa caaccaatta   2940
cttgttgaga aatagagtat aattatccta taaatataac gtttttgaac acacatgaac   3000
aaggaagtac aggacaattg attttgaaga gaatgtggat tttgatgtaa ttgttgggat   3060
tccattttta ataaggcaat aatattaggt atgtggatat actagaagtt ctcctcgagg   3120
gtcgatatgc ggtgtgaaat accgcacaga tgcgtaagga gaaaataccg catcaggaaa   3180
ttgtaaacgt taatattttg ttaaaattcg cgttaaattt ttgttaaatc agctcatttt   3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420
caagtttttt ggggtcgagg tgccgtaaag cactaaatcg gaaccctaaa gggagccccc   3480
```

```
gatttagagc ttgacgggga aagccggcga acgtggcgag aaaggaaggg aagaaagcga   3540
aaggagcggg cgctagggcg ctggcaagtg tagcggtcac gctgcgcgta accaccacac   3600
ccgccgcgct taatgcgccg ctacagggcg cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccagggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
atactaacat aactataaaa aaataaatag ggacctagac ttcaggttgt ctaactcctt   4020
ccttttcggt tagagcggat gtggggggag ggcgtgaatg taagcgtgac ataactaatt   4080
acatgatcat tcgaaatgac tgaattgttg tctcaaaact cttctcatga tcttgtttgt   4140
tgcagttcta ggtaaggatg acaatgggac aactctagta actttgaata atgggttcaa   4200
tttcttttgc aaacccaagt taaaggataa tctcaattgg ttcaaatcaa tggttgtgtc   4260
gtttgaatcc ttcaatacga aaaatatgac caattgttct ggaccaccac ccaaaggtgg   4320
aacaccaata gcagtggttt caaaaactct gtcatctact tcattacaga ctctttcgat   4380
ttcgatagaa ctaattttga taccaccgat gttcatagtg tcatcggctc taccgtgtgc   4440
atggtagtaa ccgttagagg tcaattcgaa aatgtcacca tgtcttctca atacttcacc   4500
attcaaggtt ggcataccct tgaaatagac atcgtgatga ttaccgttta acaatgtttt   4560
tgaggcacca aacataacag gacctaatgc caattcaccg atacctggct tatttttagg   4620
cattgggtaa ccgttcttat ctaatatgta caaggtgcaa cccatacatt gggatgaaaa   4680
agaacttaaa gattgagctt gcaaaaatga accagcagaa aaagcaccac cgatttctgt   4740
accaccacac atttctataa ctggcttgta gttagctcta cccattaacc acaaatattc   4800
gtctacatta gaggcttcac cggatgaaga aaagcatctt atggtggacc aatcgtaacc   4860
tgaaacacaa tttgtggatt tccatgatct tacaatagat ggtacgacac ccaacattgt   4920
gacctttgca tcttgaacaa atttagcgaa accagagact aaaggactac cgttgtacaa   4980
ggcaatagat gcaccattta acaaactagc ataaaccaac caaggaccca tcatccaacc   5040
caaattagtt ggccatacta taacgtcacc ttttctaata tccaaatgag accaaccatc   5100
agcagcagcc ttcaatgggg tggcttgtgt ccaaggaatt gcttttggtt cacctgtagt   5160
accactggag aataagatgt tagtataagc atcaacaggt tgttctctgg cagtaaactc   5220
gcagttttta aactccttgg ctctttctaa aaagtaatcc caagatatgt caccatctct   5280
caattctgca ccaatgttag aaccactaca agggataact attgccattg gggatttagc   5340
ttcaactact cttgaataca atggtattct ctttttacct ctgatgatgt gatcttgtgt   5400
gaaaattgcc ttagctttgg ataatctcaa tctagttgag atttcagggg cggaaaatga   5460
atctgctata gagacaacta cgtaaccagc caatactatg gccaaatata taacaacagc   5520
atcaacatgc attggcatat cgatggctat tgcacaacct ttttctaaac ccatttcttc   5580
caatgcataa ccaaccaacc aaactctctt tctcaattga tctaatgtca acttattcaa   5640
aggcaagtca tcgttaccct cgtctctcca aacgatcata gtatcgttca atttcttatt   5700
ggagtttacg ttcaagcaat ttttagctga gttcaagtaa ccaccaggta accattcaga   5760
accacctggg ttgttgatgt catctcttct caagatacat tctgggtcct tagagaaact   5820
```

-continued aattttcatt tcatccatca atactgttct ccaatagact tcagggtttc taacagaaaa 5880
ttcttggaag tgagaaaaag aagaaattgg atctttgtac tttacaccca aaaattcttt 5940
acctctcttt tccaacaaag cacccaaatt agttgacttg actttttcag ggtctggaat 6000
ccaagcaggt ggggctggac cgaaatcctt gtagcaacca taaaacaaca tttggtgtaa 6060
ggagaaaggc aaatctggtg acaagatatg gttagcgatg ttgatccaag tttgaggggt 6120
tgcagcacca taattacaaa cgatttctgc caatctacca tgtaatgttt ctgctacttc 6180
tgaggtgata cccaatgcga tgaaatctga ggcaacgact gaatccaagg acttatagtt 6240
tttacccatt cttttaatcg tggatccttc aaaaattctt actttttttt tggatggacg 6300
caaagaagtt taataatcat attacatggc attaccacca tatacatatc catatacata 6360
tccatatcta atcttactta tatgttgtgg aaatgtaaag agccccatta tcttagccta 6420
aaaaaacctt ctctttggaa ctttcagtaa tacgcttaac tgctcattgc tatattgaag 6480
tacggattag aagccgccga gcgggtgaca gccctccgaa ggaagactct cctccgtgcg 6540
tcctcgtctt caccggtcgc gttcctgaaa cgcagatgtg cctcgcgccg cactgctccg 6600
aacaataaag attctacaat actagctttt atggttatga agaggaaaaa ttggcagtaa 6660
cctggcccca caaaccttca aatgaacgaa tcaaattaac aaccatagga tgataatgcg 6720
attagttttt tagccttatt tctggggtaa ttaatcagcg aagcgatgat ttttgatcta 6780
ttaacagata tataaatgca aaaactgcat aaccacttta actaatactt tcaacatttt 6840
cggtttgtat tacttcttat tcaaatgtaa taaaagtatc aacaaaaaat tgttaatata 6900
cctctatact ttaacgtcaa ggagaaaaaa ccccggatcc gtaatacgac tcactataat 6960
gaatcatttg agagctgaag gtccagcttc tgttttggct attggtactg ctaatccaga 7020
aaatattttg attcaagatg aatttccaga ttattatttt agagttacta aatctgaaca 7080
tatgactcaa ttgaaagaaa aatttagaaa aatttgtgat aaatctatga ttagaaaaag 7140
aaatattttt ttgaatgaag aacatttgaa acaaaatcca aaattggttg aacatgatgt 7200
tcaaactttg gatgctagac aagatatgtt ggttgttgaa gttccaaaat tgggtaaaga 7260
tgcttgtgct aaagctatta aagaatgggg tcaaccaaaa tctaaaatta ctcatttgat 7320
ttttacttct gcttctacta ctgatatgcc aggtgctgat tatcattgtg ctaaattgtt 7380
gggtttgtct ccatctgtta aaagagttat gatgtatcaa ttgggttgtt atggtggtgg 7440
tactgttttg agaattgcta aagatattgc tgaaaataat aaaggtgcta gagttttggc 7500
tgtttgttgt gatattatgg cttgtttgtt tagaggtcca tctgattctg atttggaatt 7560
gttggttggt caagctattt ttggtgatgg tgctgctgct gttattgttg gtgctgaacc 7620
agatgaatct gttggtgaaa gaccaatttt tgaattggtt tctactggtc aaactatttt 7680
gccaaattct gaaggtacta ttggtggtca tattagagaa gctggtttga tttttgattt 7740
gcataaagat gttccaatgt tgatttctaa taatattgaa aaatgtttga ttgaagcttt 7800
tactccaatt ggtatttctg attggaattc tattttttgg attactcatc caggtggtaa 7860
agctattttg gataaagttg aagaaaaatt gcatttgaaa tctgataaat ttgttgattc 7920
tagacatgtt ttgtctgaac atggtaatat gtcttcttct actgttttgt ttgttatgga 7980
tgaattgaga aaaagatctt tggaagaagg taaatctact actggtgatg gttttgaatg 8040
gggtgttttg tttggttttg gtccaggttt gactgttgaa agagttgttg ttagatctgt 8100
tccaattaaa tatgaaggta gaggttcctt gttaacttgt ggtgacgttg aagaaaaccc 8160
aggtcctatg gccgtcaagc atttgatagt attgaagttt aaagatgaaa tcacagaagc 8220
tcaaaaggaa gaatttttca agacctacgt taatttggtc aacattatac ctgctatgaa 8280
agatgtatac tggggtaaag acgttacaca aaagaaagaa gaaggttata cacacattgt 8340
cgaagtaacc ttcgaatcag ttgaaactat ccaagattac atcattcatc cagctcacgt 8400
tggttttggt gacgtttaca gatccttctg ggaaaaattg ttgatcttcg attacacccc 8460
aagaaagtga tgatgggctg caggaattcg atatcaagct tatcgatacc gtcgacctcg 8520
agtcatgtaa ttagttatgt cacgcttaca ttcacgccct ccccccacat ccgctctaac 8580
cgaaaaggaa ggagttagac aacctgaagt ctaggtccct atttattttt ttatagttat 8640
gttagtatta agaacgttat ttatatttca aatttttctt ttttttctgt acagacgcgt 8700
gtacgcatgt aacattatac tgaaaacctt gcttgagaag gttttgggac gctcgaaggc 8760
tttaatttgc ggccggtacc cagcttttgt tccctttagt gagggttaat tccgagcttg 8820
gcgtaatcat ggtcatagct gtttcctgtg tgaaattgtt atccgctcac aattccacac 8880
aacataggag ccggaagcat aaagtgtaaa gcctggggtg cctaatgagt gaggtaactc 8940
acattaattg cgttgcgctc actgcccgct ttccagtcgg gaaacctgtc gtgccagctg 9000
cattaatgaa tcggccaacg cgcggggaga ggcggtttgc gtattgggcg ctcttccgct 9060
tcctcgctca ctgactcgct gcgctcggtc gttcggctgc ggcgagcggt atcagctcac 9120
tcaaaggcgg taatacggtt atccacagaa tcaggggata acgcaggaaa gaacatgtga 9180
gcaaaaggcc agcaaaaggc caggaaccgt aaaaaggccg cgttgctggc gtttttccat 9240
aggctcggcc cccctgacga gcatcacaaa aatcgacgct caagtcagag gtggcgaaac 9300
ccgacaggac tataaagata ccaggcgttc cccctggaa gctccctcgt gcgctctcct 9360
gttccgaccc tgccgcttac cggatacctg tccgcctttc tcccttcggg aagcgtggcg 9420
ctttctcaat gctcacgctg taggtatctc agttcggtgt aggtcgttcg ctccaagctg 9480
ggctgtgtgc acgaaccccc cgttcagccc gaccgctgcg ccttatccgg taactatcgt 9540
cttgagtcca acccggtaag acacgactta tcgccactgg cagcagccac tggtaacagg 9600
attagcagag cgaggtatgt aggcggtgct acagagttct tgaagtggtg gcctaactac 9660
ggctacacta gaaggacagt atttggtatc tgcgctctgc tgaagccagt taccttcgga 9720
aaaagagttg gtagctcttg atccggcaaa caaaccaccg ctggtagcgg tggttttttt 9780
gtttgcaagc agcagattac gcgcagaaaa aaaggatctc aagaagatcc tttgatcttt 9840
tctacggggt ctgacgctca gtggaacgaa aactcacgtt aagggatttt ggtcatgaga 9900
ttatcaaaaa ggatcttcac ctagatcctt ttaaattaaa aatgaagttt taaatcaatc 9960
taaagtatat atgagtaaac ttggtctgac agttaccaat gcttaatcag tgaggcacct 10020
atctcagcga tctgtctatt tcgttcatcc atagttgcct gactgcccgt cgtgtagata 10080
actacgatac gggagggctt accatctggc cccagtgctg caatgatacc gcgagaccca 10140
cgctcaccgg ctccagattt atcagcaata aaccagccag ccggaagggc cgagcgcaga 10200
agtggtcctg caactttatc cgcctccatc cagtctatta attgttgccg ggaagctaga 10260
gtaagtagtt cgccagttaa tagtttgcgc aacgttgttg ccattgctac aggcatcgtg 10320
gtgtcacgct cgtcgtttgg tatggcttc 10349

<210> SEQ ID NO 77
<211> LENGTH: 10349
<212> TYPE: DNA
<213> ORGANISM: Artificial Sequence
<220> FEATURE:

<223> OTHER INFORMATION: Codon Optimized

<400> SEQUENCE: 77
attcagctcc ggttcccaac gatcaaggcg agttacatga tcccccatgt tgtgaaaaaa 60
agcggttagc tccttcggtc ctccgatcgt tgtcagaagt aagttggccg cagtgttatc 120
actcatggtt atggcagcac tgcataattc tcttactgtc atgccatccg taagatgctt 180
ttctgtgact ggtgagtact caaccaagtc attctgagaa tagtgtatgc ggcgaccgag 240
ttgctcttgc ccggcgtcaa tacgggataa taccgcgcca catagcagaa ctttaaaagt 300
gctcatcatt ggaaaacgtt cttcggggcg aaaactctca aggatcttac cgctgttgag 360
atccagttcg atgtaaccca ctcgtgcacc caactgatct tcagcatctt ttactttcac 420
cagcgtttct gggtgagcaa aaacaggaag gcaaaatgcc gcaaaaaagg gaataagggc 480
gacacggaaa tgttgaatac tcatactctt cctttttcaa tattattgaa gcatttatca 540
gggttattgt ctcatgagcg gatacatatt tgaatgtatt tagaaaaata aacaaatagg 600
ggttccgcgc acatttcccc gaaaagtgcc acctgacgtc taagaaacca ttattatcat 660
gacattaacc tataaaaata ggcgtatcac gaggcccttt cgtctcgcgc gtttcggtga 720
tgacggtgaa aacctctgac acatgcagct cccggagacg gtcacagctt gtctgtaagc 780
ggatgccggg agcagacaag cccgtcaggg cgcgtcagcg ggtgttggcg ggtgtcgggg 840
ctggcttaac tatgcggcat cagagcagat tgtactgaga gtgcaccata tcgactacgt 900
cgtaaggccg tttctgacag agtaaaattc ttgagggaac tttcaccatt atgggaaatg 960
gttcaagaag gtattgactt aaactccatc aaatggtcag gtcattgagt gtttttttatt 1020 tgttgtattt tttttttttt agagaaaatc ctccaatatc aaattaggaa tcgtagtttc 1080
atgattttct gttacaccta actttttgtg tggtgccctc ctccttgtca atattaatgt 1140
taaagtgcaa ttctttttcc ttatcacgtt gagccattag tatcaatttg cttacctgta 1200
ttcctttact atcctccttt ttctccttct tgataaatgt atgtagattg cgtatatagt 1260
ttcgtctacc ctatgaacat attccatttt gtaatttcgt gtcgtttcta ttatgaattt 1320
catttataaa gtttatgtac aaatatcata aaaaaagaga atctttttaa gcaaggattt 1380
tcttaacttc ttcggcgaca gcatcaccga cttcggtggt actgttggaa ccacctaaat 1440
caccagttct gatacctgca tccaaaacct ttttaactgc atcttcaatg gccttacctt 1500
cttcaggcaa gttcaatgac aatttcaaca tcattgcagc agacaagata gtggcgatag 1560
ggtcaacctt attctttggc aaatctggag cagaaccgtg gcatggttcg tacaaaccaa 1620
atgcggtgtt cttgtctggc aaagaggcca aggacgcaga tggcaacaaa cccaaggaac 1680
ctgggataac ggaggcttca tcggagatga tatcaccaaa catgttgctg gtgattataa 1740
taccatttag gtgggttggg ttcttaacta ggatcatggc ggcagaatca atcaattgat 1800
gttgaacctt caatgtaggg aattcgttct tgatggtttc ctccacagtt tttctccata 1860
atcttgaaga ggccaaaaca ttagctttat ccaaggacca aataggcaat ggtggctcat 1920
gttgtagggc catgaaagcg gccattcttg tgattctttg cacttctgga acggtgtatt 1980
gttcactatc ccaagcgaca ccatcaccat cgtcttcctt tctcttacca aagtaaatac 2040
ctcccactaa ttctctgaca acaacgaagt cagtaccttt agcaaattgt ggcttgattg 2100
gagataagtc taaaagagag tcggatgcaa agttacatgg tcttaagttg gcgtacaatt 2160
gaagttcttt acggattttt agtaaacctt gttcaggtct aacactaccg gtaccccatt 2220
taggaccacc cacagcacct aacaaaacgg catcaacctt cttggaggct tccagcgcct 2280

-continued catctggaag tgggacacct gtagcatcga tagcagcacc accaattaaa tgattttcga 2340
aatcgaactt gacattggaa cgaacatcag aaatagcttt aagaacctta atggcttcgg 2400
ctgtgatttc ttgaccaacg tggtcacctg gcaaaacgac gatcttctta ggggcagaca 2460
taggggcaga cattagaatg gtatatcctt gaaatatata tatatattgc tgaaatgtaa 2520
aaggtaagaa aagttagaaa gtaagacgat tgctaaccac ctattggaaa aaacaatagg 2580
tccttaaata atattgtcaa cttcaagtat tgtgatgcaa gcatttagtc atgaacgctt 2640
ctctattcta tatgaaaagc cggttccggc ctctcacctt tcctttttct cccaattttt 2700
cagttgaaaa aggtatatgc gtcaggcgac ctctgaaatt aacaaaaaat ttccagtcat 2760
cgaatttgat tctgtgcgat agcgcccctg tgtgttctcg ttatgttgag gaaaaaaata 2820
atggttgcta agagattcga actcttgcat cttacgatac ctgagtattc ccacagttaa 2880
ctgcggtcaa gatatttctt gaatcaggcg ccttagaccg ctcggccaaa caaccaatta 2940
cttgttgaga aatagagtat aattatccta taaatataac gtttttgaac acacatgaac 3000
aaggaagtac aggacaattg attttgaaga gaatgtggat tttgatgtaa ttgttgggat 3060
tccattttta ataaggcaat aatattaggt atgtggatat actagaagtt ctcctcgagg 3120
gtcgatatgc ggtgtgaaat accgcacaga tgcgtaagga gaaaataccg catcaggaaa 3180
ttgtaaacgt taatattttg ttaaaattcg cgttaaattt ttgttaaatc agctcatttt 3240
ttaaccaata ggccgaaatc ggcaaaatcc cttataaatc aaaagaatag accgagatag 3300
ggttgagtgt tgttccagtt tggaacaaga gtccactatt aaagaacgtg gactccaacg 3360
tcaaagggcg aaaaaccgtc tatcagggcg atggcccact acgtgaacca tcaccctaat 3420
caagtttttt ggggtcgagg tgccgtaaag cactaaatcg gaaccctaaa gggagccccc 3480
gatttagagc ttgacgggga aagccggcga acgtggcgag aaaggaaggg aagaaagcga 3540
aaggagcggg cgctagggcg ctggcaagtg tagcggtcac gctgcgcgta accaccacac 3600
ccgccgcgct taatgcgccg ctacagggcg cgtcgcgcca ttcgccattc aggctgcgca 3660
actgttggga agggcgatcg gtgcgggcct cttcgctatt acgccagctg gcgaaggggg 3720
gatgtgctgc aaggcgatta agttgggtaa cgccagggtt ttcccagtca cgacgttgta 3780
aaacgacggc cagtgaattg taatacgact cactataggg cgaattggag ctctagtcgc 3840
aaattaaagc cttcgagcgt cccaaaacct tctcaagcaa ggttttcagt ataatgttac 3900
atgcgtacac gcgtctgtac agaaaaaaaa gaaaaatttg aaatataaat aacgttctta 3960
atactaacat aactataaaa aaataaatag ggacctagac ttcaggttgt ctaactcctt 4020
ccttttcggt tagagcggat gtgggggag ggcgtgaatg taagcgtgac ataactaatt 4080
acatgatcat tcgaaatgac tgaattgttg tctcaaaact cttctcatga tcttgtttgt 4140
tgcagttcta ggtaaggatg acaatgggac aactctagta actttgaata atgggttcaa 4200
tttcttttgc aaacccaagt taaaggataa tctcaattgg ttcaaatcaa tggttgtgtc 4260
gtttgaatcc ttcaatacga aaaatatgac caattgttct ggaccaccac ccaaaggtgg 4320
aacaccaata gcagtggttt caaaaactct gtcatctact tcattacaga ctctttcgat 4380
ttcgatagaa ctaattttga taccaccgat gttcatagtg tcatcggctc taccgtgtgc 4440
atggtagtaa ccgttagagg tcaattcgaa aatgtcacca tgtcttctca atacttcacc 4500
attcaaggtt ggcataccct tgaaatagac atcgtgatga ttaccgttta acaatgtttt 4560
tgaggcacca aacataacag gacctaatgc caattcaccg atacctggct tatttttagg 4620
cattgggtaa ccgttcttat ctaatatgta caaggtgcaa cccatacatt gggatgaaaa 4680
agaacttaaa gattgagctt gcaaaaatga accagcagaa aaagcaccac cgatttctgt 4740
accaccacac atttctataa ctggcttgta gttagctcta cccattaacc acaaatattc 4800
gtctacatta gaggcttcac cggatgaaga aaagcatctt atggtggacc aatcgtaacc 4860
tgaaacacaa tttgtggatt tccatgatct tacaatagat ggtacgacac ccaacattgt 4920
gacctttgca tcttgaacaa atttagcgaa accagagact aaaggactac cgttgtacaa 4980
ggcaatagat gcaccattta acaaactagc ataaaccaac caaggaccca tcatccaacc 5040
caaattagtt ggccatacta taacgtcacc ttttctaata tccaaatgag accaaccatc 5100
agcagcagcc ttcaatgggg tggcttgtgt ccaaggaatt gcttttggtt cacctgtagt 5160
accactggag aataagatgt tagtataagc atcaacaggt tgttctctgg cagtaaactc 5220
gcagttttta aactccttgg ctctttctaa aaagtaatcc caagatatgt caccatctct 5280
caattctgca ccaatgttag aaccactaca agggataact attgccattg ggatttagc 5340
ttcaactact cttgaataca atggtattct ctttttacct ctgatgatgt gatcttgtgt 5400
gaaaattgcc ttagctttgg ataatctcaa tctagttgag atttcagggg cggaaaatga 5460
atctgctata gagacaacta cgtaaccagc caatactatg gccaaatata taacaacagc 5520
atcaacatgc attggcatat cgatggctat tgcacaacct ttttctaaac ccatttcttc 5580
caatgcataa ccaaccaacc aaactctctt tctcaattga tctaatgtca acttattcaa 5640
aggcaagtca tcgttaccct cgtctctcca aacgatcata gtatcgttca atttcttatt 5700
ggagtttacg ttcaagcaat ttttagctga gttcaagtaa ccaccaggta accattcaga 5760
accacctggg ttgttgatgt catctcttct caagatacat tctgggtcct tagagaaact 5820
aattttcatt tcatccatca atactgttct ccaatagact tcagggtttc taacagaaaa 5880
ttcttggaag tgagaaaaag aagaaattgg atctttgtac tttacaccca aaaattcttt 5940
acctctcttt tccaacaaag cacccaaatt agttgacttg actttttcag ggtctggaat 6000
ccaagcaggt ggggctggac cgaaatcctt gtagcaacca taaaacaaca tttggtgtaa 6060
ggagaaaggc aaatctggtg acaagatatg gttagcgatg ttgatccaag tttgaggggt 6120
tgcagcacca taattacaaa cgatttctgc caatctacca tgtaatgttt ctgctacttc 6180
tgaggtgata cccaatgcga tgaaatctga ggcaacgact gaatccaagg acttatagtt 6240
tttacccatt cttttaatcg tggatccttc aaaaattctt acttttttttt tggatggacg 6300
caaagaagtt taataatcat attacatggc attaccacca tatacatatc catatacata 6360
tccatatcta atcttactta tatgttgtgg aaatgtaaag agccccatta tcttagccta 6420
aaaaaacctt ctctttggaa ctttcagtaa tacgcttaac tgctcattgc tatattgaag 6480
tacggattag aagccgccga gcgggtgaca gccctccgaa ggaagactct cctccgtgcg 6540
tcctcgtctt caccggtcgc gttcctgaaa cgcagatgtg cctcgcgccg cactgctccg 6600
aacaataaag attctacaat actagctttt atggttatga agaggaaaaa ttggcagtaa 6660
cctggcccca caaaccttca aatgaacgaa tcaaattaac aaccatagga tgataatgcg 6720
attagttttt tagccttatt tctggggtaa ttaatcagcg aagcgatgat ttttgatcta 6780
ttaacagata tataaatgca aaaactgcat aaccacttta actaatactt tcaacatttt 6840
cggtttgtat tacttcttat tcaaatgtaa taaaagtatc aacaaaaaat tgttaatata 6900
cctctatact ttaacgtcaa ggagaaaaaa ccccggatcc gtaatacgac tcactataat 6960
gaatcatttg agagctgaag gtccagcttc tgttttggct attggtactg ctaatccaga 7020

```
aaatattttg attcaagatg aatttccaga ttattatttt agagttacta aatctgaaca   7080
tatgactcaa ttgaaagaaa aatttagaaa aatttgtgat aaatctatga ttagaaaaag   7140
aaattgtttt ttgaatgaag aacatttgaa acaaaatcca agattggttg aacatgaaat   7200
gcaaactttg gatgctagac aagatatgtt ggttgttgaa gttccaaaat tgggtaaaga   7260
tgcttgtgct aaagctatta aagaatgggg tcaaccaaaa tctaaaatta ctcatttgat   7320
ttttacttct gcttctacta ctgatatgcc aggtgctgat tatcattgtg ctaaattgtt   7380
gggtttgtct ccatctgtta aaagagttat gatgtatcaa ttgggttgtt atggtggtgg   7440
tactgttttg agaattgcta aagatattgc tgaaaataat aaaggtgcta gagttttggc   7500
tgtttgttgt gatatgactg cttgtttgtt tagaggtcca tctgattcta atttggaatt   7560
gttggttggt caagctattt ttggtgatgg tgctgctgct gttattgttg gtgctgaacc   7620
agatgaatct gttggtgaaa gaccaatttt tgaattggtt tctactggtc aaactttttt   7680
gccaaattct gaaggtacta ttggtggtca tattagagaa gctggtttga tgtttgattt   7740
gcataaagat gttccaatgt tgatttctaa taatattgaa aaatgtttga ttgaagcttt   7800
tactccaatt ggtatttctg attggaattc tattttttgg attactcatc caggtggtaa   7860
agctattttg gataaagttg aagaaaaatt gcatttgaaa tctgataaat ttgttgattc   7920
tagacatgtt ttgtctgaac atggtaatat gtcttcttct actgttttgt ttgttatgga   7980
tgaattgaga aaaagatctt tggaagaagg taaatctact actggtgatg gttttgaatg   8040
gggtgttttg tttggttttg gtccaggttt gactgttgaa agagttgttt tgagatctgt   8100
tccaattaat tatgaaggta gaggttcctt gttaacttgt ggtgacgttg aagaaaaccc   8160
aggtcctatg gccgtcaagc atttgatagt attgaagttt aaagatgaaa tcacagaagc   8220
tcaaaaggaa gaatttttca agacctacgt taatttggtc aacattatac ctgctatgaa   8280
agatgtatac tggggtaaag acgttacaca aaagaaagaa gaaggttata cacacattgt   8340
cgaagtaacc ttcgaatcag ttgaaactat ccaagattac atcattcatc cagctcacgt   8400
tggttttggt gacgtttaca gatccttctg ggaaaaattg ttgatcttcg attacacccc   8460
aagaaagtga tgatgggctg caggaattcg atatcaagct tatcgatacc gtcgacctcg   8520
agtcatgtaa ttagttatgt cacgcttaca ttcacgccct ccccccacat ccgctctaac   8580
cgaaaaggaa ggagttagac aacctgaagt ctaggtccct atttattttt ttatagttat   8640
gttagtatta agaacgttat ttatatttca aatttttctt ttttttctgt acagacgcgt   8700
gtacgcatgt aacattatac tgaaaacctt gcttgagaag gttttgggac gctcgaaggc   8760
tttaatttgc ggccggtacc cagcttttgt tccctttagt gagggttaat tccgagcttg   8820
gcgtaatcat ggtcatagct gtttcctgtg tgaaattgtt atccgctcac aattccacac   8880
aacataggag ccggaagcat aaagtgtaaa gcctggggtg cctaatgagt gaggtaactc   8940
acattaattg cgttgcgctc actgcccgct ttccagtcgg gaaacctgtc gtgccagctg   9000
cattaatgaa tcggccaacg cgcggggaga ggcggtttgc gtattgggcg ctcttccgct   9060
tcctcgctca ctgactcgct gcgctcggtc gttcggctgc ggcgagcggt atcagctcac   9120
tcaaaggcgg taatacggtt atccacagaa tcaggggata acgcaggaaa gaacatgtga   9180
gcaaaaggcc agcaaaaggc caggaaccgt aaaaaggccg cgttgctggc gtttttccat   9240
aggctcggcc cccctgacga gcatcacaaa aatcgacgct caagtcagag gtggcgaaac   9300
ccgacaggac tataaagata ccaggcgttc ccccctggaa gctccctcgt gcgctctcct   9360
```

-continued

```
gttccgaccc tgccgcttac cggatacctg tccgcctttc tcccttcggg aagcgtggcg   9420

ctttctcaat gctcacgctg taggtatctc agttcggtgt aggtcgttcg ctccaagctg   9480

ggctgtgtgc acgaaccccc cgttcagccc gaccgctgcg ccttatccgg taactatcgt   9540

cttgagtcca acccggtaag acacgactta tcgccactgg cagcagccac tggtaacagg   9600

attagcagag cgaggtatgt aggcggtgct acagagttct tgaagtggtg gcctaactac   9660

ggctacacta gaaggacagt atttggtatc tgcgctctgc tgaagccagt taccttcgga   9720

aaaagagttg gtagctcttg atccggcaaa caaaccaccg ctggtagcgg tggttttttt   9780

gtttgcaagc agcagattac gcgcagaaaa aaaggatctc aagaagatcc tttgatcttt   9840

tctacggggt ctgacgctca gtggaacgaa aactcacgtt aagggatttt ggtcatgaga   9900

ttatcaaaaa ggatcttcac ctagatcctt ttaaattaaa aatgaagttt taaatcaatc   9960

taaagtatat atgagtaaac ttggtctgac agttaccaat gcttaatcag tgaggcacct  10020

atctcagcga tctgtctatt tcgttcatcc atagttgcct gactgcccgt cgtgtagata  10080

actacgatac gggagggctt accatctggc cccagtgctg caatgatacc gcgagaccca  10140

cgctcaccgg ctccagattt atcagcaata aaccagccag ccggaagggc cgagcgcaga  10200

agtggtcctg caactttatc cgcctccatc cagtctatta attgttgccg ggaagctaga  10260

gtaagtagtt cgccagttaa tagtttgcgc aacgttgttg ccattgctac aggcatcgtg  10320

gtgtcacgct cgtcgtttgg tatggcttc                                   10349
```

<210> SEQ ID NO 78
<211> LENGTH: 10367
<212> TYPE: DNA
<213> ORGANISM: Artificial Sequence
<220> FEATURE:
<223> OTHER INFORMATION: Codon Optimized

<400> SEQUENCE: 78

```
attcagctcc ggttcccaac gatcaaggcg agttacatga tcccccatgt tgtgaaaaaa     60

agcggttagc tccttcggtc ctccgatcgt tgtcagaagt aagttggccg cagtgttatc    120

actcatggtt atggcagcac tgcataattc tcttactgtc atgccatccg taagatgctt    180

ttctgtgact ggtgagtact caaccaagtc attctgagaa tagtgtatgc ggcgaccgag    240

ttgctcttgc ccggcgtcaa tacgggataa taccgcgcca catagcagaa ctttaaaagt    300

gctcatcatt ggaaaacgtt cttcggggcg aaaactctca aggatcttac cgctgttgag    360

atccagttcg atgtaaccca ctcgtgcacc caactgatct tcagcatctt ttactttcac    420

cagcgtttct gggtgagcaa aaacaggaag gcaaaatgcc gcaaaaaagg gaataagggc    480

gacacggaaa tgttgaatac tcatactctt cctttttcaa tattattgaa gcatttatca    540

gggttattgt ctcatgagcg gatacatatt tgaatgtatt tagaaaaata aacaaatagg    600

ggttccgcgc acatttcccc gaaaagtgcc acctgacgtc taagaaacca ttattatcat    660

gacattaacc tataaaaata ggcgtatcac gaggcccttt cgtctcgcgc gtttcggtga    720

tgacggtgaa aacctctgac acatgcagct cccggagacg gtcacagctt gtctgtaagc    780

ggatgccggg agcagacaag cccgtcaggg cgcgtcagcg ggtgttggcg ggtgtcgggg    840

ctggcttaac tatgcggcat cagagcagat tgtactgaga gtgcaccata tcgactacgt    900

cgtaaggccg tttctgacag agtaaaattc ttgagggaac tttcaccatt atgggaaatg    960

gttcaagaag gtattgactt aaactccatc aaatggtcag gtcattgagt gttttttatt   1020

tgttgtattt tttttttttt agagaaaatc ctccaatatc aaattaggaa tcgtagtttc   1080
```

-continued

```
atgattttct gttacaccta actttttgtg tggtgccctc ctccttgtca atattaatgt   1140
taaagtgcaa ttctttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaaagaga atctttttaa gcaaggattt   1380
tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca aagtaaatac   2040
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tccttttttct cccaattttt   2700
cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaaata   2820
atggttgcta agagattcga actcttgcat cttacgatac ctgagtattc ccacagttaa   2880
ctgcggtcaa gatatttctt gaatcaggcg ccttagaccg ctcggccaaa caaccaatta   2940
cttgttgaga aatagagtat aattatccta taaatataac gtttttgaac acacatgaac   3000
aaggaagtac aggacaattg attttgaaga gaatgtggat tttgatgtaa ttgttgggat   3060
tccatttttta ataaggcaat aatattaggt atgtggatat actagaagtt ctcctcgagg   3120
gtcgatatgc ggtgtgaaat accgcacaga tgcgtaagga gaaaataccg catcaggaaa   3180
ttgtaaacgt taatattttg ttaaaattcg cgttaaattt ttgttaaatc agctcatttt   3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420
```

caagtttttt ggggtcgagg tgccgtaaag cactaaatcg gaaccctaaa gggagccccc 3480
gatttagagc ttgacgggga aagccggcga acgtggcgag aaaggaaggg aagaaagcga 3540
aaggagcggg cgctagggcg ctggcaagtg tagcggtcac gctgcgcgta accaccacac 3600
ccgccgcgct taatgcgccg ctacagggcg cgtcgcgcca ttcgccattc aggctgcgca 3660
actgttggga agggcgatcg gtgcgggcct cttcgctatt acgccagctg gcgaaggggg 3720
gatgtgctgc aaggcgatta agttgggtaa cgccagggtt ttcccagtca cgacgttgta 3780
aaacgacggc cagtgaattg taatacgact cactataggg cgaattggag ctctagtcgc 3840
aaattaaagc cttcgagcgt cccaaaacct tctcaagcaa ggttttcagt ataatgttac 3900
atgcgtacac gcgtctgtac agaaaaaaaa gaaaaatttg aaatataaat aacgttctta 3960
atactaacat aactataaaa aaataaatag ggacctagac ttcaggttgt ctaactcctt 4020
ccttttcggt tagagcggat gtgggggag ggcgtgaatg taagcgtgac ataactaatt 4080
acatgatcat tcgaaatgac tgaattgttg tctcaaaact cttctcatga tcttgtttgt 4140
tgcagttcta ggtaaggatg acaatgggac aactctagta actttgaata atgggttcaa 4200
tttcttttgc aaacccaagt taaaggataa tctcaattgg ttcaaatcaa tggttgtgtc 4260
gtttgaatcc ttcaatacga aaaatatgac caattgttct ggaccaccac ccaaaggtgg 4320
aacaccaata gcagtggttt caaaaactct gtcatctact tcattacaga ctctttcgat 4380
ttcgatagaa ctaattttga taccaccgat gttcatagtg tcatcggctc taccgtgtgc 4440
atggtagtaa ccgttagagg tcaattcgaa aatgtcacca tgtcttctca atacttcacc 4500
attcaaggtt ggcataccct tgaaatagac atcgtgatga ttaccgttta acaatgtttt 4560
tgaggcacca aacataacag gacctaatgc caattcaccg atacctggct tatttttagg 4620
cattgggtaa ccgttcttat ctaatatgta caaggtgcaa cccatacatt gggatgaaaa 4680
agaacttaaa gattgagctt gcaaaaatga accagcagaa aaagcaccac cgatttctgt 4740
accaccacac atttctataa ctggcttgta gttagctcta cccattaacc acaaatattc 4800
gtctacatta gaggcttcac cggatgaaga aaagcatctt atggtggacc aatcgtaacc 4860
tgaaacacaa tttgtggatt tccatgatct tacaatagat ggtacgacac ccaacattgt 4920
gacctttgca tcttgaacaa atttagcgaa accagagact aaaggactac cgttgtacaa 4980
ggcaatagat gcaccattta acaaactagc ataaaccaac caaggaccca tcatccaacc 5040
caaattagtt ggccatacta taacgtcacc ttttctaata tccaaatgag accaaccatc 5100
agcagcagcc ttcaatgggg tggcttgtgt ccaaggaatt gcttttggtt cacctgtagt 5160
accactggag aataagatgt tagtataagc atcaacaggt tgttctctgg cagtaaactc 5220
gcagttttta aactccttgg ctctttctaa aaagtaatcc caagatatgt caccatctct 5280
caattctgca ccaatgttag aaccactaca agggataact attgccattg gggatttagc 5340
ttcaactact cttgaataca atggtattct ctttttacct ctgatgatgt gatcttgtgt 5400
gaaaattgcc ttagctttgg ataatctcaa tctagttgag atttcagggg cggaaaatga 5460
atctgctata gagacaacta cgtaaccagc caatactatg gccaaatata taacaacagc 5520
atcaacatgc attggcatat cgatggctat tgcacaacct ttttctaaac ccatttcttc 5580
caatgcataa ccaaccaacc aaactctctt tctcaattga tctaatgtca acttattcaa 5640
aggcaagtca tcgttaccct cgtctctcca aacgatcata gtatcgttca atttcttatt 5700
ggagtttacg ttcaagcaat ttttagctga gttcaagtaa ccaccaggta accattcaga 5760
accacctggg ttgttgatgt catctcttct caagatacat tctgggtcct tagagaaact 5820

-continued

```
aattttcatt tcatccatca atactgttct ccaatagact tcagggtttc taacagaaaa   5880
ttcttggaag tgagaaaaag aagaaattgg atctttgtac tttacaccca aaaattcttt   5940
acctctcttt tccaacaaag cacccaaatt agttgacttg actttttcag ggtctggaat   6000
ccaagcaggt ggggctggac cgaaatcctt gtagcaacca taaaacaaca tttggtgtaa   6060
ggagaaaggc aaatctggtg acaagatatg gttagcgatg ttgatccaag tttgaggggt   6120
tgcagcacca taattacaaa cgatttctgc caatctacca tgtaatgttt ctgctacttc   6180
tgaggtgata cccaatgcga tgaaatctga ggcaacgact gaatccaagg acttatagtt   6240
tttacccatt cttttaatcg tggatccttc aaaaattctt actttttttt tggatggacg   6300
caaagaagtt taataatcat attacatggc attaccacca tatacatatc catatacata   6360
tccatatcta atcttactta tatgttgtgg aaatgtaaag agccccatta tcttagccta   6420
aaaaaacctt ctctttggaa ctttcagtaa tacgcttaac tgctcattgc tatattgaag   6480
tacggattag aagccgccga gcgggtgaca gccctccgaa ggaagactct cctccgtgcg   6540
tcctcgtctt caccggtcgc gttcctgaaa cgcagatgtg cctcgcgccg cactgctccg   6600
aacaataaag attctacaat actagctttt atggttatga agaggaaaaa ttggcagtaa   6660
cctggcccca caaaccttca aatgaacgaa tcaaattaac aaccatagga tgataatgcg   6720
attagttttt tagccttatt tctggggtaa ttaatcagcg aagcgatgat ttttgatcta   6780
ttaacagata tataaatgca aaaactgcat aaccacttta actaatactt tcaacatttt   6840
cggtttgtat tacttcttat tcaaatgtaa taaaagtatc aacaaaaaat tgttaatata   6900
cctctatact ttaacgtcaa ggagaaaaaa ccccggatcc gtaatacgac tcactataat   6960
ggaagaaatt aaaggtgttt tgaaagctaa agatgttggt tgtgttgcta ctattttggc   7020
tattggtact gctaatccat tgaattgtgt taatcaagat gaatttttgc attcttattt   7080
taaattgact aataatcata ataatacttc ttttaaagaa ttgtttacta gaatttgtaa   7140
taattctatg attaaaaata gatatatgca tttgactgaa gatattttga aagaaaatcc   7200
aaatttgtgt gattatgctg ctcaatcttt gaatactaga caagatatta aaattaaaga   7260
aattccaaaa ttggctgaaa gagctgctat ggttgctatt aaagaatggg gtaaaccaat   7320
ttctaatttg actcatatta tttttcattc ttctactggt gctgctgata tgccaggtgc   7380
tgattatcaa ttggttaaat ctttgggttt gaatagatct attaaaagaa ttatgttgta   7440
taatttgggt tgttttgctg gtggtactgt tttgagagtt gctaaagatt tggttgaaaa   7500
taatttgggt gcttctgttt tggctgtttg tgctgaaatt acttctgctg atgctacttt   7560
tggtagattg tctgaagatg ataaaggtag attggttggt catgctattt ttggtgatgg   7620
tgctgctgct ttggttattg gtaatgctga tgatccagaa aataaaggtt tgtttcaaat   7680
tgtttctact tctcaaacta ttttgccaaa ttctgaaggt tgtattgaag gtcatattag   7740
agaagatggt gttactttta ctttgtctcc aagagttcca aaattgattg gtgataatat   7800
tgaaacttgt ttgatggaag cttttactcc atttaaaatt tctgattgga attctttgtt   7860
ttgggttgtt catccaggtg gtgctgctat tttgagagaa gttgaatcta gagttggttt   7920
ggaacaagaa aaattgagag cttcttggca tgttttgaga gaatatggta atatttcttc   7980
tgcttctgtt ttgtttattt tggatgaaat gagaaataaa tctttggaag aaggtagaaa   8040
aactactggt gaaggtaaaa attggggtgt tttgtttggt tttggtccag gtttgactgt   8100
tgaaactgtt gttttgcatt ctattccaat tgaaggtaga ggttccttgt taacttgtgg   8160
```

-continued

```
tgacgttgaa gaaaacccag gtcctatggc cgtcaagcat ttgatagtat tgaagtttaa   8220

agatgaaatc acagaagctc aaaaggaaga atttttcaag acctacgtta atttggtcaa   8280

cattatacct gctatgaaag atgtatactg ggtaaagac gttacacaaa agaaagaaga   8340

aggttataca cacattgtcg aagtaacctt cgaatcagtt gaaactatcc aagattacat   8400

cattcatcca gctcacgttg gttttggtga cgtttacaga tccttctggg aaaaattgtt   8460

gatcttcgat tacaccccaa gaaagtgatg atgggctgca ggaattcgat atcaagctta   8520

tcgataccgt cgacctcgag tcatgtaatt agttatgtca cgcttacatt cacgccctcc   8580

ccccacatcc gctctaaccg aaaaggaagg agttagacaa cctgaagtct aggtccctat   8640

ttattttttt atagttatgt tagtattaag aacgttattt atatttcaaa tttttctttt   8700

ttttctgtac agacgcgtgt acgcatgtaa cattatactg aaaaccttgc ttgagaaggt   8760

tttgggacgc tcgaaggctt taatttgcgg ccggtaccca gcttttgttc cctttagtga   8820

gggttaattc cgagcttggc gtaatcatgg tcatagctgt ttcctgtgtg aaattgttat   8880

ccgctcacaa ttccacacaa cataggagcc ggaagcataa agtgtaaagc ctggggtgcc   8940

taatgagtga ggtaactcac attaattgcg ttgcgctcac tgcccgcttt ccagtcggga   9000

aacctgtcgt gccagctgca ttaatgaatc ggccaacgcg cggggagagg cggtttgcgt   9060

attgggcgct cttccgcttc ctcgctcact gactcgctgc gctcggtcgt tcggctgcgg   9120

cgagcggtat cagctcactc aaaggcggta atacggttat ccacagaatc aggggataac   9180

gcaggaaaga acatgtgagc aaaaggccag caaaaggcca ggaaccgtaa aaaggccgcg   9240

ttgctggcgt ttttccatag gctcggcccc cctgacgagc atcacaaaaa tcgacgctca   9300

agtcagaggt ggcgaaaccc gacaggacta taaagatacc aggcgttccc cctggaagc   9360

tccctcgtgc gctctcctgt tccgaccctg ccgcttaccg gatacctgtc cgcctttctc   9420

ccttcgggaa gcgtggcgct ttctcaatgc tcacgctgta ggtatctcag ttcggtgtag   9480

gtcgttcgct ccaagctggg ctgtgtgcac gaaccccccg ttcagcccga ccgctgcgcc   9540

ttatccggta actatcgtct tgagtccaac ccggtaagac acgacttatc gccactggca   9600

gcagccactg gtaacaggat tagcagagcg aggtatgtag gcggtgctac agagttcttg   9660

aagtggtggc ctaactacgg ctacactaga aggacagtat ttggtatctg cgctctgctg   9720

aagccagtta ccttcggaaa aagagttggt agctcttgat ccggcaaaca aaccaccgct   9780

ggtagcggtg gtttttttgt ttgcaagcag cagattacgc gcagaaaaaa aggatctcaa   9840

gaagatcctt tgatcttttc tacggggtct gacgctcagt ggaacgaaaa ctcacgttaa   9900

gggattttgg tcatgagatt atcaaaaagg atcttcacct agatcctttt aaattaaaaa   9960

tgaagtttta aatcaatcta aagtatatat gagtaaactt ggtctgacag ttaccaatgc  10020

ttaatcagtg aggcacctat ctcagcgatc tgtctatttc gttcatccat agttgcctga  10080

ctgcccgtcg tgtagataac tacgatacgg gagggcttac catctggccc cagtgctgca  10140

atgataccgc gagacccacg ctcaccggct ccagatttat cagcaataaa ccagccagcc  10200

ggaagggccg agcgcagaag tggtcctgca actttatccg cctccatcca gtctattaat  10260

tgttgccggg aagctagagt aagtagttcg ccagttaata gtttgcgcaa cgttgttgcc  10320

attgctacag gcatcgtggt gtcacgctcg tcgtttggta tggcttc                10367
```

<210> SEQ ID NO 79
<211> LENGTH: 10349
<212> TYPE: DNA
<213> ORGANISM: Artificial Sequence
<220> FEATURE:
<223> OTHER INFORMATION: Codon Optimized

<400> SEQUENCE: 79
attcagctcc ggttcccaac gatcaaggcg agttacatga tcccccatgt tgtgaaaaaa 60
agcggttagc tccttcggtc ctccgatcgt tgtcagaagt aagttggccg cagtgttatc 120
actcatggtt atggcagcac tgcataattc tcttactgtc atgccatccg taagatgctt 180
ttctgtgact ggtgagtact caaccaagtc attctgagaa tagtgtatgc ggcgaccgag 240
ttgctcttgc ccggcgtcaa tacgggataa taccgcgcca catagcagaa ctttaaaagt 300
gctcatcatt ggaaaacgtt cttcggggcg aaaactctca aggatcttac cgctgttgag 360
atccagttcg atgtaaccca ctcgtgcacc caactgatct tcagcatctt ttactttcac 420
cagcgtttct gggtgagcaa aaacaggaag gcaaaatgcc gcaaaaaagg gaataagggc 480
gacacggaaa tgttgaatac tcatactctt cctttttcaa tattattgaa gcatttatca 540
gggttattgt ctcatgagcg gatacatatt tgaatgtatt tagaaaaata aacaaatagg 600
ggttccgcgc acatttcccc gaaaagtgcc acctgacgtc taagaaacca ttattatcat 660
gacattaacc tataaaaata ggcgtatcac gaggcccttt cgtctcgcgc gtttcggtga 720
tgacggtgaa aacctctgac acatgcagct cccggagacg gtcacagctt gtctgtaagc 780
ggatgccggg agcagacaag cccgtcaggg cgcgtcagcg ggtgttggcg ggtgtcgggg 840
ctggcttaac tatgcggcat cagagcagat tgtactgaga gtgcaccata tcgactacgt 900
cgtaaggccg tttctgacag agtaaaattc ttgagggaac tttcaccatt atgggaaatg 960
gttcaagaag gtattgactt aaactccatc aaatggtcag gtcattgagt gtttttttatt 1020 tgttgtattt ttttttttt agagaaaatc ctccaatatc aaattaggaa tcgtagtttc 1080
atgattttct gttacaccta actttttgtg tggtgccctc ctccttgtca atattaatgt 1140
taaagtgcaa ttctttttcc ttatcacgtt gagccattag tatcaatttg cttacctgta 1200
ttcctttact atcctccttt ttctccttct tgataaatgt atgtagattg cgtatatagt 1260
ttcgtctacc ctatgaacat attccatttt gtaatttcgt gtcgtttcta ttatgaattt 1320
catttataaa gtttatgtac aaatatcata aaaaaagaga atctttttaa gcaaggattt 1380
tcttaacttc ttcggcgaca gcatcaccga cttcggtggt actgttggaa ccacctaaat 1440
caccagttct gatacctgca tccaaaacct ttttaactgc atcttcaatg gccttacctt 1500
cttcaggcaa gttcaatgac aatttcaaca tcattgcagc agacaagata gtggcgatag 1560
ggtcaacctt attctttggc aaatctggag cagaaccgtg gcatggttcg tacaaaccaa 1620
atgcggtgtt cttgtctggc aaagaggcca aggacgcaga tggcaacaaa cccaaggaac 1680
ctgggataac ggaggcttca tcggagatga tatcaccaaa catgttgctg gtgattataa 1740
taccatttag gtgggttggg ttcttaacta ggatcatggc ggcagaatca atcaattgat 1800
gttgaacctt caatgtaggg aattcgttct tgatggtttc ctccacagtt tttctccata 1860
atcttgaaga ggccaaaaca ttagctttat ccaaggacca aataggcaat ggtggctcat 1920
gttgtagggc catgaaagcg gccattcttg tgattctttg cacttctgga acggtgtatt 1980
gttcactatc ccaagcgaca ccatcaccat cgtcttcctt tctcttacca aagtaaatac 2040
ctcccactaa ttctctgaca acaacgaagt cagtaccttt agcaaattgt ggcttgattg 2100
gagataagtc taaaagagag tcggatgcaa agttacatgg tcttaagttg gcgtacaatt 2160
gaagttcttt acggattttt agtaaacctt gttcaggtct aacactaccg gtaccccatt 2220

```
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tcctttttct cccaattttt   2700
cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaaata   2820
atggttgcta agagattcga actcttgcat cttacgatac ctgagtattc ccacagttaa   2880
ctgcggtcaa gatatttctt gaatcaggcg ccttagaccg ctcggccaaa caaccaatta   2940
cttgttgaga aatagagtat aattatccta taaatataac gtttttgaac acacatgaac   3000
aaggaagtac aggacaattg attttgaaga gaatgtggat tttgatgtaa ttgttgggat   3060
tccattttta ataaggcaat aatattaggt atgtggatat actagaagtt ctcctcgagg   3120
gtcgatatgc ggtgtgaaat accgcacaga tgcgtaagga gaaaataccg catcaggaaa   3180
ttgtaaacgt taatattttg ttaaaattcg cgttaaattt ttgttaaatc agctcatttt   3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420
caagtttttt ggggtcgagg tgccgtaaag cactaaatcg gaaccctaaa gggagccccc   3480
gatttagagc ttgacgggga aagccggcga acgtggcgag aaaggaaggg aagaaagcga   3540
aaggagcggg cgctagggcg ctggcaagtg tagcggtcac gctgcgcgta accaccacac   3600
ccgccgcgct taatgcgccg ctacagggcg cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccagggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
atactaacat aactataaaa aaataaatag ggacctagac ttcaggttgt ctaactcctt   4020
ccttttcggt tagagcggat gtggggggag ggcgtgaatg taagcgtgac ataactaatt   4080
acatgatcat tcgaaatgac tgaattgttg tctcaaaact cttctcatga tcttgtttgt   4140
tgcagttcta ggtaaggatg acaatgggac aactctagta actttgaata atgggttcaa   4200
tttcttttgc aaacccaagt taaaggataa tctcaattgg ttcaaatcaa tggttgtgtc   4260
gtttgaatcc ttcaatacga aaaatatgac caattgttct ggaccaccac ccaaaggtgg   4320
aacaccaata gcagtggttt caaaaactct gtcatctact tcattacaga ctctttcgat   4380
ttcgatagaa ctaattttga taccaccgat gttcatagtg tcatcggctc taccgtgtgc   4440
atggtagtaa ccgttagagg tcaattcgaa aatgtcacca tgtcttctca atacttcacc   4500
attcaaggtt ggcataccct tgaaatagac atcgtgatga ttaccgttta acaatgtttt   4560
tgaggcacca aacataacag gacctaatgc caattcaccg atacctggct tatttttagg   4620
```

-continued

```
cattgggtaa ccgttcttat ctaatatgta caaggtgcaa cccatacatt gggatgaaaa   4680
agaacttaaa gattgagctt gcaaaaatga accagcagaa aaagcaccac cgatttctgt   4740
accaccacac atttctataa ctggcttgta gttagctcta cccattaacc acaaatattc   4800
gtctacatta gaggcttcac cggatgaaga aaagcatctt atggtggacc aatcgtaacc   4860
tgaaacacaa tttgtggatt tccatgatct tacaatagat ggtacgacac ccaacattgt   4920
gacctttgca tcttgaacaa atttagcgaa accagagact aaaggactac cgttgtacaa   4980
ggcaatagat gcaccattta acaaactagc ataaaccaac caaggaccca tcatccaacc   5040
caaattagtt ggccatacta taacgtcacc ttttctaata tccaaatgag accaaccatc   5100
agcagcagcc ttcaatgggg tggcttgtgt ccaaggaatt gcttttggtt cacctgtagt   5160
accactggag aataagatgt tagtataagc atcaacaggt tgttctctgg cagtaaactc   5220
gcagttttta aactccttgg ctctttctaa aaagtaatcc caagatatgt caccatctct   5280
caattctgca ccaatgttag aaccactaca agggataact attgccattg gggatttagc   5340
ttcaactact cttgaataca atggtattct ctttttacct ctgatgatgt gatcttgtgt   5400
gaaaattgcc ttagctttgg ataatctcaa tctagttgag atttcagggg cggaaaatga   5460
atctgctata gagacaacta cgtaaccagc caatactatg gccaaatata taacaacagc   5520
atcaacatgc attggcatat cgatggctat tgcacaacct ttttctaaac ccatttcttc   5580
caatgcataa ccaaccaacc aaactctctt tctcaattga tctaatgtca acttattcaa   5640
aggcaagtca tcgttaccct cgtctctcca aacgatcata gtatcgttca atttcttatt   5700
ggagtttacg ttcaagcaat ttttagctga gttcaagtaa ccaccaggta accattcaga   5760
accacctggg ttgttgatgt catctcttct caagatacat tctgggtcct tagagaaact   5820
aattttcatt tcatccatca atactgttct ccaatagact tcagggtttc taacagaaaa   5880
ttcttggaag tgagaaaaag aagaaattgg atctttgtac tttacaccca aaaattcttt   5940
acctctcttt tccaacaaag cacccaaatt agttgacttg actttttcag ggtctggaat   6000
ccaagcaggt ggggctggac cgaaatcctt gtagcaacca taaaacaaca tttggtgtaa   6060
ggagaaaggc aaatctggtg acaagatatg gttagcgatg ttgatccaag tttgaggggt   6120
tgcagcacca taattacaaa cgatttctgc caatctacca tgtaatgttt ctgctacttc   6180
tgaggtgata cccaatgcga tgaaatctga ggcaacgact gaatccaagg acttatagtt   6240
tttacccatt cttttaatcg tggatccttc aaaaattctt actttttttt tggatggacg   6300
caaagaagtt taataatcat attacatggc attaccacca tatacatatc catatacata   6360
tccatatcta atcttactta tatgttgtgg aaatgtaaag agccccatta tcttagccta   6420
aaaaaacctt ctctttggaa ctttcagtaa tacgcttaac tgctcattgc tatattgaag   6480
tacggattag aagccgccga gcgggtgaca gccctccgaa ggaagactct cctccgtgcg   6540
tcctcgtctt caccggtcgc gttcctgaaa cgcagatgtg cctcgcgccg cactgctccg   6600
aacaataaag attctacaat actagctttt atggttatga agaggaaaaa ttggcagtaa   6660
cctggcccca caaaccttca aatgaacgaa tcaaattaac aaccatagga tgataatgcg   6720
attagttttt tagccttatt tctggggtaa ttaatcagcg aagcgatgat tttgatcta    6780
ttaacagata tataaatgca aaaactgcat aaccacttta actaatactt tcaacatttt   6840
cggtttgtat tacttcttat tcaaatgtaa taaaagtatc aacaaaaaat tgttaatata   6900
cctctatact ttaacgtcaa ggagaaaaaa ccccggatcc gtaatacgac tcactataat   6960
```

-continued gaatcatttg agagctgaag gtccagcttc tgttttggct attggtactg ctaatccaga 7020
aaatattttg attcaagatg aatttccaga ttattatttt agagttacta aatctgaaca 7080
tatgactcaa ttgaaagaaa aatttagaaa aatttgtgat aaatctatga ttagaaaaag 7140
aaattgtttt ttgaatgaag aacatttgaa acaaaatcca agattggttg aacatgaaat 7200
gcaaactttg gatgctagac aagatatgtt ggttgttgaa gttccaaaat tgggtaaaga 7260
tgcttgtgct aaagctatta aagaatgggg tcaaccaaaa tctaaaatta ctcatttgat 7320
tttacttct gcttctacta ctgatatgcc aggtgctgat tatcattgtg ctaaattgtt 7380
gggtttgtct ccatctgtta aaagagttat gatgtatcaa ttgggttgtt atggtggtgg 7440
tactgttttg agaattgcta aagatattgc tgaaaataat aaaggtgcta gagttttggc 7500
tgtttgttgt gatattatgg cttgtttgtt tagaggtcca tctgattctg atttggaatt 7560
gttggttggt caagctattt ttggtgatgg tgctgctgct gttattgttg gtgctgaacc 7620
agatgaatct gttggtgaaa gaccaatttt tgaattggtt tctactggtc aaactatttt 7680
gccaaattct gaaggtacta ttggtggtca tattagagaa gctggtttga tttttgattt 7740
gcataaagat gttccaatgt tgatttctaa taatattgaa aaatgtttga ttgaagcttt 7800
tactccaatt ggtatttctg attggaattc tattttttgg attactcatc caggtggtaa 7860
agctattttg gataaagttg aagaaaaatt gcatttgaaa tctgataaat ttgttgattc 7920
tagacatgtt ttgtctgaac atggtaatat gtcttcttct actgttttgt ttgttatgga 7980
tgaattgaga aaaagatctt tggaagaagg taaatctact actggtgatg gttttgaatg 8040
ggtgttttg tttggttttg gtccaggttt gactgttgaa agagttgttg ttagatctgt 8100
tccaattaaa tatgaaggta gaggttcctt gttaacttgt ggtgacgttg aagaaaaccc 8160
aggtcctatg gccgtcaagc atttgatagt attgaagttt aaagatgaaa tcacagaagc 8220
tcaaaaggaa gaatttttca agacctacgt taatttggtc aacattatac ctgctatgaa 8280
agatgtatac tggggtaaag acgttacaca aaagaaagaa gaaggttata cacacattgt 8340
cgaagtaacc ttcgaatcag ttgaaactat ccaagattac atcattcatc cagctcacgt 8400
tggttttggt gacgtttaca gatccttctg ggaaaaattg ttgatcttcg attacacccc 8460
aagaaagtga tgatgggctg caggaattcg atatcaagct tatcgatacc gtcgacctcg 8520
agtcatgtaa ttagttatgt cacgcttaca ttcacgccct ccccccacat ccgctctaac 8580
cgaaaaggaa ggagttagac aacctgaagt ctaggtccct atttattttt ttatagttat 8640
gttagtatta agaacgttat ttatatttca aatttttctt ttttttctgt acagacgcgt 8700
gtacgcatgt aacattatac tgaaaacctt gcttgagaag gttttgggac gctcgaaggc 8760
tttaatttgc ggccggtacc cagcttttgt tccctttagt gagggttaat tccgagcttg 8820
gcgtaatcat ggtcatagct gtttcctgtg tgaaattgtt atccgctcac aattccacac 8880
aacataggag ccggaagcat aaagtgtaaa gcctggggtg cctaatgagt gaggtaactc 8940
acattaattg cgttgcgctc actgcccgct ttccagtcgg gaaacctgtc gtgccagctg 9000
cattaatgaa tcggccaacg cgcggggaga ggcggtttgc gtattgggcg ctcttccgct 9060
tcctcgctca ctgactcgct gcgctcggtc gttcggctgc ggcgagcggt atcagctcac 9120
tcaaaggcgg taatacggtt atccacagaa tcaggggata acgcaggaaa gaacatgtga 9180
gcaaaaggcc agcaaaaggc caggaaccgt aaaaaggccg cgttgctggc gtttttccat 9240
aggctcggcc cccctgacga gcatcacaaa aatcgacgct caagtcagag gtggcgaaac 9300
ccgacaggac tataaagata ccaggcgttc ccccctggaa gctccctcgt gcgctctcct 9360

```
gttccgaccc tgccgcttac cggatacctg tccgcctttc tcccttcggg aagcgtggcg   9420
ctttctcaat gctcacgctg taggtatctc agttcggtgt aggtcgttcg ctccaagctg   9480
ggctgtgtgc acgaaccccc cgttcagccc gaccgctgcg ccttatccgg taactatcgt   9540
cttgagtcca acccggtaag acacgactta tcgccactgg cagcagccac tggtaacagg   9600
attagcagag cgaggtatgt aggcggtgct acagagttct tgaagtggtg gcctaactac   9660
ggctacacta gaaggacagt atttggtatc tgcgctctgc tgaagccagt taccttcgga   9720
aaaagagttg gtagctcttg atccggcaaa caaaccaccg ctggtagcgg tggttttttt   9780
gtttgcaagc agcagattac gcgcagaaaa aaaggatctc aagaagatcc tttgatcttt   9840
tctacggggt ctgacgctca gtggaacgaa aactcacgtt aagggatttt ggtcatgaga   9900
ttatcaaaaa ggatcttcac ctagatcctt ttaaattaaa aatgaagttt taaatcaatc   9960
taaagtatat atgagtaaac ttggtctgac agttaccaat gcttaatcag tgaggcacct  10020
atctcagcga tctgtctatt tcgttcatcc atagttgcct gactgccccgt cgtgtagata 10080
actacgatac gggagggctt accatctggc cccagtgctg caatgatacc gcgagaccca  10140
cgctcaccgg ctccagattt atcagcaata aaccagccag ccggaagggc cgagcgcaga  10200
agtggtcctg caactttatc cgcctccatc cagtctatta attgttgccg ggaagctaga  10260
gtaagtagtt cgccagttaa tagtttgcgc aacgttgttg ccattgctac aggcatcgtg  10320
gtgtcacgct cgtcgtttgg tatggcttc                                   10349
```

```
<210> SEQ ID NO 80
<211> LENGTH: 10394
<212> TYPE: DNA
<213> ORGANISM: Artificial Sequence
<220> FEATURE:
<223> OTHER INFORMATION: Codon Optimized

<400> SEQUENCE: 80
```

```
attcagctcc ggttcccaac gatcaaggcg agttacatga tcccccatgt tgtgaaaaaa     60
agcggttagc tccttcggtc ctccgatcgt tgtcagaagt aagttggccg cagtgttatc    120
actcatggtt atggcagcac tgcataattc tcttactgtc atgccatccg taagatgctt    180
ttctgtgact ggtgagtact caaccaagtc attctgagaa tagtgtatgc ggcgaccgag    240
ttgctcttgc ccggcgtcaa tacgggataa taccgcgcca catagcagaa ctttaaaagt    300
gctcatcatt ggaaaacgtt cttcggggcg aaaactctca aggatcttac cgctgttgag    360
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt cctttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gtttttttatt  1020
```

-continued

```
tgttgtattt tttttttttt agagaaaatc ctccaatatc aaattaggaa tcgtagtttc   1080
atgattttct gttacaccta actttttgtg tggtgccctc ctccttgtca atattaatgt   1140
taaagtgcaa ttctttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaaagaga atctttttaa gcaaggattt   1380
tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca aagtaaatac   2040
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tcctttttct cccaattttt   2700
cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaaata   2820
atggttgcta agagattcga actcttgcat cttacgatac ctgagtattc ccacagttaa   2880
ctgcggtcaa gatatttctt gaatcaggcg ccttagaccg ctcggccaaa caaccaatta   2940
cttgttgaga aatagagtat aattatccta taaatataac gtttttgaac acacatgaac   3000
aaggaagtac aggacaattg attttgaaga gaatgtggat tttgatgtaa ttgttgggat   3060
tccattttta ataaggcaat aatattaggt atgtggatat actagaagtt ctcctcgagg   3120
gtcgatatgc ggtgtgaaat accgcacaga tgcgtaagga gaaaataccg catcaggaaa   3180
ttgtaaacgt taatattttg ttaaaattcg cgttaaattt ttgttaaatc agctcatttt   3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420
```

caagtttttt ggggtcgagg tgccgtaaag cactaaatcg gaaccctaaa gggagccccc 3480
gatttagagc ttgacgggga aagccggcga acgtggcgag aaaggaaggg aagaaagcga 3540
aaggagcggg cgctagggcg ctggcaagtg tagcggtcac gctgcgcgta accaccacac 3600
ccgccgcgct taatgcgccg ctacagggcg cgtcgcgcca ttcgccattc aggctgcgca 3660
actgttggga agggcgatcg gtgcgggcct cttcgctatt acgccagctg gcgaaggggg 3720
gatgtgctgc aaggcgatta agttgggtaa cgccagggtt ttcccagtca cgacgttgta 3780
aaacgacggc cagtgaattg taatacgact cactataggg cgaattggag ctctagtcgc 3840
aaattaaagc cttcgagcgt cccaaaacct tctcaagcaa ggttttcagt ataatgttac 3900
atgcgtacac gcgtctgtac agaaaaaaaa gaaaaatttg aaatataaat aacgttctta 3960
atactaacat aactataaaa aaataaatag ggacctagac ttcaggttgt ctaactcctt 4020
ccttttcggt tagagcggat gtgggggag ggcgtgaatg taagcgtgac ataactaatt 4080
acatgatcat tcgaaatgac tgaattgttg tctcaaaact cttctcatga tcttgtttgt 4140
tgcagttcta ggtaaggatg acaatgggac aactctagta actttgaata atgggttcaa 4200
tttcttttgc aaacccaagt taaaggataa tctcaattgg ttcaaatcaa tggttgtgtc 4260
gtttgaatcc ttcaatacga aaaatatgac caattgttct ggaccaccac ccaaaggtgg 4320
aacaccaata gcagtggttt caaaaactct gtcatctact tcattacaga ctctttcgat 4380
ttcgatagaa ctaattttga taccaccgat gttcatagtg tcatcggctc taccgtgtgc 4440
atggtagtaa ccgttagagg tcaattcgaa aatgtcacca tgtcttctca atacttcacc 4500
attcaaggtt ggcataccct tgaaatagac atcgtgatga ttaccgttta acaatgtttt 4560
tgaggcacca aacataacag gacctaatgc caattcaccg atacctggct tatttttagg 4620
cattgggtaa ccgttcttat ctaatatgta caaggtgcaa cccatacatt gggatgaaaa 4680
agaacttaaa gattgagctt gcaaaaatga accagcagaa aaagcaccac cgatttctgt 4740
accaccacac atttctataa ctggcttgta gttagctcta cccattaacc acaaatattc 4800
gtctacatta gaggcttcac cggatgaaga aaagcatctt atggtggacc aatcgtaacc 4860
tgaaacacaa tttgtggatt tccatgatct tacaatagat ggtacgacac ccaacattgt 4920
gacctttgca tcttgaacaa atttagcgaa accagagact aaaggactac cgttgtacaa 4980
ggcaatagat gcaccattta acaaactagc ataaaccaac caaggaccca tcatccaacc 5040
caaattagtt ggccatacta taacgtcacc ttttctaata tccaaatgag accaaccatc 5100
agcagcagcc ttcaatgggg tggcttgtgt ccaaggaatt gcttttggtt cacctgtagt 5160
accactggag aataagatgt tagtataagc atcaacaggt tgttctctgg cagtaaactc 5220
gcagttttta aactccttgg ctctttctaa aaagtaatcc caagatatgt caccatctct 5280
caattctgca ccaatgttag aaccactaca agggataact attgccattg gggatttagc 5340
ttcaactact cttgaataca atggtattct ctttttacct ctgatgatgt gatcttgtgt 5400
gaaaattgcc ttagctttgg ataatctcaa tctagttgag atttcagggg cggaaaatga 5460
atctgctata gagacaacta cgtaaccagc caatactatg gccaaatata taacaacagc 5520
atcaacatgc attggcatat cgatggctat tgcacaacct ttttctaaac ccatttcttc 5580
caatgcataa ccaaccaacc aaactctctt tctcaattga tctaatgtca acttattcaa 5640
aggcaagtca tcgttaccct cgtctctcca aacgatcata gtatcgttca atttcttatt 5700
ggagtttacg ttcaagcaat ttttagctga gttcaagtaa ccaccaggta accattcaga 5760

-continued accacctggg ttgttgatgt catctcttct caagatacat tctgggtcct tagagaaact 5820
aattttcatt tcatccatca atactgttct ccaatagact tcagggtttc taacagaaaa 5880
ttcttggaag tgagaaaaag aagaaattgg atctttgtac tttacaccca aaaattcttt 5940
acctctcttt tccaacaaag cacccaaatt agttgacttg actttttcag ggtctggaat 6000
ccaagcaggt ggggctggac cgaaatcctt gtagcaacca taaaacaaca tttggtgtaa 6060
ggagaaaggc aaatctggtg acaagatatg gttagcgatg ttgatccaag tttgaggggt 6120
tgcagcacca taattacaaa cgatttctgc caatctacca tgtaatgttt ctgctacttc 6180
tgaggtgata cccaatgcga tgaaatctga ggcaacgact gaatccaagg acttatagtt 6240
tttacccatt cttttaatcg tggatccttc aaaaattctt actttttttt tggatggacg 6300
caaagaagtt taataatcat attacatggc attaccacca tatacatatc catatacata 6360
tccatatcta atcttactta tatgttgtgg aaatgtaaag agccccatta tcttagccta 6420
aaaaaacctt ctctttggaa ctttcagtaa tacgcttaac tgctcattgc tatattgaag 6480
tacggattag aagccgccga gcgggtgaca gccctccgaa ggaagactct cctccgtgcg 6540
tcctcgtctt caccggtcgc gttcctgaaa cgcagatgtg cctcgcgccg cactgctccg 6600
aacaataaag attctacaat actagctttt atggttatga agaggaaaaa ttggcagtaa 6660
cctggcccca caaaccttca aatgaacgaa tcaaattaac aaccatagga tgataatgcg 6720
attagttttt tagccttatt tctggggtaa ttaatcagcg aagcgatgat ttttgatcta 6780
ttaacagata tataaatgca aaaactgcat aaccacttta actaatactt tcaacatttt 6840
cggtttgtat tacttcttat tcaaatgtaa taaaagtatc aacaaaaaat tgttaatata 6900
cctctatact ttaacgtcaa ggagaaaaaa ccccggatcc gtaatacgac tcactataat 6960
gaatcatttg agagctgaag gtccagcttc tgttttggct attggtactg ctaatccaga 7020
aaatattttg attcaagatg aatttccaga ttattatttt agagttacta aatctgaaca 7080
tatgactcaa ttgaaagaaa aatttagaaa aatttgtgat aaatctatga ttagaaaaag 7140
aaattgtttt ttgaatgaag aacatttgaa acaaaatcca agattggttg aacatgaaat 7200
gcaaactttg gatgctagac aagatatgtt ggttgttgaa gttccaaaat tgggtaaaga 7260
tgcttgtgct aaagctatta aagaatgggg tcaaccaaaa tctaaaatta ctcatttgat 7320
ttttacttct gcttctacta ctgatatgcc aggtgctgat tatcattgtg ctaaattgtt 7380
gggtttgtct ccatctgtta aaagagttat gatgtatcaa ttgggttgtt atggtggtgg 7440
tactgttttg agaattgcta aagatattgc tgaaaataat aaaggtgcta gagttttggc 7500
tgtttgttgt gatattatgg cttgtttgtt tagaggtcca tctgattctg atttggaatt 7560
gttggttggt caagctattt ttggtgatgg tgctgctgct gttattgttg gtgctgaacc 7620
agatgaatct gttggtgaaa gaccaatttt tgaattggtt tctactggtc aaactatttt 7680
gccaaattct gaaggtacta ttggtggtca tattagagaa gctggtttga tttttgattt 7740
gcataaagat gttccaatgt tgatttctaa taatattgaa aaatgtttga ttgaagcttt 7800
tactccaatt ggtatttctg attggaattc tatttttttgg attactcatc caggtggtaa 7860
agctattttg gataaagttg aagaaaaatt gcatttgaaa tctgataaat ttgttgattc 7920
tagacatgtt ttgtctgaac atggtaatat gtcttcttct actgttttgt ttgttatgga 7980
tgaattgaga aaaagatctt tggaagaagg taaatctact actggtgatg gttttgaatg 8040
gggtgttttg tttggttttg gtccaggttt gactgttgaa agaggtagat ggagaaaagg 8100
taatttgcca ttggaaatgg atttgtctgg tgtttttttt ttgggtttgg atcaagttga 8160
aggtagaggt tccttgttaa cttgtggtga cgttgaagaa aacccaggtc ctatggccgt 8220
caagcatttg atagtattga agtttaaaga tgaaatcaca gaagctcaaa aggaagaatt 8280
tttcaagacc tacgttaatt tggtcaacat tatacctgct atgaaagatg tatactgggg 8340
taaagacgtt acacaaaaga aagaagaagg ttatacacac attgtcgaag taaccttcga 8400
atcagttgaa actatccaag attacatcat tcatccagct cacgttggtt ttggtgacgt 8460
ttacagatcc ttctgggaaa aattgttgat cttcgattac accccaagaa agtgatgatg 8520
ggctgcagga attcgatatc aagcttatcg ataccgtcga cctcgagtca tgtaattagt 8580
tatgtcacgc ttacattcac gccctccccc cacatccgct ctaaccgaaa aggaaggagt 8640
tagacaacct gaagtctagg tccctattta tttttttata gttatgttag tattaagaac 8700
gttatttata tttcaaattt ttcttttttt tctgtacaga cgcgtgtacg catgtaacat 8760
tatactgaaa accttgcttg agaaggtttt gggacgctcg aaggctttaa tttgcggccg 8820
gtacccagct tttgttccct ttagtgaggg ttaattccga gcttggcgta atcatggtca 8880
tagctgtttc ctgtgtgaaa ttgttatccg ctcacaattc cacacaacat aggagccgga 8940
agcataaagt gtaaagcctg gggtgcctaa tgagtgaggt aactcacatt aattgcgttg 9000
cgctcactgc ccgctttcca gtcgggaaac ctgtcgtgcc agctgcatta atgaatcggc 9060
caacgcgcgg ggagaggcgg tttgcgtatt gggcgctctt ccgcttcctc gctcactgac 9120
tcgctgcgct cggtcgttcg gctgcggcga gcggtatcag ctcactcaaa ggcggtaata 9180
cggttatcca cagaatcagg ggataacgca ggaaagaaca tgtgagcaaa aggccagcaa 9240
aaggccagga accgtaaaaa ggccgcgttg ctggcgtttt tccataggct ccgcccccct 9300
gacgagcatc acaaaaatcg acgctcaagt cagaggtggc gaaacccgac aggactataa 9360
agataccagg cgtttccccc tggaagctcc ctcgtgcgct ctcctgttcc gaccctgccg 9420
cttaccggat acctgtccgc ctttctccct tcgggaagcg tggcgctttc tcaatgctca 9480
cgctgtaggt atctcagttc ggtgtaggtc gttcgctcca agctgggctg tgtgcacgaa 9540
ccccccgttc agcccgaccg ctgcgcctta tccggtaact atcgtcttga gtccaacccg 9600
gtaagacacg acttatcgcc actggcagca gccactggta acaggattag cagagcgagg 9660
tatgtaggcg gtgctacaga gttcttgaag tggtggccta actacggcta cactagaagg 9720
acagtatttg gtatctgcgc tctgctgaag ccagttacct tcggaaaaag agttggtagc 9780
tcttgatccg gcaaacaaac caccgctggt agcggtggtt tttttgtttg caagcagcag 9840
attacgcgca gaaaaaaagg atctcaagaa gatcctttga tcttttctac ggggtctgac 9900
gctcagtgga acgaaaactc acgttaaggg attttggtca tgagattatc aaaaaggatc 9960
ttcacctaga tccttttaaa ttaaaaatga agttttaaat caatctaaag tatatatgag 10020
taaacttggt ctgacagtta ccaatgctta atcagtgagg cacctatctc agcgatctgt 10080
ctatttcgtt catccatagt tgcctgactg ccccgtcgtgt agataactac gatacgggag 10140
ggcttaccat ctggccccag tgctgcaatg ataccgcgag acccacgctc accggctcca 10200
gatttatcag caataaacca gccagccgga agggccgagc gcagaagtgg tcctgcaact 10260
ttatccgcct ccatccagtc tattaattgt tgccgggaag ctagagtaag tagttcgcca 10320
gttaatagtt tgcgcaacgt tgttgccatt gctacaggca tcgtggtgtc acgctcgtcg 10380
tttggtatgg cttc 10394

<210> SEQ ID NO 81

<211> LENGTH: 10361
<212> TYPE: DNA
<213> ORGANISM: Artificial Sequence
<220> FEATURE:
<223> OTHER INFORMATION: Codon Optimized

<400> SEQUENCE: 81
attcagctcc ggttcccaac gatcaaggcg agttacatga tcccccatgt tgtgaaaaaa 60
agcggttagc tccttcggtc ctccgatcgt tgtcagaagt aagttggccg cagtgttatc 120
actcatggtt atggcagcac tgcataattc tcttactgtc atgccatccg taagatgctt 180
ttctgtgact ggtgagtact caaccaagtc attctgagaa tagtgtatgc ggcgaccgag 240
ttgctcttgc ccggcgtcaa tacgggataa taccgcgcca catagcagaa ctttaaaagt 300
gctcatcatt ggaaaacgtt cttcggggcg aaaactctca aggatcttac cgctgttgag 360
atccagttcg atgtaaccca ctcgtgcacc caactgatct tcagcatctt ttactttcac 420
cagcgtttct gggtgagcaa aaacaggaag gcaaaatgcc gcaaaaaagg gaataagggc 480
gacacggaaa tgttgaatac tcatactctt cctttttcaa tattattgaa gcatttatca 540
gggttattgt ctcatgagcg gatacatatt tgaatgtatt tagaaaaata aacaaatagg 600
ggttccgcgc acatttcccc gaaaagtgcc acctgacgtc taagaaacca ttattatcat 660
gacattaacc tataaaaata ggcgtatcac gaggcccttt cgtctcgcgc gtttcggtga 720
tgacggtgaa aacctctgac acatgcagct cccggagacg gtcacagctt gtctgtaagc 780
ggatgccggg agcagacaag cccgtcaggg cgcgtcagcg ggtgttggcg ggtgtcgggg 840
ctggcttaac tatgcggcat cagagcagat tgtactgaga gtgcaccata tcgactacgt 900
cgtaaggccg tttctgacag agtaaaattc ttgagggaac tttcaccatt atgggaaatg 960
gttcaagaag gtattgactt aaactccatc aaatggtcag gtcattgagt gtttttttatt 1020 tgttgtattt tttttttttt agagaaaatc ctccaatatc aaattaggaa tcgtagtttc 1080
atgattttct gttacaccta actttttgtg tggtgccctc ctccttgtca atattaatgt 1140
taaagtgcaa ttcttttttcc ttatcacgtt gagccattag tatcaatttg cttacctgta 1200
ttcctttact atcctccttt ttctccttct tgataaatgt atgtagattg cgtatatagt 1260
ttcgtctacc ctatgaacat attccatttt gtaatttcgt gtcgtttcta ttatgaattt 1320
catttataaa gtttatgtac aaatatcata aaaaaagaga atctttttaa gcaaggattt 1380
tcttaacttc ttcggcgaca gcatcaccga cttcggtggt actgttggaa ccacctaaat 1440
caccagttct gatacctgca tccaaaacct ttttaactgc atcttcaatg gccttacctt 1500
cttcaggcaa gttcaatgac aatttcaaca tcattgcagc agacaagata gtggcgatag 1560
ggtcaacctt attctttggc aaatctggag cagaaccgtg gcatggttcg tacaaaccaa 1620
atgcggtgtt cttgtctggc aaagaggcca aggacgcaga tggcaacaaa cccaaggaac 1680
ctgggataac ggaggcttca tcggagatga tatcaccaaa catgttgctg gtgattataa 1740
taccatttag gtgggttggg ttcttaacta ggatcatggc ggcagaatca atcaattgat 1800
gttgaacctt caatgtaggg aattcgttct tgatggtttc ctccacagtt tttctccata 1860
atcttgaaga ggccaaaaca ttagctttat ccaaggacca aataggcaat ggtggctcat 1920
gttgtagggc catgaaagcg gccattcttg tgattctttg cacttctgga acggtgtatt 1980
gttcactatc ccaagcgaca ccatcaccat cgtcttcctt tctcttacca aagtaaatac 2040
ctcccactaa ttctctgaca acaacgaagt cagtaccttt agcaaattgt ggcttgattg 2100
gagataagtc taaaagagag tcggatgcaa agttacatgg tcttaagttg gcgtacaatt 2160

-continued gaagttcttt acggattttt agtaaacctt gttcaggtct aacactaccg gtaccccatt 2220
taggaccacc cacagcacct aacaaaacgg catcaacctt cttggaggct tccagcgcct 2280
catctggaag tgggacacct gtagcatcga tagcagcacc accaattaaa tgattttcga 2340
aatcgaactt gacattggaa cgaacatcag aaatagcttt aagaacctta atggcttcgg 2400
ctgtgatttc ttgaccaacg tggtcacctg gcaaaacgac gatcttctta ggggcagaca 2460
taggggcaga cattagaatg gtatatcctt gaaatatata tatatattgc tgaaatgtaa 2520
aaggtaagaa aagttagaaa gtaagacgat tgctaaccac ctattggaaa aaacaatagg 2580
tccttaaata atattgtcaa cttcaagtat tgtgatgcaa gcatttagtc atgaacgctt 2640
ctctattcta tatgaaaagc cggttccggc ctctcacctt tcctttttct cccaattttt 2700
cagttgaaaa aggtatatgc gtcaggcgac ctctgaaatt aacaaaaaat ttccagtcat 2760
cgaatttgat tctgtgcgat agcgcccctg tgtgttctcg ttatgttgag gaaaaaaata 2820
atggttgcta agagattcga actcttgcat cttacgatac ctgagtattc ccacagttaa 2880
ctgcggtcaa gatatttctt gaatcaggcg ccttagaccg ctcggccaaa caaccaatta 2940
cttgttgaga aatagagtat aattatccta taaatataac gtttttgaac acacatgaac 3000
aaggaagtac aggacaattg attttgaaga gaatgtggat tttgatgtaa ttgttgggat 3060
tccattttta ataaggcaat aatattaggt atgtggatat actagaagtt ctcctcgagg 3120
gtcgatatgc ggtgtgaaat accgcacaga tgcgtaagga gaaaataccg catcaggaaa 3180
ttgtaaacgt taatattttg ttaaaattcg cgttaaattt ttgttaaatc agctcatttt 3240
ttaaccaata ggccgaaatc ggcaaaatcc cttataaatc aaaagaatag accgagatag 3300
ggttgagtgt tgttccagtt tggaacaaga gtccactatt aaagaacgtg gactccaacg 3360
tcaaagggcg aaaaaccgtc tatcagggcg atggcccact acgtgaacca tcaccctaat 3420
caagtttttt ggggtcgagg tgccgtaaag cactaaatcg gaaccctaaa gggagccccc 3480
gatttagagc ttgacgggga aagccggcga acgtggcgag aaaggaaggg aagaaagcga 3540
aaggagcggg cgctagggcg ctggcaagtg tagcggtcac gctgcgcgta accaccacac 3600
ccgccgcgct taatgcgccg ctacagggcg cgtcgcgcca ttcgccattc aggctgcgca 3660
actgttggga agggcgatcg gtgcgggcct cttcgctatt acgccagctg gcgaaggggg 3720
gatgtgctgc aaggcgatta agttgggtaa cgccagggtt ttcccagtca cgacgttgta 3780
aaacgacggc cagtgaattg taatacgact cactataggg cgaattggag ctctagtcgc 3840
aaattaaagc cttcgagcgt cccaaaacct tctcaagcaa ggttttcagt ataatgttac 3900
atgcgtacac gcgtctgtac agaaaaaaaa gaaaaatttg aaatataaat aacgttctta 3960
atactaacat aactataaaa aaataaatag ggacctagac ttcaggttgt ctaactcctt 4020
ccttttcggt tagagcggat gtggggggag ggcgtgaatg taagcgtgac ataactaatt 4080
acatgatcat tcgaaatgac tgaattgttg tctcaaaact cttctcatga tcttgtttgt 4140
tgcagttcta ggtaaggatg acaatgggac aactctagta actttgaata atgggttcaa 4200
tttcttttgc aaacccaagt taaaggataa tctcaattgg ttcaaatcaa tggttgtgtc 4260
gtttgaatcc ttcaatacga aaaatatgac caattgttct ggaccaccac ccaaaggtgg 4320
aacaccaata gcagtggttt caaaaactct gtcatctact tcattacaga ctctttcgat 4380
ttcgatagaa ctaattttga taccaccgat gttcatagtg tcatcggctc taccgtgtgc 4440
atggtagtaa ccgttagagg tcaattcgaa aatgtcacca tgtcttctca atacttcacc 4500

-continued

```
attcaaggtt ggcataccct tgaaatagac atcgtgatga ttaccgttta acaatgtttt   4560
tgaggcacca aacataacag gacctaatgc caattcaccg atacctggct tatttttagg   4620
cattgggtaa ccgttcttat ctaatatgta caaggtgcaa cccatacatt gggatgaaaa   4680
agaacttaaa gattgagctt gcaaaaatga accagcagaa aaagcaccac cgatttctgt   4740
accaccacac atttctataa ctggcttgta gttagctcta cccattaacc acaaatattc   4800
gtctacatta gaggcttcac cggatgaaga aaagcatctt atggtggacc aatcgtaacc   4860
tgaaacacaa tttgtggatt tccatgatct tacaatagat ggtacgacac ccaacattgt   4920
gacctttgca tcttgaacaa atttagcgaa accagagact aaaggactac cgttgtacaa   4980
ggcaatagat gcaccattta acaaactagc ataaaccaac caaggaccca tcatccaacc   5040
caaattagtt ggccatacta taacgtcacc ttttctaata tccaaatgag accaaccatc   5100
agcagcagcc ttcaatgggg tggcttgtgt ccaaggaatt gcttttggtt cacctgtagt   5160
accactggag aataagatgt tagtataagc atcaacaggt tgttctctgg cagtaaactc   5220
gcagttttta aactccttgg ctctttctaa aaagtaatcc caagatatgt caccatctct   5280
caattctgca ccaatgttag aaccactaca agggataact attgccattg gggatttagc   5340
ttcaactact cttgaataca atggtattct ctttttacct ctgatgatgt gatcttgtgt   5400
gaaaattgcc ttagctttgg ataatctcaa tctagttgag atttcagggg cggaaaatga   5460
atctgctata gagacaacta cgtaaccagc caatactatg gccaaatata taacaacagc   5520
atcaacatgc attggcatat cgatggctat tgcacaacct ttttctaaac ccatttcttc   5580
caatgcataa ccaaccaacc aaactctctt tctcaattga tctaatgtca acttattcaa   5640
aggcaagtca tcgttaccct cgtctctcca aacgatcata gtatcgttca atttcttatt   5700
ggagtttacg ttcaagcaat ttttagctga gttcaagtaa ccaccaggta accattcaga   5760
accacctggg ttgttgatgt catctcttct caagatacat tctgggtcct tagagaaact   5820
aattttcatt tcatccatca atactgttct ccaatagact tcagggtttc taacagaaaa   5880
ttcttggaag tgagaaaaag aagaaattgg atctttgtac tttacaccca aaaattcttt   5940
acctctcttt tccaacaaag cacccaaatt agttgacttg actttttcag ggtctggaat   6000
ccaagcaggt ggggctggac cgaaatcctt gtagcaacca taaaacaaca tttggtgtaa   6060
ggagaaaggc aaatctggtg acaagatatg gttagcgatg ttgatccaag tttgaggggt   6120
tgcagcacca taattacaaa cgatttctgc caatctacca tgtaatgttt ctgctacttc   6180
tgaggtgata cccaatgcga tgaaatctga ggcaacgact gaatccaagg acttatagtt   6240
tttacccatt cttttaatcg tggatccttc aaaaattctt actttttttt tggatggacg   6300
caaagaagtt taataatcat attacatggc attaccacca tatacatatc catatacata   6360
tccatatcta atcttactta tatgttgtgg aaatgtaaag agccccatta tcttagccta   6420
aaaaaacctt ctctttggaa ctttcagtaa tacgcttaac tgctcattgc tatattgaag   6480
tacggattag aagccgccga gcgggtgaca gccctccgaa ggaagactct cctccgtgcg   6540
tcctcgtctt caccggtcgc gttcctgaaa cgcagatgtg cctcgcgccg cactgctccg   6600
aacaataaag attctacaat actagctttt atggttatga agaggaaaaa ttggcagtaa   6660
cctggcccca caaaccttca aatgaacgaa tcaaattaac aaccatagga tgataatgcg   6720
attagttttt tagccttatt tctggggtaa ttaatcagcg aagcgatgat ttttgatcta   6780
ttaacagata tataaatgca aaaactgcat aaccacttta actaatactt tcaacatttt   6840
cggtttgtat tacttcttat tcaaatgtaa taaaagtatc aacaaaaaat tgttaatata   6900
```

-continued

```
cctctatact ttaacgtcaa ggagaaaaaa ccccggatcc gtaatacgac tcactataat   6960
ggttactgtt gaagaattta gaaaagctca aagagctgaa ggtccagcta ctattatggc   7020
tattggtact gctactccag ctaattgtgt tttgcaatct gaatatccag attattattt   7080
tagaattact aattctgaac ataaaactga attgaaagaa aaatttaaaa gaatgtgtga   7140
taaatctatg attagaaaaa gatatatgca tttgactgaa gaaattttga aagaaaatcc   7200
aaatttgtgt gcttatgaag ctccatcttt ggatgctaga caagatatgg ttgttgttga   7260
agttccaaaa ttgggtaaag aagctgctac taaagctatt aaagaatggg gtcaaccaaa   7320
atctaaaatt actcatttgg ttttttgtac tacttctggt gttgatatgc caggtgctga   7380
ttatcaattg actaaattgt tgggtttgag accatctgtt aaaagattga tgatgtatca   7440
acaaggttgt tttgctggtg gtactgtttt gagattggct aaagatttgg ctgaaaataa   7500
taaaggtgct agagttttgg ttgtttgttc tgaaattact gctgttactt ttagaggtcc   7560
aaatgatact catttggatt ctttggttgg tcaagctttg tttggtgatg gttctgctgc   7620
tttgattgtt ggttctgatc caattccaga agttgaaaaa ccaatttttg aattggtttc   7680
tgctgctcaa actattttgc cagattctga tggtgctatt gatggtcatt tgagagaagt   7740
tggtttgact tttcatttgt tgaaagatgt tccaggtttg atttctaaaa atattgaaaa   7800
atctttgaat gaagctttta aaccattggg tatttctgat tggaattctt tgttttggat   7860
tgctcatcca ggtggtccag ctattttgga tcaagttgaa tctaaattgg ctttgaaaac   7920
tgaaaaattg agagctacta gacatgtttt gtctgaatat ggtaatatgt cttctgcttg   7980
tgttttgttt attttggatg aaatgagaag aaaatgtgtt gaagatggtt tgaatactac   8040
tggtgaaggt ttggaatggg gtgttttgtt tggttttggt ccaggtttga ctgttgaaac   8100
tgttgttttg cattctgttg ctattgaagg tagaggttcc ttgttaactt gtggtgacgt   8160
tgaagaaaac ccaggtccta tggccgtcaa gcatttgata gtattgaagt ttaaagatga   8220
aatcacagaa gctcaaaagg aagaattttt caagacctac gttaatttgg tcaacattat   8280
acctgctatg aaagatgtat actggggtaa agacgttaca caaaagaaag aagaaggtta   8340
tacacacatt gtcgaagtaa ccttcgaatc agttgaaact atccaagatt acatcattca   8400
tccagctcac gttggttttg gtgacgttta cagatccttc tgggaaaaat tgttgatctt   8460
cgattacacc ccaagaaagt gatgatgggc tgcaggaatt cgatatcaag cttatcgata   8520
ccgtcgacct cgagtcatgt aattagttat gtcacgctta cattcacgcc ctccccccac   8580
atccgctcta accgaaaagg aaggagttag acaacctgaa gtctaggtcc ctatttattt   8640
ttttatagtt atgttagtat taagaacgtt atttatattt caaatttttc ttttttttct   8700
gtacagacgc gtgtacgcat gtaacattat actgaaaacc ttgcttgaga aggttttggg   8760
acgctcgaag gctttaattt gcggccggta cccagctttt gttcccttta gtgagggtta   8820
attccgagct tggcgtaatc atggtcatag ctgtttcctg tgtgaaattg ttatccgctc   8880
acaattccac acaacatagg agccggaagc ataaagtgta aagcctgggg tgcctaatga   8940
gtgaggtaac tcacattaat tgcgttgcgc tcactgcccg ctttccagtc gggaaacctg   9000
tcgtgccagc tgcattaatg aatcggccaa cgcgcgggga gaggcggttt gcgtattggg   9060
cgctcttccg cttcctcgct cactgactcg ctgcgctcgg tcgttcggct gcggcgagcg   9120
gtatcagctc actcaaaggc ggtaatacgg ttatccacag aatcagggga taacgcagga   9180
aagaacatgt gagcaaaagg ccagcaaaag gccaggaacc gtaaaaaggc cgcgttgctg   9240
```

-continued gcgtttttcc ataggctcgg ccccccctgac gagcatcaca aaaatcgacg ctcaagtcag 9300
aggtggcgaa acccgacagg actataaaga taccaggcgt tccccccctgg aagctccctc 9360 gtgcgctctc ctgttccgac cctgccgctt accggatacc tgtccgcctt tctcccttcg 9420
ggaagcgtgg cgctttctca atgctcacgc tgtaggtatc tcagttcggt gtaggtcgtt 9480
cgctccaagc tgggctgtgt gcacgaaccc cccgttcagc ccgaccgctg cgccttatcc 9540
ggtaactatc gtcttgagtc caacccggta agacacgact tatcgccact ggcagcagcc 9600
actggtaaca ggattagcag agcgaggtat gtaggcggtg ctacagagtt cttgaagtgg 9660
tggcctaact acggctacac tagaaggaca gtatttggta tctgcgctct gctgaagcca 9720
gttaccttcg gaaaaagagt tggtagctct tgatccggca aacaaaccac cgctggtagc 9780
ggtggttttt ttgtttgcaa gcagcagatt acgcgcagaa aaaaaggatc tcaagaagat 9840
cctttgatct tttctacggg gtctgacgct cagtggaacg aaaactcacg ttaagggatt 9900
ttggtcatga gattatcaaa aaggatcttc acctagatcc ttttaaatta aaaatgaagt 9960
tttaaatcaa tctaaagtat atatgagtaa acttggtctg acagttacca atgcttaatc 10020
agtgaggcac ctatctcagc gatctgtcta tttcgttcat ccatagttgc ctgactgccc 10080
gtcgtgtaga taactacgat acgggagggc ttaccatctg gccccagtgc tgcaatgata 10140
ccgcgagacc cacgctcacc ggctccagat ttatcagcaa taaaccagcc agccggaagg 10200
gccgagcgca gaagtggtcc tgcaacttta tccgcctcca tccagtctat taattgttgc 10260
cgggaagcta gagtaagtag ttcgccagtt aatagtttgc gcaacgttgt tgccattgct 10320
acaggcatcg tggtgtcacg ctcgtcgttt ggtatggctt c 10361

<210> SEQ ID NO 82
<211> LENGTH: 9767
<212> TYPE: DNA
<213> ORGANISM: Artificial Sequence
<220> FEATURE:
<223> OTHER INFORMATION: Codon Optimized

<400> SEQUENCE: 82
attcagctcc ggttcccaac gatcaaggcg agttacatga tcccccatgt tgtgaaaaaa 60
agcggttagc tccttcggtc ctccgatcgt tgtcagaagt aagttggccg cagtgttatc 120
actcatggtt atggcagcac tgcataattc tcttactgtc atgccatccg taagatgctt 180
ttctgtgact ggtgagtact caaccaagtc attctgagaa tagtgtatgc ggcgaccgag 240
ttgctcttgc ccggcgtcaa tacgggataa taccgcgcca catagcagaa ctttaaaagt 300
gctcatcatt ggaaaacgtt cttcggggcg aaaactctca aggatcttac cgctgttgag 360
atccagttcg atgtaaccca ctcgtgcacc caactgatct tcagcatctt ttactttcac 420
cagcgtttct gggtgagcaa aaacaggaag gcaaaatgcc gcaaaaaagg gaataagggc 480
gacacggaaa tgttgaatac tcatactctt cctttttcaa tattattgaa gcatttatca 540
gggttattgt ctcatgagcg gatacatatt tgaatgtatt tagaaaaata aacaaatagg 600
ggttccgcgc acatttcccc gaaaagtgcc acctgacgtc taagaaacca ttattatcat 660
gacattaacc tataaaaata ggcgtatcac gaggcccttt cgtctcgcgc gtttcggtga 720
tgacggtgaa aacctctgac acatgcagct cccggagacg gtcacagctt gtctgtaagc 780
ggatgccggg agcagacaag cccgtcaggg cgcgtcagcg ggtgttggcg ggtgtcgggg 840
ctggcttaac tatgcggcat cagagcagat tgtactgaga gtgcaccata tcgactacgt 900
cgtaaggccg tttctgacag agtaaaattc ttgagggaac tttcaccatt atgggaaatg 960
gttcaagaag gtattgactt aaactccatc aaatggtcag gtcattgagt gttttttatt 1020
tgttgtattt tttttttttt agagaaaatc ctccaatatc aaattaggaa tcgtagtttc 1080
atgattttct gttacaccta actttttgtg tggtgccctc ctccttgtca atattaatgt 1140
taaagtgcaa ttctttttcc ttatcacgtt gagccattag tatcaatttg cttacctgta 1200
ttcctttact atcctccttt ttctccttct tgataaatgt atgtagattg cgtatatagt 1260
ttcgtctacc ctatgaacat attccatttt gtaatttcgt gtcgtttcta ttatgaattt 1320
catttataaa gtttatgtac aaatatcata aaaaaagaga atctttttaa gcaaggattt 1380
tcttaacttc ttcggcgaca gcatcaccga cttcggtggt actgttggaa ccacctaaat 1440
caccagttct gatacctgca tccaaaacct ttttaactgc atcttcaatg gccttacctt 1500
cttcaggcaa gttcaatgac aatttcaaca tcattgcagc agacaagata gtggcgatag 1560
ggtcaacctt attctttggc aaatctggag cagaaccgtg gcatggttcg tacaaaccaa 1620
atgcggtgtt cttgtctggc aaagaggcca aggacgcaga tggcaacaaa cccaaggaac 1680
ctgggataac ggaggcttca tcggagatga tatcaccaaa catgttgctg gtgattataa 1740
taccatttag gtgggttggg ttcttaacta ggatcatggc ggcagaatca atcaattgat 1800
gttgaacctt caatgtaggg aattcgttct tgatggtttc ctccacagtt tttctccata 1860
atcttgaaga ggccaaaaca ttagctttat ccaaggacca aataggcaat ggtggctcat 1920
gttgtagggc catgaaagcg gccattcttg tgattctttg cacttctgga acggtgtatt 1980
gttcactatc ccaagcgaca ccatcaccat cgtcttcctt tctcttacca aagtaaatac 2040
ctcccactaa ttctctgaca acaacgaagt cagtaccttt agcaaattgt ggcttgattg 2100
gagataagtc taaaagagag tcggatgcaa agttacatgg tcttaagttg gcgtacaatt 2160
gaagttcttt acggattttt agtaaacctt gttcaggtct aacactaccg gtaccccatt 2220
taggaccacc cacagcacct aacaaaacgg catcaacctt cttggaggct tccagcgcct 2280
catctggaag tgggacacct gtagcatcga tagcagcacc accaattaaa tgattttcga 2340
aatcgaactt gacattggaa cgaacatcag aaatagcttt aagaacctta atggcttcgg 2400
ctgtgatttc ttgaccaacg tggtcacctg gcaaaacgac gatcttctta ggggcagaca 2460
taggggcaga cattagaatg gtatatcctt gaaatatata tatatattgc tgaaatgtaa 2520
aaggtaagaa aagttagaaa gtaagacgat tgctaaccac ctattggaaa aaacaatagg 2580
tccttaaata atattgtcaa cttcaagtat tgtgatgcaa gcatttagtc atgaacgctt 2640
ctctattcta tatgaaaagc cggttccggc ctctcacctt tcctttttct cccaattttt 2700
cagttgaaaa aggtatatgc gtcaggcgac ctctgaaatt aacaaaaaat ttccagtcat 2760
cgaatttgat tctgtgcgat agcgcccctg tgtgttctcg ttatgttgag gaaaaaaata 2820
atggttgcta agagattcga actcttgcat cttacgatac ctgagtattc ccacagttaa 2880
ctgcggtcaa gatatttctt gaatcaggcg ccttagaccg ctcggccaaa caaccaatta 2940
cttgttgaga aatagagtat aattatccta taaatataac gtttttgaac acacatgaac 3000
aaggaagtac aggacaattg attttgaaga gaatgtggat tttgatgtaa ttgttgggat 3060
tccattttta ataaggcaat aatattaggt atgtggatat actagaagtt ctcctcgagg 3120
gtcgatatgc ggtgtgaaat accgcacaga tgcgtaagga gaaaataccg catcaggaaa 3180
ttgtaaacgt taatattttg ttaaaattcg cgttaaattt ttgttaaatc agctcatttt 3240
ttaaccaata ggccgaaatc ggcaaaatcc cttataaatc aaaagaatag accgagatag 3300

-continued

```
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420
caagtttttt ggggtcgagg tgccgtaaag cactaaatcg gaaccctaaa gggagccccc   3480
gatttagagc ttgacgggga aagccggcga acgtggcgag aaaggaaggg aagaaagcga   3540
aaggagcggg cgctagggcg ctggcaagtg tagcggtcac gctgcgcgta accaccacac   3600
ccgccgcgct taatgcgccg ctacagggcg cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccagggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
atactaacat aactataaaa aaataaatag ggacctagac ttcaggttgt ctaactcctt   4020
ccttttcggt tagagcggat gtggggggag ggcgtgaatg taagcgtgac ataactaatt   4080
acatgatcat tcgaaatgac tgaattgttg tctcaaaact cttctcatga tcttgtttgt   4140
tgcagttcta ggtaaggatg acaatgggac aactctagta actttgaata atgggttcaa   4200
tttcttttgc aaacccaagt taaaggataa tctcaattgg ttcaaatcaa tggttgtgtc   4260
gtttgaatcc ttcaatacga aaaatatgac caattgttct ggaccaccac ccaaaggtgg   4320
aacaccaata gcagtggttt caaaaactct gtcatctact tcattacaga ctctttcgat   4380
ttcgatagaa ctaattttga taccaccgat gttcatagtg tcatcggctc taccgtgtgc   4440
atggtagtaa ccgttagagg tcaattcgaa aatgtcacca tgtcttctca atacttcacc   4500
attcaaggtt ggcataccct tgaaatagac atcgtgatga ttaccgttta acaatgtttt   4560
tgaggcacca aacataacag gacctaatgc caattcaccg atacctggct tatttttagg   4620
cattgggtaa ccgttcttat ctaatatgta caaggtgcaa cccatacatt gggatgaaaa   4680
agaacttaaa gattgagctt gcaaaaatga accagcagaa aaagcaccac cgatttctgt   4740
accaccacac atttctataa ctggcttgta gttagctcta cccattaacc acaaatattc   4800
gtctacatta gaggcttcac cggatgaaga aaagcatctt atggtggacc aatcgtaacc   4860
tgaaacacaa tttgtggatt tccatgatct tacaatagat ggtacgacac ccaacattgt   4920
gacctttgca tcttgaacaa atttagcgaa accagagact aaaggactac cgttgtacaa   4980
ggcaatagat gcaccattta acaaactagc ataaaccaac caaggaccca tcatccaacc   5040
caaattagtt ggccatacta taacgtcacc ttttctaata tccaaatgag accaaccatc   5100
agcagcagcc ttcaatgggg tggcttgtgt ccaaggaatt gcttttggtt cacctgtagt   5160
accactggag aataagatgt tagtataagc atcaacaggt tgttctctgg cagtaaactc   5220
gcagttttta aactccttgg ctctttctaa aaagtaatcc caagatatgt caccatctct   5280
caattctgca ccaatgttag aaccactaca agggataact attgccattg gggatttagc   5340
ttcaactact cttgaataca atggtattct ctttttacct ctgatgatgt gatcttgtgt   5400
gaaaattgcc ttagctttgg ataatctcaa tctagttgag atttcagggg cggaaaatga   5460
atctgctata gagacaacta cgtaaccagc caatactatg gccaaatata taacaacagc   5520
atcaacatgc attggcatat cgatggctat tgcacaacct ttttctaaac ccatttcttc   5580
caatgcataa ccaaccaacc aaactctctt tctcaattga tctaatgtca acttattcaa   5640
aggcaagtca tcgttaccct cgtctctcca aacgatcata gtatcgttca atttcttatt   5700
```

-continued ggagtttacg ttcaagcaat ttttagctga gttcaagtaa ccaccaggta accattcaga 5760
accacctggg ttgttgatgt catctcttct caagatacat tctgggtcct tagagaaact 5820
aattttcatt tcatccatca atactgttct ccaatagact tcagggtttc taacagaaaa 5880
ttcttggaag tgagaaaaag aagaaattgg atctttgtac tttacaccca aaaattcttt 5940
acctctcttt tccaacaaag cacccaaatt agttgacttg actttttcag ggtctggaat 6000
ccaagcaggt ggggctggac cgaaatcctt gtagcaacca taaaacaaca tttggtgtaa 6060
ggagaaaggc aaatctggtg acaagatatg gttagcgatg ttgatccaag tttgaggggt 6120
tgcagcacca taattacaaa cgatttctgc caatctacca tgtaatgttt ctgctacttc 6180
tgaggtgata cccaatgcga tgaaatctga ggcaacgact gaatccaagg acttatagtt 6240
tttacccatt cttttaatcg tggatccttc aaaaattctt actttttttt tggatggacg 6300
caaagaagtt taataatcat attacatggc attaccacca tatacatatc catatacata 6360
tccatatcta atcttactta tatgttgtgg aaatgtaaag agccccatta tcttagccta 6420
aaaaaacctt ctctttggaa ctttcagtaa tacgcttaac tgctcattgc tatattgaag 6480
tacggattag aagccgccga gcgggtgaca gccctccgaa ggaagactct cctccgtgcg 6540
tcctcgtctt caccggtcgc gttcctgaaa cgcagatgtg cctcgcgccg cactgctccg 6600
aacaataaag attctacaat actagctttt atggttatga agaggaaaaa ttggcagtaa 6660
cctggcccca caaaccttca aatgaacgaa tcaaattaac aaccatagga tgataatgcg 6720
attagttttt tagccttatt tctggggtaa ttaatcagcg aagcgatgat tttgatcta 6780
ttaacagata tataaatgca aaaactgcat aaccacttta actaatactt tcaacatttt 6840
cggtttgtat tacttcttat tcaaatgtaa taaaagtatc aacaaaaaat tgttaatata 6900
cctctatact ttaacgtcaa ggagaaaaaa ccccggatcc gtaatacgac tcactataat 6960
gaatcatttg agagctgaag gtccagcttc tgttttggct attggtactg ctaatccaga 7020
aaatattttg attcaagatg aatttccaga ttattatttt agagttacta aatctgaaca 7080
tatgactcaa ttgaaagaaa aatttagaaa aatttgtgat aaatctatga ttagaaaaag 7140
aaattgtttt ttgaatgaag aacatttgaa acaaaatcca agattggctg aacatgaaat 7200
gcaaactttg gatgctagac aagatatgtt ggttgttgaa gttccaaaat tgggtaaaga 7260
tgcttgtgct aaagctatta aagaatgggg tcaaccaaaa tctaaaatta ctcatttgat 7320
tttacttct gcttctacta ctgatatgcc aggtgctgat tatcattgtg ctaaattgtt 7380
gggtttgtct ccatctgtta aaagagttat gatgtatcaa ttgggttgtt atggtggtgg 7440
tactgttttg agaattgcta aagatattgc tgaaaataat aaaggtgcta gagttttggc 7500
tgtttgttgt gatattatgg cttttttttt tgaaggtaga ggttccttgt taacttgtgg 7560
tgacgttgaa gaaaacccag gtcctatggc cgtcaagcat ttgatagtat tgaagtttaa 7620
agatgaaatc acagaagctc aaaaggaaga atttttcaag acctacgtta atttggtcaa 7680
cattatacct gctatgaaag atgtatactg gggtaaagac gttacacaaa agaaagaaga 7740
aggttataca cacattgtcg aagtaacctt cgaatcagtt gaaactatcc aagattacat 7800
cattcatcca gctcacgttg gttttggtga cgtttacaga tccttctggg aaaaattgtt 7860
gatcttcgat tacaccccaa gaaagtgatg atgggctgca ggaattcgat atcaagctta 7920
tcgataccgt cgacctcgag tcatgtaatt agttatgtca cgcttacatt cacgccctcc 7980
ccccacatcc gctctaaccg aaaaggaagg agttagacaa cctgaagtct aggtccctat 8040

-continued ttattttttt atagttatgt tagtattaag aacgttattt atatttcaaa tttttctttt 8100
ttttctgtac agacgcgtgt acgcatgtaa cattatactg aaaaccttgc ttgagaaggt 8160
tttgggacgc tcgaaggctt taatttgcgg ccggtaccca gcttttgttc cctttagtga 8220
gggttaattc cgagcttggc gtaatcatgg tcatagctgt ttcctgtgtg aaattgttat 8280
ccgctcacaa ttccacacaa cataggagcc ggaagcataa agtgtaaagc ctggggtgcc 8340
taatgagtga ggtaactcac attaattgcg ttgcgctcac tgcccgcttt ccagtcggga 8400
aacctgtcgt gccagctgca ttaatgaatc ggccaacgcg cggggagagg cggtttgcgt 8460
attgggcgct cttccgcttc ctcgctcact gactcgctgc gctcggtcgt tcggctgcgg 8520
cgagcggtat cagctcactc aaaggcggta atacggttat ccacagaatc aggggataac 8580
gcaggaaaga acatgtgagc aaaaggccag caaaaggcca ggaaccgtaa aaaggccgcg 8640
ttgctggcgt ttttccatag gctcggcccc cctgacgagc atcacaaaaa tcgacgctca 8700
agtcagaggt ggcgaaaccc gacaggacta taaagatacc aggcgttccc cctggaagc 8760 tccctcgtgc gctctcctgt tccgaccctg ccgcttaccg gatacctgtc cgcctttctc 8820
ccttcgggaa gcgtggcgct ttctcaatgc tcacgctgta ggtatctcag ttcggtgtag 8880
gtcgttcgct ccaagctggg ctgtgtgcac gaaccccccg ttcagcccga ccgctgcgcc 8940
ttatccggta actatcgtct tgagtccaac ccggtaagac acgacttatc gccactggca 9000
gcagccactg gtaacaggat tagcagagcg aggtatgtag gcggtgctac agagttcttg 9060
aagtggtggc ctaactacgg ctacactaga aggacagtat ttggtatctg cgctctgctg 9120
aagccagtta ccttcggaaa aagagttggt agctcttgat ccggcaaaca aaccaccgct 9180
ggtagcggtg gtttttttgt ttgcaagcag cagattacgc gcagaaaaaa aggatctcaa 9240
gaagatcctt tgatcttttc tacggggtct gacgctcagt ggaacgaaaa ctcacgttaa 9300
gggattttgg tcatgagatt atcaaaaagg atcttcacct agatcctttt aaattaaaaa 9360
tgaagtttta aatcaatcta aagtatatat gagtaaactt ggtctgacag ttaccaatgc 9420
ttaatcagtg aggcacctat ctcagcgatc tgtctatttc gttcatccat agttgcctga 9480
ctgcccgtcg tgtagataac tacgatacgg gagggcttac catctggccc cagtgctgca 9540
atgataccgc gagacccacg ctcaccggct ccagatttat cagcaataaa ccagccagcc 9600
ggaagggccg agcgcagaag tggtcctgca actttatccg cctccatcca gtctattaat 9660
tgttgccggg aagctagagt aagtagttcg ccagttaata gtttgcgcaa cgttgttgcc 9720
attgctacag gcatcgtggt gtcacgctcg tcgtttggta tggcttc 9767

<210> SEQ ID NO 83
<211> LENGTH: 9791
<212> TYPE: DNA
<213> ORGANISM: Artificial Sequence
<220> FEATURE:
<223> OTHER INFORMATION: Codon Optimized

<400> SEQUENCE: 83
attcagctcc ggttcccaac gatcaaggcg agttacatga tcccccatgt tgtgaaaaaa 60
agcggttagc tccttcggtc ctccgatcgt tgtcagaagt aagttggccg cagtgttatc 120
actcatggtt atggcagcac tgcataattc tcttactgtc atgccatccg taagatgctt 180
ttctgtgact ggtgagtact caaccaagtc attctgagaa tagtgtatgc ggcgaccgag 240
ttgctcttgc ccggcgtcaa tacgggataa taccgcgcca catagcagaa ctttaaaagt 300
gctcatcatt ggaaaacgtt cttcggggcg aaaactctca aggatcttac cgctgttgag 360

-continued

```
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt cctttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gtttttttatt   1020
tgttgtattt tttttttttt agagaaaatc ctccaatatc aaattaggaa tcgtagtttc   1080
atgattttct gttacaccta actttttgtg tggtgccctc ctccttgtca atattaatgt   1140
taaagtgcaa ttctttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaaagaga atctttttaa gcaaggattt   1380
tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca aagtaaatac   2040
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tcctttttct cccaattttt   2700
```

-continued

```
cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaaata   2820
atggttgcta agagattcga actcttgcat cttacgatac ctgagtattc ccacagttaa   2880
ctgcggtcaa gatatttctt gaatcaggcg ccttagaccg ctcggccaaa caaccaatta   2940
cttgttgaga aatagagtat aattatccta taaatataac gtttttgaac acacatgaac   3000
aaggaagtac aggacaattg attttgaaga gaatgtggat tttgatgtaa ttgttgggat   3060
tccattttta ataaggcaat aatattaggt atgtggatat actagaagtt ctcctcgagg   3120
gtcgatatgc ggtgtgaaat accgcacaga tgcgtaagga gaaaataccg catcaggaaa   3180
ttgtaaacgt taatattttg ttaaaattcg cgttaaattt ttgttaaatc agctcatttt   3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420
caagtttttt ggggtcgagg tgccgtaaag cactaaatcg gaaccctaaa gggagccccc   3480
gatttagagc ttgacgggga aagccggcga acgtggcgag aaaggaaggg aagaaagcga   3540
aaggagcggg cgctagggcg ctggcaagtg tagcggtcac gctgcgcgta accaccacac   3600
ccgccgcgct taatgcgccg ctacagggcg cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccagggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
atactaacat aactataaaa aaataaatag ggacctagac ttcaggttgt ctaactcctt   4020
ccttttcggt tagagcggat gtgggggag ggcgtgaatg taagcgtgac ataactaatt   4080
acatgatcat tcgaaatgac tgaattgttg tctcaaaact cttctcatga tcttgtttgt   4140
tgcagttcta ggtaaggatg acaatgggac aactctagta actttgaata atgggttcaa   4200
tttcttttgc aaacccaagt taaaggataa tctcaattgg ttcaaatcaa tggttgtgtc   4260
gtttgaatcc ttcaatacga aaaatatgac caattgttct ggaccaccac ccaaaggtgg   4320
aacaccaata gcagtggttt caaaaactct gtcatctact tcattacaga ctctttcgat   4380
ttcgatagaa ctaatttga taccaccgat gttcatagtg tcatcggctc taccgtgtgc   4440
atggtagtaa ccgttagagg tcaattcgaa aatgtcacca tgtcttctca atacttcacc   4500
attcaaggtt ggcataccct tgaaatagac atcgtgatga ttaccgttta acaatgtttt   4560
tgaggcacca aacataacag gacctaatgc caattcaccg atacctggct tatttttagg   4620
cattgggtaa ccgttcttat ctaatatgta caaggtgcaa cccatacatt gggatgaaaa   4680
agaacttaaa gattgagctt gcaaaaatga accagcagaa aaagcaccac cgatttctgt   4740
accaccacac atttctataa ctggcttgta gttagctcta cccattaacc acaaatattc   4800
gtctacatta gaggcttcac cggatgaaga aaagcatctt atggtggacc aatcgtaacc   4860
tgaaacacaa tttgtggatt tccatgatct tacaatagat ggtacgacac ccaacattgt   4920
gacctttgca tcttgaacaa atttagcgaa accagagact aaaggactac cgttgtacaa   4980
ggcaatagat gcaccattta acaaactagc ataaaccaac caaggaccca tcatccaacc   5040
caaattagtt ggccatacta taacgtcacc ttttctaata tccaaatgag accaaccatc   5100
```

agcagcagcc ttcaatgggg tggcttgtgt ccaaggaatt gcttttggtt cacctgtagt 5160
accactggag aataagatgt tagtataagc atcaacaggt tgttctctgg cagtaaactc 5220
gcagtttta aactccttgg ctctttctaa aaagtaatcc caagatatgt caccatctct 5280
caattctgca ccaatgttag aaccactaca agggataact attgccattg gggatttagc 5340
ttcaactact cttgaataca atggtattct ctttttacct ctgatgatgt gatcttgtgt 5400
gaaaattgcc ttagctttgg ataatctcaa tctagttgag atttcagggg cggaaaatga 5460
atctgctata gagacaacta cgtaaccagc caatactatg gccaaatata taacaacagc 5520
atcaacatgc attggcatat cgatggctat tgcacaacct ttttctaaac ccatttcttc 5580
caatgcataa ccaaccaacc aaactctctt tctcaattga tctaatgtca acttattcaa 5640
aggcaagtca tcgttaccct cgtctctcca aacgatcata gtatcgttca atttcttatt 5700
ggagtttacg ttcaagcaat ttttagctga gttcaagtaa ccaccaggta accattcaga 5760
accacctggg ttgttgatgt catctcttct caagatacat tctgggtcct tagagaaact 5820
aattttcatt tcatccatca atactgttct ccaatagact tcagggtttc taacagaaaa 5880
ttcttggaag tgagaaaaag aagaaattgg atctttgtac tttacaccca aaaattcttt 5940
acctctcttt tccaacaaag cacccaaatt agttgacttg actttttcag ggtctggaat 6000
ccaagcaggt ggggctggac cgaaatcctt gtagcaacca taaaacaaca tttggtgtaa 6060
ggagaaaggc aaatctggtg acaagatatg gttagcgatg ttgatccaag tttgaggggt 6120
tgcagcacca taattacaaa cgatttctgc caatctacca tgtaatgttt ctgctacttc 6180
tgaggtgata cccaatgcga tgaaatctga ggcaacgact gaatccaagg acttatagtt 6240
tttacccatt cttttaatcg tggatccttc aaaaattctt actttttttt tggatggacg 6300
caaagaagtt taataatcat attacatggc attaccacca tatacatatc catatacata 6360
tccatatcta atcttactta tatgttgtgg aaatgtaaag agccccatta tcttagccta 6420
aaaaaacctt ctctttggaa ctttcagtaa tacgcttaac tgctcattgc tatattgaag 6480
tacggattag aagccgccga gcgggtgaca gccctccgaa ggaagactct cctccgtgcg 6540
tcctcgtctt caccggtcgc gttcctgaaa cgcagatgtg cctcgcgccg cactgctccg 6600
aacaataaag attctacaat actagctttt atggttatga agaggaaaaa ttggcagtaa 6660
cctggcccca caaaccttca aatgaacgaa tcaaattaac aaccatagga tgataatgcg 6720
attagttttt tagccttatt tctggggtaa ttaatcagcg aagcgatgat tttgatcta 6780
ttaacagata tataaatgca aaaactgcat aaccacttta actaatactt tcaacatttt 6840
cggtttgtat tacttcttat tcaaatgtaa taaaagtatc aacaaaaaat tgttaatata 6900
cctctatact ttaacgtcaa ggagaaaaaa ccccggatcc gtaatacgac tcactataat 6960
ggcttgtttg tttagaggtc catctgaatc tgatttggaa ttgttggttg gtcaagctat 7020
ttttggtgat ggtgctgctg ctgttattgt tggtgctgaa ccagatgaat ctgttggtga 7080
aagaccaatt tttgaattgg tttctactgg tcaaactatt ttgccaaatt ctgaaggtac 7140
tattggtggt catattagag aagctggttt gatttttgat ttgcataaag atgttccaat 7200
gttgatttct aataatattg aaaaatgttt gattgaagct tttactccaa ttggtatttc 7260
tgattggaat tctatttttt ggattactca tccaggtggt aaagctattt tggataaagt 7320
tgaagaaaaa ttgcatttga aatctgataa atttgttgat tctagacatg ttttgtctga 7380
acatggtaat atgtcttctt ctactgtttt gtttgttatg gatgaattga gaaaaagatc 7440

-continued

```
tttggaagaa ggtaaatcta ctactggtga tggttttgaa tggggtgttt tgtttggttt   7500
tggtccaggt ttgactgttg aaagagttgt tgttagatct gttccaatta aatatgaagg   7560
tagaggttcc ttgttaactt gtggtgacgt tgaagaaaac ccaggtccta tggccgtcaa   7620
gcatttgata gtattgaagt ttaaagatga aatcacagaa gctcaaaagg aagaattttt   7680
caagacctac gttaatttgg tcaacattat acctgctatg aaagatgtat actggggtaa   7740
agacgttaca caaaagaaag aagaaggtta tacacacatt gtcgaagtaa ccttcgaatc   7800
agttgaaact atccaagatt acatcattca tccagctcac gttggttttg gtgacgttta   7860
cagatccttc tgggaaaaat tgttgatctt cgattacacc ccaagaaagt gatgatgggc   7920
tgcaggaatt cgatatcaag cttatcgata ccgtcgacct cgagtcatgt aattagttat   7980
gtcacgctta cattcacgcc ctccccccac atccgctcta accgaaaagg aaggagttag   8040
acaacctgaa gtctaggtcc ctatttattt ttttatagtt atgttagtat taagaacgtt   8100
atttatattt caaatttttc ttttttttct gtacagacgc gtgtacgcat gtaacattat   8160
actgaaaacc ttgcttgaga aggttttggg acgctcgaag gctttaattt gcggccggta   8220
cccagctttt gttcccttta gtgagggtta attccgagct tggcgtaatc atggtcatag   8280
ctgtttcctg tgtgaaattg ttatccgctc acaattccac acaacatagg agccggaagc   8340
ataaagtgta aagcctgggg tgcctaatga gtgaggtaac tcacattaat tgcgttgcgc   8400
tcactgcccg ctttccagtc gggaaacctg tcgtgccagc tgcattaatg aatcggccaa   8460
cgcgcgggga gaggcggttt gcgtattggg cgctcttccg cttcctcgct cactgactcg   8520
ctgcgctcgg tcgttcggct gcggcgagcg gtatcagctc actcaaaggc ggtaatacgg   8580
ttatccacag aatcagggga taacgcagga aagaacatgt gagcaaaagg ccagcaaaag   8640
gccaggaacc gtaaaaaggc cgcgttgctg gcgtttttcc ataggctcgg ccccccctgac   8700
gagcatcaca aaaatcgacg ctcaagtcag aggtggcgaa acccgacagg actataaaga   8760
taccaggcgt ttccccctgg aagctccctc gtgcgctctc ctgttccgac cctgccgctt   8820
accggatacc tgtccgcctt tctcccttcg ggaagcgtgg cgctttctca atgctcacgc   8880
tgtaggtatc tcagttcggt gtaggtcgtt cgctccaagc tgggctgtgt gcacgaaccc   8940
cccgttcagc ccgaccgctg cgccttatcc ggtaactatc gtcttgagtc caacccggta   9000
agacacgact tatcgccact ggcagcagcc actggtaaca ggattagcag agcgaggtat   9060
gtaggcggtg ctacagagtt cttgaagtgg tggcctaact acggctacac tagaaggaca   9120
gtatttggta tctgcgctct gctgaagcca gttaccttcg gaaaaagagt tggtagctct   9180
tgatccggca aacaaaccac cgctggtagc ggtggttttt ttgtttgcaa gcagcagatt   9240
acgcgcagaa aaaaaggatc tcaagaagat cctttgatct tttctacggg gtctgacgct   9300
cagtggaacg aaaactcacg ttaagggatt ttggtcatga gattatcaaa aaggatcttc   9360
acctagatcc ttttaaatta aaaatgaagt tttaaatcaa tctaaagtat atatgagtaa   9420
acttggtctg acagttacca atgcttaatc agtgaggcac ctatctcagc gatctgtcta   9480
tttcgttcat ccatagttgc ctgactgccc gtcgtgtaga taactacgat acgggagggc   9540
ttaccatctg gccccagtgc tgcaatgata ccgcgagacc cacgctcacc ggctccagat   9600
ttatcagcaa taaaccagcc agccggaagg gccgagcgca gaagtggtcc tgcaacttta   9660
tccgcctcca tccagtctat taattgttgc cgggaagcta gagtaagtag ttcgccagtt   9720
aatagtttgc gcaacgttgt tgccattgct acaggcatcg tggtgtcacg ctcgtcgttt   9780
ggtatggctt c                                                        9791
```

<210> SEQ ID NO 84
<211> LENGTH: 10130
<212> TYPE: DNA
<213> ORGANISM: Artificial Sequence
<220> FEATURE:
<223> OTHER INFORMATION: Codon Optimized

<400> SEQUENCE: 84
attcagctcc ggttcccaac gatcaaggcg agttacatga tcccccatgt tgtgaaaaaa 60
agcggttagc tccttcggtc ctccgatcgt tgtcagaagt aagttggccg cagtgttatc 120
actcatggtt atggcagcac tgcataattc tcttactgtc atgccatccg taagatgctt 180
ttctgtgact ggtgagtact caaccaagtc attctgagaa tagtgtatgc ggcgaccgag 240
ttgctcttgc ccggcgtcaa tacgggataa taccgcgcca catagcagaa ctttaaaagt 300
gctcatcatt ggaaaacgtt cttcggggcg aaaactctca aggatcttac cgctgttgag 360
atccagttcg atgtaaccca ctcgtgcacc caactgatct tcagcatctt ttactttcac 420
cagcgtttct gggtgagcaa aaacaggaag gcaaaatgcc gcaaaaaagg gaataagggc 480
gacacggaaa tgttgaatac tcatactctt cctttttcaa tattattgaa gcatttatca 540
gggttattgt ctcatgagcg gatacatatt tgaatgtatt tagaaaaata aacaaatagg 600
ggttccgcgc acatttcccc gaaaagtgcc acctgacgtc taagaaacca ttattatcat 660
gacattaacc tataaaaata ggcgtatcac gaggcccttt cgtctcgcgc gtttcggtga 720
tgacggtgaa aacctctgac acatgcagct cccggagacg gtcacagctt gtctgtaagc 780
ggatgccggg agcagacaag cccgtcaggg cgcgtcagcg ggtgttggcg ggtgtcgggg 840
ctggcttaac tatgcggcat cagagcagat tgtactgaga gtgcaccata tcgactacgt 900
cgtaaggccg tttctgacag agtaaaattc ttgagggaac tttcaccatt atgggaaatg 960
gttcaagaag gtattgactt aaactccatc aaatggtcag gtcattgagt gtttttttatt 1020 tgttgtattt ttttttttt agagaaaatc ctccaatatc aaattaggaa tcgtagtttc 1080
atgattttct gttacaccta actttttgtg tggtgccctc ctccttgtca atattaatgt 1140
taaagtgcaa ttctttttcc ttatcacgtt gagccattag tatcaatttg cttacctgta 1200
ttcctttact atcctccttt ttctccttct tgataaatgt atgtagattg cgtatatagt 1260
ttcgtctacc ctatgaacat attccatttt gtaatttcgt gtcgtttcta ttatgaattt 1320
catttataaa gtttatgtac aaatatcata aaaaaagaga atctttttaa gcaaggattt 1380
tcttaacttc ttcggcgaca gcatcaccga cttcggtggt actgttggaa ccacctaaat 1440
caccagttct gatacctgca tccaaaacct ttttaactgc atcttcaatg gccttacctt 1500
cttcaggcaa gttcaatgac aatttcaaca tcattgcagc agacaagata gtggcgatag 1560
ggtcaacctt attctttggc aaatctggag cagaaccgtg gcatggttcg tacaaaccaa 1620
atgcggtgtt cttgtctggc aaagaggcca aggacgcaga tggcaacaaa cccaaggaac 1680
ctgggataac ggaggcttca tcggagatga tatcaccaaa catgttgctg gtgattataa 1740
taccatttag gtgggttggg ttcttaacta ggatcatggc ggcagaatca atcaattgat 1800
gttgaacctt caatgtaggg aattcgttct tgatggtttc ctccacagtt tttctccata 1860
atcttgaaga ggccaaaaca ttagctttat ccaaggacca aataggcaat ggtggctcat 1920
gttgtagggc catgaaagcg gccattcttg tgattctttg cacttctgga acggtgtatt 1980
gttcactatc ccaagcgaca ccatcaccat cgtcttcctt tctcttacca aagtaaatac 2040

-continued

```
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tcctttttct cccaattttt   2700
cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaaata   2820
atggttgcta agagattcga actcttgcat cttacgatac ctgagtattc ccacagttaa   2880
ctgcggtcaa gatatttctt gaatcaggcg ccttagaccg ctcggccaaa caaccaatta   2940
cttgttgaga aatagagtat aattatccta taaatataac gtttttgaac acacatgaac   3000
aaggaagtac aggacaattg attttgaaga gaatgtggat tttgatgtaa ttgttgggat   3060
tccatttta ataaggcaat aatattaggt atgtggatat actagaagtt ctcctcgagg    3120
gtcgatatgc ggtgtgaaat accgcacaga tgcgtaagga gaaaataccg catcaggaaa   3180
ttgtaaacgt taatattttg ttaaaattcg cgttaaattt ttgttaaatc agctcatttt   3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaaccgtc tatcagggcg atggcccact acgtgaacca tcaccctaat   3420
caagtttttt ggggtcgagg tgccgtaaag cactaaatcg gaaccctaaa gggagccccc   3480
gatttagagc ttgacgggga aagccggcga acgtggcgag aaaggaaggg aagaaagcga   3540
aaggagcggg cgctagggcg ctggcaagtg tagcggtcac gctgcgcgta accaccacac   3600
ccgccgcgct taatgcgccg ctacagggcg cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccagggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
atactaacat aactataaaa aaataaatag ggacctagac ttcaggttgt ctaactcctt   4020
ccttttcggt tagagcggat gtgggggggag ggcgtgaatg taagcgtgac ataactaatt 4080
acatgatcat tcgaaatgac tgaattgttg tctcaaaact cttctcatga tcttgtttgt   4140
tgcagttcta ggtaaggatg acaatgggac aactctagta actttgaata atgggttcaa   4200
tttcttttgc aaacccaagt taaaggataa tctcaattgg ttcaaatcaa tggttgtgtc   4260
gtttgaatcc ttcaatacga aaaatatgac caattgttct ggaccaccac ccaaaggtgg   4320
aacaccaata gcagtggttt caaaaactct gtcatctact tcattacaga ctctttcgat   4380
ttcgatagaa ctaattttga taccaccgat gttcatagtg tcatcggctc taccgtgtgc   4440
```

```
atggtagtaa ccgttagagg tcaattcgaa aatgtcacca tgtcttctca atacttcacc   4500
attcaaggtt ggcataccct tgaaatagac atcgtgatga ttaccgttta acaatgtttt   4560
tgaggcacca aacataacag gacctaatgc caattcaccg atacctggct tatttttagg   4620
cattgggtaa ccgttcttat ctaatatgta caaggtgcaa cccatacatt gggatgaaaa   4680
agaacttaaa gattgagctt gcaaaaatga accagcagaa aaagcaccac cgatttctgt   4740
accaccacac atttctataa ctggcttgta gttagctcta cccattaacc acaaatattc   4800
gtctacatta gaggcttcac cggatgaaga aaagcatctt atggtggacc aatcgtaacc   4860
tgaaacacaa tttgtggatt tccatgatct tacaatagat ggtacgacac ccaacattgt   4920
gacctttgca tcttgaacaa atttagcgaa accagagact aaaggactac cgttgtacaa   4980
ggcaatagat gcaccattta acaaactagc ataaaccaac caaggaccca tcatccaacc   5040
caaattagtt ggccatacta taacgtcacc ttttctaata tccaaatgag accaaccatc   5100
agcagcagcc ttcaatgggg tggcttgtgt ccaaggaatt gcttttggtt cacctgtagt   5160
accactggag aataagatgt tagtataagc atcaacaggt tgttctctgg cagtaaactc   5220
gcagttttta aactccttgg ctctttctaa aaagtaatcc caagatatgt caccatctct   5280
caattctgca ccaatgttag aaccactaca agggataact attgccattg gggatttagc   5340
ttcaactact cttgaataca atggtattct ctttttacct ctgatgatgt gatcttgtgt   5400
gaaaattgcc ttagctttgg ataatctcaa tctagttgag atttcagggg cggaaaatga   5460
atctgctata gagacaacta cgtaaccagc caatactatg gccaaatata taacaacagc   5520
atcaacatgc attggcatat cgatggctat tgcacaacct ttttctaaac ccatttcttc   5580
caatgcataa ccaaccaacc aaactctctt tctcaattga tctaatgtca acttattcaa   5640
aggcaagtca tcgttaccct cgtctctcca aacgatcata gtatcgttca atttcttatt   5700
ggagtttacg ttcaagcaat ttttagctga gttcaagtaa ccaccaggta accattcaga   5760
accacctggg ttgttgatgt catctcttct caagatacat tctgggtcct tagagaaact   5820
aattttcatt tcatccatca atactgttct ccaatagact tcagggtttc taacagaaaa   5880
ttcttggaag tgagaaaaag aagaaattgg atctttgtac tttacaccca aaaattcttt   5940
acctctcttt tccaacaaag cacccaaatt agttgacttg actttttcag ggtctggaat   6000
ccaagcaggt ggggctggac cgaaatcctt gtagcaacca taaaacaaca tttggtgtaa   6060
ggagaaaggc aaatctggtg acaagatatg gttagcgatg ttgatccaag tttgaggggt   6120
tgcagcacca taattacaaa cgatttctgc caatctacca tgtaatgttt ctgctacttc   6180
tgaggtgata cccaatgcga tgaaatctga ggcaacgact gaatccaagg acttatagtt   6240
tttacccatt cttttaatcg tggatccttc aaaaattctt actttttttt tggatggacg   6300
caaagaagtt taataatcat attacatggc attaccacca tatacatatc catatacata   6360
tccatatcta atcttactta tatgttgtgg aaatgtaaag agccccatta tcttagccta   6420
aaaaaacctt ctctttggaa ctttcagtaa tacgcttaac tgctcattgc tatattgaag   6480
tacggattag aagccgccga gcgggtgaca gccctccgaa ggaagactct cctccgtgcg   6540
tcctcgtctt caccggtcgc gttcctgaaa cgcagatgtg cctcgcgccg cactgctccg   6600
aacaataaag attctacaat actagctttt atggttatga agaggaaaaa ttggcagtaa   6660
cctggcccca caaaccttca aatgaacgaa tcaaattaac aaccatagga tgataatgcg   6720
attagttttt tagccttatt tctggggtaa ttaatcagcg aagcgatgat tttgatcta    6780
```

-continued

```
ttaacagata tataaatgca aaaactgcat aaccacttta actaatactt tcaacatttt   6840
cggtttgtat tacttcttat tcaaatgtaa taaaagtatc aacaaaaaat tgttaatata   6900
cctctatact ttaacgtcaa ggagaaaaaa ccccggatcc gtaatacgac tcactataat   6960
gaatttggaa aatattgata aagttaattc tccaggtact gaagataaag attttgattc   7020
tagagcttct ggttctaaaa ctaatggttg tgaatcttct gataatgaag ttgaatcttc   7080
tattaatgct aatccaaatt ctatttctgg ttcttcttct ggttttggta atggtaaaag   7140
agaaggtgtt aaaagagctg ctccaggtga tattgctcca acttctagac attatagatc   7200
tttgtctatg gattcttata tgggttcttt gcaatttgat gatgaatctt tgaaattgtt   7260
gccattgggt actggtgttg gtttgcaatc tccaaattct ttggctgatg gtaattctac   7320
taaatttggt atggaatttc caaatggtga atttaatgct gttgaattga aaaaaattat   7380
ggaatctgaa aaattgactg aaattgcttt gtctgatcca aaaagagcta aaagaatttt   7440
ggctaataga caatctgctg ctagatctaa agaaagaaga tctagatata tttctgaatt   7500
ggaacataaa gttcaaactt tgcaaactga agctactact ttgtctgctc aagttactaa   7560
attgcaaaga gattctgttg gtttgacttc tcaaaattct gaattgaaat ttagagttca   7620
agctatggaa caacaagctc aattgaaaga tgctttgaat gatgctttga gagctgaagt   7680
tcaaagattg aaattgactg ctgctgaatt gtctggtgaa gctcatttgt ctaattgtat   7740
ggctcaacaa ttgtctatta atcaacaaat gtatcaaatg caacatagac aaactgttca   7800
attgaatttg tatcaaatgc aacaacaaca acaacataat gaaatgtctt ctcaaccatg   7860
ttctggtgaa gttactgaac atgaatcttc taaagaaggt agaggttcct tgttaacttg   7920
tggtgacgtt gaagaaaacc caggtcctat ggccgtcaag catttgatag tattgaagtt   7980
taaagatgaa atcacagaag ctcaaaagga agaatttttc aagacctacg ttaatttggt   8040
caacattata cctgctatga aagatgtata ctggggtaaa gacgttacac aaaagaaaga   8100
agaaggttat acacacattg tcgaagtaac cttcgaatca gttgaaacta tccaagatta   8160
catcattcat ccagctcacg ttggttttgg tgacgtttac agatccttct gggaaaaatt   8220
gttgatcttc gattacaccc caagaaagtg atgatgggct gcaggaattc gatatcaagc   8280
ttatcgatac cgtcgacctc gagtcatgta attagttatg tcacgcttac attcacgccc   8340
tccccccaca tccgctctaa ccgaaaagga aggagttaga caacctgaag tctaggtccc   8400
tatttatttt tttatagtta tgttagtatt aagaacgtta tttatatttc aaatttttct   8460
tttttttctg tacagacgcg tgtacgcatg taacattata ctgaaaacct tgcttgagaa   8520
ggttttggga cgctcgaagg ctttaatttg cggccggtac ccagcttttg ttccctttag   8580
tgagggttaa ttccgagctt ggcgtaatca tggtcatagc tgtttcctgt gtgaaattgt   8640
tatccgctca caattccaca caacatagga gccggaagca taaagtgtaa agcctggggt   8700
gcctaatgag tgaggtaact cacattaatt gcgttgcgct cactgcccgc tttccagtcg   8760
ggaaacctgt cgtgccagct gcattaatga atcggccaac gcgcggggag aggcggtttg   8820
cgtattgggc gctcttccgc ttcctcgctc actgactcgc tgcgctcggt cgttcggctg   8880
cggcgagcgg tatcagctca ctcaaaggcg gtaatacggt tatccacaga atcaggggat   8940
aacgcaggaa agaacatgtg agcaaaaggc cagcaaaagg ccaggaaccg taaaaaggcc   9000
gcgttgctgg cgtttttcca taggctcggc ccccctgacg agcatcacaa aaatcgacgc   9060
tcaagtcaga ggtggcgaaa cccgacagga ctataaagat accaggcgtt tccccctgga   9120
agctccctcg tgcgctctcc tgttccgacc ctgccgctta ccggatacct gtccgccttt   9180
```

ctcccttcgg gaagcgtggc gctttctcaa tgctcacgct gtaggtatct cagttcggtg 9240
taggtcgttc gctccaagct gggctgtgtg cacgaacccc ccgttcagcc cgaccgctgc 9300
gccttatccg gtaactatcg tcttgagtcc aacccggtaa gacacgactt atcgccactg 9360
gcagcagcca ctggtaacag gattagcaga gcgaggtatg taggcggtgc tacagagttc 9420
ttgaagtggt ggcctaacta cggctacact agaaggacag tatttggtat ctgcgctctg 9480
ctgaagccag ttaccttcgg aaaaagagtt ggtagctctt gatccggcaa acaaaccacc 9540
gctggtagcg gtggtttttt tgtttgcaag cagcagatta cgcgcagaaa aaaaggatct 9600
caagaagatc ctttgatctt ttctacgggg tctgacgctc agtggaacga aaactcacgt 9660
taagggattt tggtcatgag attatcaaaa aggatcttca cctagatcct tttaaattaa 9720
aaatgaagtt ttaaatcaat ctaaagtata tatgagtaaa cttggtctga cagttaccaa 9780
tgcttaatca gtgaggcacc tatctcagcg atctgtctat ttcgttcatc catagttgcc 9840
tgactgcccg tcgtgtagat aactacgata cgggagggct taccatctgg ccccagtgct 9900
gcaatgatac cgcgagaccc acgctcaccg gctccagatt tatcagcaat aaaccagcca 9960
gccggaaggg ccgagcgcag aagtggtcct gcaactttat ccgcctccat ccagtctatt 10020
aattgttgcc gggaagctag agtaagtagt tcgccagtta atagtttgcg caacgttgtt 10080
gccattgcta caggcatcgt ggtgtcacgc tcgtcgtttg gtatggcttc 10130

<210> SEQ ID NO 85
<211> LENGTH: 2274
<212> TYPE: DNA
<213> ORGANISM: Artificial Sequence
<220> FEATURE:
<223> OTHER INFORMATION: Codon Optimized

<400> SEQUENCE: 85
atgtatatgt atcaagaagt ttatttggtt ccaactttgt cttatttgta tttggttgtt 60
gttttgttgc catctatttt tttttctttt agaagaatgg cttttaaatc tttggattct 120
gttacttctt ctgatattgc tgctttgggt attgaaccac aattggctca ttctttgcat 180
ggtagattgg ctgaaattgt ttctaatcat ggttctgcta ctccacatac ttggagatgt 240
atttcttctc atttgttgtc tccagatttg ccattttctt tgcatcaaat gttgtattat 300
ggttgttata aagattttgg tccagatcca ccagcttgga ttccagatgc tgaaaatgct 360
atttctacta atgttggtaa attgttggaa aaaagaggta aagaattttt gggtgttaaa 420
tataaagatc caatttctaa tttttctgat tttcaagaat tttctgttac taatccagaa 480
gtttattgga gaactatttt ggatgaaatg aatatttctt tttctaaacc accagaatgt 540
attttgagag aaaatttttc tagagatggt caaattttga atccaggtgg tgaatggttg 600
ccaggtgctt ttattaatcc agctaaaaat tgtttggatt tgaattgtaa atctttggat 660
gatactatga ttttgtggag agatgaaggt aaagatgatt tgccagttaa taaaatgact 720
ttgaaagaat tgagatctga agtttggttg gttgcttatg ctttgaaaga attggaattg 780
gaaggtggtt ctgctattgc tattgatatg ccaatgaatg ttcattctgt tgttatttat 840
ttggctattg ttttggctgg ttatgttgtt gtttctattg ctgattcttt tgctgctcca 900
gaaatttcta ctagattgaa aatttctaaa gctaaagcta tttttactca agatttgatt 960
gttagaggtg aaaaaactat tccattgtat tctagaattg ttgaagctca atctccattg 1020
gctattgtta ttccatctaa aggtttttct gtttctgctc aattgagaca tggtgatgtt 1080
tcttggcatg atttttgaa tagagctaat aaatttaaaa attatgaatt tgctgctgtt 1140
gaacaaccaa ttgatgctta tactaatatt ttgttttctt ctggtactac tggtgaacca 1200
aaagctattc catggactca agctactcca tttaaagctg ctgctgatgc ttggtgtcat 1260
atggatattc aaaaaggtga tgttgttgct tggccaacta atttgggttg gatgatgggt 1320
ccatggttgg tttatgcttc tttgttgaat ggtgcttcta ttgctttgta taatggttct 1380
ccattgggtt ctggttttgc taaatttgtt caagatgcta aagttactat gttgggtgtt 1440
attccatcta ttgttagaac ttggaaatct actaattgtg ttgctggtta tgattggtct 1500
actattagat gtttttcttc tactggtgaa gcttctaata ttgatgaata tttgtggttg 1560
atgggtagag cttattataa accagttatt gaatattgtg gtggtactga aattggtggt 1620
ggttttgtta ctggttcttt gttgcaagct caatctttgg ctgctttttc tactccagct 1680
atgggttgtt ctttgtttat tttgggttct gatggttatc caattccaaa acataaacca 1740
ggtattggtg aattggcttt gggtccattg atgtttggtg cttctaaaac tttgttgaat 1800
gctgatcatt atgatgttta ttttaaaaga atgccatctt tgaatggtaa agttttgaga 1860
agacatggtg atatgtttga attgacttct aaaggttatt atcatgctca tggtagagct 1920
gatgatacta tgaatttggg tggtattaaa gtttcttctg ttgaaattga aagaatttgt 1980
aatgaagctg atgaaaaagt tttggaaact gctgctattg gtgttccacc attggctggt 2040
ggtccagaac aattggttat tgctgttgtt ttgaaaaatt ctgatagaac tactgttgat 2100
ttgaatcaat tgagattgtc ttttaattct gctgttcaaa aaaaattgaa tccattgttt 2160
agagtttcta gagttgttcc attgtcttct ttgccaagaa ctgctactaa taaagttatg 2220
agaagaattt tgagacaaca atttactcaa ttggataaat cttctaaaat ttaa 2274

<210> SEQ ID NO 86
<211> LENGTH: 2331
<212> TYPE: DNA
<213> ORGANISM: Artificial Sequence
<220> FEATURE:
<223> OTHER INFORMATION: Codon Optimized

<400> SEQUENCE: 86
atggctttgg aattgccaca tttgttgcca tataaattgg ttaaaggtca aactttggtt 60
gctcaagctg ctagagctga attggcttct tcttcttctt cttctgttat tttgaaatct 120
aattttatta ataataatta tattaattat tgtaataata ataataataa tgaaagaaga 180
ttggttgtta gaagagattg ggaaactatg gcttcttctc catctcattc tagaaataat 240
aatgatatta gaactattaa tcatttgaga catgttgatt ctatggctac tatgccatct 300
ggtgctggta aaattccaag attgaatgct gttattttgg gtgaagcttt ggctactgaa 360
gaaaatgatt tggtttttcc aactgatgaa ttttctcaac aagctcatgt tccatctcca 420
caaaaatatt tggaaatgta taaaagatct attgaagatc cagctggttt ttggtctgaa 480
attgcttctc aattttattg gaaacaaaaa tgggatgatt ctgtttattc tgaaaatttg 540
gatgtttcta aaggtagagt taatattgaa tggtttaaag gtggtattac taatatttgt 600
tataattgtt tggataaaaa tgttgaagct ggtttgggtg ataaaattgc tttgtattgg 660
gaaggtaatg atactggttt tgatgattct ttgacttatt ctcaattgtt gcataaagtt 720
tgtcaattgg ctaattattt gaaagatatg ggtgttcaaa aaggtgatgc tgttgttatt 780
tatttgccaa tgttgttgga attgccaatt actatgttgg cttgtgctag aattggtgct 840
gttcattctg ttgtttttgc tggtttttct gctgaatctt tgtctcaaag aattattgat 900

```
tgtaaaccaa aagttgttat tacttgtaat gctgttaaaa gaggtccaaa aattattcat    960
ttgaaagata ttgttgatgc tgctttggtt gaatctgcta aaactggtgt tccaattgat   1020
acttgtttgg tttatgaaaa tcaattggct atgaaaagag atattactaa atggcaagat   1080
ggtagagata tttggtggca agatgttatt ccaaaatatc caactgaatg tgctgttgaa   1140
tgggttgatg ctgaagatcc attgtttttg ttgtatactt ctggttctac tggtaaacca   1200
aaaggtgttt tgcatactac tggtggttat atggtttata ctgctactac ttttaaatat   1260
gcttttgatt ataaaccatc tgatgtttat tggtgtactg ctgattgtgg ttggattact   1320
ggtcattctt atgttactta tggtccattg ttgaatggtg cttcttgtat tgtttttgaa   1380
ggtgctccaa attatccaga ttctggtaga tgttgggata ttgttgataa atataaagtt   1440
actatttttt atactgctcc aactttggtt agatctttga tgagagatgg tgatgaatat   1500
gttactagat attctagaaa atctttgaga attttgggtt ctgttggtga accaattaat   1560
ccatctgctt ggagatggtt ttataatgtt gttggtgatt ctagatgtcc aatttctgat   1620
acttggtggc aaactgaaac tggtggtttt atgattactc cattgccagg tgcttggcca   1680
caaaaaccag gttctgctac ttttccattt tttggtgtta aaccagttat tgttgatgaa   1740
aaaggtgttg aaattgaagg tgaatgttct ggttatttgt gtgttaaagg ttcttggcca   1800
ggtgctttta gaactttgta tggtgattat gaaagatatg aaactactta ttttaaacca   1860
tttactggtt attattttac tggtgatggt tgttctagag ataaagatgg ttatcattgg   1920
ttgactggta gagttgatga tgttattaat gtttctggtc atagaattgg tactgctgaa   1980
gttgaatctg ctttggtttc tcatccaaaa tgtgctgaag ctgctgttgt tggtattgaa   2040
catgaagtta aaggtcaagc tatttatgct tttgttactt tggttgaagg tgaaccatat   2100
tctgaagaat tgagaaaatc tttgattttg tctgttagaa aacaaattgg tgcttttgct   2160
gctccagaaa gaattcattg ggctccaggt ttgccaaaaa ctagatctgg taaaattatg   2220
agaagaattt tgagaaaaat tgcttctggt caattggatg aattgggtga tacttctact   2280
ttggctgatc caaatgttgt tgaacaattg atttctttgt ctaattgtta g            2331
```

<210> SEQ ID NO 87
<211> LENGTH: 1662
<212> TYPE: DNA
<213> ORGANISM: Artificial Sequence
<220> FEATURE:
<223> OTHER INFORMATION: Codon Optimized

<400> SEQUENCE: 87

```
atggaaaaaa aacaagataa tcataataat aataataata atggtgatga acaagaagaa     60
tttattttta gatctaaatt gccagatatt tatattccaa atcatccacc attgcattct    120
tattgttttg aaaatatttc tcaatttaaa gatagaccat gtttgattaa tggtgctact    180
ggtgaaacta ttacttatgc tgatgttgat ttgacttcta gaaaagttgc tgctggtttg    240
gataaaattg gtattaaaca aggtgatgtt attatgttgt tgttgagaaa ttgtccagaa    300
tttgtttatt ctttttggc tgcttctcat attggtgctg ttgttactac tgctaatcca    360
ttttatactg ctgctgaagt tgctaaacaa gctgctgctt ctaatactaa attggttatt    420
actttgtctg gttttattga taaagttaga gattttactg gtgatggtat taaagttgtt    480
tgtgttgatg ctccaccaga tgaatctgaa tatttgcatt tttctgtttt gactcaagct    540
gatgaatctg aaattccaga tgttgaaatt aaaccagatg atgttgttgc tttgccatat    600
```

tcttctggta ctactggttt gccaaaaggt gttatgttga ctcatagagt tatggttact 660
ggtgttgctc aacaagttga tggtgataat ccaaattggc attttcatca aaatgatgtt 720
attttgtgtg ttttgccagt tttcatatt tattgtttga atgctatttt gttgtgtggt 780
ttgagagttg gtgcttctat tttgattatg gaaaaatttg aaatgaaaaa aatggttgaa 840
ttgattgaaa aatttaaagt tactattgct ccagttgttc caccaattgt tttgtctgtt 900
gttaaatttc cagatttgca tagatatgat ttgtcttcta ttagaactat tatgtctggt 960
ggtgctccaa tgggtaaaga tttggaagaa gctgttaaag aaaaatttcc acatgttact 1020
ttgggtcaag gttatggtat gactgaagct gaatgtttgt ctttgtgttt gggttttgct 1080
aaagaaccat ttccaactaa atttggtact tgtggtactg ttgttagaaa tgctgaaatg 1140
aaaattgttg atccaaatac tggtgcttct ttgccaagaa atcaatctgg tgaaatttgt 1200
attagaggta aacaaattat gaaaggttat attaatgatt ttgaagctac taaaggtact 1260
attgatgaag ctggttggtt gcatactggt gatattggtt ttgttgatga tgatgatgaa 1320
ttgtttattg ttgatagatt gaaagaattg attaaatata aaggttttca agttgctcca 1380
gctgaattgg aatctttgtt gattgctcat ccaaatattt ctgatgctgc tgttgttcca 1440
atgaaagatg aagctgctgg tgaagttcca gttgcttttg ttgttagatc taatggttct 1500
aaaatttctg aagaagatat taaacaatat atttctaaac aagttgtttt ttataaaaga 1560
attgctaaag tttttttat tgaagaaatt ccaaaatctc cagctggtaa aattttgaga 1620
aaatctttga gagctagatt ggttactgaa caagctattt aa 1662

<210> SEQ ID NO 88
<211> LENGTH: 1719
<212> TYPE: DNA
<213> ORGANISM: Artificial Sequence
<220> FEATURE:
<223> OTHER INFORMATION: Codon Optimized

<400> SEQUENCE: 88
atgatttcta ttgctccacc attgaaaact caaaataaac aagaaatttc tactattgat 60
cataatgatc ataatcaaga acatattttt aaatctaaat tgccagaaat tccaatttct 120
aataatattc cattgcattc ttatattttt caaaatttgc cagaaaaatc taatagacca 180
tgtttgatta ctggtactac tactcaaact acttattctt attctcaaac tcatcatatt 240
gctaaaaaaa ttgctaaagg tttgtctaaa ttgaatatta ataaaaatga tgttattatg 300
attttgttgc caaattgtcc agaatttatt ttttcttttt ttggtgcttc tatgattggt 360
gctgctatta ctactgctaa tccattttat acttctccag aaatttttaa acaattgcaa 420
atttctaaag ctaaattggt tattactcaa actcaatttg tttctaaatt gattgatttt 480
ccagaaaaag ttattggtag agattttact gttgttactg ttgatggtga tgaaaatcca 540
tctccagaaa attgtttgcc attttctatt ttgactggtg aagatgaaac tgaagaaatt 600
tctattgatc caaatgatcc aattgctatt ccattttctt ctggtactac tggtttgcca 660
aaaggtgttg ttttgactca taaaaatttg attacttctg ttgctcaaca agttgatggt 720
gataatccaa atatgtattt gagatctgat gatgttgttt tgtgtgtttt gccattgttt 780
catatttatt ctttgaattc tgttttgttg tgtgctttga gagttggtgc ttctgttttg 840
ttggttccaa aatttgaaat tggtactttg ttggaattga ttcaaaaaca tagagttact 900
gttgctccag ttgttccacc attggttttg ggtttggcta aaaatccagt tgtttctgaa 960
tttgatttgt cttctattag aatggttttg tctggtgctg ctccattggg tatggaattg 1020

```
gaagatgctt tgagaagaag agttccacaa gctgttattg gtcaaggtta tggtatgact   1080

gaagctggtc cagttttgtc tatgtgtttg gcttttgcta aacaaccatt tccaactaaa   1140

tctggttctt gtggtactgt tgttagaaat gctcaattga aagttattga tccagaaact   1200

ggtgcttctt tgtcttataa tcaaccaggt gaaatttgta ttagaggtca tcaaattatg   1260

aaaggttatt tggataattc tgatgctact gctaatacta ttgatgttga tggttggttg   1320

catactggtg atattggtta tgttgatgat gatgatgaaa tttttattgt tgatagagtt   1380

aaagaaatta ttaaatttaa aggttttcaa gttccaccag ctgaattgga agctttgttg   1440

atttctcatc catctattgc tgatgctgct gttgttccac aaaaagatga agttgctggt   1500

gaagttccag ttgcttttgt tgttaaatct aataataaag attttgattt gtctgaagat   1560

gctgttaaag aatttattgc taaacaagtt gtttttata aaaaattgca taaagtttat     1620

tttgttcatt ctattccaaa atctccatct ggtaaaattt tgagaaaaga tttggttgct   1680

aaattggctt tggcttctac tttgattatt tcttcttaa                           1719
```

<210> SEQ ID NO 89
<211> LENGTH: 2184
<212> TYPE: DNA
<213> ORGANISM: Artificial Sequence
<220> FEATURE:
<223> OTHER INFORMATION: Condon Optimized

<400> SEQUENCE: 89

```
atgggtagaa aatctatttc tgaagttggt gttgaagatt tggttcaagc tggtttgact     60

actgaagaag ctactggttt tcaaagagtt ttgaaagatt ctttgtcttg tactaaaggt    120

tctgatccat ctgaagtttg gagacatttg gttgctagaa gagttttgaa accatggcat    180

ccacatggtt tgcatcaatt ggtttattat tctgtttatg ctcattggga tgtttcttct    240

aaaggtccac caccatattg gtttccatct ttgtatgaat ctaaacatac taatatgggt    300

ggtattatgg aaaaacatgg ttcttctttg ttgggtccat tgtataaaga tccaattact    360

tcttattctt tgtttcaaaa attttctgct caacatccag aagcttattg gtctattgtt    420

ttgaaagaat tgtctgtttc ttttcaagaa gaaccaaaat gtattttgga tagatctgat    480

ttgaaatcta aacatggtgg ttcttggttg ccaggttctg ttttgaatat tgctgaatgt    540

tgtttgttgc caactgctta tccaagaaaa gatgatgatt ctttggctat tgtttggaga    600

gatgaaggtt gtgatgattc tggtattaat attattactt tgaaacaatt gagagaacaa    660

gttatttctg ttgctaaagc tttggatgct atgttttcta aaggtgatgc tattgctatt    720

gatatgccaa tgactgctaa tgctgttatt atttatttgg ctattatttt gtctggtttg    780

gttgttgttt ctattgctga ttcttttgct ccaaaagaaa tttctattag attgagagtt    840

tctcaagcta aagctatttt tactcaagat tttattttga gaggttctag aaaatttcca    900

ttgtattcta gagttgttga agctgctcca gataaagtta ttgttttgcc agctattggt    960

tctaatgttg gtattcaatt gagagaacaa gatatgtctt ggggtgattt tttgtcttct   1020

gttggtacta gatctagaaa ttattctcca tgttatcaac cagttgatac tttgattaat   1080

attttgtttt cttctggtac tactggtgaa ccaaaagcta ttccatggac tcaattgtct   1140

ccaattagat gtgctgctga atcttgggct catatggata tgcaagttgg tgatgttttt   1200

tgttggccaa ctaatttggg ttgggttatg ggtccaattt tgattttttc ttctttttg    1260

tctggtgcta ctttggcttt gtatcatggt tctccattgg gttatggttt tggtaaattt   1320
```

-continued

```
gttcaagatg ctggtgttac taaattgggt actgttccat ctttggttaa agcttggaaa   1380

aatactcaat gtatgaatgg tttggattgg actaaaatta aatgttttgc ttctactggt   1440

gaaacttcta atgttgatga tgatttgtgg ttgtcttcta gagcttatta taaaccagtt   1500

attgaatgtt gtggtggtac tgaattgtct tcttcttata ttcaaggttc tttgttgcaa   1560

ccacaagctt ttggtgcttt ttctactact tctatgacta cttctttggt tattttggat   1620

gaacatggta atccatttcc agatgatcaa gcttgtattg gtgaagttgg tttgtttcca   1680

ttgtatttgg gtgctactga tagattgttg aatgctgatc atgaagaagt ttattttaaa   1740

ggtatgccat tgtataaagg tatgagattg agaagacatg gtgatattat taaaagaact   1800

gttggtggtt attttattgt tcaaggtaga gctgatgata ctatgaattt gggtggtatt   1860

aaaacttctt ctgttgaaat tgaaagagtt tgtgatagag ctgatgaatc tattgttgaa   1920

actgctgctg tttctgtttc tccagttgat ggtggtccag aacaattggt tatgtttgtt   1980

gttttgaaaa atggttataa ttctgaagct gaaaatttga gaactaaatt ttctaaagct   2040

attcaatcta atttgaatcc attgtttaaa gttagatttg ttaaaattgt tccagaattt   2100

ccaagaactg cttctaataa attgttgaga agagttttga gagatcaaat taaacatgaa   2160

ttgtctgctc attctagaat ttaa                                         2184
```

```
<210> SEQ ID NO 90
<211> LENGTH: 2172
<212> TYPE: DNA
<213> ORGANISM: Artificial Sequence
<220> FEATURE:
<223> OTHER INFORMATION: Codon Optimized

<400> SEQUENCE: 90

atgtctattt ctgaagttgg tgttgaagat ttggttcaag ctggtttgac tactgaagaa     60

gctactggtt ttcaaagagt tttgaaagat tctttgtctt gtactaaagg ttctgatcca    120

tctgaagttt ggagacattt ggttgctaga agagctttga aaccatggca tccacatggt    180

ttgcatcaat tggtttatta ttctgtttat gctcattggg atgtttcttc taaaggtcca    240

ccaccatatt ggtttccatc tttgtatgaa tctaaacata ctaatatggg tggtattatg    300

gaaaaacatg gttcttcttt gttgggtcca ttgtataaag atccaattac ttcttattct    360

ttgtttcaaa aattttctgc tcaacatcca gaagcttatt ggtctattgt tttgaaagaa    420

ttgtctgttt cttttcaaga agaaccaaaa tgtattttgg atagatctga tttgaaatct    480

aaacatggtg gttcttggtt gccaggttct gttttgaatg ttgctgaatg ttgtttgttg    540

ccaactgctt atccaagaaa agatgatgat tctttggcta ttgtttggag agatgaaggt    600

tgtgatgatt ctggtattaa tattattact ttgaaacaat tgagagaaca agttatttct    660

gttgctaaag ctttggatgc tatgttttct aaaggtgatg ctattgctat tgatatgcca    720

atgactgcta atgctgttat tatttatttg gctattattt tgtctggttt ggttgttgtt    780

tctattgctg attcttttgc tccaaaagaa atttctatta gattgagagt ttctcaagct    840

aaagctattt ttactcaaga ttttattttg agaggttcta gaaaatttcc attgtattct    900

agagttgttg aagctgctcc agataaagtt attgttttgc cagctattgg ttctaatgtt    960

ggtattcaat tgagagaaca agatatgtct tggggtgatt ttttgtcttc tgttggtact   1020

agatctagaa attattctcc atgttatcaa ccagttgata ctttgattaa tattttgttt   1080

tcttctggta ctactggtga accaaaagct attccatgga ctcaattgtc tccaattaga   1140

tgtgctgctg aatcttgggc tcatatggat atgcaagttg gtgatgtttt ttgttggcca   1200
```

actaatttgg gttgggttat gggtccaatt ttgatttttt cttctttttt gtctggtgct 1260
actttggctt tgtatcatgg ttctccattg ggttatggtt ttggtaaatt tgttcaagat 1320
gctggtgtta ctaaattggg tactgttcca tctttggtta aagcttggaa aaatactcaa 1380
tgtatgaatg gtttggattg gactaaaatt aaatgttttg cttctactgg tgaaacttct 1440
aatgttgatg atgatttgtg gttgtcttct agagcttatt ataaaccagt tattgaatgt 1500
tgtggtggta ctgaattgtc ttcttcttat attcaaggtt ctttgttgca accacaagct 1560
tttggtgctt tttctactac ttctatgact acttctttgg ttattttgga tgaacatggt 1620
aatccatttc cagatgatca agcttgtatt ggtgaagttg gtttgtttcc attgtatttg 1680
ggtgctactg atagattgtt gaatgctgat catgaagaag tttattttaa agaatgtcat 1740
tatactaaag aatgtgcttc tgaaacttgg agatattatc aaagaactgt tggtggttat 1800
tttattgttc aaggtagagc tgatgatact atgaatttgg gtggtattaa aacttcttct 1860
gttgaaattg aaagagtttg tgatagagct gatgaatcta ttgttgaaac tgctgctgtt 1920
tctgtttctc cagttgatgg tggtccagaa caattggtta tgtttgttgt tttgaaaaat 1980
ggttataatt ctgaagctga aaatttgaga actaaatttt ctaaagctat tcaatctaat 2040
ttgaatccat tgtttaaagt tagatttgtt aaaattgttc cagaatttcc aagaactgct 2100
tctaataaat tgttgagaag agttttgaga gatcaaatta aacatgaatt gtctgctcat 2160
tctagaattt aa 2172

<210> SEQ ID NO 91
<211> LENGTH: 2148
<212> TYPE: DNA
<213> ORGANISM: Artificial Sequence
<220> FEATURE:
<223> OTHER INFORMATION: Codon Optimized

<400> SEQUENCE: 91
atgggttcta aatctatttc tgaagttggt gttgatgatt tggttcaagc tggtttgact 60
actgaagaag ctactggttt tcaaagagtt ttgaaagatt ctttgtcttg tactaaaggt 120
tctgatccat ctgaagtttg gagacatttg gttgctagaa gagttttgaa accatggtct 180
gtttatgctc attgggatgt ttcttctaaa ggtccaccac catattggtt tccatctttg 240
tatcattcta aagatactaa tttgggtaga ttgatggaaa aacatggtcc atctttgttg 300
ggtccattgt ataaagatcc aattacttct tattctttgt ttcaaaaatt ttctgttgaa 360
catccagaag tttattggtc tattgctttg aaagaattgt ctgtttcttt tcaagaagaa 420
ccaaaatgta ttttggataa atctgataaa tctaaacatg gtggttcttg gttgccaggt 480
gctgttttga atattgctga atgttgtttg ttgccaactt cttatccaag aaaagatgat 540
gattctttgg ctattgtttg gagagatgaa ggttctgatg attcttctgt taatttgatt 600
actttgaaac aattgagaga acaagttatt tctgttgcta aatctttgga tgctatgttt 660
tctaaaggtg atgctattgc tatggatatg ccaatgactg ctaatgctgt tattatttat 720
ttggctatta ttttgtctgg tttggttgtt gtttctattg ctgattcttt tgctccaaaa 780
gaaattgctt ctagattgca tgtttctcaa gctaaagcta tttttactca agattttatt 840
ttgagaggtg gtagaaaatt tccattgtat tctagagttg ttgaagctgc tccagataga 900
gttattgttt tgccagctac tggttctaat attggtattc aattgagaga acaagatatg 960
tcttggggtg attttttgtc ttctgttggt actagatcta gaaaatattc tccatgttat 1020
caaccagttg attctttgat taatattttg ttttcttctg gtactactgg tgaaccaaaa 1080
gctattccat ggactcattt gtctccaatt agatgttctt ctgatttttg ggcttatatg 1140
gatattaaag ttggtgatgt tgtttgttgg ccaactaatt tgggttgggc tttgggtcca 1200
tttattttgt ttacttgttt tttgtctggt gctgttttgg ctttgtatca tggttctcca 1260
ttgggtagag gttttggtaa atttgttcaa gatgcttctg ttactaaatt gggtactgtt 1320
ccatctttgg ttaaaacttg gaaaaatact caatgtatga aaggtttgga ttggactaaa 1380
attaaatctt ttgcttctac tggtgaaact tctaatgttg atgatgattt gtggttgtct 1440
tctcaagctt attataaacc agttattgaa tgttgtggtg gtactgaatt ggcttcttct 1500
tatattcaag gttctttgtt gcaaccacaa gcttttggtg cttttaatac tgctactatg 1560
actacttctt ttgttattat tgatgaacat ggtaatccat atccagatga tcaagcttgt 1620
actggtgaag ttggtttgat tccattgtat ttgggtgctt ctgatagatt gttgaatgct 1680
gatcatgaag aagtttattt taaaggtatg ccattgtata aaggtatgag attgagaaga 1740
catggtgata ttattaatag aactgttggt ggttatttta ttgttcaagg tagagctgat 1800
gatactatga atttgggtgg tattaaaact tcttcttttg aaattgaaca tgtttgtgat 1860
agagctgatg attctatttt ggaaactgct gctgtttctg tttctccaat tggtggtggt 1920
ccagaacaat tggttatgtt tgttgttttg aaaaatggtt atgatgctga agctgaaaat 1980
ttgagaacta aattttctaa agctattcaa tctaatttga atccattgtt taaagttact 2040
gctgttaaaa ttgttcatga atttccaaga actatgtcta ataaattgtt gagaagagtt 2100
ttgagagatc aattgaatag agaattttct attcaatcta aaatttag 2148

<210> SEQ ID NO 92
<211> LENGTH: 303
<212> TYPE: DNA
<213> ORGANISM: Artificial Sequence
<220> FEATURE:
<223> OTHER INFORMATION: Codon Optimized

<400> SEQUENCE: 92
atggctgtta aacatttgat tattttgaaa tttaaagatg aaattactga agctcaaaaa 60
gaagaatttt ttaaaactta tgttaatttg gttaatatta ttccagctat gaaagatgtt 120
tattggggta aagatgttac tcaaaaaaat aaagaagaag gttatactca tattgttgaa 180
gttacttttg aatctgttga aactattcaa gattatatta ttcatccagc tcatgttggt 240
tttggtgatg tttatagatg tttttgggaa aaattgttga tttttgatta tactccaaga 300
aaa 303

<210> SEQ ID NO 93
<211> LENGTH: 330
<212> TYPE: DNA
<213> ORGANISM: Artificial Sequence
<220> FEATURE:
<223> OTHER INFORMATION: Codon Optimized

<400> SEQUENCE: 93
atggaagaag ctaaaggtgt tgttaaacat gttttgttgg ctaaatttaa agaaggtact 60
tctgatgatc aaattcaaca attgattaaa ggttatgcta atttgttgaa tttgattcca 120
tctatgaaat cttttcattg ggtaaagat gtttcttttg aaaatttgca tcaaggtttt 180
actcatattt ttgaatctac ttttgaaaat actgaaggtg ttgctgaata tgttgctcat 240
ccagctcatg ttgaatttgc taatgttttt ttgtctaatt tggataaagt tgttgttttt 300
gattataaac caactactgt tttgttgcca 330

<210> SEQ ID NO 94
<211> LENGTH: 42
<212> TYPE: DNA
<213> ORGANISM: Artificial Sequence
<220> FEATURE:
<223> OTHER INFORMATION: Primer

<400> SEQUENCE: 94
aggaaacgaa gataaatctc gagtttatca ttatcaatac tg 42

<210> SEQ ID NO 95
<211> LENGTH: 37
<212> TYPE: DNA
<213> ORGANISM: Artificial Sequence
<220> FEATURE:
<223> OTHER INFORMATION: Primer

<400> SEQUENCE: 95
ggaaaaatca gtcaaggcaa attaaagcct tcgagcg 37

<210> SEQ ID NO 96
<211> LENGTH: 27
<212> TYPE: DNA
<213> ORGANISM: Artificial Sequence
<220> FEATURE:
<223> OTHER INFORMATION: Primer

<400> SEQUENCE: 96
gatgggggat ccactagttc tagaatc 27

<210> SEQ ID NO 97
<211> LENGTH: 25
<212> TYPE: DNA
<213> ORGANISM: Artificial Sequence
<220> FEATURE:
<223> OTHER INFORMATION: Primer

<400> SEQUENCE: 97
tgatgggctg caggaattcg atatc 25

<210> SEQ ID NO 98
<211> LENGTH: 38
<212> TYPE: DNA
<213> ORGANISM: Artificial Sequence
<220> FEATURE:
<223> OTHER INFORMATION: Primer

<400> SEQUENCE: 98
gaactagtgg atcccccatc atgaaccatt tgagagcc 38

<210> SEQ ID NO 99
<211> LENGTH: 32
<212> TYPE: DNA
<213> ORGANISM: Artificial Sequence
<220> FEATURE:
<223> OTHER INFORMATION: Primer

<400> SEQUENCE: 99
tattttggct ttaactttct tggggtgtaa tc 32

<210> SEQ ID NO 100

<211> LENGTH: 43
<212> TYPE: DNA
<213> ORGANISM: Artificial Sequence
<220> FEATURE:
<223> OTHER INFORMATION: Primer

<400> SEQUENCE: 100
agaaagttaa agccaaaata atgataacga gaataatatc aag 43

<210> SEQ ID NO 101
<211> LENGTH: 28
<212> TYPE: DNA
<213> ORGANISM: Artificial Sequence
<220> FEATURE:
<223> OTHER INFORMATION: Primer

<400> SEQUENCE: 101
ataaacccat ggcgcagacc tgtgagag 28

<210> SEQ ID NO 102
<211> LENGTH: 28
<212> TYPE: DNA
<213> ORGANISM: Artificial Sequence
<220> FEATURE:
<223> OTHER INFORMATION: Primer

<400> SEQUENCE: 102
ggtctgcgcc atgggtttat catccgtc 28

<210> SEQ ID NO 103
<211> LENGTH: 41
<212> TYPE: DNA
<213> ORGANISM: Artificial Sequence
<220> FEATURE:
<223> OTHER INFORMATION: Primer

<400> SEQUENCE: 103
cgaattcctg cagcccatca gtgtctatgt ctaggtaaag g 41

<210> SEQ ID NO 104
<211> LENGTH: 25
<212> TYPE: DNA
<213> ORGANISM: Artificial Sequence
<220> FEATURE:
<223> OTHER INFORMATION: Primer

<400> SEQUENCE: 104
tgatgggctg caggaattcg atatc 25

<210> SEQ ID NO 105
<211> LENGTH: 27
<212> TYPE: DNA
<213> ORGANISM: Artificial Sequence
<220> FEATURE:
<223> OTHER INFORMATION: Primer

<400> SEQUENCE: 105
gatgggggat ccactagttc tagaatc 27

<210> SEQ ID NO 106
<211> LENGTH: 33
<212> TYPE: DNA
<213> ORGANISM: Artificial Sequence
<220> FEATURE:
<223> OTHER INFORMATION: Primer

<400> SEQUENCE: 106
caccagaacc gaaggtagag gttctttgtt aac 33

<210> SEQ ID NO 107
<211> LENGTH: 45
<212> TYPE: DNA
<213> ORGANISM: Artificial Sequence
<220> FEATURE:
<223> OTHER INFORMATION: Primer

<400> SEQUENCE: 107
cgaattcctg cagcccatca ctttgatctc ttgtagacct tattc 45

<210> SEQ ID NO 108
<211> LENGTH: 42
<212> TYPE: DNA
<213> ORGANISM: Artificial Sequence
<220> FEATURE:
<223> OTHER INFORMATION: Primer

<400> SEQUENCE: 108
gaactagtgg atcccccatc atggtttcca atcacttgtt tg 42

<210> SEQ ID NO 109
<211> LENGTH: 29
<212> TYPE: DNA
<213> ORGANISM: Artificial Sequence
<220> FEATURE:
<223> OTHER INFORMATION: Primer

<400> SEQUENCE: 109
ctctaccttc ggttctggtg tataagtcg 29

<210> SEQ ID NO 110
<211> LENGTH: 22
<212> TYPE: DNA
<213> ORGANISM: Artificial Sequence
<220> FEATURE:
<223> OTHER INFORMATION: Primer

<400> SEQUENCE: 110
gatccactag ttctagaatc cg 22

<210> SEQ ID NO 111
<211> LENGTH: 35
<212> TYPE: DNA
<213> ORGANISM: Artificial Sequence
<220> FEATURE:
<223> OTHER INFORMATION: Primer

<400> SEQUENCE: 111
tctagaacta gtggatcatg aaccatttga gagcc 35

<210> SEQ ID NO 112
<211> LENGTH: 28
<212> TYPE: DNA
<213> ORGANISM: Artificial Sequence
<220> FEATURE:
<223> OTHER INFORMATION: Primer

<400> SEQUENCE: 112
tcgttatcac tttcttgggg tgtaatcg 28

<210> SEQ ID NO 113

<211> LENGTH: 36
<212> TYPE: DNA
<213> ORGANISM: Artificial Sequence
<220> FEATURE:
<223> OTHER INFORMATION: Primer

<400> SEQUENCE: 113
ccaagaaagt gataacgaga ataatatcaa gaatac 36

<210> SEQ ID NO 114
<211> LENGTH: 44
<212> TYPE: DNA
<213> ORGANISM: Artificial Sequence
<220> FEATURE:
<223> OTHER INFORMATION: Primer

<400> SEQUENCE: 114
aggtcgacgg tatcgttaaa taaaaacgta taccaaatat tcag 44

<210> SEQ ID NO 115
<211> LENGTH: 18
<212> TYPE: DNA
<213> ORGANISM: Artificial Sequence
<220> FEATURE:
<223> OTHER INFORMATION: Primer

<400> SEQUENCE: 115
cgataccgtc gacctcga 18

<210> SEQ ID NO 116
<211> LENGTH: 32
<212> TYPE: DNA
<213> ORGANISM: Artificial Sequence
<220> FEATURE:
<223> OTHER INFORMATION: Primer

<400> SEQUENCE: 116
ggttaaacta gtatgggtaa aaactataag tc 32

<210> SEQ ID NO 117
<211> LENGTH: 33
<212> TYPE: DNA
<213> ORGANISM: Artificial Sequence
<220> FEATURE:
<223> OTHER INFORMATION: Primer

<400> SEQUENCE: 117
gtgcccgtcg actcattcga aatgactgaa ttg 33

<210> SEQ ID NO 118
<211> LENGTH: 3952
<212> TYPE: DNA
<213> ORGANISM: Artificial Sequence
<220> FEATURE:
<223> OTHER INFORMATION: Codon Optimized

<400> SEQUENCE: 118
tcattatcaa tactgccatt tcaaagaata cgtaaataat taatagtagt gattttccta 60
actttattta gtcaaaaaat tagcctttta attctgctgt aacccgtaca tgcccaaaat 120
agggggcggg ttacacagaa tatataacat cgtaggtgtc tgggtgaaca gtttattcct 180
ggcatccact aaatataatg gagcccgctt tttaagctgg catccagaaa aaaaaagaat 240
cccagcacca aaatattgtt ttcttcacca accatcagtt cataggtcca ttctcttagc 300
gcaactacag agaacagggg cacaaacagg caaaaaacgg gcacaacctc aatggagtga 360

-continued

```
tgcaacctgc ctggagtaaa tgatgacaca aggcaattga cccacgcatg tatctatctc    420
attttcttac accttctatt accttctgct ctctctgatt tggaaaaagc tgaaaaaaaa    480
ggttgaaacc agttccctga aattattccc ctacttgact aataagtata taaagacggt    540
aggtattgat tgtaattctg taaatctatt tcttaaactt cttaaattct acttttatag    600
ttagtctttt ttttagtttt aaaacaccaa gaacttagtt tcgaataaac acacataaac    660
aaacaaaatg aaattgttaa catttccagg tcaaggtact tctatttcta tttctatatt    720
gaaggctata ataagaaaca agtcaagaga atttcaaaca atcttgagtc aaaatggtaa    780
agaatctaac gatttgttgc aatacatctt ccaaaatcca tcttcacctg gttcaatcgc    840
tgtttgttcc aatttgttct atcaattgta ccaaatcttg tctaacccat cagatcctca    900
agaccaagca cctaaaaata tgacaaagat cgatagtcct gacaaaaagg ataacgaaca    960
atgttatttg ttgggtcatt ctttgggtga attaacttgc ttgtccgtta atagtttatt   1020
ttctttgaag gacttatttg atattgcaaa cttcagaaac aaattaatgg tcacttcaac   1080
agaaaagtac ttggttgccc acaacataaa cagatccaat aagttcgaaa tgtgggcttt   1140
atccagtcca agagcaaccg atttgcctca agaagttcaa aagttgttaa attcaccaaa   1200
cttgttatct tcatcccaaa acactatttc agtagccaat gctaactccg tcaaacaatg   1260
tgttgtaact ggtttagtag atgacttgga atcattaaga acagaattga acttaagatt   1320
ccctagattg agaatcacag aattgaccaa tccatacaac attcctttcc ataattccac   1380
tgtcttaaga ccagttcaag aacctttgta cgactatatt tgggatattt tgaaaaagaa   1440
tggtactcat actttgatgg aattaaacca cccaatcatt gccaatttgg atggtaacat   1500
ctcatactac atccatcacg ctttggatag attcgttaag tgttcttcaa gaactgtaca   1560
attcacaatg tgctatgaca ccattaatag tggtactcca gttgaaatcg ataagtctat   1620
ttgtttcggt cctggtaacg taatatacaa cttaatcaga agaaactgcc ctcaagttga   1680
taccatcgaa tacacttctt tggcaacaat cgatgcctac cataaagctg cagaagaaaa   1740
taaggattaa tcatgtaatt agttatgtca cgcttacatt cacgccctcc ccccacatcc   1800
gctctaaccg aaaaggaagg agttagacaa cctgaagtct aggtccctat ttattttttt   1860
atagttatgt tagtattaag aacgttattt atatttcaaa tttttctttt ttttctgtac   1920
agacgcgtgt acgcatgtaa cattatactg aaaaccttgc ttgagaaggt tttgggacgc   1980
tcgaaggctt taatttgccc tcgagggggg gcccggtacc caattcgccc tatagtgagt   2040
cgtattacgc gcgctcactg gccgtcgttt tacaacgtcg tgactgggaa aaccctggcg   2100
ttacccaact taatcgcctt gcagcacatc ccccttcgc cagctggcgt aatagcgaag   2160
aggcccgcac cgatcgccct tcccaacagt tgcgcagcct gaatggcgaa tggcgcgacg   2220
cgccctgtag cggcgcatta agcgcggcgg gtgtggtggt tacgcgcagc gtgaccgcta   2280
cacttgccag cgccctagcg cccgctcctt tcgctttctt cccttccttt ctcgccacgt   2340
tcgccggctt tccccgtcaa gctctaaatc gggggctccc tttagggttc cgatttagtg   2400
ctttacggca cctcgacccc aaaaaacttg attagggtga tggttcacgt agtgggccat   2460
cgccctgata gacggttttt cgccctttga cgttggagtc cacgttcttt aatagtggac   2520
tcttgttcca aactggaaca acactcaacc ctatctcggt ctattctttt gatttataag   2580
ggattttgcc gatttcggcc tattggttaa aaaatgagct gatttaacaa aaatttaacg   2640
cgaattttaa caaaatatta acgtttacaa tttcctgatg cggtattttc tccttacgca   2700
```

-continued

```
tctgtgcggt atttcacacc gcatagatcc gtcgagttca agagaaaaaa aaagaaaaag   2760

caaaaagaaa aaaggaaagc gcgcctcgtt cagaatgaca cgtatagaat gatgcattac   2820

cttgtcatct tcagtatcat actgttcgta tacatactta ctgacattca taggtataca   2880

tatatacaca tgtatatata tcgtatgctg cagctttaaa taatcggtgt cattagtttt   2940

gctggccgca tcttctcaaa tatgcttccc agcctgcttt tctgtaacgt tcaccctcta   3000

ccttagcatc ccttcccttt gcaaatagtc ctcttccaac aataataatg tcagatcctg   3060

tagagaccac atcatccacg gttctatact gttgacccaa tgcgtctccc ttgtcatcta   3120

aacccacacc gggtgtcata atcaaccaat cgtaaccttc atctcttcca cccatgtctc   3180

tttgagcaat aaagccgata acaaaatctt tgtcgctctt cgcaatgtca acagtaccct   3240

tagtatattc tccagtagat agggagccct tgcatgacaa ttctgctaac atcaaaaggc   3300

ctctaggttc ctttgttact tcttctgccg cctgcttcaa accgctaaca atacctgggc   3360

ccaccacacc gtgtgcattc gtaatgtctg cccattctgc tattctgtat acacccgcag   3420

agtactgcaa tttgactgta ttaccaatgt cagcaaattt tctgtcttcg aagagtaaaa   3480

aattgtactt ggcggataat gcctttagcg gcttaactgt gccctccatg gaaaaatcag   3540

tcaagatatc cacatgtgtt tttagtaaac aaattttggg acctaatgct tcaactaact   3600

ccagtaattc cttggtggta cgaacatcca atgaagcaca caagtttgtt tgcttttcgt   3660

gcatgatatt aaatagcttg gcagcaacag gactaggatg agtagcagca cgttccttat   3720

atgtagcttt cgacatgatt tatcttcgtt tcctgcaggt tttgttctg tgcagttggg    3780

ttaagaatac tgggcaattt catgtttctt caacactaca tatgcgtata tataccaatc   3840

taagtctgtg ctccttcctt cgttcttcct tctgttcgga gattaccgaa tcaaaaaaat   3900

ttcaaagaaa ccgaaatcaa aaaaaagaat aaaaaaaaaa tgatgaattg aa           3952
```

<210> SEQ ID NO 119
<211> LENGTH: 3718
<212> TYPE: DNA
<213> ORGANISM: Artificial Sequence
<220> FEATURE:
<223> OTHER INFORMATION: Codon Optimized

<400> SEQUENCE: 119

```
tcattatcaa tactgccatt tcaaagaata cgtaaataat taatagtagt gattttccta     60

actttattta gtcaaaaaat tagcctttta attctgctgt aacccgtaca tgcccaaaat    120

agggggcggg ttacacagaa tatataacat cgtaggtgtc tgggtgaaca gtttattcct    180

ggcatccact aaatataatg gagcccgctt tttaagctgg catccagaaa aaaaaagaat    240

cccagcacca aaatattgtt ttcttcacca accatcagtt cataggtcca ttctcttagc    300

gcaactacag agaacagggg cacaaacagg caaaaaacgg gcacaacctc aatggagtga    360

tgcaacctgc ctggagtaaa tgatgacaca aggcaattga cccacgcatg tatctatctc    420

attttcttac accttctatt accttctgct ctctctgatt tggaaaaagc tgaaaaaaaa    480

ggttgaaacc agttccctga aattattccc ctacttgact aataagtata taaagacggt    540

aggtattgat tgtaattctg taaatctatt tcttaaactt cttaaattct acttttatag    600

ttagtctttt ttttagtttt aaaacaccaa gaacttagtt tcgaataaac acacataaac    660

aaacaaaatg aaaaaggttt gtgtcatcgg tgctggtact atgggttctg gtattgctca    720

agcatttgct gcaaaaggtt tcgaagttgt attgagagat ataaaggacg aatttgttga    780

tagaggttta gacttcatca ataagaactt gagtaaattg gttaagaaag gtaaaatcga    840
```

-continued

```
agaagctact aaggttgaaa tattgacaag aatatctggt actgtagatt tgaacatggc    900
cgctgattgt gacttagtaa ttgaagcagc cgtcgaaaga atggatatta agaaacaaat    960
attcgctgat ttggataata tttgcaagcc agaaactata ttggcatcta acacatcttc   1020
attatcaatt accgaagtcg cctccgctac taagacaaac gataaggtta taggcatgca   1080
tttctttaac ccagcccctg ttatgaaatt ggttgaagta ataagaggta tcgcaacctc   1140
acaagaaact ttcgatgcag ttaaggaaac atccattgcc attggtaaag atccagtcga   1200
agttgcagaa gcccctggtt tcgtcgttaa cagaatcttg ataccaatga taaacgaagc   1260
tgtaggtata ttagctgaag gtatcgcatc cgtcgaagat attgacaaag ccatgaagtt   1320
aggtgctaac catccaatgg gtcctttgga attaggtgac tttataggtt tggacatctg   1380
cttagctatt atggatgttt tgtattccga aactggtgac agtaaataca gacctcacac   1440
attgttgaag aaatatgtta gagcaggttg gttaggtaga aagagtggta aaggtttcta   1500
cgattactct aaataatcat gtaattagtt atgtcacgct tacattcacg ccctcccccc   1560
acatccgctc taaccgaaaa ggaaggagtt agacaacctg aagtctaggt ccctatttat   1620
ttttttatag ttatgttagt attaagaacg ttatttatat ttcaaatttt tctttttttt   1680
ctgtacagac gcgtgtacgc atgtaacatt atactgaaaa ccttgcttga gaaggttttg   1740
ggacgctcga aggctttaat ttgccctcga ggggggcccc ggtacccaat tcgccctata   1800
gtgagtcgta ttacgcgcgc tcactggccg tcgttttaca acgtcgtgac tgggaaaacc   1860
ctggcgttac ccaacttaat cgccttgcag cacatccccc tttcgccagc tggcgtaata   1920
gcgaagaggc ccgcaccgat cgcccttccc aacagttgcg cagcctgaat ggcgaatggc   1980
gcgacgcgcc ctgtagcggc gcattaagcg cggcgggtgt ggtggttacg cgcagcgtga   2040
ccgctacact tgccagcgcc ctagcgcccg ctcctttcgc tttcttccct tcctttctcg   2100
ccacgttcgc cggctttccc cgtcaagctc taaatcgggg gctcccttta gggttccgat   2160
ttagtgcttt acggcacctc gaccccaaaa aacttgatta gggtgatggt tcacgtagtg   2220
ggccatcgcc ctgatagacg gtttttcgcc ctttgacgtt ggagtccacg ttctttaata   2280
gtggactctt gttccaaact ggaacaacac tcaaccctat ctcggtctat tcttttgatt   2340
tataagggat tttgccgatt tcggcctatt ggttaaaaaa tgagctgatt taacaaaaat   2400
ttaacgcgaa ttttaacaaa atattaacgt ttacaatttc ctgatgcggt attttctcct   2460
tacgcatctg tgcggtattt cacaccgcat agatccgtcg agttcaagag aaaaaaaaag   2520
aaaaagcaaa aagaaaaaag gaaagcgcgc ctcgttcaga atgacacgta tagaatgatg   2580
cattaccttg tcatcttcag tatcatactg ttcgtataca tacttactga cattcatagg   2640
tatacatata tacacatgta tatatatcgt atgctgcagc tttaaataat cggtgtcatt   2700
agttttgctg gccgcatctt ctcaaatatg cttcccagcc tgcttttctg taacgttcac   2760
cctctacctt agcatccctt ccctttgcaa atagtcctct tccaacaata ataatgtcag   2820
atcctgtaga gaccacatca tccacggttc tatactgttg acccaatgcg tctcccttgt   2880
catctaaacc cacaccgggt gtcataatca accaatcgta accttcatct cttccaccca   2940
tgtctctttg agcaataaag ccgataacaa aatctttgtc gctcttcgca atgtcaacag   3000
taccccttagt atattctcca gtagataggg agcccttgca tgacaattct gctaacatca   3060
aaaggcctct aggttccttt gttacttctt ctgccgcctg cttcaaaccg ctaacaatac   3120
ctgggcccac cacaccgtgt gcattcgtaa tgtctgccca ttctgctatt ctgtatacac   3180
```

ccgcagagta ctgcaatttg actgtattac caatgtcagc aaattttctg tcttcgaaga 3240
gtaaaaaatt gtacttggcg gataatgcct ttagcggctt aactgtgccc tccatggaaa 3300
aatcagtcaa gatatccaca tgtgttttta gtaaacaaat tttgggacct aatgcttcaa 3360
ctaactccag taattccttg gtggtacgaa catccaatga agcacacaag tttgtttgct 3420
tttcgtgcat gatattaaat agcttggcag caacaggact aggatgagta gcagcacgtt 3480
ccttatatgt agctttcgac atgatttatc ttcgtttcct gcaggttttt gttctgtgca 3540
gttgggttaa gaatactggg caatttcatg tttcttcaac actacatatg cgtatatata 3600
ccaatctaag tctgtgctcc ttccttcgtt cttccttctg ttcggagatt accgaatcaa 3660
aaaaatttca aagaaaccga aatcaaaaaa aagaataaaa aaaaaatgat gaattgaa 3718

<210> SEQ ID NO 120
<211> LENGTH: 3655
<212> TYPE: DNA
<213> ORGANISM: Artificial Sequence
<220> FEATURE:
<223> OTHER INFORMATION: Codon Optimized

<400> SEQUENCE: 120
tcattatcaa tactgccatt tcaaagaata cgtaaataat taatagtagt gattttccta 60
actttattta gtcaaaaaat tagcctttta attctgctgt aacccgtaca tgcccaaaat 120
agggggcggg ttacacagaa tatataacat cgtaggtgtc tgggtgaaca gtttattcct 180
ggcatccact aaatataatg gagcccgctt tttaagctgg catccagaaa aaaaaagaat 240
cccagcacca aaatattgtt ttcttcacca accatcagtt cataggtcca ttctcttagc 300
gcaactacag agaacagggg cacaaacagg caaaaaacgg gcacaacctc aatggagtga 360
tgcaacctgc ctggagtaaa tgatgacaca aggcaattga cccacgcatg tatctatctc 420
attttcttac accttctatt accttctgct ctctctgatt tggaaaaagc tgaaaaaaaa 480
ggttgaaacc agttccctga aattattccc ctacttgact aataagtata taaagacggt 540
aggtattgat tgtaattctg taaatctatt tcttaaactt cttaaattct acttttatag 600
ttagtctttt ttttagtttt aaaacaccaa gaacttagtt tcgaataaac acacataaac 660
aaacaaaatg gaactaaaca atgtcatcct tgaaaaggaa ggtaaagttg ctgtagttac 720
cattaacaga cctaaagcat taaatgcgtt aaatagtgat acactaaaag aaatggatta 780
tgttataggt gaaattgaaa atgatagcga agtacttgca gtaattttaa ctggagcagg 840
agaaaaatca tttgtagcag gagcagatat ttctgagatg aaggaaatga ataccattga 900
aggtagaaaa ttcgggatac ttggaaataa agtgtttaga agattagaac ttcttgaaaa 960
gcctgtaata gcagctgtta atggttttgc tttaggaggc ggatgcgaaa tagctatgtc 1020
ttgtgatata agaatagctt caagcaacgc aagatttggt caaccagaag taggtctcgg 1080
aataacacct ggttttggtg gtacacaaag actttcaaga ttagttggaa tgggcatggc 1140
aaagcagctt atatttactg cacaaaatat aaaggcagat gaagcattaa gaatcggact 1200
tgtaaataag gtagtagaac ctagtgaatt aatgaataca gcaaaagaaa ttgcaaacaa 1260
aattgtgagc aatgctccag tagctgttaa gttaagcaaa caggctatta atagaggaat 1320
gcagtgtgat attgatactg ctttagcatt tgaatcagaa gcatttggag aatgcttttc 1380
aacagaggat caaaaggatg caatgacagc tttcatagag aaaagaaaaa ttgaaggctt 1440
caaaaataga tagtcatgta attagttatg tcacgcttac attcacgccc tccccccaca 1500
tccgctctaa ccgaaaagga aggagttaga caacctgaag tctaggtccc tatttatttt 1560
tttatagtta tgttagtatt aagaacgtta tttatatttc aaatttttct tttttttctg 1620
tacagacgcg tgtacgcatg taacattata ctgaaaacct tgcttgagaa ggttttggga 1680
cgctcgaagg ctttaatttg ccctcgaggg ggggcccggt acccaattcg ccctatagtg 1740
agtcgtatta cgcgcgctca ctggccgtcg ttttacaacg tcgtgactgg gaaaaccctg 1800
gcgttaccca acttaatcgc cttgcagcac atcccccttt cgccagctgg cgtaatagcg 1860
aagaggcccg caccgatcgc ccttcccaac agttgcgcag cctgaatggc gaatggcgcg 1920
acgcgccctg tagcggcgca ttaagcgcgg cgggtgtggt ggttacgcgc agcgtgaccg 1980
ctacacttgc cagcgcccta gcgcccgctc ctttcgcttt cttcccttcc tttctcgcca 2040
cgttcgccgg ctttccccgt caagctctaa atcgggggct ccctttaggg ttccgattta 2100
gtgctttacg gcacctcgac cccaaaaaac ttgattaggg tgatggttca cgtagtgggc 2160
catcgccctg atagacggtt tttcgccctt tgacgttgga gtccacgttc tttaatagtg 2220
gactcttgtt ccaaactgga acaacactca accctatctc ggtctattct tttgatttat 2280
aagggatttt gccgatttcg gcctattggt taaaaaatga gctgatttaa caaaaattta 2340
acgcgaattt taacaaaata ttaacgttta caatttcctg atgcggtatt ttctccttac 2400
gcatctgtgc ggtatttcac accgcataga tccgtcgagt tcaagagaaa aaaaaagaaa 2460
aagcaaaaag aaaaaaggaa agcgcgcctc gttcagaatg acacgtatag aatgatgcat 2520
taccttgtca tcttcagtat catactgttc gtatacatac ttactgacat tcataggtat 2580
acatatatac acatgtatat atatcgtatg ctgcagcttt aaataatcgg tgtcattagt 2640
tttgctggcc gcatcttctc aaatatgctt cccagcctgc ttttctgtaa cgttcaccct 2700
ctaccttagc atcccttccc tttgcaaata gtcctcttcc aacaataata atgtcagatc 2760
ctgtagagac cacatcatcc acggttctat actgttgacc caatgcgtct cccttgtcat 2820
ctaaacccac accgggtgtc ataatcaacc aatcgtaacc ttcatctctt ccacccatgt 2880
ctctttgagc aataaagccg ataacaaaat ctttgtcgct cttcgcaatg tcaacagtac 2940
ccttagtata ttctccagta gatagggagc ccttgcatga caattctgct aacatcaaaa 3000
ggcctctagg ttcctttgtt acttcttctg ccgcctgctt caaaccgcta acaatacctg 3060
ggcccaccac accgtgtgca ttcgtaatgt ctgcccattc tgctattctg tatacacccg 3120
cagagtactg caatttgact gtattaccaa tgtcagcaaa ttttctgtct tcgaagagta 3180
aaaaattgta cttggcggat aatgccttta gcggcttaac tgtgccctcc atggaaaaat 3240
cagtcaagat atccacatgt gtttttagta aacaaatttt gggacctaat gcttcaacta 3300
actccagtaa ttccttggtg gtacgaacat ccaatgaagc acacaagttt gtttgctttt 3360
cgtgcatgat attaaatagc ttggcagcaa caggactagg atgagtagca gcacgttcct 3420
tatatgtagc tttcgacatg atttatcttc gtttcctgca ggtttttgtt ctgtgcagtt 3480
gggttaagaa tactgggcaa tttcatgttt cttcaacact acatatgcgt atatatacca 3540
atctaagtct gtgctccttc cttcgttctt ccttctgttc ggagattacc gaatcaaaaa 3600
aatttcaaag aaaccgaaat caaaaaaaag aataaaaaaa aaatgatgaa ttgaa 3655

<210> SEQ ID NO 121
<211> LENGTH: 4054
<212> TYPE: DNA
<213> ORGANISM: Artificial Sequence
<220> FEATURE:
<223> OTHER INFORMATION: Codon Optimized

<400> SEQUENCE: 121

```
tcattatcaa tactgccatt tcaaagaata cgtaaataat taatagtagt gattttccta     60
actttattta gtcaaaaaat tagcctttta attctgctgt aacccgtaca tgcccaaaat    120
agggggcggg ttacacagaa tatataacat cgtaggtgtc tgggtgaaca gtttattcct    180
ggcatccact aaatataatg gagcccgctt tttaagctgg catccagaaa aaaaaagaat    240
cccagcacca aaatattgtt ttcttcacca accatcagtt cataggtcca ttctcttagc    300
gcaactacag agaacagggg cacaaacagg caaaaaaacgg gcacaacctc aatggagtga   360
tgcaacctgc ctggagtaaa tgatgacaca aggcaattga cccacgcatg tatctatctc    420
attttcttac accttctatt accttctgct ctctctgatt tggaaaaagc tgaaaaaaaa    480
ggttgaaacc agttccctga aattattccc ctacttgact aataagtata taaagacggt    540
aggtattgat tgtaattctg taaatctatt tcttaaactt cttaaattct acttttatag    600
ttagtctttt ttttagtttt aaaacaccaa gaacttagtt tcgaataaac acacataaac    660
aaacaaaatg aaaaattgtg tcatagtttc tgccgttaga actgctatcg gttcttttaa    720
cggttcattg gcatctactt cagctatcga tttgggtgct acagtaatca aagctgcaat    780
tgaaagagca aagatagatt ccttgcatat agacgaagtt atcatgggta atgtattgca    840
agctggttta ggtcaaaacc cagctagaca agcattgtta aaatcaggtt tagcagaaac    900
cgtatgtggt ttcactgtca ataaggtttg cggttccggt ttgaagagtg tcgctttagc    960
cgctcaagcc attcaagctg gtcaagcaca atccatagtt gccggtggta tggaaaacat   1020
gagtttggca ccttatttgt tagatgccaa ggctagatct ggttatagat taggtgacgg   1080
tcaagtatac gacgtcattt tgagagatgg tttaatgtgc gctactcatg gttatcacat   1140
gggtataact gctgaaaacg ttgcaaagga atacggtatc acaagagaaa tgcaagatga   1200
attggcttta cactctcaaa gaaaggcagc cgctgcaatc gaatcaggtg cctttaccgc   1260
tgaaattgta ccagtcaacg ttgtaactag aaagaaaact ttcgttttct ctcaagacga   1320
atttccaaaa gctgattcaa ctacagaagc attgggtgcc ttaagacctg ccttcgacaa   1380
ggctggtact gtaactgctg gtaatgcatc cggtataaac gatggtgccg ctgcattggt   1440
catcatggaa gaaagtgccg ctttagcagc cggtttgaca cctttagcta gaattaaatc   1500
ctacgcaagt ggtggtgtcc cacctgcttt gatgggtatg ggtccagttc ctgcaacaca   1560
aaagaccttg caattagcag gtttgcaatt agccgatatt gacttaatag aagccaatga   1620
agcatttgct gcacaattct tggctgttgg taaaacttta ggtttcgact ctgaaaaggt   1680
taatgtaaac ggtggtgcaa tcgccttggg tcatccaatt ggtgcatcag gtgccagaat   1740
tttagttaca ttgttacacg ctatgcaagc aagagataaa acattgggtt tagctacctt   1800
gtgtattggt ggtggtcaag gtattgcaat ggttatagaa agattaaatt aatcatgtaa   1860
ttagttatgt cacgcttaca ttcacgccct ccccccacat ccgctctaac cgaaaaggaa   1920
ggagttagac aacctgaagt ctaggtccct atttattttt ttatagttat gttagtatta   1980
agaacgttat ttatatttca aatttttctt ttttttctgt acagacgcgt gtacgcatgt   2040
aacattatac tgaaaacctt gcttgagaag gttttgggac gctcgaaggc tttaatttgc   2100
cctcgagggg gggcccggta cccaattcgc cctatagtga gtcgtattac gcgcgctcac   2160
tggccgtcgt tttacaacgt cgtgactggg aaaaccctgg cgttacccaa cttaatcgcc   2220
ttgcagcaca tccccctttc gccagctggc gtaatagcga agaggcccgc accgatcgcc   2280
cttcccaaca gttgcgcagc ctgaatggcg aatggcgcga cgcgccctgt agcggcgcat   2340
```

taagcgcggc gggtgtggtg gttacgcgca gcgtgaccgc tacacttgcc agcgccctag 2400
cgcccgctcc tttcgctttc ttcccttcct ttctcgccac gttcgccggc tttccccgtc 2460
aagctctaaa tcgggggctc cctttagggt tccgatttag tgctttacgg cacctcgacc 2520
ccaaaaaact tgattagggt gatggttcac gtagtgggcc atcgccctga tagacggttt 2580
ttcgcccttt gacgttggag tccacgttct ttaatagtgg actcttgttc caaactggaa 2640
caacactcaa ccctatctcg gtctattctt ttgatttata agggattttg ccgatttcgg 2700
cctattggtt aaaaaatgag ctgatttaac aaaaatttaa cgcgaatttt aacaaaatat 2760
taacgtttac aatttcctga tgcggtattt tctccttacg catctgtgcg gtatttcaca 2820
ccgcatagat ccgtcgagtt caagagaaaa aaaaagaaaa agcaaaaaga aaaaaggaaa 2880
gcgcgcctcg ttcagaatga cacgtataga atgatgcatt accttgtcat cttcagtatc 2940
atactgttcg tatacatact tactgacatt cataggtata catatataca catgtatata 3000
tatcgtatgc tgcagcttta aataatcggt gtcattagtt ttgctggccg catcttctca 3060
aatatgcttc ccagcctgct tttctgtaac gttcaccctc taccttagca tcccttccct 3120
ttgcaaatag tcctcttcca acaataataa tgtcagatcc tgtagagacc acatcatcca 3180
cggttctata ctgttgaccc aatgcgtctc ccttgtcatc taaacccaca ccgggtgtca 3240
taatcaacca atcgtaacct tcatctcttc cacccatgtc tctttgagca ataaagccga 3300
taacaaaatc tttgtcgctc ttcgcaatgt caacagtacc cttagtatat tctccagtag 3360
atagggagcc cttgcatgac aattctgcta acatcaaaag gcctctaggt tcctttgtta 3420
cttcttctgc cgcctgcttc aaaccgctaa caatacctgg gcccaccaca ccgtgtgcat 3480
tcgtaatgtc tgcccattct gctattctgt atacacccgc agagtactgc aatttgactg 3540
tattaccaat gtcagcaaat tttctgtctt cgaagagtaa aaaattgtac ttggcggata 3600
atgcctttag cggcttaact gtgccctcca tggaaaaatc agtcaagata tccacatgtg 3660
tttttagtaa acaaattttg ggacctaatg cttcaactaa ctccagtaat tccttggtgg 3720
tacgaacatc caatgaagca cacaagtttg tttgcttttc gtgcatgata ttaaatagct 3780
tggcagcaac aggactagga tgagtagcag cacgttcctt atatgtagct ttcgacatga 3840
tttatcttcg tttcctgcag gtttttgttc tgtgcagttg ggttaagaat actgggcaat 3900
ttcatgtttc ttcaacacta catatgcgta tatataccaa tctaagtctg tgctccttcc 3960
ttcgttcttc cttctgttcg gagattaccg aatcaaaaaa atttcaaaga aaccgaaatc 4020
aaaaaaaaga ataaaaaaaa aatgatgaat tgaa 4054

<210> SEQ ID NO 122
<211> LENGTH: 4054
<212> TYPE: DNA
<213> ORGANISM: Artificial Sequence
<220> FEATURE:
<223> OTHER INFORMATION: Codon Optimized

<400> SEQUENCE: 122
tcattatcaa tactgccatt tcaaagaata cgtaaataat taatagtagt gattttccta 60
actttattta gtcaaaaaat tagcctttta attctgctgt aacccgtaca tgcccaaaat 120
agggggcggg ttacacagaa tatataacat cgtaggtgtc tgggtgaaca gtttattcct 180
ggcatccact aaatataatg gagcccgctt tttaagctgg catccagaaa aaaaaagaat 240
cccagcacca aaatattgtt ttcttcacca accatcagtt cataggtcca ttctcttagc 300

-continued

```
gcaactacag agaacagggg cacaaacagg caaaaaacgg gcacaacctc aatggagtga    360
tgcaacctgc ctggagtaaa tgatgacaca aggcaattga cccacgcatg tatctatctc    420
attttcttac accttctatt accttctgct ctctctgatt tggaaaaagc tgaaaaaaaa    480
ggttgaaacc agttccctga aattattccc ctacttgact aataagtata taaagacggt    540
aggtattgat tgtaattctg taaatctatt tcttaaactt cttaaattct acttttatag    600
ttagtctttt ttttagtttt aaaacaccaa gaacttagtt tcgaataaac acacataaac    660
aaacaaaatg actagagaag ttgtagtcgt ttctggtgtt agaacagcta ttggtacttt    720
tggtggttca ttaaaagatg ttgctccagc agaattgggt gcattagtag tcagagaagc    780
cttggctaga gcacaagtat ccggtgacga cgtcggtcat gttgtattcg gtaatgttat    840
ccaaacagaa ccaagagata tgtatttggg tagagtcgct gcagttaatg gtggtgtaac    900
tattaacgcc cctgctttaa cagtcaacag attgtgtggt tccggtttac aagctatagt    960
tagtgccgct caaacaatct tgttaggtga caccgacgtt gctattggtg gtggtgctga   1020
atctatgtca agagccccat acttagctcc tgcagccaga tggggtgcca gaatgggtga   1080
cgctggtttg gttgacatga tgttgggtgc tttacatgat cctttccata gaatacacat   1140
gggtgttact gcagaaaacg tagccaagga atacgatatt tcaagagcac aacaagacga   1200
agctgcattg gaatctcaca gaagagcatc agccgctatc aaagccggtt actttaagga   1260
tcaaattgtt ccagtcgttt caaaaggtag aaagggtgac gtcaccttcg atactgacga   1320
acatgttaga cacgacgcta ctattgatga catgacaaaa ttgagacctg ttttcgtaaa   1380
ggaaaatggt actgttacag ccggtaatgc ttccggtttg aacgatgcag ccgctgcagt   1440
agtcatgatg gaaagagcag aagccgaaag aagaggtttg aaaccattag ctagattggt   1500
ttcttatggt catgctggtg ttgatccaaa agcaatgggt attggtccag ttcctgctac   1560
caagatagca ttggaaagag ccggtttaca agtctctgat ttggacgtta tagaagcaaa   1620
tgaagccttt gccgctcaag catgtgcagt tacaaaagca ttgggtttag atccagcaaa   1680
agtaaatcct aacggttccg gtatcagttt aggtcatcca attggtgcta ccggtgcatt   1740
gattactgtt aaggctttac acgaattgaa cagagttcaa ggtagatacg cattagtaac   1800
aatgtgcata ggtggtggtc aaggtattgc agccatattc gaaagaatct aatcatgtaa   1860
ttagttatgt cacgcttaca ttcacgccct ccccccacat ccgctctaac cgaaaaggaa   1920
ggagttagac aacctgaagt ctaggtccct atttattttt ttatagttat gttagtatta   1980
agaacgttat ttatatttca aatttttctt ttttttctgt acagacgcgt gtacgcatgt   2040
aacattatac tgaaaacctt gcttgagaag gttttgggac gctcgaaggc tttaatttgc   2100
cctcgagggg gggcccggta cccaattcgc cctatagtga gtcgtattac gcgcgctcac   2160
tggccgtcgt tttacaacgt cgtgactggg aaaaccctgg cgttacccaa cttaatcgcc   2220
ttgcagcaca tccccctttc gccagctggc gtaatagcga agaggcccgc accgatcgcc   2280
cttcccaaca gttgcgcagc ctgaatggcg aatggcgcga cgcgccctgt agcggcgcat   2340
taagcgcggc gggtgtggtg gttacgcgca gcgtgaccgc tacacttgcc agcgccctag   2400
cgcccgctcc tttcgctttc ttcccttcct ttctcgccac gttcgccggc tttccccgtc   2460
aagctctaaa tcgggggctc cctttagggt tccgatttag tgctttacgg cacctcgacc   2520
ccaaaaaact tgattagggt gatggttcac gtagtgggcc atcgccctga tagacggttt   2580
ttcgcccttt gacgttggag tccacgttct ttaatagtgg actcttgttc caaactggaa   2640
caacactcaa ccctatctcg gtctattctt ttgatttata agggattttg ccgatttcgg   2700
```

```
cctattggtt aaaaaatgag ctgatttaac aaaaatttaa cgcgaatttt aacaaaatat   2760

taacgtttac aatttcctga tgcggtattt tctccttacg catctgtgcg gtatttcaca   2820

ccgcatagat ccgtcgagtt caagagaaaa aaaaagaaaa agcaaaaaga aaaaaggaaa   2880

gcgcgcctcg ttcagaatga cacgtataga atgatgcatt accttgtcat cttcagtatc   2940

atactgttcg tatacatact tactgacatt cataggtata catatataca catgtatata   3000

tatcgtatgc tgcagcttta aataatcggt gtcattagtt ttgctggccg catcttctca   3060

aatatgcttc ccagcctgct tttctgtaac gttcaccctc taccttagca tcccttccct   3120

ttgcaaatag tcctcttcca acaataataa tgtcagatcc tgtagagacc acatcatcca   3180

cggttctata ctgttgaccc aatgcgtctc ccttgtcatc taaacccaca ccgggtgtca   3240

taatcaacca atcgtaacct tcatctcttc cacccatgtc tctttgagca ataaagccga   3300

taacaaaatc tttgtcgctc ttcgcaatgt caacagtacc cttagtatat tctccagtag   3360

atagggagcc cttgcatgac aattctgcta acatcaaaag gcctctaggt tcctttgtta   3420

cttcttctgc cgcctgcttc aaaccgctaa caatacctgg gcccaccaca ccgtgtgcat   3480

tcgtaatgtc tgcccattct gctattctgt atacacccgc agagtactgc aatttgactg   3540

tattaccaat gtcagcaaat ttctgtcttc cgaagagtaa aaaattgtac ttggcggata   3600

atgcctttag cggcttaact gtgccctcca tggaaaaatc agtcaagata tccacatgtg   3660

tttttagtaa acaaattttg ggacctaatg cttcaactaa ctccagtaat tccttggtgg   3720

tacgaacatc caatgaagca cacaagtttg tttgcttttc gtgcatgata ttaaatagct   3780

tggcagcaac aggactagga tgagtagcag cacgttcctt atatgtagct ttcgacatga   3840

tttatcttcg tttcctgcag gtttttgttc tgtgcagttg ggttaagaat actgggcaat   3900

ttcatgtttc ttcaacacta catatgcgta tatataccaa tctaagtctg tgctccttcc   3960

ttcgttcttc cttctgttcg gagattaccg aatcaaaaaa atttcaaaga aaccgaaatc   4020

aaaaaaaaga ataaaaaaaa aatgatgaat tgaa                               4054
```

<210> SEQ ID NO 123
<211> LENGTH: 4063
<212> TYPE: DNA
<213> ORGANISM: Artificial Sequence
<220> FEATURE:
<223> OTHER INFORMATION: Codon Optimized

<400> SEQUENCE: 123

```
tcattatcaa tactgccatt tcaaagaata cgtaaataat taatagtagt gattttccta     60

actttattta gtcaaaaaat tagcctttta attctgctgt aacccgtaca tgcccaaaat    120

agggggcggg ttacacagaa tatataacat cgtaggtgtc tgggtgaaca gtttattcct    180

ggcatccact aaatataatg gagcccgctt tttaagctgg catccagaaa aaaaaagaat    240

cccagcacca aaatattgtt ttcttcacca accatcagtt cataggtcca ttctcttagc    300

gcaactacag agaacagggg cacaaacagg caaaaaacgg gcacaacctc aatggagtga    360

tgcaacctgc ctggagtaaa tgatgacaca aggcaattga cccacgcatg tatctatctc    420

attttcttac accttctatt accttctgct ctctctgatt tggaaaaagc tgaaaaaaaa    480

ggttgaaacc agttccctga aattattccc ctacttgact aataagtata taaagacggt    540

aggtattgat tgtaattctg taaatctatt tcttaaactt cttaaattct acttttatag    600

ttagtctttt ttttagtttt aaaacaccaa gaacttagtt tcgaataaac acacataaac    660
```

-continued

```
aaacaaaatg atcgtcaagc caatggttag aaacaacatt tgtttgaacg cccatcctca    720
aggttgcaaa aagggtgttg aagatcaaat cgaatacact aaaaagagaa tcacagcaga    780
agtaaaagct ggtgcaaagg cccctaaaaa tgttttggta ttgggttgtt ccaacggtta    840
tggtttggct agtagaataa ccgctgcatt tggttacggt gccgctacta tcggtgtttc    900
cttcgaaaaa gcaggtagtg aaaccaagta tggtactcca ggttggtaca ataacttggc    960
ctttgatgaa gcagccaaga gagaaggttt gtactctgtc actatagatg gtgacgcttt   1020
ctcagatgaa attaaagcac aagtaataga agaagccaaa aagaaaggta tcaagttcga   1080
tttgatcgtt tactctttgg catcaccagt aagaacagat cctgacaccg gtataatgca   1140
caagtcagta ttgaagccat tcggtaaaac tttcacaggt aaaaccgtcg atcctttcac   1200
tggtgaattg aaggaaatat ctgcagaacc agccaatgat gaagaagctg cagccactgt   1260
caaagttatg ggtggtgaag actgggaaag atggattaaa caattgtcca aggaaggttt   1320
gttagaagaa ggttgtatca cattggctta ctcttacata ggtcctgaag ctacacaagc   1380
attgtataga aaaggtacta tcggtaaagc taaagaacat ttggaagcta ctgcacacag   1440
attgaataag gaaaacccat ctatcagagc attcgtatca gtcaataagg gtttagttac   1500
aagagcctcc gctgttatcc cagtaattcc tttgtactta gctagtttgt ttaaagttat   1560
gaaggaaaag ggtaaccatg aaggttgcat agaacaaatc acaagattgt acgcagaaag   1620
attgtacaga aaggatggta ctattccagt tgacgaagaa aacagaatta gaatcgatga   1680
ctgggaattg gaagaagacg tacaaaaagc cgtctctgct ttaatggaaa aggttactgg   1740
tgaaaacgct gaatcattga cagatttggc aggttataga cacgactttt tagcctctaa   1800
tggtttcgat gtcgaaggta ttaactacga agctgaagtt gaaagatttg acagaatata   1860
atcatgtaat tagttatgtc acgcttacat tcacgccctc cccccacatc cgctctaacc   1920
gaaaaggaag gagttagaca acctgaagtc taggtcccta tttatttttt tatagttatg   1980
ttagtattaa gaacgttatt tatatttcaa atttttcttt tttttctgta cagacgcgtg   2040
tacgcatgta acattatact gaaaaccttg cttgagaagg ttttgggacg ctcgaaggct   2100
ttaatttgcc ctcgaggggg ggcccggtac ccaattcgcc ctatagtgag tcgtattacg   2160
cgcgctcact ggccgtcgtt ttacaacgtc gtgactggga aaaccctggc gttacccaac   2220
ttaatcgcct tgcagcacat ccccctttcg ccagctggcg taatagcgaa gaggcccgca   2280
ccgatcgccc ttcccaacag ttgcgcagcc tgaatggcga atggcgcgac gcgccctgta   2340
gcggcgcatt aagcgcggcg ggtgtggtgg ttacgcgcag cgtgaccgct acacttgcca   2400
gcgccctagc gcccgctcct ttcgctttct tcccttcctt tctcgccacg ttcgccggct   2460
ttccccgtca agctctaaat cgggggctcc ctttagggtt ccgatttagt gctttacggc   2520
acctcgaccc caaaaaactt gattagggtg atggttcacg tagtgggcca tcgccctgat   2580
agacggtttt tcgccctttg acgttggagt ccacgttctt taatagtgga ctcttgttcc   2640
aaactggaac aacactcaac cctatctcgg tctattcttt tgatttataa gggattttgc   2700
cgatttcggc ctattggtta aaaaatgagc tgatttaaca aaaatttaac gcgaatttta   2760
acaaaatatt aacgtttaca atttcctgat gcggtatttt ctccttacgc atctgtgcgg   2820
tatttcacac cgcatagatc cgtcgagttc aagagaaaaa aaaagaaaaa gcaaaaagaa   2880
aaaaggaaag cgcgcctcgt tcagaatgac acgtatagaa tgatgcatta ccttgtcatc   2940
ttcagtatca tactgttcgt atacatactt actgacattc ataggtatac atatatacac   3000
atgtatatat atcgtatgct gcagctttaa ataatcggtg tcattagttt tgctggccgc   3060
```

```
atcttctcaa atatgcttcc cagcctgctt ttctgtaacg ttcaccctct accttagcat   3120

cccttccctt tgcaaatagt cctcttccaa caataataat gtcagatcct gtagagacca   3180

catcatccac ggttctatac tgttgaccca atgcgtctcc cttgtcatct aaacccacac   3240

cgggtgtcat aatcaaccaa tcgtaacctt catctcttcc acccatgtct ctttgagcaa   3300

taaagccgat aacaaaatct ttgtcgctct tcgcaatgtc aacagtaccc ttagtatatt   3360

ctccagtaga tagggagccc ttgcatgaca attctgctaa catcaaaagg cctctaggtt   3420

cctttgttac ttcttctgcc gcctgcttca aaccgctaac aatacctggg cccaccacac   3480

cgtgtgcatt cgtaatgtct gcccattctg ctattctgta tacacccgca gagtactgca   3540

atttgactgt attaccaatg tcagcaaatt ttctgtcttc gaagagtaaa aaattgtact   3600

tggcggataa tgcctttagc ggcttaactg tgccctccat ggaaaaatca gtcaagatat   3660

ccacatgtgt ttttagtaaa caaattttgg gacctaatgc ttcaactaac tccagtaatt   3720

ccttggtggt acgaacatcc aatgaagcac acaagtttgt ttgcttttcg tgcatgatat   3780

taaatagctt ggcagcaaca ggactaggat gagtagcagc acgttcctta tatgtagctt   3840

tcgacatgat ttatcttcgt ttcctgcagg tttttgttct gtgcagttgg gttaagaata   3900

ctgggcaatt tcatgtttct tcaacactac atatgcgtat atataccaat ctaagtctgt   3960

gctccttcct tcgttcttcc ttctgttcgg agattaccga atcaaaaaaa tttcaaagaa   4020

accgaaatca aaaaaaagaa taaaaaaaaa atgatgaatt gaa                     4063
```

<210> SEQ ID NO 124
<211> LENGTH: 5497
<212> TYPE: DNA
<213> ORGANISM: Artificial Sequence
<220> FEATURE:
<223> OTHER INFORMATION: Codon Optimized

<400> SEQUENCE: 124

```
tcattatcaa tactgccatt tcaaagaata cgtaaataat taatagtagt gattttccta     60

actttattta gtcaaaaaat tagccttttta attctgctgt aacccgtaca tgcccaaaat    120

agggggcggg ttacacagaa tatataacat cgtaggtgtc tgggtgaaca gtttattcct    180

ggcatccact aaatataatg gagcccgctt tttaagctgg catccagaaa aaaaaagaat    240

cccagcacca aaatattgtt ttcttcacca accatcagtt cataggtcca ttctcttagc    300

gcaactacag agaacagggg cacaaacagg caaaaaacgg gcacaacctc aatggagtga    360

tgcaacctgc ctggagtaaa tgatgacaca aggcaattga cccacgcatg tatctatctc    420

attttcttac accttctatt accttctgct ctctctgatt tggaaaaagc tgaaaaaaaa    480

ggttgaaacc agttccctga aattattccc ctacttgact aataagtata taaagacggt    540

aggtattgat tgtaattctg taaatctatt tcttaaactt cttaaattct acttttatag    600

ttagtctttt ttttagtttt aaaacaccaa gaacttagtt tcgaataaac acacataaac    660

aaacaaaatg gtttccaatc acttgtttga cgcaatgaga gccgctgccc ctggtaacgc    720

ccctttcata agaatagata atactagaac ttggacatac gatgacgcct ttgctttatc    780

tggtagaata gcatcagcta tggatgcttt gggtatcaga ccaggtgaca gagtcgcagt    840

tcaagtagaa aaatccgctg aagcattgat cttgtatttg gcttgtttga gaagtggtgc    900

agtttatttg ccattgaata ctgcctacac attagctgaa ttggattact tcataggtga    960

cgcagaacct agattggttg tagtcgcctc ttcagccaga gctggtgtag aaacaattgc   1020
```

-continued

```
taaaccaaga ggtgcaatag tcgaaacctt agatgctgct ggttctggta gtttgttaga   1080
tttggccaga gacgaacctg ctgattttgt tgacgcttca agatcagccg atgacttagc   1140
cgctattttg tacacctctg gtactacagg tagatcaaag ggtgctatgt tgactcatgg   1200
taatttgttg tcaaacgcat taaccttgag agatttctgg agagttactg ccggtgacag   1260
attaatccac gctttgccaa tttttcatac tcacggttta ttcgttgcta ccaacgtaac   1320
tttgttagca ggtgcctcca tgttcttgtt gagtaagttc gatccagaag aaatattatc   1380
tttgatgcct caagctacta tgttgatggg tgtcccaaca ttctacgtta gattgttaca   1440
atcacctaga ttagataagc aagctgttgc aaacatcaga ttgtttatat ccggtagtgc   1500
tccattgtta gcagaaaccc atactgaatt tcaagcaaga acaggtcacg ccattttaga   1560
aagatacggt atgacagaaa ccaatatgaa cacttctaac ccttatgaag gtaaaagaat   1620
agctggtaca gttggttttc cattgcctga tgtcacagtt agagtaaccg acccagccac   1680
tggtttagct ttgccacctg aacaaactgg tatgatcgaa attaaaggtc caaacgtttt   1740
taagggttac tggagaatgc ctgaaaagac tgctgctgag tttactgctg atggtttctt   1800
tatctctggt gacttaggta aaattgatag agacggttat gtccatattg ttggtcgtgg   1860
taaagatttg gttatatccg gtggttataa catctaccct aaggaagtag aaggtgaaat   1920
agatcaaatc gaaggtgttg tagaatcagc tgtaataggt gtcccacatc ctgattttgg   1980
tgaaggtgtt acagcagtcg ttgtaagaaa accaggtgct gcattagatg aaaaggcaat   2040
tgtttctgcc ttacaagaca gattggctag atacaagcaa ccaaagagaa taatcttcgc   2100
agaagatttg cctagaaata ctatgggtaa agtacaaaag aacatcttga gacaacaata   2160
cgccgactta tacaccagaa ccgaaggtag aggttctttg ttaacatgtg gtgacgttga   2220
agaaaatcca ggtcctatgg cttcagaaaa ggaaataaga agagaaagat tcttgaacgt   2280
attcccaaag ttagttgaag aattgaacgc tagtttgtta gcttatggta tgcctaaaga   2340
agcctgcgat tggtatgctc actctttaaa ctacaatact ccaggtggta aattgaatag   2400
aggtttgagt gtagttgata cttatgctat cttgtctaac aaaaccgttg aacaattagg   2460
tcaagaagaa tacgaaaagg tcgctatctt gggttggtgt attgaattgt tgcaagcata   2520
ctttttggtt gccgatgaca tgatggataa gtctataaca agaagaggtc aaccatgctg   2580
gtacaaagtt ccagaagttg gtgaaatagc cataaatgat gcttttatgt tggaagccgc   2640
tatctataaa ttgttgaagt cacatttcag aaacgaaaag tactacatcg atattaccga   2700
attattccac gaagttactt tccaaacaga attgggtcaa ttgatggatt tgataactgc   2760
acctgaagat aaagttgact tgtcaaagtt ttccttgaag aaacattcat tcatcgtcac   2820
ctttgaaact gcttattact ccttctattt gccagtcgcc ttggctatgt acgtagctgg   2880
tattactgat gaaaaagact tgaagcaagc aagagatgtt ttgatacctt tgggtgaata   2940
cttccaaatc caagatgact acttagactg tttcggtact ccagaacaaa taggtaaaat   3000
cggtacagat attcaagaca ataagtgcag ttgggttatt aacaaggctt tggaattagc   3060
atctgccgaa caaagaaaga ctttggatga aaactacggt aaaaaggact cagttgctga   3120
agcaaagtgt aagaaaattt ttaatgattt gaagattgaa caattgtacc atgaatacga   3180
agaatccatc gctaaagact taaaggcaaa gattagtcaa gttgatgaat caagaggttt   3240
taaagccgac gttttgacag ctttcttgaa taaggtctac aagagatcaa agtgatcatg   3300
taattagtta tgtcacgctt acattcacgc cctcccccca catccgctct aaccgaaaag   3360
gaaggagtta gacaacctga agtctaggtc cctatttatt tttttatagt tatgttagta   3420
```

-continued

```
ttaagaacgt tatttatatt tcaaattttt cttttttttc tgtacagacg cgtgtacgca   3480
tgtaacatta tactgaaaac cttgcttgag aaggttttgg gacgctcgaa ggctttaatt   3540
tgccctcgag ggggggcccg gtacccaatt cgccctatag tgagtcgtat tacgcgcgct   3600
cactggccgt cgttttacaa cgtcgtgact gggaaaaccc tggcgttacc caacttaatc   3660
gccttgcagc acatccccct ttcgccagct ggcgtaatag cgaagaggcc cgcaccgatc   3720
gcccttccca acagttgcgc agcctgaatg gcgaatggcg cgacgcgccc tgtagcggcg   3780
cattaagcgc ggcgggtgtg gtggttacgc gcagcgtgac cgctacactt gccagcgccc   3840
tagcgcccgc tcctttcgct ttcttccctt cctttctcgc cacgttcgcc ggctttcccc   3900
gtcaagctct aaatcggggg ctccctttag ggttccgatt tagtgcttta cggcacctcg   3960
accccaaaaa acttgattag ggtgatggtt cacgtagtgg gccatcgccc tgatagacgg   4020
tttttcgccc tttgacgttg gagtccacgt tctttaatag tggactcttg ttccaaactg   4080
gaacaacact caaccctatc tcggtctatt cttttgattt ataagggatt ttgccgattt   4140
cggcctattg gttaaaaaat gagctgattt aacaaaaatt taacgcgaat tttaacaaaa   4200
tattaacgtt tacaatttcc tgatgcggta ttttctcctt acgcatctgt gcggtatttc   4260
acaccgcata gatccgtcga gttcaagaga aaaaaaaaga aaaagcaaaa agaaaaaagg   4320
aaagcgcgcc tcgttcagaa tgacacgtat agaatgatgc attaccttgt catcttcagt   4380
atcatactgt tcgtatacat acttactgac attcataggt atacatatat acacatgtat   4440
atatatcgta tgctgcagct ttaaataatc ggtgtcatta gttttgctgg ccgcatcttc   4500
tcaaatatgc ttcccagcct gcttttctgt aacgttcacc ctctacctta gcatcccttc   4560
cctttgcaaa tagtcctctt ccaacaataa taatgtcaga tcctgtagag accacatcat   4620
ccacggttct atactgttga cccaatgcgt ctcccttgtc atctaaaccc acaccgggtg   4680
tcataatcaa ccaatcgtaa ccttcatctc ttccacccat gtctctttga gcaataaagc   4740
cgataacaaa atctttgtcg ctcttcgcaa tgtcaacagt acccttagta tattctccag   4800
tagataggga gcccttgcat gacaattctg ctaacatcaa aaggcctcta ggttcctttg   4860
ttacttcttc tgccgcctgc ttcaaaccgc taacaatacc tgggcccacc acaccgtgtg   4920
cattcgtaat gtctgcccat tctgctattc tgtatacacc cgcagagtac tgcaatttga   4980
ctgtattacc aatgtcagca aattttctgt cttcgaagag taaaaaattg tacttggcgg   5040
ataatgcctt tagcggctta actgtgccct ccatggaaaa atcagtcaag atatccacat   5100
gtgtttttag taaacaaatt ttgggaccta atgcttcaac taactccagt aattccttgg   5160
tggtacgaac atccaatgaa gcacacaagt ttgtttgctt ttcgtgcatg atattaaata   5220
gcttggcagc aacaggacta ggatgagtag cagcacgttc cttatatgta gctttcgaca   5280
tgatttatct tcgtttcctg caggtttttg ttctgtgcag ttgggttaag aatactgggc   5340
aatttcatgt ttcttcaaca ctacatatgc gtatatatac caatctaagt ctgtgctcct   5400
tccttcgttc ttccttctgt tcggagatta ccgaatcaaa aaaatttcaa agaaaccgaa   5460
atcaaaaaaa agaataaaaa aaaaatgatg aattgaa                            5497
```